(12) United States Patent
Ma et al.

(10) Patent No.: US 11,999,964 B2
(45) Date of Patent: Jun. 4, 2024

(54) SYNTHETIC MAMMALIAN SIGNALING CIRCUITS FOR ROBUST CELL POPULATION CONTROL

(71) Applicant: California Institute of Technology, Pasadena, CA (US)

(72) Inventors: Yitong Ma, Pasadena, CA (US); Mark W. Budde, Pasadena, CA (US); Michaelle N. Mayalu, Pasadena, CA (US); Michael B. Elowitz, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 89 days.

(21) Appl. No.: 17/460,120

(22) Filed: Aug. 27, 2021

(65) Prior Publication Data

US 2022/0064666 A1 Mar. 3, 2022

Related U.S. Application Data

(60) Provisional application No. 63/072,014, filed on Aug. 28, 2020.

(51) Int. Cl.
| | | |
|---|---|---|
| *C12N 15/85* | (2006.01) | |
| *C07K 14/415* | (2006.01) | |
| *C12N 9/02* | (2006.01) | |
| *C12N 9/86* | (2006.01) | |
| *C12N 15/11* | (2006.01) | |

(52) U.S. Cl.
CPC .......... *C12N 15/85* (2013.01); *C07K 14/415* (2013.01); *C12N 9/0069* (2013.01); *C12N 9/86* (2013.01); *C12N 15/11* (2013.01); *C12Y 113/12003* (2013.01); *C07K 2319/00* (2013.01); *C12N 2310/20* (2017.05); *C12N 2800/107* (2013.01); *C12N 2810/10* (2013.01)

(58) Field of Classification Search
CPC .......... C07K 14/415; C07K 2319/95; C12N 9/0069; C12N 9/86; C12Y 113/12003
See application file for complete search history.

(56) References Cited

U.S. PATENT DOCUMENTS

| | | |
|---|---|---|
| 5,260,291 A | 11/1993 | Lunt et al. |
| 5,747,498 A | 5/1998 | Schnur et al. |
| 6,326,193 B1 | 12/2001 | Liu et al. |
| 6,703,199 B1 | 3/2004 | Koide |
| 2008/0139587 A1 | 6/2008 | Huang et al. |
| 2020/0071723 A1 | 3/2020 | Gao et al. |
| 2020/0277333 A1 | 9/2020 | Chong et al. |
| 2021/0171582 A1 | 6/2021 | Flynn et al. |

FOREIGN PATENT DOCUMENTS

| | | |
|---|---|---|
| EP | 0564409 | 3/1993 |
| EP | 0566226 | 11/1995 |
| EP | 0520722 | 12/1996 |
| EP | 0787722 | 8/1997 |
| EP | 0837063 | 4/1998 |
| WO | WO1996033980 | 10/1996 |
| WO | WO1997002266 | 1/1997 |
| WO | WO1997030034 | 8/1997 |
| WO | WO1997038983 | 10/1997 |
| WO | WO1997049688 | 12/1997 |
| WO | WO1998010767 | 3/1998 |
| WO | WO1999003854 | 1/1999 |
| WO | WO2001029058 | 4/2001 |
| WO | WO2001096584 | 12/2001 |
| WO | WO2002022577 | 3/2002 |
| WO | WO2003013541 | 2/2003 |
| WO | WO2019147478 | 8/2019 |

OTHER PUBLICATIONS

Powers et al (Regulation of auxin transcriptional responses. Developmental dynamics, Nov. 2019) (Year: 2019).*
Sekine et al (Molecular Cloning of a Gene for Indole-3-Acetamide Hydrolase from Bradyrhizobium japonicum. Journal of Bacteriology, vol. 171, Mar. 1989). (Year: 1989).*
Jasik et al (PIN2 Turnover in *Arabidopsis* Root Epidermal Cells Explored by the Photoconvertible Protein Dendra2. PLoS One, vol. 8, Apr. 2013) (Year: 2013).*
Kanke et al (Auxin-inducible protein depletion system in fission yeast. BMC Cell Biology, 2011) (Year: 2011).*
Trost et al (Regulated protein depletion by the auxin-inducible degradation system in *Drosophila melanogaster*. Fly, vol. 10, 2016). (Year: 2016).*
Gao et al (Programmable protein circuits in living cells. Science, vol. 361, Sep. 2018). (Year: 2018).*
Anderson et al (Glutamate metabolism and recycling at the excitatory synapse in health and neurodegeneration. Neuropharmacology, vol. 196, 2021) (Year: 2021).*
Costello et al (Synthetic Biological Circuits within an Orthogonal Central Dogma. Trends in Biotech, vol. 39, Jan. 2021) ( Year: 2021).*

(Continued)

*Primary Examiner* — Valarie E Bertoglio
*Assistant Examiner* — Matasha Dhar
(74) *Attorney, Agent, or Firm* — Sheppard, Mullin, Richter & Hampton LLP

(57) ABSTRACT

Disclosed herein include circuits, compositions, nucleic acids, populations, systems, and methods enabling cells to sense, control, and/or respond to their own population size. In some embodiments, an orthogonal communication channel allows specific communication between engineered cells. Also described herein, in some embodiments, is an evolutionarily robust 'paradoxical' regulatory circuit architecture in which orthogonal signals both stimulate and inhibit net cell growth at different signal concentrations. In some embodiments, engineered cells autonomously reach designed densities and/or activate therapeutic or safety programs at specific density thresholds. Methods of treatment are also provided in some embodiments.

11 Claims, 41 Drawing Sheets

(41 of 41 Drawing Sheet(s) Filed in Color)

(56) References Cited

OTHER PUBLICATIONS

Gao et al (Auxin Biosynthesis and Catabolismchapter 2 in Auxin and Its Role in Plant Development, E. Zazimalova et al. (eds.), Springer, 2014) (Year: 2014).*
Adamowski et al., "PIN-Dependent Auxin Transport: Action, Regulation, and Evolution," The Plant Cell 2015, 27, 20-32.
Aggen et al., "Single-Chain VαVβ T Cell Receptors Function Without Mispairing With Endogenous TCR Chains," Gene Therapy 2012, 19(4), 365-374.
Alon, "An Introduction to Systems Biology Design Principles of Biological Circuits," Second Edition 2020, in 343 pages.
Bacchus et al., "Synthetic two-way communication between mammalian cells," Nature Biotechnology 2012, 30(10), 991-1016.
Balagaddé et al., "Long-term monitoring of bacteria undergoing programmed population control in microchemostat," Science 2005, 309, 137-140.
Berg et al., "ilastik: interactive machine learning for (bio)image analysis," 2020, 1-9.
Bier & De Robertis, "BMP gradients: A paradigm for morphogen-mediated developmental patterning," Science 2015, 348(6242), aaa5838, in 14 pages.
Boyman & Sprent, "The role of interleukin-2 during homeostasis and activation of the immune system," Nature 2012, 12, 180-190.
Chevalier et al., "Design and Analysis of a Proportional-Integral-Derivative Controller with Biological Molecules," Cell 2019, 9, 338-353.
Chiang et al., "Organ-Level Quorum Sensing Directs Regeneration in Hair Stem Cell Populations," Cell 2015, 161, 277-290.
Chmielewski et al., "IL-12 Release by Engineered T Cells Expressing Chimeric Antigen Receptors Can Effectively Muster an Antigen-Independent Macrophage Response on Tumor Cells That Have Shut Down Tumor Antigen Expression," American Association for Cancer Research 2011, 71(17), 5697-5706.
Choi et al., "CAR-T cells secreting BiTEs circumvent antigen escape without detectable toxicity," Nature Biotechnology 2019, 37, 1049-1058.
Dao et al., "Targeting the Intracellular WT1 Oncogene Product with a Therapeutic Human Antibody," Sci Transl Med 2013, 5(176), in 22 pages.
Daringer et al., "Modular Extracellular Sensor Architecture for Engineering Mammalian Cell-based Devices," American Chemical Society 2014, 3, 892-902.
Del Vecchio & Murray, "Biomolecular Feedback Systems," Princeton 2014, in 282 pages.
Dharmasiri et al., "The F-box protein TIR1 is an auxin receptor," Nature 2005, 435, 441-445.
Din et al., "Synchronized cycles of bacterial lysis for in vivo delivery," Nature 2016, 536(7614), 81-85.
Di Stasi et al., "Inducible Apoptosis as a Safety Switch for Adoptive Cell Therapy," N Engl J Med 2011, 365(18), 1673-1683.
Early & Martin, "Photoperiodic Regulation of Vegetative Growth and Gibberellin Metabolism in Strawberry," Hortscience 1990, 25(9), 392, in 1 page.
Finkelstein, "Abscisic Acid Synthesis and Response," American Society of Plant Biologists 2013, e0166, in 36 pages.
Gao et al., "Programmable protein circuits in living cells," Science 2018, 361, 1252-1258.
Gibb et al., "The segmentation clock mechanism moves up a notch," Trends in Cell Biology 2010, 10(2), 593-600.
Gibson et al., "Enzymatic assembly of DNA molecules up to several hundred kilobases," Nature Methods 2009, 6(5), 343-345.
Guindon et al., "New algorithms and methods to estimate maximum-likelihood phylogenies: assessing the performance of PhyML 3.0," University of Zurich 2010, 10(5167), in 16 pages.
Harborth et al., "Identification of essential genes in cultured mammalian cells using small interfering RNAs," Journal of Cell Science 2001, 114(24), 4557-4565.
Hart et al., "Design principles of cell circuits with paradoxical components," PNAS 2012, 109(21), 8346-8351.
Hart et al., "Paradoxical Signaling by a Secreted Molecule Leads to Homeostasis of Cell Levels," Cell 2014, 158, 1022-1032.
Holcik & Sonenberg, "Translational control in stress apoptosis," Nature Reviews Molecular Cell Biology 2005, 6, 318-327.
Hollinger & Hudson, "Engineered antibody fragments and the rise of single domains," Nature Biotechnology 2005, 23(9), 1126-1136.
Hong et al., "Synthetic quorum-sensing circuit to control consortial biofilm formation and dispersal in a micro fluidic device," Nature Communications 2012, 3(613), 1-8.
Hu et al., "Augmentation of Antitumor Immunity by Human and Mouse CAR T Cells Secreting IL-18," Cell Rep. 2017, 20(13), 3025-3033.
International Search Report and Written Opinion dated Dec. 20, 2021 in PCT Patent Application No. PCT/US2021/048100.
Karin & Alon, "Biphasic response as a mechanism against mutant takeover in tissue homeostasis circuits," Molecular Systems Biology 2017, 13(933), 1-12.
Kawaguchi et al., "The Presence of an Enzyme that Converts Indole-3-acetamide IAA in Wild and Cultivate Rice," Plan Cell Physiology 1991, 32(2), 143-149.
Keener & Sneyd, "Mathematical Physiology II: Systems Physiology," vol. 2, 2009.
Khakhar et al., "Cell-cell communication in yeast using auxin biosynthesis and auxin responsive CRISPR transcription factors," bioRxiv 2015, 020487, in 15 pages. doi: https://doi.org/10.1101/020487.
Landgraf et al., "Segregation of molecules at cell division reveals native protein localization," Nat Methods 2013, 9(5), 480-482.
Langmead & Salzberg, "Fast gapped-read alignment with Bowtie 2," Nat Methods 2013, 9(4), 357-359.
Li & Elowitz, "Communication codes in developmental signaling pathways," Development 2019, 146, in 12 pages.
Liang et al., "Engineering the ABA Plant Stress Pathway for Regulation of Induced Proximity," Sci Signal 2011, 4(164), rs2, in 18 pages.
Liao et al., "Rock-paper-scissors: Engineered population dynamics increase genetic stability," Science 2019, 365(6457), 1045-1049.
Ma et al., "Synthetic mammalian signaling circuits for robust cell population control," bioRxiv 2020, 278564, in 39 pages. doi: https://doi.org/10.1101/2020.09.02.278564.
Maetzig et al., "Gammaretroviral Vectors: Biology, Technology and Application," Viruses 2011, 3(6), 677-713.
Mashiguchi et al., "The main auxin biosynthesis pathway in *Arabidopsis*," PNAS 2011, 108(45), 18512-18517.
Matsuda et al., "Synthetic Signal Propagation Through Direct Cell-Cell Interaction," Science Signaling 2017, 5(220), 1-9.
Mendoza-Ochoa et al., "A fast and tuneable auxin-inducible degron for depletion of target proteins in budding yeast," Yeast 2019, 36, 75-81.
Milone et al., "Chimeric Receptors Containing CD137 Signal Transduction Domains Mediate Enhanced Survival of T Cells and Increased Antileukemic Efficacy In Vivo," Molecular Therapy 2009, 17(8), 1453-1464.
Miyamoto et al., "Rapid and Orthogonal Logic Gating with a Gibberellin-induced Dimerization System," Nat Chem Biol 2012, 8(5), 465-470.
Morsut et al., "Engineering Customized Cell Sensing and Response Behaviors Using Synthetic Notch Receptors," Cell 2016, 164, 780-791.
Muldoon et al., "Macrophages employ quorum licensing to regulate collective activation," Nature Communications 2020, 11(878), 1-14.
Natsume et al., "Rapid Protein Depletion in Human Cells by Auxin-Inducible Degron Tagging with Short Homology Donors," Cell Reports 2016, 15, 210-218.
Nishimura et al., "An auxin-based degron system for the rapid depletion of proteins in nonplant cells," Nature Methods 2009, 6(12), 917-922.
Park et al., "Bacterial quorum sensing and anti-quorum sensing," Korean Journal of Microbiology and Biotechnology 2004, 32(1), 1-10.
Papenfort & Bassler, "Quorum-Sensing Signal-Response Systems in Gram-Negative Bacteria," Nat Rev Microbiol 2016, 14(9), 576-588.

(56) References Cited

OTHER PUBLICATIONS

Petrášek, "Pin Proteins Perform a Rate-Limiting Function in Cellular Auxin Efflux," Science 2006, 312, 914-918.
Raven, "Transport of Indoleacetic Acid in Plant Cells in Relation to PH and Electrical Potential Gradients, and Its Significance for Polar IAA Transport," New Phytol 1975, 74, 163-172.
Reitsma et al., "Composition and regulation of the cellular repertoire of SCF ubiquitin ligases," Cell 2017, 171(6), 1326-1339.
Richards et al., "A Flexible Growth Function for Empirical Use," Journal of Experimental Botany 1959, 10(29), 290-300.
Robinson et al., "Measurement of diffusion coefficients of some indoles and ascorbic acid by flow injection analysis," J. Phys. Chem. 1990, 94(2), 1003-1005.
Sastry et al., "Targeting Hepatitis B Virus-Infected Cells with a T-Cell Receptor-Like Antibody," Journal of Virology 2011, 85(5), 1935-1942.
Satyanarayana & Kaldis, "Mammalian cell-cycle regulation: several Cdks, numerous cyclins and diverse compensatory mechanisms," Oncogene 2009, 28, 2925-2939.
Scott & Hasty, "Quorum Sensing Communication Modules for Microbial Consortia," ACS Synth Biol 2016, 5(9), 969-977.
Sekine et al., "Synthetic mammalian pattern formation driven by differential diffusivity of Nodal and Lefty," Nature Communications 2018, 9(5456), 1-11.
Sekine et al., "Detection of the IAA Biosynthetic Pathway from Tryptophan via Indole-3-Acetamide in *Bradyrhizobium* spp," Plant Cell Physiol 1988, 29(5), 867-874.
Sergeeva et al., "An anti-PR1/HLA-A2 T-cell receptor-like antibody mediates complement-dependent cytotoxicity against acute myeloid leukemia progenitor cells," Blood 2011, 117(16), 4262- 4272.
Sharrock et al., "NTR 2.0: a rationally-engineered prodrug converting enzyme with substantially enhanced efficacy for targeted cell ablation," bioRxiv 2020, 111427, in 26 pages. doi: https://doi.org/10.1101/2020.05.22.111427.
Sievers et al., "Fast, scalable generation of high-quality protein multiple sequence alignments using Clustal Omega," Molecular Systems Biology 2011, 7(539), 1-6.
Sitbon et al., "Transgenic Tobacco Plants Coexpressing the Agrobacterium *tumefaciens iaaM* and *iaaH* Genes Display Altered Growth and Indoleacetic Acid Metabolism," Plant Physiol 1992, 99, 1062- 1069.
Stirling et al., "Rational Design of Evolutionarily Stable Microbial Kill Switches," Molecular Cell 2017, 68(4), 686-697.
Straathof et al., "An inducible caspase 9 safety switch for T-cell therapy," Blood 2005, 105(11), 4247-4254.
Szymczak et al., "Correction of multi-gene deficiency in vivo using a single 'self-cleaving' 2A peptide-based retroviral vector," Nature Biotechnology 2004, 22(5), 589-594.
Tanaka et al., "Spatiotemporal asymmetric auxin distribution: a means to coordinate plant development," Cell. Mol. Life Sci. 2006, 63, 2738-2754.
Tassev et al., "Retargeting NK92 cells using an HLA-A2-restricted, EBNA3C-specific chimeric antigen receptor," Cancer Gene Therapy 2012, 19, 84-100.
Teague et al., "Synthetic Morphogenesis," Cold Spring Harb Perspect Biol 2016, 8(a023929), in 15 pages.
Toda et al., "Programming self-organizing multicellular structures with synthetic cell-cell signaling," Science 2018, 361(6398), 156-162.
Trask et al., "Phase I Study of Adenoviral Delivery of the HSV-tk Gene and Ganciclovir Administration in Patients with Recurrent Malignant Brain Tumors." Molecular Therapy 2000, 1(2), 195-203.
Turing, "The Chemical Basis of Morphogenesis," Philosophical Transactions of the Royal Society of London. Series B, Biological Sciences 1952, 237(641), 37-72.
Verma et al., "TCR Mimic Monoclonal Antibody Targets a Using Breast Cancer Models Significantly Impedes Tumor Growth In Vivo Specific Peptide/HLA Class I Complex and Significantly Impedes Tumor Growth In Vivo Using Breast Cancer Models," J Immunol 2010, 184, 2156-2165.
Waters & Bassler, "Quorum Sensing: Cell-to-Cell Communication in Bacteria," Annu. Rev. Cell Dev. Biol. 2005, 21, 319-346.
Willemsen et al., "Grafting primary human T lymphocytes with cancer-specific chimeric single chain and two chain TCR," Gene Therapy 2000, 7, 1369-1377.
Willemsen et al., "A phage display selected Fab fragment with MHC class I-restricted specificity for MAGE-A1 allows for retargeting of primary human T lymphocytes," Gene Therapy 2001, 8, 1601-1608.
You et al., "Programmed population control by cell-cell communication and regulated killing," Nature 2004, in 4 pages.
Zhang et al., "Transgenic TCR expression: comparison of single chain with full-length receptor constructs for T-cell function," Cancer Gene Therapy 2004, 11, 487-496.
Zhou et al., "Circuit design features of a stable two-cell system," Cell 2018, 172(4), 744-757.

\* cited by examiner

Reactions of Indole-3-acetamide hydrolases (e.g. iaaH, aux2, AMI1, etc.)

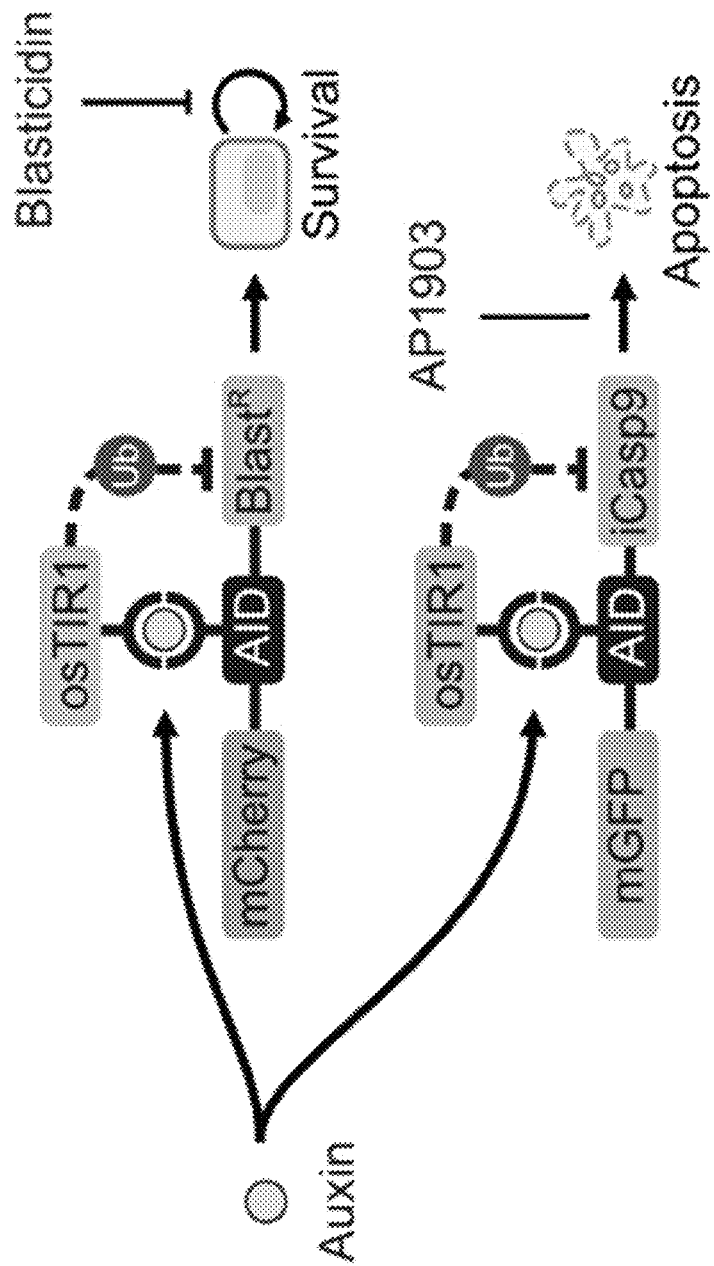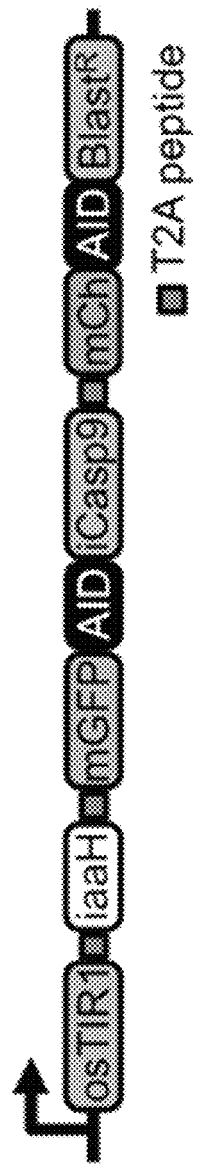
FIG. 4B
FIG. 4C

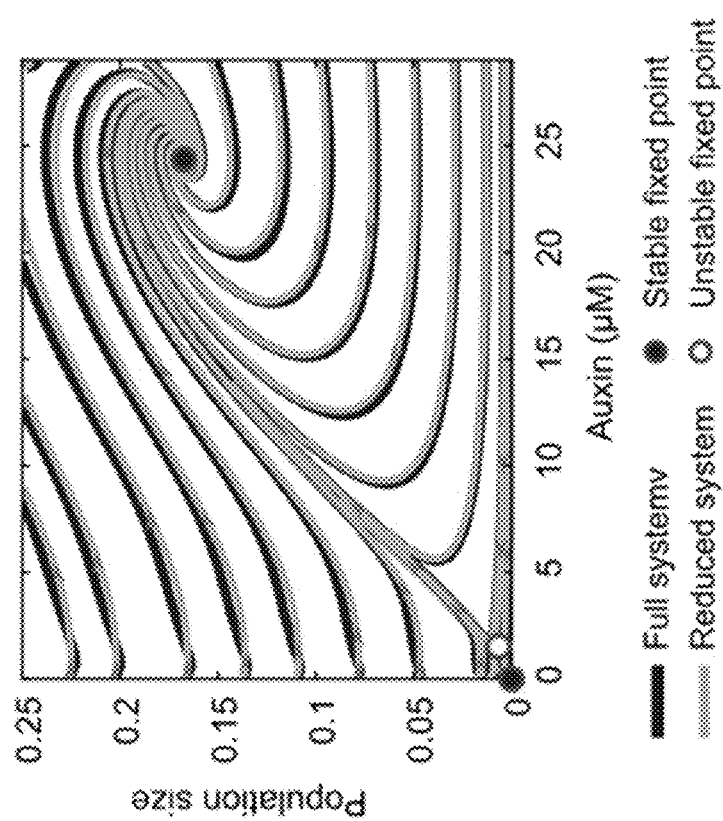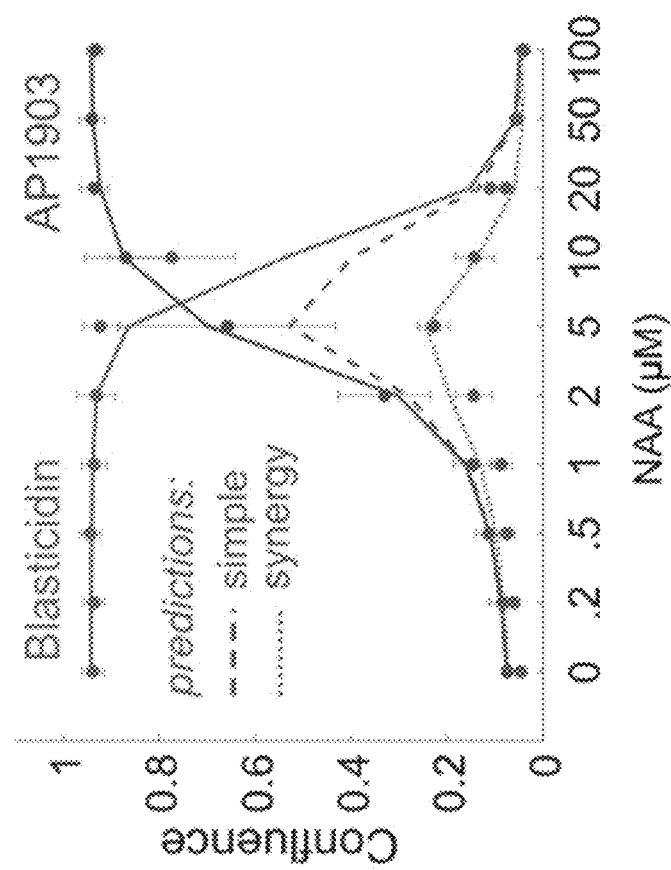
FIG. 8B
FIG. 8A

SYNTHETIC MAMMALIAN SIGNALING CIRCUITS FOR ROBUST CELL POPULATION CONTROL

RELATED APPLICATIONS

This application claims the benefit under 35 U.S.C. § 119(e) of U.S. Provisional Patent Application Ser. No. 63/072,014, filed Aug. 28, 2020, the content of this related application is incorporated herein by reference in its entirety for all purposes.

STATEMENT REGARDING FEDERALLY SPONSORED R&D

This invention was made with government support under Grant No. HR0011-17-2-0008 awarded by DARPA. The government has certain rights in the invention.

FIELD

Background

The present disclosure relates generally to the field of synthetic biology.

Description of the Related Art

Engineered cell therapies have enormous potential to address diseases that would be difficult or impossible to control with drugs alone. Once in a patient, the ability of engineered therapeutic cells to function correctly depends on their population density at different sites in the body. However, current cell therapies generally lack rationally designed systems that would enable engineered cells to control their own population density. There is a need for synthetic circuits that enable cells to sense, control, and respond to their own population size to provide this capability, allowing engineered cells to autonomously reach designed densities, or to activate therapeutic or safety programs at specific density thresholds. However, any circuit that limits growth can be susceptible to mutations that inactivate it. There is a need for circuits that can enable population control in a way that is robust to such mutations, and thus make such systems more stable and reliable.

SUMMARY

Disclosed herein include nucleic acid compositions. In some embodiments, the nucleic acid composition comprises: a first polynucleotide encoding a first synthase, wherein the first synthase is capable of catalyzing the synthesis of an orthogonal signal from a first precursor molecule.

Disclosed herein include nucleic acid compositions. In some embodiments, the nucleic acid composition comprises: a second polynucleotide encoding a second synthase, wherein the second synthase is capable of catalyzing the synthesis of a first precursor molecule from a second precursor molecule.

Disclosed herein include nucleic acid compositions. In some embodiments, the nucleic acid composition comprises: a third polynucleotide encoding a transporter capable of transporting an orthogonal signal, a first precursor molecule, and/or a second precursor molecule across a cell membrane.

Disclosed herein include nucleic acid compositions. In some embodiments, the nucleic acid composition comprises: a fourth polynucleotide encoding a signal-binding protein; and a fifth polynucleotide encoding a first fusion protein comprising a signal-responsive domain and a pro-growth protein; wherein the signal-binding protein is capable of binding an orthogonal signal, wherein a signal-binding protein bound to the orthogonal signal is capable of reducing the stability, localization, and/or activity of a protein comprising a signal-responsive domain.

Disclosed herein include nucleic acid compositions. In some embodiments, the nucleic acid composition comprises: a fourth polynucleotide encoding a signal-binding protein; a fifth polynucleotide encoding a first fusion protein comprising a signal-responsive domain and a pro-growth protein; and a sixth polynucleotide encoding a second fusion protein comprising a signal-responsive domain and a pro-death protein, wherein the signal-binding protein is capable of binding an orthogonal signal, wherein a signal-binding protein bound to the orthogonal signal is capable of reducing the stability, localization, and/or activity of a protein comprising a signal-responsive domain.

Disclosed herein include nucleic acid compositions. In some embodiments, the nucleic acid composition comprises: a fourth polynucleotide encoding a signal-binding protein; and a seventh polynucleotide encoding a third fusion protein comprising a signal-responsive domain and target protein, wherein the signal-binding protein is capable of binding an orthogonal signal, wherein a signal-binding protein bound to the orthogonal signal is capable of reducing the stability, localization, and/or activity of a protein comprising a signal-responsive domain.

Disclosed herein include nucleic acid compositions. In some embodiments, the nucleic acid composition comprises: two or more of the nucleic acid compositions of any one of the nucleic acid compositions (e.g., circuits) provided herein.

In some embodiments, the target protein can diminish immune cell function. In some embodiments, the target protein is an activity regulator. In some embodiments, the activity regulator is capable of reducing T cell activity. In some embodiments, the activity regulator comprises a ubiquitin ligase involved in TCR/CAR signal transduction selected from the group comprising c-CBL, CBL-B, ITCH, R F125, R F128, WWP2, or any combination thereof. In some embodiments, the activity regulator comprises a negative regulatory enzyme selected from the group comprising SHP1, SHP2, SHTP1, SHTP2, CD45, CSK, CD148, PTPN22, DGKalpha, DGKzeta, DRAK2, HPK1, HPK1, STS1, STS2, SLAT, or any combination thereof. In some embodiments, the activity regulator is a negative regulatory scaffold/adapter protein selected from the group comprising PAG, LIME, NTAL, LAX31, SIT, GAB2, GRAP, ALX, SLAP, SLAP2, DOK1, DOK2, or any combination thereof. In some embodiments, the activity regulator is a dominant negative version of an activating TCR signaling component selected from the group comprising ZAP70, LCK, FYN, NCK, VAV1, SLP76, ITK, ADAP, GADS, PLCgammal, LAT, p85, SOS, GRB2, NFAT, p50, p65, API, RAP1, CRKII, C3G, WAVE2, ARP2/3, ABL, ADAP, RIAM, SKAP55, or any combination thereof. In some embodiments, the activity regulator comprises the cytoplasmic tail of a negative co-regulatory receptor selected from the group comprising CD5, PD1, CTLA4, BTLA, LAG3, B7-H1, B7-1, CD160, TFM3, 2B4, TIGIT, or any combination thereof. In some embodiments, the activity regulator is targeted to the plasma membrane with a targeting sequence derived from LAT, PAG, LCK, FYN, LAX, CD2, CD3, CD4, CD5, CD7, CD8a, PD1, SRC, LYN, or any combination thereof. In some embodiments, the activity regulator reduces or abrogates a pathway and/or a function selected from the group comprising Ras signaling, PKC signaling, calcium-dependent signaling, NF-kappaB signaling, NFAT signaling, cytokine secretion, T cell survival, T cell proliferation, CTL activity, degranulation, tumor cell killing, differentiation, or any combination thereof.

In some embodiments, the concentration, localization, stability, and/or activity of one or more payloads are under control of the orthogonal signal (e.g., via regulation through an AID-tagged protein). The nucleic acid composition can comprise: an eighth polynucleotide encoding one or more payloads. In some embodiments, the target protein is capable of modulating the concentration, localization, stability, and/or activity of the one or more payloads. In some embodiments, the target protein is capable of repressing the transcription of the one or more payloads. In some embodiments, a payload transcript is capable of being translated to generate a payload protein, and wherein the target protein is capable of reducing the concentration, localization, stability, and/or activity of the payload protein. In some embodiments, the concentration, localization, stability, and/or activity of the payload protein is inversely related to the concentration, localization, stability, and/or activity of the target protein. In some embodiments, the target protein comprises a protease. In some embodiments, the payload protein comprises a degron and a cut site the protease is capable of cutting to expose the degron, and wherein the degron of the payload protein being exposed changes the payload protein to a payload protein destabilized state. In some embodiments, the protease comprises tobacco etch virus (TEV) protease, tobacco vein mottling virus (TVMV) protease, hepatitis C virus protease (HCVP), derivatives thereof, or any combination thereof. In some embodiments, the payload protein comprises a cage polypeptide. In some embodiments, the cage polypeptide comprises: (a) a helical bundle, comprising between 2 and 7 alpha-helices, wherein the helical bundle comprises: (i) a structural region; and (ii) a latch region, wherein the latch region comprises a degron located within the latch region, wherein the structural region interacts with the latch region to prevent activity of the degron; and (b) amino acid linkers connecting each alpha helix. In some embodiments, the target protein comprises a key polypeptide capable of binding to the cage polypeptide structural region, thereby displacing the latch region and activating the degron.

In some embodiments, the payload encodes a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof. In some embodiments, the payload protein comprises a synthetic protein circuit component. In some embodiments, the payload comprises a bispecific T cell engager (BiTE). In some embodiments, the payload protein comprises a cytokine. In some embodiments, the cytokine is selected from the group consisting of interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, granulocyte macrophage colony stimulating factor (GM-CSF), M-CSF, SCF, TSLP, oncostatin M, leukemia-inhibitory factor (LIF), CNTF, Cardiotropin-1, NNT-1/BSF-3, growth hormone, Prolactin, Erythropoietin, Thrombopoietin, Leptin, G-CSF, or receptor or ligand thereof. In some embodiments, the payload protein comprises a member of the TGF-β/BMP family selected from the group consisting of TGF-β1, TGF-β2, TGF-β3, BMP-2, BMP-3a, BMP-3b, BMP-4, BMP-5, BMP-6, BMP-7, BMP-8a, BMP-8b, BMP-9, BMP-10, BMP-11, BMP-15, BMP-16, endometrial bleeding associated factor (EBAF), growth differentiation factor-1 (GDF-1), GDF-2, GDF-3, GDF-5, GDF-6, GDF-7, GDF-8, GDF-9, GDF-12, GDF-14, mullerian inhibiting substance (MIS), activin-1, activin-2, activin-3, activin-4, and activin-5. In some embodiments, the payload protein comprises a member of the TNF family of cytokines selected from the group consisting of TNF-alpha, TNF-beta, LT-beta, CD40 ligand, Fas ligand, CD 27 ligand, CD 30 ligand, and 4-1 BBL. In some embodiments, the payload protein comprises a member of the immunoglobulin superfamily of cytokines selected from the group consisting of B7.1 (CD80) and B7.2 (B70). In some embodiments, the payload protein comprises an interferon (e.g., interferon alpha, interferon beta, or interferon gamma). In some embodiments, the payload protein comprises a chemokine. In some embodiments, the chemokine is selected from CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13, or CXCL15. In some embodiments, the payload protein comprises a interleukin (e.g., IL-10 IL-12, IL-1, IL-6, IL-7, IL-15, IL-2, IL-18 or IL-21). In some embodiments, the payload protein comprises a tumor necrosis factor (TNF), such as, for example, TNF-alpha, TNF-beta, TNF-gamma, CD252, CD154, CD178, CD70, CD153, or 4-1BBL. In some embodiments, the payload protein comprises a factor locally down-regulating the activity of endogenous immune cells. In some embodiments, the payload protein is capable of remodeling a tumor microenvironment and/or reducing immunosuppression at a target site of a subject.

In some embodiments, the payload protein comprises a chimeric antigen receptor (CAR) or T-cell receptor (TCR). In some embodiments, the CAR and/or TCR comprises one or more of an antigen binding domain, a transmembrane domain, and an intracellular signaling domain. In some embodiments, the intracellular signaling domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCER1G), FcR beta (Fc Epsilon Rib), CD79a, CD79b, Fcgamma RIIa, DAP10, and DAP12, or a functional variant thereof. In some embodiments, the costimulatory domain comprises a functional domain of one or more proteins selected from the group consisting of CD27, CD28, 4-1BB (CD137), OX40, CD28-OX40, CD28-4-1BB, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D, or a functional variant thereof. In some embodiments, the antigen binding domain binds a tumor antigen (e.g., a solid tumor antigen).

In some embodiments, the tumor antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bD-Galp(1-4)bDG1cp(1-1)Cer); TNF receptor family member B cell maturation (BCMA); Tn antigen ((Tn Ag) or (GalNAca-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-ab1); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDG1cp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; survivin; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the tumor antigen is selected from the group comprising CD150, 5T4, ActRIIA, B7, BMCA, CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, GD2, GD3, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NY-ESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-1, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D1), ephrinB2, epithelial tumor antigen, estrogen receptor, fetal acethycholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, 02-Microglobulin, Fc Receptor-like 5 (FcRL5), or molecules expressed by HIV, HCV, HBV, or other pathogens.

In some embodiments, the antigen binding domain comprises an antibody, an antibody fragment, an scFv, a Fv, a Fab, a (Fab')2, a single domain antibody (SDAB), a VH or VL domain, a camelid VHH domain, a Fab, a Fab', a F(ab')2, a Fv, a scFv, a dsFv, a diabody, a triabody, a tetrabody, a multispecific antibody formed from antibody fragments, a single-domain antibody (sdAb), a single chain comprising anticomplementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof. In some embodiments, the antigen binding domain is connected to the transmembrane domain by a hinge region. In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7Rα, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C, or a functional variant thereof. In some embodiments, the CAR or TCR further comprises a leader peptide. In some embodiments, the TCR further comprises a constant region and/or CDR4.

In some embodiments, the payload protein comprises fluorescence activity, polymerase activity, protease activity, phosphatase activity, kinase activity, SUMOylating activity, deSUMOylating activity, ribosylation activity, deribosylation activity, myristoylation activity demyristoylation activity, or any combination thereof. In some embodiments, the payload protein comprises nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, adenylation activity, deadenylation activity, or any combination thereof. In some embodiments, the payload protein comprises a CRE recombinase, GCaMP, a cell therapy component, a knock-down gene therapy component, a cell-surface exposed epitope, or any combination thereof. In some embodiments, the payload protein comprises a diagnostic agent (e.g., green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, mruby3, rsCherry, rsCherryRev, derivatives thereof, or any combination thereof).

In some embodiments, the payload protein comprises a programmable nuclease. In some embodiments, the programmable nuclease is selected from the group comprising: SpCas9 or a derivative thereof; VRER, VQR, EQR SpCas9; xCas9-3.7; eSpCas9; Cas9-HF1; HypaCas9; evoCas9; HiFi Cas9; ScCas9; StCas9; NmCas9; SaCas9; CjCas9; CasX; Cas9 H940A nickase; Cas12 and derivatives thereof; dcas9-APOBEC1 fusion, BE3, and dcas9-deaminase fusions; dcas9-Krab, dCas9-VP64, dCas9-Tet1, and dcas9-transcriptional regulator fusions; Dcas9-fluorescent protein fusions; Cas13-fluorescent protein fusions; RCas9-fluorescent protein fusions; Cas13-adenosine deaminase fusions. In some embodiments, the programmable nuclease comprises a zinc finger nuclease (ZFN) and/or transcription activator-like effector nuclease (TALEN). In some embodiments, the programmable nuclease comprises *Streptococcus pyogenes* Cas9 (SpCas9), *Staphylococcus aureus* Cas9 (SaCas9), a zinc finger nuclease, TAL effector nuclease, meganuclease, MegaTAL, Tev-m TALEN, MegaTev, homing endonuclease, Cas1, Cas1B, Cas2, Cas3, Cas4, Cas5, Cash, Cas7, Cas8, Cas9, Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb 1, Csb2, Csb3, Csx17, Csx14, Csx10, Csx16, CsaX, Csx3, Csx1, Csx15, Csf1, Csf2, Csf3, Csf4, Cpf1, C2c1, C2c3, Cas12a, Cas12b, Cas12c, Cas12d, Cas12e, Cas13a, Cas13b, Cas13c, derivatives thereof, or any combination thereof. The nucleic acid composition can comprise: a polynucleotide encoding (i) a targeting molecule and/or (ii) a donor nucleic acid. In some embodiments, the targeting molecule is capable of associating with the programmable nuclease. In some embodiments, wherein the targeting molecule comprises single strand DNA or single strand RNA. In some embodiments, the targeting molecule comprises a single guide RNA (sgRNA). In some embodiments, the orthogonal signal triggers cellular differentiation. In some embodiments, the payload encodes a cellular reprogramming factor capable of converting an at least partially differentiated cell to a less differentiated cell (e.g., Oct-3, Oct-4, Sox2, c-Myc, Klf4, Nanog, Lin28, ASCL1, MYT1L, TBX3b, SV40 large T, hTERT, miR-291, miR-294, miR-295, or any combinations thereof). In some embodiments, the payload encodes a cellular reprogramming factor capable of differentiating a given cell into a desired differentiated state (e.g., nerve growth factor (NGF), fibroblast growth factor (FGF), interleukin-6 (IL-6), bone morphogenic protein (BMP), neurogenin3 (Ngn3), pancreatic and duodenal homeobox 1 (Pdx1), Mafa, or any combination thereof).

In some embodiments, the orthogonal signal triggers a permanent switch in a receiver cell, such as, for example, a recombinase-based permanent switch. In some embodiments, one or more of the payloads comprise a recombinase. The nucleic acid composition can comprise: a second promoter and a ninth polynucleotide comprising a payload gene, wherein, in the absence of a recombination event, the second promoter and the ninth polynucleotide are not operably linked, wherein the recombinase is capable of catalyzing the recombination event, and wherein the second promoter and the ninth polynucleotide are operably linked after the recombination event such that the second promoter is capable of inducing transcription of the payload gene to generate a payload transcript. In some embodiments, the recombination event comprises removal of a sequence flanked by recombinase target sites or an inversion of a sequence flanked by recombinase target sites. In some embodiments, the ninth polynucleotide is flanked by recombinase target sites. In some embodiments, prior to the recombination event, the sequence of the payload gene is inverted relative to the second promoter. The nucleic acid composition can comprise: at least one stop cassette situated between the second promoter and the payload gene, wherein the stop cassette comprises one or more stop sequences, and wherein the one or more stop cassettes are flanked by recombinase target sites. In some embodiments, the payload transcript is capable of being translated to generate a payload protein. In some embodiments, the at least one stop cassette is configured to prevent transcription of the payload gene and/or translation of the payload transcript. In some embodiments, the one or more stop sequences comprise a polyadenylation signal, a stop codon, a frame-shifting mutation, or any combination thereof. In some embodiments, the recombinase is Cre, Dre, Flp, KD, B2, B3, λ, HK022, HP1, γ6, ParA, Tn3, Gin, ΦC31, Bxb1, R4, derivatives thereof, or any combination thereof. In some embodiments, the recombinase is a Flp recombinase and the recombinase target sites are FRT sites. In some embodiments, the recombinase is a Cre recombinase and the recombinase target sites are loxP sites.

In some embodiments, the first synthase comprises an indole-3-acetic acid hydrolase (e.g., iaaH, aux2 and/or AMI1, *A. tumefaciens* iaaH, or any combination thereof). In some embodiments, the second synthase comprises tryptophan 2-monooxygenase (iaaM). In some embodiments, the transporter is auxin exporter PIN2 (e.g., *Arabidopsis thaliana* PIN2). In some embodiments, the first precursor molecule and/or the second precursor molecule is an endogenous molecule of a cell (e.g., L-tryptophan). In some embodiments, the orthogonal signal comprises indole-3-acetic acid (IAA), 1-napthalenatic acid (NAA), derivatives thereof, or any combination thereof. In some embodiments, the first precursor molecule comprises indole-3-acetamide (IAM) and/or 1-naphthaleneacetamide (NAM). In some embodiments, the signal-binding protein comprises TIR1 (e.g., osTIR1). In some embodiments, the signal-responsive domain comprises an auxin inducible degron (AID), such as a minimal auxin inducible degron (mAID). In some embodiments, the signal-responsive domain and/or signal-binding protein does not modulate endogenous mammalian proteins. In some embodiments, the orthogonal signal exhibits minimal immunogenicity in a subject. In some embodiments, the orthogonal signal is capable of diffusing through a target site of a subject. In some embodiments, the target site is a tissue of interest. In some embodiments, the orthogonal signal is orthogonal to the intrinsic signaling pathways of a subject. In some embodiments, the orthogonal signal is a small molecule, such as, for example, a hormone (e.g., a plant hormone, such as auxin, abscisic acid or gibberellin).

In some embodiments, the plant hormone is selected from the group comprising an auxin, a cytokinin, a phenolic plant hormone, an isoprenoid plant hormone, an aromatic plant hormone, a lipid plant hormone, a gibberellin, a salicylate, derivatives thereof, or any combination thereof. In some embodiments, the salicylate is or includes salicylic acid. In some embodiments, the auxin is selected from the group comprising indole-3-acetic acid (IAA), indole-3-acetic acid ethyl ester, indole-3-acetyl-glycine (IAGly), indole-3-acetyl-L-alanine (IAA1a), indole-3-carboxylic acid (I3CA), indole-3-carboxylic acid methyl, indole-3-butyric acid (IBA), indole-3-glyoxylic acid methyl ester, DL-indole-3-lactic acid (ILA), indole-3-carboxaldehyde (IAld), tryptophol (IEt), derivatives thereof, or any combination thereof. In some embodiments, the isoprenoid plant hormones is or includes an abscisic acid and/or an isoprenoid cytokinin. In some embodiments, the abscisic acid comprises (+)-cis, trans-abscisic acid (ABA). In some embodiments, the isoprenoid cytokinin is N6-isopentenyladenine (iP) and/or cis-zeatin (cZ). In some embodiments, the one or more aromatic plant hormones comprises an aromatic cytokinin. In some embodiments, the one or more aromatic cytokinins is selected from the group comprising N6-benzyladenine (BA), ortho-topolin (oT), and para-topolin (pT). In some embodiments, the one or more lipid plant hormones comprises a jasmonate (e.g., (−)-jasmonic acid (JA) and/or (−)-jasmonic acid methyl ester). In some embodiments, the gibberellin is selected from the group comprising gibberellic acid (GA) 1, GA2, GA3, GA4, GA5, GA6, GA7, GA8, GA9, GA10, GA11, GA12, GA13, GA14, GA15, GA16, GA17, GA18, GA19, GA20, GA21, GA22, GA23, GA24, GA25, GA26, GA27, GA28, GA29, GA30, GA31, GA32, GA33, GA34, GA35, GA36, GA37, GA38, GA39, GA40, GA41, GA42, GA43, GA44, GA45, GA46, GA47, GA48, GA49, GA50, GA51, GA52, GA53, GA54, GA55, GA56, GA57, GA58, GA59, GA60, GA61, GA62, GA63, GA64, GA65, GA66, GA67, GA68, GA69, GA70, GA71, GA72, GA73, GA74, GA75, GA76, GA77, GA78, GA79, GA80, GA81, GA82, GA83, GA84, GA85, GA86, GA87, GA88, GA89, GA90, GA91, GA92, GA93, GA94, GA95, GA96, GA97, GA98, GA99, GA100, GA101, GA102, GA103, GA104, GA105, GA106, GA107, GA108, GA109, GA110, GA111, GA112, GA113, GA114, GA115, GA116, GA117, GA118, GA119, GA120, GA121, GA122, GA123, GA124, GA125, GA126, GA127, GA128, GA129, GA130, GA131, GA132, GA133, GA134, GA135, GA136, derivatives thereof, or any combination thereof. In some embodiments, the cytokinin is selected from the group comprising zeatin, zeatin, N6-benzyl adenine, N6-(delta-2-isopentyl) adenine, 1,3-diphenyl urea, thidiazuron, CPPU (forchlorfenuron), kinetin, derivatives thereof, or any combination thereof.

In some embodiments, the pro-growth protein is essential for survival and/or cell cycle progression (e.g., a cell-cycle regulator). In some embodiments, the pro-growth protein is essential for survival and/or cell cycle progression in the presence of an exogenous agent. In some embodiments, the exogenous agent is an antibiotic. In some embodiments, the pro-growth protein provides antibiotic resistance. In some embodiments, the pro-growth protein comprises a cyclin-dependent kinase (CDK), cyclin, an aurora kinase, a cell division cycle (CDC) protein, or any combination thereof. In some embodiments, the pro-growth protein comprises lamin B1, lamin B2, NUP153, GAS41, ARC21, cytoplasmic dynein, the protein kinase cdk1, β-actin, and γ-actin, Cdk1, Cdk2, Cdk3, Cdk4, Cdk6, Cyclin A, Cyclin D, Cyclin D, Cyclin E, Cyclin B, or any combination thereof. In some embodiments, the pro-growth protein comprises FoxO1, HDAC, DP-1, E2F, ABL, AMPK, BRK, BRSK I, BRSK2, BTK, CAMKK1, CAMKK alpha, CAMKK beta, Rb, Suv39HI, SCF, p19INK4D, GSK-3, pi 8 INK4, myc, cyclin E, CDK2, CDK9, CDG4/6, Cycline D, p16 INK4A, cdc25A, BMI1, SCF, Akt, CHK1/2, C 1 delta, CK1 gamma, C 2, CLK2, CSK, DDR2, DYRK1A/2/3, EF2K, EPH-A2/A4/B1/B2/B3/B4, EIF2A3, Smad2, Smad3, Smad4, Smad7, p53, p21 Cip1, PAX, Fyn, CAS, C3G, SOS, Tal, Raptor, RACK-1, CRK, Rap1, Rac, KRas, NRas, HRas, GRB2, FAK, PI3K, spred, Spry, mTOR, MPK, LKB1, PAK 1/2/4/5/6, PDGFRA, PYK2, Src, SRPK1, PLC, PKC, PKA, PKB alpha/beta, PKC alpha/gamma/zeta, PKD, PLK1, PRAK, PRK2, RIPK2, WAVE-2, TSC2, DAPK1, BAD, IMP, C-TAK1, TAK1, TAO1, TBK1, TESK1, TGFBR1, TIE2, TLK1, TrkA, TSSK1, TTBK1/2, TTK, Tp12/cotl, MEK1, MEK2, PLDL Erk1, Erk2, Erk5, Erk8, p9ORSK, PEA-15, SRF, p27 KIP1, TIF 1a, HMGN1, ER81, MKP-3, c-Fos, FGF-R1, GCK, GSK3 beta, HER4, HIPK1/2/3/, IGF-1R, cdc25, UBF, LAMTOR2, Statl, StaO, CREB, JAK, Src, PTEN, NF-kappaB, HECTH9, Bax, HSP70, HSP90, Apaf-1, Cyto c, BCL-2, Bcl-xL, Smac, XIAP, Caspase-9, Caspase-3, Caspase-6, Caspase-7, CDC37, TAB, IKK, TRADD, TRAF2, R1P1, FLIP, TAK1, JNK1/2/3, Lck, A-Raf, B-Raf, C-Raf, MOS, MLK1/3, MN 1/2, MSK1, MST2/3/4, MPSK1, MEKK1, ME K4, MEL, ASK1, MINK1, MKK 1/2/3/4/6/7, NE 2a/6/7, NUAK1, OSR1, SAP, STK33, Syk, Lyn, PDK1, PHK, PIM 1/2/3, Ataxin-1, mTORC1, MDM2, p21 Wafl, Cyclin Dl, Lamin A, Tp12, Myc, catenin, Wnt, IKK-beta, IKK-gamma, IKK-alpha, IKK-epsilon, ELK, p65RelA, IRAKI, IRA 2, IRAK4, IRR, FADD, TRAF6, TRAF3, MKK3, MKK6, ROCK2, RSK1/2, SGK 1, SmMLCK, SIK2/3, ULK1/2, VEGFR1, WNK 1, YES1, ZAP70, MAP4K3, MAP4K5, MAPK1b, MAPKAP-K2 K3, p38 alpha/beta/delta/gamma MAPK, Aurora A, Aurora B, Aurora C, MCAK, Clip, MAPKAPK, FAK, MARK 1/2/3/4, Mud, SHC, CXCR4, Gap-1, Myc, beta-catenin/TCF, Cb1, BRM, Mcl1, BRD2, BRD3, BRD4, AR, RAS, ErbB3, EGFR, IRE1, HPK1, RIPK2, Era, or any combination thereof.

In some embodiments, the pro-death protein is capable of halting cell growth and/or inducing cell death. In some embodiments, the pro-death protein comprises cytosine deaminase, thymidine kinase, Bax, Bid, Bad, Bak, BCL2L11, p53, PUMA, Diablo/SMAC, S-TRAIL, Cas9, Cas9n, hSpCas9, hSpCas9n, HSVtk, cholera toxin, diphtheria toxin, alpha toxin, anthrax toxin, exotoxin, pertussis toxin, Shiga toxin, shiga-like toxin Fas, TNF, caspase 2, caspase 3, caspase 6, caspase 7, caspase 8, caspase 9, caspase 10, caspase 11, caspase 12, purine nucleoside phosphorylase, or any combination thereof. In some embodiments, the pro-death protein is capable of halting cell growth and/or inducing cell death in the presence of a pro-death agent. In some embodiments, the pro-death protein comprises Caspase-9 and the pro-death agent comprises AP1903; the pro-death protein comprises HSV thymidine kinase (TK) and the pro-death agent Ganciclovir (GCV), Ganciclovir elaidic acid ester, Penciclovir (PCV), Acyclovir (ACV), Valacyclovir (VCV), (E)-5-(2-bromovinyl)-2'-deoxyuridine (BVDU), Zidovuline (AZT), and/or 2'-exo-methanocarbathymidine (MCT); the pro-death protein comprises Cytosine Deaminase (CD) and the pro-death agent comprises 5-fluorocytosine (5-FC); the pro-death protein comprises Purine nucleoside phosphorylase (PNP) and the pro-death agent comprises 6-methylpurine deoxyriboside (MEP) and/or fludarabine (FAMP); the pro-death protein comprises a Cytochrome p450 enzyme (CYP) and the pro-death agent comprises Cyclophosphamide (CPA), Ifosfamide (IFO), and/or 4-ipomeanol (4-IM); the pro-death protein comprises a Carboxypeptidase (CP) and the pro-death agent comprises 4-[(2-chloroethyl)(2-mesyloxyethyl)amino]benzoyl-L-glutamic acid (CMDA), Hydroxy- and amino-aniline mustards, Anthracycline glutamates, and/or Methotrexate α-peptides (MTX-Phe); the pro-death protein comprises Carboxylesterase (CE) and the pro-death agent comprises Irinotecan (IRT), and/or Anthracycline acetals; the pro-death protein comprises Nitroreductase (NTR) and the pro-death agent comprises dinitroaziridinylbenzamide CB1954, dinitrobenzamide mustard SN23862, 4-Nitrobenzyl carbamates, and/or Quinones; the pro-death protein comprises Horse radish peroxidase (HRP) and the pro-death agent comprises Indole-3-acetic acid (IAA) and/or 5-Fluoroindole-3-acetic acid (FIAA); the pro-death protein comprises Guanine Ribosyltransferase (XGRTP) and the pro-death agent comprises 6-Thioxanthine (6-TX); the pro-death protein comprises a glycosidase enzyme and the pro-death agent comprises HM1826 and/or Anthracycline acetals; the pro-death protein comprises Methionine-α,γ-lyase (MET) and the pro-death agent comprises Selenomethionine (Se-MET); and/or the pro-death protein comprises thymidine phosphorylase (TP) and the pro-death agent comprises 5'-Deoxy-5-fluorouridine (5'-DFU).

In some embodiments, the fifth polynucleotide, the sixth polynucleotide, and/or the seventh polynucleotide are operably linked to a tandem gene expression element. In some embodiments, the tandem gene expression element is an internal ribosomal entry site (IRES), foot-and-mouth disease virus 2A peptide (F2A), equine rhinitis A virus 2A peptide (E2A), porcine teschovirus 2A peptide (P2A) or Thosea asigna virus 2A peptide (T2A), or any combination thereof. In some embodiments, a first promoter is operably linked to the fifth polynucleotide, the sixth polynucleotide, and/or the seventh polynucleotide, wherein first promoter is capable of inducing transcription of the fifth polynucleotide, the sixth polynucleotide, and/or the seventh polynucleotide to generate a polycistronic transcript, and wherein the polycistronic transcript is capable of being translated to generate the signal-binding protein, the first fusion protein, the second fusion protein, and/or the third fusion protein. In some embodiments, the first promoter and/or second promoter comprises a ubiquitous promoter. In some embodiments, the ubiquitous promoter is selected from the group comprising a cytomegalovirus (CMV) immediate early promoter, a CMV promoter, a viral simian virus 40 (SV40) (e.g., early or late), a Moloney murine leukemia virus (MoMLV) LTR promoter, a Rous sarcoma virus (RSV) LTR, an RSV promoter, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus, a Ubiquitin C promoter (UBC), a phosphoglycerate kinase-1 (PGK) promoter, 3-phosphoglycerate kinase promoter, a cytomegalovirus enhancer, human β-actin (HBA) promoter, chicken β-actin (CBA) promoter, a CAG promoter, a CBH promoter, or any combination thereof. In some embodiments, a signal-binding protein bound to the orthogonal signal is capable of triggering the ubiquitylation and proteasomal degradation of a protein comprising a signal-responsive domain. In some embodiments, the first polynucleotide, the second polynucleotide, the third polynucleotide, the fourth polynucleotide, the fifth polynucleotide, the sixth polynucleotide, the seventh polynucleotide, the eighth polynucleotide, and/or the ninth polynucleotide further comprises a transcript stabilization element (e.g., woodchuck hepatitis post-translational regulatory element (WPRE), bovine growth hormone polyadenylation (bGH-polyA) signal sequence, human growth hormone polyadenylation (hGH-polyA) signal sequence, or any combination thereof). In some embodiments, the first polynucleotide, the second polynucleotide, the third polynucleotide, the fourth polynucleotide, the fifth polynucleotide, the sixth polynucleotide, the seventh polynucleotide, the eighth polynucleotide, and/or the ninth polynucleotide is evolutionarily stable for at least about 10 days, about 20 days, about 40 days, about 80 days, about 80 days, or about 100 days, of serial passaging.

In some embodiments, the orthogonal signal informs receiver cells about various types of 'information' concerning the senders (e.g., population size, location, cellular activity). In some embodiments, the expression and/or activity of the first synthase, second synthase, and/or transporter is configured to be responsive to changes in: cell localization; one or more signal transduction pathways regulating cell survival, cell growth, cell proliferation, cell adhesion, cell migration, cell metabolism, cell morphology, cell differentiation, apoptosis, or any combination thereof; and/or T cell activity (e.g., one or more of T cell simulation, T cell activation, cytokine secretion, T cell survival, T cell proliferation, CTL activity, T cell degranulation, and T cell differentiation). In some embodiments, a synthetic protein circuit component modulates the expression and/or activity of the first synthase, second synthase, and/or transporter. In some embodiments, the expression and/or activity of the first synthase, second synthase, and/or transporter is configured to be responsive to immune cell stimulation. In some embodiments, immune cell stimulation comprises signal transduction induced by binding of a stimulatory molecule with its cognate ligand on the surface of an immune cell. In some embodiments, the cognate ligand is a CAR or a TCR.

In some embodiments, the first fusion protein, the second fusion protein, and/or the third fusion protein further comprises a diagnostic agent (e.g., green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, mruby3, rsCherry, rsCherryRev, derivatives thereof, or any combination thereof).

In some embodiments, the nucleic acid composition comprises one or more vectors. In some embodiments, at least one of the one or more vectors is a viral vector, a plasmid, a naked DNA vector, a lipid nanoparticle, or any combination thereof. In some embodiments, the viral vector is an AAV vector, a lentivirus vector, a retrovirus vector, an integration-deficient lentivirus (IDLV) vector.

Disclosed herein include compositions. In some embodiments, the composition comprises: one or more of the nucleic acid compositions (e.g., circuits) provided herein. In some embodiments, the composition comprises one or more vectors, a ribonucleoprotein (RNP) complex, a liposome, a nanoparticle, an exosome, a microvesicle, or any combination thereof. In some embodiments, the vector is a viral vector, a plasmid, a naked DNA vector, a lipid nanoparticle, or any combination thereof. In some embodiments, the viral vector is an AAV vector, a lentivirus vector, a retrovirus vector, an integration-deficient lentivirus (IDLV) vector. In some embodiments, the AAV vector comprises single-stranded AAV (ssAAV) vector or a self-complementary AAV (scAAV) vector.

Disclosed herein include populations of cells. In some embodiments, the population of cells comprises: one or more sender cells comprising one or more of the nucleic acid compositions (e.g., circuits) provided herein; one or more receiver cells comprising one or more of the nucleic acid compositions (e.g., circuits) provided herein; and/or one or more sender-receiver cells comprising one or more of the nucleic acid compositions (e.g., circuits) provided herein.

Disclosed herein include populations of cells. In some embodiments, the population of cells comprises: a first cell type comprising one or more of the nucleic acid compositions (e.g., circuits) provided herein; and a second cell type comprising one or more of the nucleic acid compositions (e.g., circuits) provided herein, wherein the first cell type and second cell type are sender-receiver cells configured to grow in the presence of both cell types.

In some embodiments, one or more cells of the population of cells is capable of actively sensing, responding to, and/or controlling the cell population size and/or density. In some embodiments, the sender cells and/or the sender-receiver cells are configured to secrete the orthogonal signal at a constant rate. In some embodiments, the sender cells and/or the sender-receiver cells are configured to secrete the orthogonal signal in response to an intracellular state and/or extracellular environment. In some embodiments, the orthogonal signal is capable of stimulating and inhibiting net cell growth of the population of cells at different concentrations of the orthogonal signal. In some embodiments, sender-receiver cells are capable of simultaneous production and perception of the orthogonal signal. In some embodiments, the sender cells and/or the sender-receiver cells are capable of secreting the orthogonal signal to generate a shared orthogonal signal pool, wherein the shared orthogonal signal pool is capable of being sensed by the receiver cells and/or the sender-receiver cells.

In some embodiments, net growth of the population of cells occurs between a lower tuned orthogonal signal threshold and an upper tuned orthogonal signal threshold of a tuned orthogonal signal range. In some embodiments, the lower tuned orthogonal signal threshold and/or the upper tuned orthogonal signal threshold of a tuned orthogonal signal range can be modulated by: adjusting the concentration of the first precursor molecule, the second precursor molecule, the exogenous agent, the pro-death agent, or any combination thereof; and/or adjusting the expression level of the signal-binding protein, the first fusion protein, the second fusion protein, the third fusion protein, the transporter, the first synthase, the second synthase, or any combination thereof. In some embodiments, the difference between the lower tuned orthogonal signal threshold and the upper tuned orthogonal signal threshold of the tuned orthogonal signal range is greater than about one order of magnitude. In some embodiments, the difference between the lower tuned orthogonal signal threshold and the upper tuned orthogonal signal threshold of the tuned orthogonal signal range is less than about one order of magnitude.

In some embodiments, one or more cells of the population of cells is configured to activate a therapeutic program in the presence of a critical orthogonal signal threshold (e.g., a local critical orthogonal signal threshold at a target site). In some embodiments, the therapeutic program comprises expression of one or more payloads. In some embodiments, one or more cells of the population of cells are immune cells is configured to switch from an immune cell inactivated state to an immune cell activated state in the presence of a critical orthogonal signal threshold (e.g., a local critical orthogonal signal threshold at a target site). In some embodiments, the sender cells and/or the sender-receiver cells are detector cells capable of trafficking to a tumor site. In some embodiments, the receiver cells and/or the sender-receiver cells comprise a killer cell type. In some embodiments, one or more cells of the population of cells is configured to differentiate into one or more cell types in the presence of orthogonal signal threshold (e.g., a local critical orthogonal signal threshold at a target site). In some embodiments, one or more cells of the population of cells is configured to differentiate into one or more cell types in the presence of a critical orthogonal signal threshold (e.g., a local critical orthogonal signal threshold at a target site). In some embodiments, one or more cells of the population of cells is configured to switch cell states in the presence of orthogonal signal threshold (e.g., a local critical orthogonal signal threshold at a target site).

In some embodiments, the population of cells is configured such that steady state population size and/or density remains between a lower tuned threshold and an upper tuned threshold of a tuned cell population size and/or density range. In some embodiments, the population of cells remains within the tuned cell population size and/or density range for at least about 10 days, about 20 days, about 40 days, about 80 days, about 80 days, or about 100 days, of continuous culture and/or presence in a subject. In some embodiments, the population of cells oscillate between a lower tuned threshold and an upper tuned threshold of a tuned cell population size and/or density range. In some embodiments, the lower tuned threshold and/or the upper tuned threshold of a tuned cell population size and/or density range can be modulated by: adjusting the concentration of the first precursor molecule, the second precursor molecule, the exogenous agent, the pro-death agent, or any combination thereof and/or adjusting the expression level of the signal-binding protein, the first fusion protein, the second fusion protein, the third fusion protein, the transporter, the first synthase, the second synthase, or any combination thereof. In some embodiments, the difference between the lower untuned threshold and the upper untuned threshold of the tuned cell population size and/or density range is greater than about one order of magnitude. In some embodiments, the difference between the lower tuned threshold and the upper tuned threshold of the tuned cell population size and/or density range is less than about one order of magnitude.

In some embodiments, one or more cells of the population of cells is configured to activate a therapeutic program upon the cell population reaching a critical cell population size and/or density threshold. In some embodiments, the therapeutic program comprises expression of one or more payloads. In some embodiments, one or more cells of the population of cells are immune cells is configured to switch from an immune cell inactivated state to an immune cell activated state upon the cell population reaching a critical cell population size and/or density threshold (e.g., a local critical cell population size and/or density threshold at a target site). In some embodiments, the sender cells and/or the sender-receiver cells are detector cells capable of trafficking to a tumor site. In some embodiments, receiver cells and/or the sender-receiver cells comprise a killer cell type. In some embodiments, one or more cells of the population of cells is configured to differentiate into one or more cell types upon the cell population reaching a critical cell population size and/or density threshold (e.g., a local critical cell population size and/or density threshold at a target site). In some embodiments, one or more cells of the population of cells is configured to differentiate into one or more cell types upon the cell population reaching a critical cell population size and/or density threshold (e.g., a local critical cell population size and/or density threshold at a target site). In some embodiments, one or more cells of the population of cells is configured to switch cell states upon the cell population reaching a critical cell population size and/or density threshold (e.g., a local critical cell population size and/or density threshold at a target site). In some embodiments, the population of cells are capable of being employed in synthetic organogenesis and/or tissue repair. In some embodiments, the population of cells is evolutionarily robust to mutations reducing or abrogating orthogonal signal-based control of population size and/or density. In some embodiments, the population of cells is robust to said mutations for at least about 10 days, about 20 days, about 40 days, about 80 days, about 80 days, or about 100 days, of continuous culture and/or presence in a subject.

In some embodiments, the first cell type, second cell type, sender cell, receiver cell, and/or sender-receiver cell comprise a eukaryotic cell. In some embodiments, the eukaryotic cell comprises an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, myoblast, myocyte, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, a zymogenic cell, or any combination thereof. In some embodiments, the stem cell comprises an embryonic stem cell, an induced pluripotent stem cell (iPSC), a hematopoietic stem/progenitor cell (HSPC), or any combination thereof.

In some embodiments, the first cell type, second cell type, sender cell, receiver cell, and/or sender-receiver cell further comprises one or more targeting moieties configured to bind a component of a target site of a subject. In some embodiments, the critical cell population size and/or density threshold comprises a local critical cell population size and/or density threshold at a target site. In some embodiments, the one or more targeting moieties are selected from the group comprising mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, and an RGD peptide or RGD peptide mimetic. In some embodiments, the one or more targeting moieties comprise one or more of the following: an antibody or antigen-binding fragment thereof, a peptide, a polypeptide, an enzyme, a peptidomimetic, a glycoprotein, a lectin, a nucleic acid, a monosaccharide, a disaccharide, a trisaccharide, an oligosaccharide, a polysaccharide, a glycosaminoglycan, a lipopolysaccharide, a lipid, a vitamin, a steroid, a hormone, a cofactor, a receptor, a receptor ligand, and analogs and derivatives thereof. In some embodiments, the antibody or antigen-binding fragment thereof comprises a Fab, a Fab', a F(ab')$_2$, a Fv, a scFv, a dsFv, a diabody, a triabody, a tetrabody, a multispecific antibody formed from antibody fragments, a single-domain antibody (sdAb), a single chain comprising complementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof. In some embodiments, the one or more targeting moieties are configured to bind one or more of the following: CD3, CD4, CD5, CD6, CD7, CD8, CD9, CD10, CD1 1a, CD1 1b, CD1 1c, CD12w, CD14, CD15, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49b, CD49c, CD51, CD52, CD53, CD54, CD55, CD56, CD58, CD59, CD61, CD62E, CD62L, CD62P, CD63, CD66, CD68, CD69, CD70, CD72, CD74, CD79, CD79a, CD79b, CD80, CD81, CD82, CD83, CD86, CD87, CD88, CD89, CD90, CD91, CD95, CD96, CD98, CD100, CD103, CD105, CD106, CD109, CD117, CD120, CD125, CD126, CD127, CD133, CD134, CD135, CD137, CD138, CD141, CD142, CD143, CD144, CD147, CD151, CD147, CD152, CD154, CD156, CD158, CD163, CD166, CD168, CD174, CD180, CD184, CDw186, CD194, CD195, CD200, CD200a, CD200b, CD209, CD221, CD227, CD235a, CD240, CD262, CD271, CD274, CD276 (B7-H3), CD303, CD304, CD309, CD326, 4-1BB, 5 AC, 5T4 (Trophoblast glycoprotein, TPBG, 5T4, Wnt-Activated Inhibitory Factor 1 or WAIF1), Adenocarcinoma antigen, AGS-5, AGS-22M6, Activin receptor like kinase 1, AFP, AKAP-4, ALK, Alpha integrin, Alpha v beta6, Amino-peptidase N, Amyloid beta, Androgen receptor, Angiopoietin 2, Angiopoietin 3, Annexin A1, Anthrax toxin protective antigen, Anti-transferrin receptor, AOC3 (VAP-1), B7-H3, *Bacillus anthracis* anthrax, BAFF (B-cell activating factor), B-lymphoma cell, bcr-ab1, Bombesin, BORIS, C5, C242 antigen, CA125 (carbohydrate antigen 125, MUC16), CA-IX (CAIX, carbonic anhydrase 9), CALLA, CanAg, *Canis lupus familiaris* IL31, Carbonic anhydrase IX, Cardiac myosin, CCL11(C-C motif chemokine 11), CCR4 (C-C chemokine receptor type 4, CD194), CCR5, CD3E (epsilon), CEA (Carcinoembryonic antigen), CEACAM3, CEACAM5 (carcinoembryonic antigen), CFD (Factor D), Ch4D5, Cholecystokinin 2 (CCK2R), CLDN18 (Claudin-18), Clumping factor A, CRIPTO, FCSF1R (Colony stimulating factor 1 receptor, CD 115), CSF2 (colony stimulating factor 2, Granulocyte-macrophage colony-stimulating factor (GM-CSF)), CTLA4 (cytotoxic T-lymphocyte-associated protein 4), CTAA16.88 tumor antigen, CXCR4 (CD 184), C—X—C chemokine receptor type 4, cyclic ADP ribose hydrolase, Cyclin B 1, CYP1B 1, Cytomegalovirus, Cytomegalovirus glycoprotein B, Dabigatran, DLL4 (delta-like-ligand 4), DPP4 (Dipeptidyl-peptidase 4), DR5 (Death receptor 5), *E. coli* Shiga toxin type-1, *E. coli* Shiga toxin type-2, ED-B, EGFL7 (EGF-like domain-containing protein 7), EGFR, EGFRII, EGFRvIII, Endoglin (CD 105), Endothelin B receptor, Endotoxin, EpCAM (epithelial cell adhesion molecule), EphA2, Episialin, ERBB2 (Epidermal Growth Factor Receptor 2), ERBB3, ERG (TMPRSS2 ETS fusion gene), *Escherichia coli*, ETV6-AML, FAP (Fibroblast activation protein alpha), FCGR1, alpha-Fetoprotein, Fibrin II, beta chain, Fibronectin extra domain-B, FOLR (folate receptor), Folate receptor alpha, Folate hydrolase, Fos-related antigen 1.F protein of respiratory syncytial virus, Frizzled receptor, Fucosyl GM1, GD2 ganglioside, G-28 (a cell surface antigen glycolipid), GD3 idiotype, GloboH, Glypican 3, N-glycolylneuraminic acid, GM3, GMCSF receptor α-chain, Growth differentiation factor 8, GP100, GPNMB (Transmembrane glycoprotein NMB), GUCY2C (Guanylate cyclase 2C, guanylyl cyclase C(GC-C), intestinal Guanylate cyclase, Guanylate cyclase-C receptor, Heat-stable enterotoxin receptor (hSTAR)), Heat shock proteins, Hemagglutinin, Hepatitis B surface antigen, Hepatitis B virus, HER1 (human epidermal growth factor receptor 1), HER2, HER2/neu, HER3 (ERBB-3), IgG4, HGF/SF (Hepatocyte growth factor/scatter factor), HHGFR, HIV-1, Histone complex, HLA-DR (human leukocyte antigen), HLA-DR10, HLA-DRB, HMWMAA, Human chorionic gonadotropin, HNGF, Human scatter factor receptor kinase, HPV E6/E7, Hsp90, hTERT, ICAM-1 (Intercellular Adhesion Molecule 1), Idiotype, IGF1R (IGF-1, insulin-like growth factor 1 receptor), IGHE, IFN-γ, Influenza hemagglutinin, IgE, IgE Fc region, IGHE, IL-1, IL-2 receptor (interleukin 2 receptor), IL-4, IL-5, IL-6, IL-6R (interleukin 6 receptor), IL-9, IL-10, IL-12, IL-13, IL-17, IL-17A, IL-20, IL-22, IL-23, IL31RA, ILGF2 (Insulin-like growth factor 2), Integrins (α4, $\alpha_U\beta_3$, αVβ3, $\alpha_4\beta_7$, α5β1, α6β4, α7β7, α11β3, α5β5, αvβ5), Interferon gamma-induced protein, ITGA2, ITGB2, KIR2D, LCK, Le, Legumain, Lewis-Y antigen, LFA-1(Lymphocyte function-associated antigen 1, CD1 1a), LHRH, LINGO-1, Lipoteichoic acid, LIV1A, LMP2, LTA, MAD-CT-1, MAD-CT-2, MAGE-1, MAGE-2, MAGE-3, MAGE A1, MAGE A3, MAGE 4, MARTI, MCP-1, MIF (Macrophage migration inhibitory factor, or glycosylation inhibiting factor (GIF)), MS4A1 (membrane-spanning 4-domains subfamily A member 1), MSLN (mesothelin), MUC1 (Mucin 1, cell surface associated (MUC1) or polymorphic epithelial mucin (PEM)), MUC1-KLH, MUC16 (CA125), MCP1 (monocyte chemotactic protein 1), MelanA/MART1, ML-IAP, MPG, MS4A1 (membrane-spanning 4-domains subfamily A), MYCN, Myelin-associated glycoprotein, Myostatin, NA17, NARP-1, NCA-90 (granulocyte antigen), Nectin-4 (ASG-22ME), NGF, Neural apoptosis-regulated proteinase 1, NOGO-A, Notch receptor, Nucleolin, Neu oncogene product, NY-BR-1, NY-ESO-1, OX-40, OxLDL (Oxidized low-density lipoprotein), OY-TES 1, P21, p53 nonmutant, P97, Page4, PAP, Paratope of anti-(N-glycolylneuraminic acid), PAX3, PAX5, PCSK9, PDCD1 (PD-1, Programmed cell death protein 1, CD279), PDGF-Ra (Alpha-type platelet-derived growth factor receptor), PDGFR-β, PDL-1, PLAC1, PLAP-like testicular alkaline phosphatase, Platelet-derived growth factor receptor beta, Phosphate-sodium co-transporter, PMEL 17, Polysialic acid, Proteinase3 (PR1), Prostatic carcinoma, PS (Phosphatidylserine), Prostatic carcinoma cells, *Pseudomonas aeruginosa*, PSMA, PSA, PSCA, Rabies virus glycoprotein, RHD (Rh polypeptide 1 (RhPI), CD240), Rhesus factor, RANKL, RhoC, Ras mutant, RGS5, ROBO4, Respiratory syncytial virus, RON, Sarcoma translocation breakpoints, SART3, Sclerostin, SLAMF7 (SLAM family member 7), Selectin P, SDC1 (Syndecan 1), sLe(a), Somatomedin C, SIP (Sphingosine-1-phosphate), Somatostatin, Sperm protein 17, SSX2, STEAP1 (six-transmembrane epithelial antigen of the prostate 1), STEAP2, STn, TAG-72 (tumor associated glycoprotein 72), Survivin, T-cell receptor, T cell transmembrane protein, TEM1 (Tumor endothelial marker 1), TENB2, Tenascin C (TN-C), TGF-α, TGF-β (Transforming growth factor beta), TGF-β1, TGF-β2 (Transforming growth factor-beta 2), Tie (CD202b), Tie2, TIM-1 (CDX-014), Tn, TNF, TNF-α, TNFRSF8, TNFRSF10B (tumor necrosis factor receptor superfamily member 10B), TNFRSF13B (tumor necrosis factor receptor superfamily member 13B), TPBG (trophoblast glycoprotein), TRAIL-R1 (Tumor necrosis apoptosis Inducing ligand Receptor 1), TRAILR2 (Death receptor 5 (DR5)), tumor-associated calcium signal transducer 2, tumor specific glycosylation of MUC1, TWEAK receptor, TYRP1 (glycoprotein 75), TRP-2, Tyrosinase, VCAM-1 (CD 106), VEGF, VEGF-A, VEGF-2 (CD309), VEGFR-1, VEGFR2, or vimentin, WT1, XAGE 1, or cells expressing any insulin growth factor receptors, or any epidermal growth factor receptors.

Disclosed herein include methods for treating a disease or disorder in a subject. In some embodiments, the method comprises: introducing into two or more cells one or more of the nucleic acid compositions (e.g., circuits) provided herein or one or more of the compositions provided herein, thereby generating a population of cells; and administering to the subject an effective amount of the population of cells. The method can comprise: isolating the two or more cells from the subject prior to the introducing step. In some embodiments, the introducing step is performed in vivo, in vitro, and/or ex vivo. In some embodiments, the introducing step comprises calcium phosphate transfection, DEAE-dextran mediated transfection, cationic lipid-mediated transfection, electroporation, electrical nuclear transport, chemical transduction, electrotransduction, Lipofectamine-mediated transfection, Effectene-mediated transfection, lipid nanoparticle (LNP)-mediated transfection, or any combination thereof.

Disclosed herein include methods for treating a disease or disorder in a subject. In some embodiments, the method comprises: administering to the subject an effective amount of a population of cells provided herein. The method can comprise: administering to the subject an effective amount of the first precursor molecule, the second precursor molecule, the exogenous agent, the pro-death agent, or any combination thereof.

In some embodiments, a target site of a subject comprises a site of disease or disorder or is proximate to a site of a disease or disorder. In some embodiments, the target site comprises a tissue. In some embodiments, the tissue is inflamed tissue, cancerous tissue, and/or infected tissue. In some embodiments, the tissue comprises adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue. In some embodiments, the tissue comprises: (i) grade I, grade II, grade III or grade IV cancerous tissue; (ii) metastatic cancerous tissue; (iii) mixed grade cancerous tissue; (iv) a sub-grade cancerous tissue; (v) healthy or normal tissue; and/or (vi) cancerous or abnormal tissue.

In some embodiments, the disease is associated with expression of a tumor antigen, wherein the disease associated with expression of a tumor antigen is selected from the group consisting of a proliferative disease, a precancerous condition, a cancer, and a non-cancer related indication associated with expression of the tumor antigen. In some embodiments, the disease or disorder is a blood disease, an immune disease, a neurological disease or disorder, a cancer, a solid tumor, an infectious disease, a genetic disease, a disorder caused by aberrant mtDNA, a metabolic disease, a disorder caused by aberrant cell cycle, a disorder caused by aberrant angiogenesis, a disorder cause by aberrant DNA damage repair, or any combination thereof. In some embodiments, the cancer is selected from the group consisting of colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers. In some embodiments, the cancer is a hematologic cancer chosen from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or pre-leukemia.

The method can comprise: administering one or more additional agents to the subject. In some embodiments, the one or more additional agents comprise a protein phosphatase inhibitor, a kinase inhibitor, a cytokine, an inhibitor of an immune inhibitory molecule, and/or or an agent that decreases the level or activity of a TREG cell. In some embodiments, the one or more additional agents comprise an immune modulator, an anti-metastatic, a chemotherapeutic, a hormone or a growth factor antagonist, an alkylating agent, a TLR agonist, a cytokine antagonist, a cytokine antagonist, or any combination thereof. In some embodiments, the one or more additional agents comprise an agonistic or antagonistic antibody specific to a checkpoint inhibitor or checkpoint stimulator molecule such as PD1, PD-L1, PD-L2, CD27, CD28, CD40, CD137, OX40, GITR, ICOS, A2AR, B7-H3, B7-H4, BTLA, CTLA4, IDO, KIR, LAG3, PD-1, TIM-3. In some embodiments, the one or more additional agents are selected from the group consisting of alkylating agents (nitrogen mustards, ethylenimine derivatives, alkyl sulfonates, nitrosoureas and triazenes); uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®); bendamustine (Treakisym®, Ribomustin®, Treanda®); chlormethine (Mustargen®); cyclophosphamide (Cytoxan®, Neosar®, Clafen®, Endoxan®, Procytox®, Revimmune™); ifosfamide (Mitoxana®); melphalan (Alkeran®); Chlorambucil (Leukeran®); pipobroman (Amedel®, Vercyte®); triethylenemelamine (Hemel®, Hexylen®, Hexastat®); triethylenethiophosphoramine; Temozolomide (Temodar®); thiotepa (Thioplex®); busulfan (Busilvex®, Myleran®); carmustine (BiCNU®); lomustine (CeeNU®); streptozocin (Zanosar®); estramustine (Emcyt®, Estracit®); fotemustine; irofulven; mannosulfan; mitobronitol; nimustine; procarbazine; ranimustine; semustine; triaziquone; treosulfan; and Dacarbazine (DTIC-Dome®); anti-EGFR antibodies (e.g., cetuximab (Erbitux®), panitumumab (Vectibix®), and gefitinib (Iressa®)); anti-Her-2 antibodies (e.g., trastuzumab (Herceptin®) and other antibodies from Genentech); antimetabolites (including, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), carmofur, cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®), decitabine (Dacogen®), enocitabine (Sunrabin®), sapacitabine, tegafururacil, tiazofurine, tioguanine, trofosfamide, and gemcitabine (Gemzar®); *vinca* alkaloids: vinblastine (Velban®, Velsar®), vincristine (Vincasar®, Oncovin®), vindesine (Eldisine®), vinorelbine (Navelbine®), vinflunine (Javlor®); platinum-based agents: carboplatin (Paraplat®, Paraplatin®), cisplatin (Platinol®), oxaliplatin (Eloxatin®), nedaplatin, satraplatin, and triplatin; anthracyclines: daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®), aclarubicin, amrubicin, liposomal doxorubicin, liposomal daunorubicin, pirarubicin, pixantrone, and zorubicin; topoisomerase inhibitors: topotecan (Hycamtin®), irinotecan (Camptosar®), etoposide (Toposar®, VePesid®), teniposide (Vumon®), lamellarin D, SN-38, camptothecin (e.g., IT-101), belotecan, and rubitecan; taxanes: paclitaxel (Taxol®), docetaxel (Taxotere®), larotaxel, cabazitaxel, ortataxel, and tesetaxel; antibiotics: actinomycin (Cosmegen®), bleomycin (Blenoxane®), hydroxyurea (Droxia®, Hydrea®), mitomycin (Mitozytrex®, Mutamycin®); immunomodulators: lenalidomide (Revlimid®), thalidomide (Thalomid®); immune cell antibodies: alemtuzamab (Campath®), gemtuzumab (Myelotarg®), rituximab (Rituxan®), tositumomab (Bexxar®); interferons (e.g., IFN-alpha (Alferon®, Roferon-A®, Intron®-A) or IFN-gamma (Actimmune®)); interleukins: IL-2 (Proleukin®), IL-24, IL-6 (Sigosix®), IL-12; HSP90 inhibitors (e.g., geldanamycin or any of its derivatives). In certain embodiments, the HSP90 inhibitor is selected from geldanamycin, 17-alkylamino-17-desmethoxygeldanamycin ("17-AAG") or 17-(2-dimethylaminoethyl)amino-17-desmethoxygeldanamycin ("17-DMAG"); anti-androgens which include, without limitation nilutamide (Nilandron®) and bicalutamide (Caxodex®); antiestrogens which include, without limitation tamoxifen (Nolvadex®), toremifene (Fareston®), letrozole (Femara®), testolactone (Teslac®), anastrozole (Arimidex®), bicalutamide (Casodex®), exemestane (Aromasin®), flutamide (Eulexin®), fulvestrant (Faslodex®), raloxifene (Evista®, Keoxifene®) and raloxifene hydrochloride; anti-hypercalcaemia agents which include without limitation gallium (III) nitrate hydrate (Ganite®) and pamidronate disodium (Aredia®); apoptosis inducers which include without limitation ethanol, 2-[[3-(2,3-dichlorophenoxy)propyl]amino]-(9C1), gambogic acid, elesclomol, embelin and arsenic trioxide (Trisenox®); Aurora kinase inhibitors which include without limitation binucleine 2; Bruton's tyrosine kinase inhibitors which include without limitation terreic acid; calcineurin inhibitors which include without limitation cypermethrin, deltamethrin, fenvalerate and tyrphostin 8; CaM kinase II inhibitors which include without limitation 5-Isoquinolinesulfonic acid, 4-[{2S)-2-[(5-isoquinolinylsulfonyl)methylamino]-3-oxo-3-{4-phenyl-1-piperazinyl)propyl]phenyl ester and benzenesulfonamide; CD45 tyrosine phosphatase inhibitors which include without limitation phosphonic acid; CDC25 phosphatase inhibitors which include without limitation 1,4-naphthalene dione, 2,3-bis[(2-hydroxyethyl)thio]-(9C1); CHK kinase inhibitors which include without limitation debromohymenialdisine; cyclooxygenase inhibitors which include without limitation 1H-indole-3-acetamide, 144-chlorobenzoyl)-5-m ethoxy-2-methyl-N-(2-phenyl ethyl)-(9C1), 5-alkyl substituted 2-arylaminophenylacetic acid and its derivatives (e.g., celecoxib (Celebrex®), rofecoxib (Vioxx®), etoricoxib (Arcoxia®), lumiracoxib (Prexige®), valdecoxib (Bextra®) or 5-alkyl-2-arylaminophenylacetic acid); cRAF kinase inhibitors which include without limitation 3-(3,5-dibromo-4-hydroxybenzylidene)-5-iodo-1,3-dihydroindo1-2-one and benzamide, 3-(dimethylamino)-N-[3-[(4-hydroxybenzoyl)amino]-4-methylphenyl]-(9C1); cyclin dependent kinase inhibitors which include without limitation olomoucine and its derivatives, purvalanol B, roascovitine (Seliciclib®), indirubin, kenpaullone, purvalanol A and indirubin-3'-monooxime; cysteine protease inhibitors which include without limitation 4-morpholinecarboxamide, N-[(1S)-3-fluoro-2-oxo-1-(2-phenylethyl)propyl]amino]-2-oxo-1-(phenylmethyl)ethyl]-(9C1); DNA intercalators which include without limitation plicamycin (Mithracin®) and daptomycin (Cubicin®); DNA strand breakers which include without limitation bleomycin (Blenoxane®); E3 ligase inhibitors which include without limitation N-((3,3,3-trifluoro-2-trifluoromethyl)propionyl)sulfanilamide; EGF Pathway Inhibitors which include, without limitation tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980; farnesyltransferase inhibitors which include without limitation ahydroxyfarnesylphosphonic acid, butanoic acid, 2-[(2 S)-2-[[(2 S,3 S)-2-[[(2R)-2-amino-3-mercaptopropyl]amino]-3-methylpent-yl]oxy]-1-oxo-3-phenylpropyl]amino]-4-(methylsulfonyl)-1-methylethylester (2S)-(9C1), tipifarnib (Zarnestra®), and manumycin A; Flk-1 kinase inhibitors which include without limitation 2-propenamide, 2-cyano-3-[4-hydroxy-3,5-bis(1-methylethyl)phenyl]-N-(3-phenylpropyl)-(2E-)-(9C1); glycogen synthase kinase-3 (GSK3) inhibitors which include without limitation indirubin-3'-monooxime; histone deacetylase (HDAC) inhibitors which include without limitation suberoylanilide hydroxamic acid (SAHA), [4-(2-amino-phenylcarbamoyl)-benzyl]carbamic acid pyridine-3-ylmethylester and its derivatives, butyric acid, pyroxamide, trichostatin A, oxamflatin, apicidin, depsipeptide, depudecin, trapoxin, vorinostat (Zolinza®), and compounds disclosed in WO 02/22577; I-kappa B-alpha kinase inhibitors (IKK) which include without limitation 2-propenenitrile, 3-[(4-methylphenyl)sulfonyl]-(2E)-(9C1); imidazotetrazinones which include without limitation temozolomide (Methazolastone®, Temodar®) and its derivatives (e.g., as disclosed generically and specifically in U.S. Pat. No. 5,260,291) and Mitozolomide; insulin tyrosine kinase inhibitors which include without limitation hydroxyl-2-naphthalenylmethylphosphonic acid; c-Jun-N-terminal kinase (JNK) inhibitors which include without limitation pyrazoleanthrone and epigallocatechin gallate; mitogen-activated protein kinase (MAP) inhibitors which include without limitation benzenesulfonamide, N-[2-[[[3-(4-chlorophenyl)-2-propenyl]methyl]amino]methyl]phenyl]-N-(2-hy-droxyethyl)-4-methoxy-(9C1); MDM2 inhibitors which include without limitation trans-4-iodo, 4'-boranyl-chalcone; MEK inhibitors which include without limitation butanedinitrile, bis[amino[2-aminophenyl)thio]methylene]-(9C1); MMP inhibitors which include without limitation Actinonin, epigallocatechin gallate, collagen peptidomimetic and non-peptidomimetic inhibitors, tetracycline derivatives marimastat (Marimastat®), prinomastat, incyclinide (Metastat®), shark cartilage extract AE-941 (Neovastat®), Tanomastat, TAA211, MMI270B or AAJ996; mTor inhibitors which include without limitation rapamycin (Rapamune®), and analogs and derivatives thereof, AP23573 (also known as ridaforolimus, deforolimus, or MK-8669), CCI-779 (also known as temsirolimus) (Torisel®) and SDZ-RAD; NGFR tyrosine kinase inhibitors which include without limitation tyrphostin AG 879; p38 MAP kinase inhibitors which include without limitation Phenol, 4-[4-(4-fluorophenyl)-5-(4-pyridinyl)-1H-imidazol-2-yl]-(9C1), and benzamide, 3-(dimethylamino)-N-[3-[(4-hydroxybenzoyl)amino]-4-methylphenyl]-(9C1); p56 tyrosine kinase inhibitors which include without limitation damnacanthal and tyrphostin 46; PDGF pathway inhibitors which include without limitation tyrphostin AG 1296, tyrphostin 9, 1,3-butadiene-1,1,3-tricarbonitrile, 2-amino-4-(1H-indol-5-yl)-(9C1), imatinib (Gleevec®) and gefitinib (Iressa®) and those compounds generically and specifically disclosed in European Patent No.: 0 564 409 and PCT Publication No.: WO 99/03854; phosphatidylinositol 3-kinase inhibitors which include without limitation wortmannin, and quercetin dihydrate; phosphatase inhibitors which include without limitation cantharidic acid, cantharidin, and L-leucinamide; protein phosphatase inhibitors which include without limitation cantharidic acid, cantharidin, L-P-bromotetramisole oxalate, 2(5H)-furanone, 4-hydroxy-5-(hydroxymethyl)-3-(1-oxohexadecyl)-(5R)-(9C1) and benzylphosphonic acid; PKC inhibitors which include without limitation 1-H-pyrollo-2,5-dione, 3-[1-3-(dimethylamino)propyl]-1H-indol-3-yl]-4-(1H-indol-3-yl)-(9C1), Bisindolylmaleimide IX, Sphinogosine, staurosporine, and Hypericin; PKC delta kinase inhibitors which include without limitation rottlerin; polyamine synthesis inhibitors which include without limitation DMFO; PTP1B inhibitors which include without limitation L-leucinamide; protein tyrosine kinase inhibitors which include, without limitation tyrphostin Ag 216, tyrphostin Ag 1288, tyrphostin Ag 1295, geldanamycin, genistein and 7H-pyrrolo[2,3-d]pyrimidine derivatives as generically and specifically described in PCT Publication No.: WO 03/013541 and U.S. Publication No.: 2008/0139587; SRC family tyrosine kinase inhibitors which include without limitation PP1 and PP2; Syk tyrosine kinase inhibitors which include without limitation piceatannol; Janus (JAK-2 and/or JAK-3) tyrosine kinase inhibitors which include without limitation tyrphostin AG 490 and 2-naphthyl vinyl ketone; retinoids which include without limitation isotretinoin (Accutane®, Amnesteem®, Cistane®, Claravis®, Sotret®) and tretinoin (Aberel®, Aknoten®, Avita®, Renova®, Retin-A®, Retin-A MICRO®, Vesanoid®); RNA polymerase H elongation inhibitors which include without limitation 5, 6-dichloro-1-beta-D-ribofuranosylbenzimidazole; serine/Threonine kinase inhibitors which include without limitation 2-aminopurine; sterol biosynthesis inhibitors which include without limitation squalene epoxidase and CYP2D6; VEGF pathway inhibitors, which include without limitation anti-VEGF antibodies, e.g., bevacizumab, and small molecules, e.g., sunitinib (Sutent®), sorafinib (Nexavar®), ZD6474 (also known as vandetanib) (Zactima™), SU6668, CP-547632 and AZD2171 (also known as cediranib) (Recentin™). In some embodiments, administering comprises aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, intradermal injection, or any combination thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) Left: an ideal mammalian private-channel communication system would allow engineered cells to send and respond to an orthogonal signal that does not interact with host cells. Middle: Engineered cells that can send and receive the signal simultaneously can respond to their own population size. Right: coupling the sending-receiving function with cell survival in a negative feedback can enable population control. (FIG. 1B) Auxin Receiver cells constitutively express a fluorescent target fusion protein, mCherry-AID-BlastR, as well as the F-box protein osTIR1. In the presence of auxin (yellow circle), osTIR1 and the AID-tagged target protein can be assembled into a SCF complex, which allows ubiquitylation (red dots) of the target protein, leading to target degradation. Both proteins are encoded on a single transcript, with an intervening T2A ribosomal skip sequence to yield separate proteins. (FIG. 1C) Auxin regulates intracellular protein levels. The circuit described in FIG. 1B was stably integrated into CHO-K1 cells to generate the Receiver cell line. The response of mCherry fluorescence to two different species of auxin (IAA and NAA) was measured after two days of treatment (dots). The responses follow Michaelis-Menten kinetics (fitted lines, Method), with indicated $EC^{50}$ values. (FIG. 1D) Auxin regulates cell density. Cells were treated with a combination of IAA and blasticidin at different concentrations for four days and passaged once. Cells were counted by flow cytometry (n=3, error bar=standard deviation). Note for both FIG. 1C and FIG. 1D, the x axis is arranged in symmetric log scale to include value at zero.

(FIG. 2A) Indole-3-acetic acid hydrolases such as iaaH, aux2, and AMI1 hydrolyze inactive auxin precursors (IAM and NAM) to their respective active form (IAA and NAA). (FIG. 2B) Stable expression of iaaH in Receiver cells allows them to produce auxin from precursors (blue square). (FIG. 2C) Conditioned media experiment (schematic). Fresh culture media with or without precursors was added to plated sender cells, collected, mixed at 1:1 ratio with standard fresh media, and then applied to receiver cells. (FIG. 2D) iaaH can produce IAA and NAA auxins from IAM and NAM precursors, respectively. Standard media, with or without precursors, was conditioned by Sender-Receivers or standard CHO-K1 cells for 48 hours and applied to Receiver cells for another two days. Receivers cultured with fresh media with or without auxins were also assayed as controls. Data are normalized to Receiver cell fluorescence treated with media conditioned by CHO-K1 cells. Error bars represent standard deviation of 3 replicates. (FIG. 2E) Auxin senders can generate an auxin gradient. Sender-Receivers (green) were seeded within a 7 mm×7 mm square at the edge of a 60 mm dish, and Receivers were plated everywhere else (no fluorescence or red). One day after plating, the media was replaced with fresh media containing low-melting-point agarose, with or without IAM (Methods). Plates were imaged after two additional days of culture. Inset: Quantification of the average pixel intensity of mCherry expression in cells shows that mCherry inhibition depends on distance from Sender-Receiver region. Error bars are the standard deviation of the four images making up each column in the mosaic.

(FIGS. 3A-3B) Sender-Receiver and Sender-Receiver-PIN2 cells perform quorum sensing. For both plots, cells were seeded at different densities and induction conditions, with either of the two auxins (saturating signaling) or their precursors (to allow quorum sensing). mCherry fluorescence was assayed after two days as a reporter of auxin sensing. Inset: Cells in B express the transporter PIN2, which actively exports auxin. Data were fitted onto an inverted Michaelis-Menten's function on log scale (see FIG. 7B for fitted parameters). (FIG. 3C) Sender-Receiver-PIN2 cells sense population size per unit volume. Cells were grown for two days at 6 different densities for each media volume, and cultured on a rocker for better mixing. (FIG. 3D) Sender-Receiver-PIN2 triggers cell death at high population density. Cells were seeded at different confluence levels, grown for four days in media with 50 µg/ml blasticidin and IAM, IAA, or no auxin (Error bars are standard deviation, n=3)).

FIGS. 4A-4G depict non-limiting exemplary embodiments and data showing paradoxical architecture reduces susceptibility to cheater mutations. (FIG. 4A) In the paradoxical architecture, the same signal inhibits growth (red pathway) and death (green pathway). This can produce a window of auxin concentrations leading to positive net growth (light blue region). Without mutation, the paradoxical and negative feedback circuits operate similarly around a stable equilibrium point of large population size (solid dots in the left panels). Mutations that eliminate sensing make both death and growth independent of auxin concentration (right panels), which selects against mutations in the paradoxical circuit due to negative net growth (FIG. 4B) In the paradoxical circuit implementation, auxin regulates growth through $Blast^R$ (upper path), and also regulates apoptosis via iCasp9 (lower path), each with distinct fluorescent protein readouts and a small molecule (blasticidin and AP1903) as a control switch. (FIG. 4C) The full paradoxical circuit can be encoded as a single open reading frame, with distinct proteins separated by T2A peptides (grey squares). (FIG. 4D) Paradaux cells respond to auxin in a biphasic manner. Cells were seeded at about 1/8 confluence (grey dashed line) and pretreated with NAA for one day, then treated with combinations of NAA, blasticidin (20 µg/ml) and AP1903 (50 nM) for another 3 days, and imaged. Pink, green, and blue dots show the mean and standard deviation of three replicates in the presence of AP1903, blasticidin, or both, respectively. Solid red and green lines indicate fits of these data to the model. Blue dashed lines indicate predictions for the fully operational circuit based on the green and red curves. Dotted blue line is the model prediction when the synergy term is included. (FIG. 4E) Different classes of behavior can occur in different parameter regimes. Using the model auxin-dependent growth was simulated in different parameter regimes and identified five distinct regimes (indicated schematically as insets). Using this classification, growth curves were numerically analyzed and sorted for each concentration of blasticidin and AP1903 (central plot). The blue dot indicates the blasticidin and AP1903 concentrations used in the time-lapse movie analysis. The grey region indicates curves that could not be classified into one of these categories (0.68% of total, see FIG. 9F and Supplementary text). (FIG. 4F). For each expression level, the percent of blasticidin-AP1903 concentrations that generate paradoxical behavior was analyzed, similar to FIG. 4E. Optimizing the expression and ratio of Blast R and iCasp9 can widen the paradoxical regime. (FIG. 4G) Dynamic simulations show the Paradoxical Control circuit provides evolutionary robustness. For the negative feedback system, tic and $\beta_C$ and $\beta_{syn}$ are set to zero. Mutated strains were simulated with auxin (A) fixed to zero, representing sensing deficient mutations. On day 25, 50, 75 and 100, mutant cells (1% of the population cap) were introduced into the simulated system to test robustness to mutations. These mutants take over in the negative feedback circuit (top) but not the paradoxical circuit (bottom). Dashed line indicates carrying capacity.

FIGS. 5A-5I depict non-limiting exemplary embodiments and data showing the paradoxical circuit allows mutationally robust population control. (FIG. 5A) Composite kymograph of long-term cultures with no control (100 µM NAM; upper panel), negative feedback (100 µM NAM and 50 µg/ml blasticidin; middle panel), or paradoxical feedback (100 µM NAM, 50 µg/ml blasticidin, and 50 nM AP1903; lower panel). For visualization, the images were analyzed in ilastik and 30-pixel-wide strips from each timepoint were combined to make the kymograph. (FIG. 5B) Population dynamics for the three conditions reveal delayed mutational escape for the paradoxical circuit (shaded envelope represents the standard deviation across 25 positions). Upper panel shows mutational escape of all negative feedback cell lines by 30 days, whereas the lower panel shows that the paradoxical control circuit prevents mutational escape during the same time period. Cells were seeded at varying densities as indicated in legend. Grey lines indicate uncontrolled growth (redrawn in both panels). Arrow (a) indicates exposure adjustment across all the positions; Arrow (b) indicates a brief disruption (~12 hours) of $CO_2$ supply. (FIG. 5C) Isolates from all long term cultures show correlated Blast R and iCasp9 expressions. (FIG. 5D) Isolates from negative feedback, but not paradoxical feedback, showed upregulation in $Blast^R$, compared to control. (FIG. 5E) Isolates from negative feedback showed diminished dynamic range compared to both control and paradoxical groups. (FIGS. 5C-5E) Isolates were treated with nothing or 10 μM NAA for two days prior to flow cytometry assay for mCherry and mGFP fluorescence, co-expressed with Blast R and iCasp9 respectively. Bars represent standard deviation from triplicates (FIGS. 5C-5D), or bootstrapping (FIG. 5E). (FIGS. 5F-5G) Blast R and iCasp9 expression levels affect survival rates across different conditions. Cells were seeded in 96-well imaging plates with IAA or standard media for one day, and the other drug (blasticidin for FIG. 5F, and AP1903 for FIG. 5G) was added on the second day and imaged to estimate confluency at day 4. Each isolate was tested with and without Blasticidin (FIG. 5F) or AP1903 (FIG. 5G) to normalize survival rates. The blue arrow in F highlights the strain that grew to high density in FIG. 9A. Values and error were calculated by bootstrapping (Methods). (FIG. 5H) A schematic showing how the paradoxical architecture, but not negative feedback, eliminates cells that lose the ability to sense auxin.

(FIG. 6A) Twelve candidate indole-3-acetamide hydrolases were screened for the ability to convert IAM to IAA. The phylogenetic tree was created with CLUSTAL-OMEGA and phyML3.0 using default settings. Candidate enzymes were transfected into Receiver cells, and auxin production was assessed by mCherry-AID degradation (FIG. 2B) after 48 hours. The fluorescent results are normalized to the control without auxin. Candidates that could down-regulate the mCherry by over 50% are highlighted in yellow. iaaH from *A. tumefaciens* (black arrow) was selected for subsequent experiments. (FIG. 6B) IAA can be synthesized from L-tryptophan (L-Trp) in a two-step pathway. (FIG. 6C) Media conditioned by iaaM expressing cells contains substrate for auxin production by iaaH. Cells transfected with iaaM were used to condition the media for 48 hours, as shown in FIG. 2C. Conditioned media was combined with an equal amount of fresh media and then applied to reporter cells for 48 hours before flow cytometry. (FIG. 6D) Auxin diffusion observed in FIG. 2E matches theoretical predictions.

(FIG. 7A) The right-shifted auxin response curve of PIN2 expressing cells is consistent with active export of IAA from the cells. Two PIN2-expressing cell lines were incubated with IAA for 48 hours and then assayed for mCherry fluorescence. The data were fitted with the same method in FIG. 1C. (FIG. 7B) Quantitative analysis of FIGS. 3A and 3B showed that the expression of PIN2 rescued dynamic range (indicated by the bracket in the left panel) lost to self-sensing (Supplementary text). (FIG. 7C) A pilot experiment showed that the Sender-Receiver-PIN2 cells escape regulation after 15 days of continuous culture. Cells were seeded into a 24-well imaging plate with 50 μg/ml of blasticidin solely (Circuit off) or also with 100 μM IAA or IAM (Circuit on). Each trace reflects an average of 12 positions in a sample well. Shaded envelopes represent the standard deviation of the averages. (FIG. 7D) Cheater cells collected from the end of the movie in (FIG. 7C) have high survival rates when grown in IAA with blasticidin for 4 days as compared to parental cells. Cell counts measured with flow cytometry were normalized to matched cells grown without drugs. Bars represent standard deviation from triplicates.

FIGS. 8A-8G depict non-limiting exemplary data showing model and parameter fitting of the paradoxical circuit. (FIG. 8A) A second Paradaux line responds to auxin in a biphasic manner. 4 nM of AP1903 and/or 50 μg/ml blasticidin were used; other parameters were the same as those used in FIG. 5D. Curves are fitted directly from the survival data because the maximum growth rate is not available. (FIG. 8B) The complete and reduced (approximate) versions of the model show similar dynamics, (overlap of black and cyan trajectories, see Modeling in Supplementary Text). (FIG. 8C) Generalized logistic growth (Equation 2) fits PC1' s growth curve better than a standard logistic growth curve. Data are from the first 120 hours of the control well in FIG. 9A, seeded at 3000 cells per well. Data is smoothed with a Gaussian filter. Fitting results: α=0.0395/hr; v=2.26. (FIG. 8D) Calculation of auxin secretion rate ($\lambda_A$). 2.09 μM/$10^6$ cell·hr. Sender-Receivers were seeded at 10,000 cells per well. After different durations (0 to 73.5 hours), conditioned media was collected to assay auxin concentration and cells were counted to estimate exponential growth rate. To determine the auxin concentration, the conditioned media was applied to Receivers at 1×, 0.5×, or 0.25× concentrations, and then Receiver fluorescence was compared to a standard curve. (FIG. 8E) Dynamic simulation of the system shows biphasic growth. Simulations were initiated at different cell densities. For each initial cell density, the initial auxin concentration was determined by setting Equation 1 to equal zero. (FIG. 8F) Simulation with delay (τ) incorporated show oscillated behaviours. Cells were seeded at 0.1, and the delay is applied onto the blasticidin related response (Equation S15). (FIG. 8G) An sub-sampling of the "unclassified" curves from FIG. 4E shows that they are intermediate between "permissive" and "paradoxical" categories.

(FIG. 9A) A replicate time-lapse movie experiment confirmed that the paradoxical design allows more robust population control compared to negative feedback. Culture and imaging conditions were similar to that shown in FIGS. 5A and 5B, with different seeding density (Methods). (FIG. 9B) Shifting traces based on their growth rate show consistent dynamics for the first oscillation. The growth rate is measured from the control sample with 100,000 seeding density, with a generalized logistic model (Equation 2 and FIG. 8C).

(FIG. 10A) Isolates that evolved in the same conditions cluster together, based on variance-stabilizing transformed (VST) read count across the whole transcriptome. Genes that are significantly differentially expressed between the groups (analyzed by DEseq2, fold change >32, adjusted p<0.01) are shown here. Genes that lack annotation in RefSeq are manually annotated, with the RefSeq number in parentheses. (FIG. 10B) Pathway enrichment analysis shows that the negative feedback and paradoxical feedback affect different sets of pathways. Enrichment analysis was performed with Gene Set Enrichment Analysis' (GSEA) ranked method against MSigDB's curated version of KEGG canonical pathways. (FIG. 10C) The negative and paradoxical circuit design exert different evolutionary pressures on the proteasome pathway. Direct comparison of the KEGG proteasome pathway between the paradoxical and negative group was analyzed by GSEA.

(FIG. 11A) Isogenic, independent cell cultures were observed in different conditions by time lapse microscopy for 17 days and then collected, sequenced, and tested for responsiveness to auxin. (FIG. 11B) Filmstrip of Sender-Receiver-PIN2 cells, with or without the 100 μM IAM precursor. Both samples were seeded with 2,000 cells per well. (FIG. 11C) Quantification of time lapse movies shows that population dynamics pulse in the presence of 100 μM precursor. Cells were seeded at the indicated density per well in a 24-well plate with 200 μg/ml of blasticidin (n=12 locations were analyzed in each well). Note that the sawtooth behavior of the control sample reflects the periodic 12 hour media changes. Data is missing on day 6 due to a data acquisition error. (FIG. 11D) Blasticidin concentration controls the population size limit, as measured from the initial peak of the time trace (inset). (FIG. 11E) Long-term culture leads to changes in auxin responsiveness. Cells were harvested, cultured for at least two passages, and assayed for mCherry-AID-Blast R expression. Auxin responsiveness is defined as the basal fluorescence divided by fluorescence in the presence of 10 μM IAA. The grey circle indicates 95% expectation (p=0.05) for a cell line with phenotype from the parental and uncontrolled growth group (2-D Gaussian assumption).

(FIG. 12A) Cell lines evolved under paradoxical conditions are phenotypically different from cheaters evolved under negative feedback. Each dot represents one culture. Cells evolved under the negative feedback conditions form a tight cluster, which is fitted with a 2-D gaussian to show the 95 percentile (orange dashed ellipse). In contrast, cell lines evolved under paradoxical control showed significantly different phenotypes compared to the negative feedback cluster (p=<1e-10, 0.001, 0.007, and <1e-10, top to bottom). (FIG. 12B) Under paradoxical, but not negative feedback, conditions, mutations that reduce auxin sensing lead to apoptosis in cheaters (red inhibitory arrow), preventing unregulated growth and mutational escape. (FIG. 12C) Activation of iCasp9 by AP1903 kills cheaters from the negative feedback condition (red dots) as compared to the parental cells (gray bars), even in the presence of NAA. Cells were incubated with different levels of NAA for 6 hours, and then 50 nM of AP1903 was added (except in controls) for another two days. Confluencies were measured and normalized to the no AP1903 control (n=3).

(FIGS. 14A-14B) Long-term culture traces under 50 μg/ml and 100 μg/ml blasticidin conditions. Experimental setups are the same as FIG. 11B. (FIG. 14C) Auxin does not sensitize cheater cells from long-term cultures to blasticidin. A cell line collected from the experiment described in (FIG. 14D) was cultured, in parallel with the parental line, with different IAA and blasticidin combinations for 4 days. Survival rates were normalized to the parental line, and each bar is from a triplet. (FIG. 14D) A separate pilot experiment showed that the parental line does not contain cheater cells. Cells were seeded into a 24-well imaging plate with 50 μg/ml of blasticidin solely or with 100 μM IAA or IAM, and no cells survived the combined IAA and blasticidin treatment. Each trace reflects an average of 12 positions in a sample well.

DETAILED DESCRIPTION

Figure 1A:
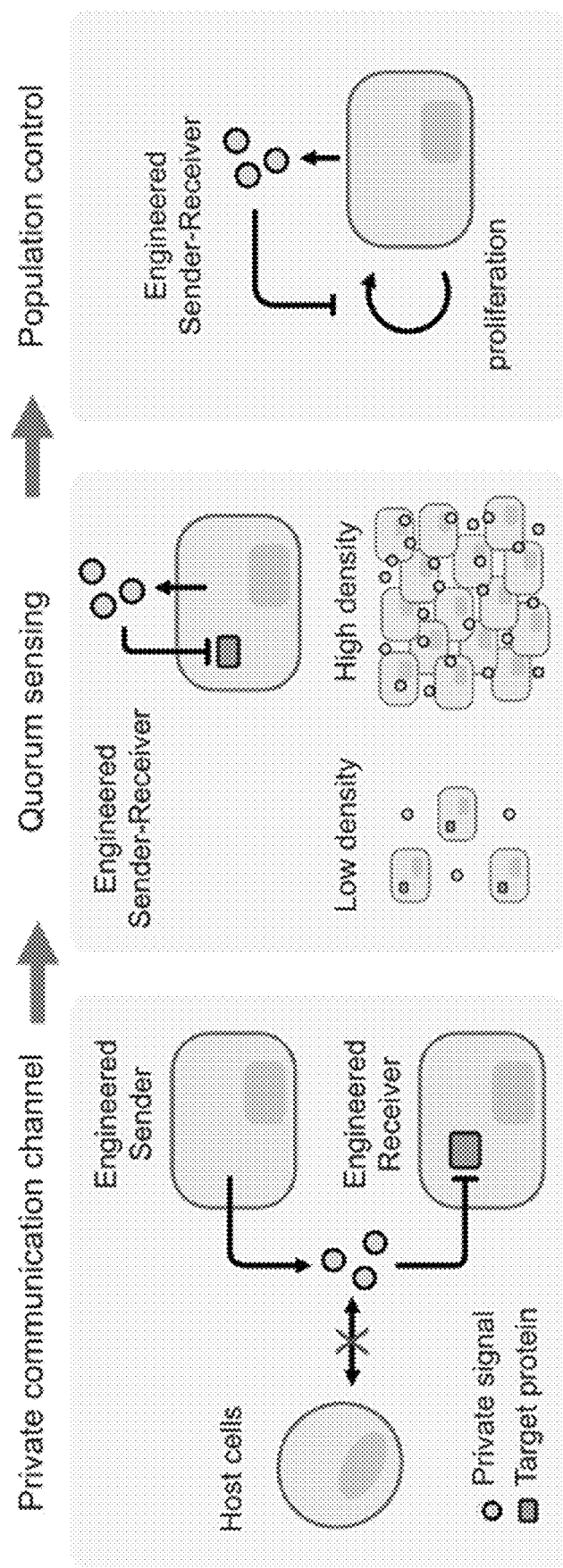
FIGS. 1A-1D depict non-limiting exemplary embodiments and data showing the plant hormone auxin allows private-channel mammalian cell-cell communication.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include nucleic acid compositions. In some embodiments, the nucleic acid composition comprises: a first polynucleotide encoding a first synthase, wherein the first synthase is capable of catalyzing the synthesis of an orthogonal signal from a first precursor molecule.

Disclosed herein include nucleic acid compositions. In some embodiments, the nucleic acid composition comprises: a second polynucleotide encoding a second synthase, wherein the second synthase is capable of catalyzing the synthesis of a first precursor molecule from a second precursor molecule.

Disclosed herein include nucleic acid compositions. In some embodiments, the nucleic acid composition comprises: a third polynucleotide encoding a transporter capable of transporting an orthogonal signal, a first precursor molecule, and/or a second precursor molecule across a cell membrane.

Disclosed herein include nucleic acid compositions. In some embodiments, the nucleic acid composition comprises: a fourth polynucleotide encoding a signal-binding protein; and a fifth polynucleotide encoding a first fusion protein comprising a signal-responsive domain and a pro-growth protein; wherein the signal-binding protein is capable of binding an orthogonal signal, wherein a signal-binding protein bound to the orthogonal signal is capable of reducing the stability, localization, and/or activity of a protein comprising a signal-responsive domain.

Disclosed herein include nucleic acid compositions. In some embodiments, the nucleic acid composition comprises: a fourth polynucleotide encoding a signal-binding protein; a fifth polynucleotide encoding a first fusion protein comprising a signal-responsive domain and a pro-growth protein; and a sixth polynucleotide encoding a second fusion protein comprising a signal-responsive domain and a pro-death protein, wherein the signal-binding protein is capable of binding an orthogonal signal, wherein a signal-binding protein bound to the orthogonal signal is capable of reducing the stability, localization, and/or activity of a protein comprising a signal-responsive domain.

Disclosed herein include nucleic acid compositions. In some embodiments, the nucleic acid composition comprises: a fourth polynucleotide encoding a signal-binding protein; and a seventh polynucleotide encoding a third fusion protein comprising a signal-responsive domain and target protein, wherein the signal-binding protein is capable of binding an orthogonal signal, wherein a signal-binding protein bound to the orthogonal signal is capable of reducing the stability, localization, and/or activity of a protein comprising a signal-responsive domain.

Disclosed herein include nucleic acid compositions. In some embodiments, the nucleic acid composition comprises: two or more of the nucleic acid compositions of any one of the Disclosed herein include compositions. In some embodiments, the composition comprises: one or more of the nucleic acid compositions (e.g., circuits) provided herein. In some embodiments, the composition comprises one or more vectors, a ribonucleoprotein (RNP) complex, a liposome, a nanoparticle, an exosome, a microvesicle, or any combination thereof. In some embodiments, the vector is a viral vector, a plasmid, a naked DNA vector, a lipid nanoparticle, or any combination thereof. In some embodiments, the viral vector is an AAV vector, a lentivirus vector, a retrovirus vector, an integration-deficient lentivirus (IDLV) vector. In some embodiments, the AAV vector comprises single-stranded AAV (ssAAV) vector or a self-complementary AAV (scAAV) vector.

Disclosed herein include populations of cells. In some embodiments, the population of cells comprises: one or more sender cells comprising one or more of the nucleic acid compositions (e.g., circuits) provided herein; one or more receiver cells comprising one or more of the nucleic acid compositions (e.g., circuits) provided herein; and/or one or more sender-receiver cells comprising one or more of the nucleic acid compositions (e.g., circuits) provided herein.

Disclosed herein include populations of cells. In some embodiments, the population of cells comprises: a first cell type comprising one or more of the nucleic acid compositions (e.g., circuits) provided herein; and a second cell type comprising one or more of the nucleic acid compositions (e.g., circuits) provided herein, wherein the first cell type and second cell type are sender-receiver cells configured to grow in the presence of both cell types.

Disclosed herein include methods for treating a disease or disorder in a subject. In some embodiments, the method comprises: introducing into two or more cells one or more of the nucleic acid compositions (e.g., circuits) provided herein or one or more of the compositions provided herein, thereby generating a population of cells; and administering to the subject an effective amount of the population of cells. The method can comprise: isolating the two or more cells from the subject prior to the introducing step. In some embodiments, the introducing step is performed in vivo, in vitro, and/or ex vivo. In some embodiments, the introducing step comprises calcium phosphate transfection, DEAE-dextran mediated transfection, cationic lipid-mediated transfection, electroporation, electrical nuclear transport, chemical transduction, electrotransduction, Lipofectamine-mediated transfection, Effectene-mediated transfection, lipid nanoparticle (LNP)-mediated transfection, or any combination thereof.

Disclosed herein include methods for treating a disease or disorder in a subject. In some embodiments, the method comprises: administering to the subject an effective amount of a population of cells provided herein. The method can comprise: administering to the subject an effective amount of the first precursor molecule, the second precursor molecule, the exogenous agent, the pro-death agent, or any combination thereof.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, N Y 1989). For purposes of the present disclosure, the following terms are defined below.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

The term "vector" as used herein, can refer to a vehicle for carrying or transferring a nucleic acid. Non-limiting examples of vectors include plasmids and viruses (for example, AAV viruses).

The term "construct," as used herein, refers to a recombinant nucleic acid that has been generated for the purpose of the expression of a specific nucleotide sequence(s), or that is to be used in the construction of other recombinant nucleotide sequences.

As used herein, the term "plasmid" refers to a nucleic acid that can be used to replicate recombinant DNA sequences within a host organism. The sequence can be a double stranded DNA.

The term "element" refers to a separate or distinct part of something, for example, a nucleic acid sequence with a separate function within a longer nucleic acid sequence. The term "regulatory element" and "expression control element" are used interchangeably herein and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

As used herein, the term "enhancer" refers to a type of regulatory element that can increase the efficiency of transcription, regardless of the distance or orientation of the enhancer relative to the start site of transcription.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

The term "construct," as used herein, refers to a recombinant nucleic acid that has been generated for the purpose of the expression of a specific nucleotide sequence(s), or that is to be used in the construction of other recombinant nucleotide sequences.

As used herein, a "subject" refers to an animal that is the object of treatment, observation or experiment. "Animal" includes cold- and warm-blooded vertebrates and invertebrates such as fish, shellfish, reptiles, and in particular, mammals. "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees and apes, and, in particular, humans. In some embodiments, the mammal is a human. However, in some embodiments, the mammal is not a human.

As used herein, the term "treatment" refers to an intervention made in response to a disease, disorder or physiological condition manifested by a patient. The aim of treatment may include, but is not limited to, one or more of the alleviation or prevention of symptoms, slowing or stopping the progression or worsening of a disease, disorder, or condition and the remission of the disease, disorder or condition. The term "treat" and "treatment" includes, for example, therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. As used herein, the term "prevention" refers to any activity that reduces the burden of the individual later expressing those symptoms. This can take place at primary, secondary and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications. The term "prevent" does not require the 100% elimination of the possibility of an event. Rather, it denotes that the likelihood of the occurrence of the event has been reduced in the presence of the compound or method.

As used herein, the term "effective amount" refers to an amount sufficient to effect beneficial or desirable biological and/or clinical results.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counterions such as sodium, and nonionic surfactants such as Tween™, polyethylene glycol (PEG), and Pluronics™. Auxiliary, stabilizer, emulsifier, lubricant, binder, pH adjustor controller, isotonic agent and other conventional additives may also be added to the carriers.

The term "antibody fragment" shall be given its ordinary meaning, and shall also refers to at least one portion of an antibody, that retains the ability to specifically interact with (e.g., by binding, steric hindrance, stabilizing/destabilizing, spatial distribution) an epitope of an antigen. Examples of antibody fragments include, but are not limited to, Fab, Fab', F(ab')$_2$, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3) (see U.S. Pat. No. 6,703,199, which describes fibronectin polypeptide minibodies).

The term "autologous" shall be given its ordinary meaning, and shall also refer to any material derived from the same individual to whom it is later to be re-introduced into the individual.

The term "allogeneic" shall be given its ordinary meaning, and shall also refer to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "stimulation," shall be given its ordinary meaning, and shall also refer to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules.

As used herein, 2A sequences or elements refer to small peptides introduced as a linker between two proteins, allowing autonomous intraribosomal self-processing of polyproteins (See e.g., de Felipe. Genetic Vaccines and Ther. 2: 13 (2004); de Felipe et al. Traffic 5:616-626 (2004)). These short peptides allow co-expression of multiple proteins from a single vector. Many 2A elements are known in the art. Examples of 2A sequences that can be used in the methods and system disclosed herein, without limitation, include 2A sequences from the foot-and-mouth disease virus (F2A), equine rhinitis A virus (E2A), Thosea asigna virus (T2A), and porcine teschovirus-1 (P2A).

Synthetic Mammalian Signaling Circuits for Robust Cell Population Control

The ability to engineer cells that can sense, control, and respond to their own population density can, in some embodiments provided herein, employ a small molecule signal that mammalian cells can produce and sense, and which can diffuse through a tissue of interest. This signal can be orthogonal to the intrinsic pathways used by the organism. Simultaneous production and perception of the signal by all cells in the population can enable coordination of population-level behaviors. Coupling such a 'quorum sensing' system to control cell proliferation and/or death can enable cells disclosed herein to autonomously limit their own population density, avoiding problems associated with overgrowth. However, any circuit that limits growth can be susceptible to mutations that inactivate it. There are provided, in some embodiments, circuits that enable population control in a way that is robust to such mutations, and thereby making the system more stable and reliable.

There are provided, in some embodiments, circuits, compositions, nucleic acids, populations, systems, and methods for orthogonal communication channels through which mammalian cells can be engineered to synthesize, sense, and respond to an orthogonal signal (e.g., the plant hormone auxin). In some embodiments, biological circuits link signaling to the control of cell survival and death to achieve autonomous cellular control of population density. There are provided, in some embodiments, a negative feedback circuit, in which cells constitutively produce signals that reduce antibiotic tolerance. Also described herein, in some embodiments, is an evolutionarily robust 'paradoxical' regulatory architecture, in which signals both stimulate and inhibit net cell growth at different signal concentrations and provide the necessary robustness for this population control circuit. In addition to auxin, the circuits, compositions, nucleic acids, populations, systems, and methods allow other small molecules (e.g. abscisic acid or gibberellin) to be used as independent communication channels. The circuits, compositions, nucleic acids, populations, systems, and methods provided herein enable new multicellular mammalian circuits which can be employed in a broad range of applications.

Directional Cell-Cell Communication Based on Sending Orthogonal Signals from One Cell to Another Cell Intercellular communication is an function that enables the coordination of multicellular behaviours. There are provided, in some embodiments, circuits, compositions, nucleic acids, populations, systems, and methods wherein one cell produces the diffusive signals, and the signal regulates the behavior of adjacent or distant cells.

Communication Between Groups of Different Cell Types.

Interaction between cell types can be essential for circuits that require collaboration between two or more cell types. There are provided, in some embodiments, circuits, compositions, nucleic acids, populations, systems, and methods that can be used in systems where one or more cell types produce auxin or another orthogonal signal provided herein (senders), and another subset of cell types (receivers) sensing it. The signal can, in some embodiments, be used to inform the receivers about population size, cellular activity or relative locations of the senders. For example, in a two component immunotherapy circuit, a detector cell type (e.g. macrophages) with better capability trafficking into the tumor site, can provide locational information to guide a killer cell type (e.g. CAT-T or NK cells) to only activate at a specific location.

Engineered Consortia of Multiple Cell Types

The auxin biosynthetic pathway from tryptophan to indole-3-acetamide (IAM) and from IAM to indole-3-acetic acid (IAA) is a two-step process. These steps can be designed to occur in different cell types, thereby requiring, in some embodiments, both cell types in close proximity for IAA production. This can be used for a coincidence detector or a proximity-dependent AND gate. Furthermore, by making both cell types require IAA for growth, a consortium can be designed that will only grow in the presence of both cell types.

Population Size and Density Sensing

In some embodiments of the circuits, compositions, nucleic acids, populations, systems, and methods provided herein, cells produce and/or sense the signal constantly and/or simultaneously. Due to the constant production rate per cell in some embodiments, the environmental concentration of the signal can serve as a readout of local population density. This can allow cells to activate a response such as therapeutic cytokine production only when they reach a critical density threshold.

Population Control with Negative Feedback

There are provided, in some embodiments, circuits, compositions, nucleic acids, populations, systems, and methods that limit or cap the population size, to prevent overgrowth of the modified cells. In some embodiments, this can be achieved by sensing the population size, and causing cells to stop growing or die if the population size exceeds a threshold. The negative feedback circuits described herein, in some embodiments, achieve this function.

Evolutionary Robust Population Control

Circuits relying on a single negative feedback loop to achieve population control can be susceptible to "cheater" mutations that break the circuit. To overcome this issue, there are provided, in some embodiments, engineered circuits in which the signal regulates both positive and negative growth rate simultaneously, and it provides the necessary robustness for population control.

Population-Level Behavior Activation

In some embodiments of the circuits, compositions, nucleic acids, populations, systems, and methods provided herein, modified immune cells, such as CAR-T or natural killer (NK) cells, are engineered to only attack once they have accumulated to a critical population threshold. In some embodiments, this reduces undesirable side effects from off-target cell killing.

Population-Level Density-Dependent Differentiation and Cell State Switching

In some embodiments of the circuits, compositions, nucleic acids, populations, systems, and methods provided herein, mammalian cells are engineered to grow to a certain population size before differentiating into the target cell type or switching states. There are provided, in some embodiments, circuits, compositions, nucleic acids, populations, systems, and methods for synthetic organogenesis or tissue repair.

Some embodiments of the circuits, compositions, nucleic acids, populations, systems, and methods provided herein are configured to achieve more than one of the functions provided herein (such as those discussed immediately above). For example, in some embodiments, circuits are configured to achieve both evolutionary robust population control and population-level density-dependent differentiation and cell state switching. Various combinations of the nucleic acid compositions are provided herein. Cells can comprise, depending on the needs of the user, any one or more of the nucleic acid compositions provided herein to perform the functions for which they are configured. In some embodiments, the cells configured to activate a therapeutic program in the presence of a critical orthogonal signal threshold and/or upon the cell population reaching a critical cell population size and/or density threshold. The relative location of the orthogonal signal can, in some embodiments can provide locational information (e.g., to guide a killer cell type (e.g. CAT-T or NK cells) to only activate at a specific location.

Circuit Components

Disclosed herein include nucleic acid compositions (e.g., circuits). In some embodiments, the nucleic acid composition comprises: a first polynucleotide encoding a first synthase, wherein the first synthase is capable of catalyzing the synthesis of an orthogonal signal from a first precursor molecule. In some embodiments, the nucleic acid composition comprises: a second polynucleotide encoding a second synthase, wherein the second synthase is capable of catalyzing the synthesis of a first precursor molecule from a second precursor molecule. In some embodiments, the nucleic acid composition comprises: a third polynucleotide encoding a transporter capable of transporting an orthogonal signal, a first precursor molecule, and/or a second precursor molecule across a cell membrane. In some embodiments, the nucleic acid composition comprises: a fourth polynucleotide encoding a signal-binding protein; and a fifth polynucleotide encoding a first fusion protein comprising a signal-responsive domain and a pro-growth protein; wherein a signal-binding protein in the presence of the orthogonal signal is capable of reducing the stability, localization, and/or activity of a protein comprising a signal-responsive domain. In some embodiments, the nucleic acid composition comprises: a fourth polynucleotide encoding a signal-binding protein; a fifth polynucleotide encoding a first fusion protein comprising a signal-responsive domain and a pro-growth protein; and a sixth polynucleotide encoding a second fusion protein comprising a signal-responsive domain and a pro-death protein, wherein a signal-binding protein in the presence of the orthogonal signal is capable of reducing the stability, localization, and/or activity of a protein comprising a signal-responsive domain. In some embodiments, the nucleic acid composition comprises: a fourth polynucleotide encoding a signal-binding protein; and a seventh polynucleotide encoding a third fusion protein comprising a signal-responsive domain and target protein, wherein a signal-binding protein in the presence of the orthogonal signal is capable of reducing the stability, localization, and/or activity of a protein comprising a signal-responsive domain. In some embodiments, the nucleic acid composition comprises: two or more of the nucleic acid compositions of any one of the nucleic acid compositions (e.g., circuits) provided herein. In some embodiments, the signal-binding protein is capable of binding the orthogonal signal. In some embodiments, the signal-binding protein in the presence of (but not necessarily bound to) the orthogonal signal is capable of reducing the stability, localization, and/or activity of a protein comprising a signal-responsive domain. In some embodiments, the signal-responsive domain comprises a degron.

The fifth polynucleotide, the sixth polynucleotide, and/or the seventh polynucleotide can be operably linked to a tandem gene expression element. The tandem gene expression element can be an internal ribosomal entry site (IRES), foot-and-mouth disease virus 2A peptide (F2A), equine rhinitis A virus 2A peptide (E2A), porcine teschovirus 2A peptide (P2A) or Thosea asigna virus 2A peptide (T2A), or any combination thereof.

A first promoter can be operably linked to the fifth polynucleotide, the sixth polynucleotide, and/or the seventh polynucleotide. The first promoter can be capable of inducing transcription of the fifth polynucleotide, the sixth polynucleotide, and/or the seventh polynucleotide to generate a polycistronic transcript. The polycistronic transcript can be capable of being translated to generate the signal-binding protein, the first fusion protein, the second fusion protein, and/or the third fusion protein.

The first promoter and/or second promoter can comprise a ubiquitous promoter. The ubiquitous promoter can be selected from the group comprising a cytomegalovirus (CMV) immediate early promoter, a CMV promoter, a viral simian virus 40 (SV40) (e.g., early or late), a Moloney murine leukemia virus (MoMLV) LTR promoter, a Rous sarcoma virus (RSV) LTR, an RSV promoter, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus, a Ubiquitin C promoter (UBC), a phosphoglycerate kinase-1 (PGK) promoter, 3-phosphoglycerate kinase promoter, a cytomegalovirus enhancer, human β-actin (HBA) promoter, chicken β-actin (CBA) promoter, a CAG promoter, a CBH promoter, or any combination thereof.

A signal-binding protein bound to the orthogonal signal can be capable of triggering the ubiquitylation and proteasomal degradation of a protein comprising a signal-responsive domain.

The first polynucleotide, the second polynucleotide, the third polynucleotide, the fourth polynucleotide, the fifth polynucleotide, the sixth polynucleotide, the seventh polynucleotide, the eighth polynucleotide, and/or the ninth polynucleotide further can comprise a transcript stabilization element (e.g., woodchuck hepatitis post-translational regulatory element (WPRE), bovine growth hormone polyadenylation (bGH-polyA) signal sequence, human growth hormone polyadenylation (hGH-polyA) signal sequence, or any combination thereof).

The first polynucleotide, the second polynucleotide, the third polynucleotide, the fourth polynucleotide, the fifth polynucleotide, the sixth polynucleotide, the seventh polynucleotide, the eighth polynucleotide, and/or the ninth polynucleotide can be evolutionarily stable for at least about 10 days, about 20 days, about 40 days, about 80 days, about 80 days, or about 100 days, of serial passaging.

The nucleic acid can comprise at least one regulatory element for expression of the synthetic protein circuit. The nucleic acid can comprise a vector, such as any of the viral vectors described in U.S. application Ser. No. 16/555,604, filed on Aug. 29, 2019, the content of which is incorporated herein by reference in its entirety. In some embodiments, the vector can comprise an adenovirus vector, an adeno-associated virus vector, an Epstein-Barr virus vector, a Herpes virus vector, an attenuated HIV vector, a retroviral vector, a vaccinia virus vector, or any combination thereof. In some embodiments, the vector can comprise an RNA viral vector. In some embodiments, the vector can be derived from one or more negative-strand RNA viruses of the order Mononegavirales. In some embodiments, the vector can be a rabies viral vector. Many such vectors useful for transferring exogenous genes into target mammalian cells are available. The vectors may be episomal, e.g. plasmids, virus-derived vectors such cytomegalovirus, adenovirus, etc., or may be integrated into the target cell genome, through homologous recombination or random integration, e.g. retrovirus-derived vectors such as MMLV, HIV-1, ALV, etc. In some embodiments, combinations of retroviruses and an appropriate packaging cell line may also find use, where the capsid proteins will be functional for infecting the target cells. Retroviral vectors can be "defective", i.e. unable to produce viral proteins required for productive infection. Replication of the vector can require growth in the packaging cell line. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression of an RNA or polypeptide (e.g., a synthetic protein circuit component) from nucleic acid sequences contained therein linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5' UTR) or "leader" sequences and 3' UTR or "trailer" sequences, as well as intervening sequences (introns) between individual coding segments (exons).

Integrating vectors have their delivered RNA/DNA permanently incorporated into the host cell chromosomes. Non-integrating vectors remain episomal which means the nucleic acid contained therein is never integrated into the host cell chromosomes. Examples of integrating vectors include retroviral vectors, lentiviral vectors, hybrid adenoviral vectors, and herpes simplex viral vector. One example of a non-integrative vector is a non-integrative viral vector. Non-integrative viral vectors eliminate the risks posed by integrative retroviruses, as they do not incorporate their genome into the host DNA. One example is the Epstein Barr oriP/Nuclear Antigen-1 ("EBNA1") vector, which is capable of limited self-replication and known to function in mammalian cells. As containing two elements from Epstein-Barr virus, oriP and EBNA1, binding of the EBNA1 protein to the virus replicon region oriP maintains a relatively long-term episomal presence of plasmids in mammalian cells. This particular feature of the oriP/EBNA1 vector makes it ideal for generation of integration-free iPSCs. Another non-integrative viral vector is adenoviral vector and the adeno-associated viral (AAV) vector. Other non-integrative viral vectors contemplated herein are single-strand negative-sense RNA viral vectors, such Sendai viral vector and rabies viral vector. Another example of a non-integrative vector is a minicircle vector. Minicircle vectors are circularized vectors in which the plasmid backbone has been released leaving only the eukaryotic promoter and cDNA(s) that are to be expressed. As used herein, the term "viral vector" refers to a nucleic acid vector construct that includes at least one element of viral origin and has the capacity to be packaged into a viral vector particle. The viral vector can contain a nucleic acid encoding a polypeptide as described herein in place of nonessential viral genes. The vector and/or particle may be utilized for the purpose of transferring nucleic acids into cells either in vitro or in vivo. Numerous forms of viral vectors are known in the art.

In some embodiment, the vectors can include a regulatory sequence that allows, for example, the translation of multiple proteins from a single mRNA. Non-limiting examples of such regulatory sequences include internal ribosome entry site (IRES) and 2A self-processing sequence. In some embodiments, the 2A sequence is a 2A peptide site from foot-and-mouth disease virus (F2A sequence). In some embodiments, the F2A sequence has a standard furin cleavage site. In some embodiments, the vector can also comprise regulatory control elements known to one of skill in the art to influence the expression of the RNA and/or protein products encoded by the polynucleotide within desired cells of the subject. In some embodiments, functionally, expression of the polynucleotide is at least in part controllable by the operably linked regulatory elements such that the element(s) modulates transcription of the polynucleotide, transport, processing and stability of the RNA encoded by the polynucleotide and, as appropriate, translation of the transcript. A specific example of an expression control element is a promoter, which is usually located 5' of the transcribed sequence. Another example of an expression control element is an enhancer, which can be located 5' or 3' of the transcribed sequence, or within the transcribed sequence. Another example of a regulatory element is a recognition sequence for a microRNA. Another example of a regulatory element is an ration and the splice donor and splice acceptor sequences that regulate the splicing of said intron. Another example of a regulatory element is a transcription termination signal and/or a polyadenylation sequence.

Expression control elements and promoters include those active in a particular tissue or cell type, referred to herein as a "tissue-specific expression control elements/promoters." Tissue-specific expression control elements are typically active in specific cell or tissue (for example in the liver, brain, central nervous system, spinal cord, eye, retina or lung). Expression control elements are typically active in these cells, tissues or organs because they are recognized by transcriptional activator proteins, or other regulators of transcription, that are unique to a specific cell, tissue or organ type.

Expression control elements also include ubiquitous or promiscuous promoters/enhancers which are capable of driving expression of a polynucleotide in many different cell types. Such elements include, but are not limited to, the cytomegalovirus (CMV) immediate early promoter/enhancer sequences, the Rous sarcoma virus (RSV) promoter/enhancer sequences and the other viral promoters/enhancers active in a variety of mammalian cell types; promoter/enhancer sequences from ubiquitously or promiscuously expressed mammalian genes including, but not limited to, beta actin, ubiquitin or EF1 alpha; or synthetic elements that are not present in nature.

Expression control elements also can confer expression in a manner that is regulatable, that is, a signal or stimuli increases or decreases expression of the operably linked polynucleotide. A regulatable element that increases expression of the operably linked polynucleotide m response to a signal or stimuli is also referred to as an "inducible element" (that is, it is induced by a signal). Particular examples include, but are not limited to, a hormone (for example, steroid) inducible promoter. A regulatable element that decreases expression of the operably linked polynucleotide in response to a signal or stimuli is referred to as a "repressible element" (that is, the signal decreases expression such that when the signal, is removed or absent, expression is increased). Typically, the amount of increase or decrease conferred by such elements is proportional to the amount of signal or stimuli present: the greater the amount of signal or stimuli, the greater the increase or decrease in expression The nucleic acid composition can comprise one or more vectors. At least one of the one or more vectors can be a viral vector, a plasmid, a naked DNA vector, a lipid nanoparticle, or any combination thereof. The viral vector can be an AAV vector, a lentivirus vector, a retrovirus vector, an integration-deficient lentivirus (IDLV) vector. Disclosed herein include compositions. In some embodiments, the composition comprises: one or more of the nucleic acid compositions (e.g., circuits) provided herein. The composition can comprise one or more vectors, a ribonucleoprotein (RNP) complex, a liposome, a nanoparticle, an exosome, a microvesicle, or any combination thereof. The vector can be a viral vector, a plasmid, a naked DNA vector, a lipid nanoparticle, or any combination thereof. The viral vector can be an AAV vector, a lentivirus vector, a retrovirus vector, an integration-deficient lentivirus (IDLV) vector. The AAV vector can comprise single-stranded AAV (ssAAV) vector or a self-complementary AAV (scAAV) vector.

Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, e.g., a gammaretroviral vector. A gammaretroviral vector may include, e.g., a promoter, a packaging signal (w), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

The term "lentivirus" refers to a genus of the Retroviridae family Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

Vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells (e.g., immune cells). For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

The nucleic acid composition can be single-stranded or double-stranded. The nucleic acid composition can contain two or more nucleic acids. The two or more nucleic acids can be in the same form (e.g., a first plasmid and a second plasmid) or different in forms (e.g., a first plasmid and a first viral vector).

Permanent Switches

In some embodiments, the orthogonal signal triggers a permanent switch in a receiver cell, such as, for example, a recombinase-based permanent switch. In some embodiments, one or more of the payloads comprise a recombinase. The nucleic acid composition can comprise: a second promoter and a ninth polynucleotide comprising a payload gene, wherein, in the absence of a recombination event, the second promoter and the ninth polynucleotide are not operably linked, wherein the recombinase is capable of catalyzing the recombination event, and wherein the second promoter and the ninth polynucleotide are operably linked after the recombination event such that the second promoter is capable of inducing transcription of the payload gene to generate a payload transcript.

The recombination event can comprise removal of a sequence flanked by recombinase target sites or an inversion of a sequence flanked by recombinase target sites. The ninth polynucleotide can be flanked by recombinase target sites. In some embodiments, prior to the recombination event, the sequence of the payload gene can be inverted relative to the second promoter. The nucleic acid composition can comprise: at least one stop cassette situated between the second promoter and the payload gene, wherein the stop cassette comprises one or more stop sequences, and wherein the one or more stop cassettes are flanked by recombinase target sites. The payload transcript can be capable of being translated to generate a payload protein. The at least one stop cassette can be configured to prevent transcription of the payload gene and/or translation of the payload transcript. In some embodiments, the one or more stop sequences comprise a polyadenylation signal, a stop codon, a frame-shifting mutation, or any combination thereof. The recombinase can be Cre, Dre, Flp, KD, B2, B3, λ, HK022, HP1, γ6, ParA, Tn3, Gin, ΦC31, Bxb1, R4, derivatives thereof, or any combination thereof. The recombinase can be a Flp recombinase and the recombinase target sites can be FRT sites. The recombinase can be a Cre recombinase and the recombinase target sites can be loxP sites.

Additional Synthetic Protein Circuits

In some embodiments of the circuits, compositions, nucleic acids, populations, systems, and methods provided herein, one or more components of the disclosed circuits interfaces with (e.g., modulates and/or is modulated by) another synthetic protein circuit component. The payload protein(s), target protein(s), fusion protein(s), synthase(s), transporter(s), and/or signal-binding protein(s) described herein can comprise, be under the control of, or modulate (directly or indirectly) a synthetic protein circuit component. Synthetic biology allows for rational design of circuits that confer new functions in living cells. Many natural cellular functions are implemented by protein-level circuits, in which proteins specifically modify each other's activity, localization, or stability. Synthetic protein circuits have been described in, Gao, Xiaojing J., et al. "Programmable protein circuits in living cells." *Science* 361.6408 (2018): 1252-1258; and PCT Application Publication No. WO 2019/147478; the content of each of these, including any supporting or supplemental information or material, is incorporated herein by reference in its entirety. In some embodiments, synthetic protein circuits respond to inputs only above or below a certain tunable threshold concentration, such as those provided in U.S. patent application Ser. No. 16/738,664, published as US Patent Publication No. 2020/0277333, the content of which is incorporated herein by reference in its entirety. In some embodiments, synthetic protein circuits comprise one or more synthetic protein circuit design components and/or concepts of U.S. application Ser. No. 16/556,063, filed on Aug. 29, 2019, the content of which is incorporated herein by reference in its entirety. In some embodiments, synthetic protein circuits comprise rationally designed circuits, including miRNA-level and/or protein-level incoherent feed-forward loop circuits, that maintain the expression of a payload at an efficacious level, such as those provided in US Patent Publication No. 2021/0171582, the content of which is incorporated herein by reference in its entirety.

Orthogonal Signals

The orthogonal signal can be capable of diffusing through a target site of a subject. The target site can be a tissue of interest. In some embodiments, the orthogonal signal exhibits minimal immunogenicity in a subject. The orthogonal signal can be orthogonal to the intrinsic signaling pathways of a subject. The orthogonal signal can comprise indole-3-acetic acid (IAA), 1-napthalenatic acid (NAA), derivatives thereof, or any combination thereof. The first synthase can comprise an indole-3-acetic acid hydrolase (e.g., iaaH, aux2 and/or AMI1, *A. tumefaciens* iaaH, or any combination thereof). The second synthase can comprise tryptophan 2-monooxygenase (iaaM). The transporter can be auxin exporter PIN2 (e.g., *Arabidopsis thaliana* PIN2). The first precursor molecule and/or the second precursor molecule can be an endogenous molecule of a cell (e.g., L-tryptophan). The first precursor molecule can comprise indole-3-acetamide (IAM) and/or 1-naphthaleneacetamide (NAM). The signal-binding protein can comprise TIR1 (e.g., osTIR1). The signal-responsive domain can comprise an auxin inducible degron (AID), such as a minimal auxin inducible degron (mAID). In some embodiments, the signal-responsive domain and/or signal-binding protein does not modulate endogenous mammalian proteins.

The orthogonal signal can be a small molecule, such as, for example, a hormone (e.g., a plant hormone, such as auxin, abscisic acid or gibberellin). The plant hormone can be selected from the group comprising an auxin, a cytokinin, a phenolic plant hormone, an isoprenoid plant hormone, an aromatic plant hormone, a lipid plant hormone, a gibberellin, a salicylate, derivatives thereof, or any combination thereof. The salicylate can be or include salicylic acid. The auxin can be selected from the group comprising indole-3-acetic acid (IAA), indole-3-acetic acid ethyl ester, indole-3-acetyl-glycine (IAGly), indole-3-acetyl-L-alanine (IAA1a), indole-3-carboxylic acid (I3CA), indole-3-carboxylic acid methyl, indole-3-butyric acid (IBA), indole-3-glyoxylic acid methyl ester, DL-indole-3-lactic acid (ILA), indole-3-carboxaldehyde (IAld), tryptophol (IEt), derivatives thereof, or any combination thereof. The isoprenoid plant hormones can be or include an abscisic acid and/or an isoprenoid cytokinin. The abscisic acid can comprise (+)-cis,trans-abscisic acid (ABA). The isoprenoid cytokinin can be N6-isopentenyladenine (iP) and/or cis-zeatin (cZ). The one or more aromatic plant hormones can comprise an aromatic cytokinin. The one or more aromatic cytokinins can be selected from the group comprising N6-benzyladenine (BA), ortho-topolin (oT), and para-topolin (pT). The one or more lipid plant hormones can comprise a jasmonate (e.g., (−)-jasmonic acid (JA) and/or (−)-jasmonic acid methyl ester). The gibberellin can be selected from the group comprising gibberellic acid (GA) 1, GA2, GA3, GA4, GA5, GA6, GA7, GA8, GA9, GA10, GA11, GA12, GA13, GA14, GA15, GA16, GA17, GA18, GA19, GA20, GA21, GA22, GA23, GA24, GA25, GA26, GA27, GA28, GA29, GA30, GA31, GA32, GA33, GA34, GA35, GA36, GA37, GA38, GA39, GA40, GA41, GA42, GA43, GA44, GA45, GA46, GA47, GA48, GA49, GA50, GA51, GA52, GA53, GA54, GA55, GA56, GA57, GA58, GA59, GA60, GA61, GA62, GA63, GA64, GA65, GA66, GA67, GA68, GA69, GA70, GA71, GA72, GA73, GA74, GA75, GA76, GA77, GA78, GA79, GA80, GA81, GA82, GA83, GA84, GA85, GA86, GA87, GA88, GA89, GA90, GA91, GA92, GA93, GA94, GA95, GA96, GA97, GA98, GA99, GA100, GA101, GA102, GA103, GA104, GA105, GA106, GA107, GA108, GA109, GA110, GA111, GA112, GA113, GA114, GA115, GA116, GA117, GA118, GA119, GA120, GA121, GA122, GA123, GA124, GA125, GA126, GA127, GA128, GA129, GA130, GA131, GA132, GA133, GA134, GA135, GA136, derivatives thereof, or any combination thereof. The cytokinin can be selected from the group comprising zeatin, zeatin, N6-benzyl adenine, N6-(delta-2-isopentyl) adenine, 1,3-diphenyl urea, thidiazuron, CPPU (forchlorfenuron), kinetin, derivatives thereof, or any combination thereof.

Target Proteins & Payload Proteins

The concentration, localization, stability, and/or activity of one or more payloads can be under control of the orthogonal signal (e.g., via regulation through an AID-tagged protein). The nucleic acid composition can comprise: an eighth polynucleotide encoding one or more payloads. The target protein can be capable of modulating the concentration, localization, stability, and/or activity of the one or more payloads.

The target protein can be capable of repressing the transcription of the one or more payloads. A payload transcript can be capable of being translated to generate a payload protein, and the target protein can be capable of reducing the concentration, localization, stability, and/or activity of the payload protein. The concentration, localization, stability, and/or activity of the payload protein can be inversely related to the concentration, localization, stability, and/or activity of the target protein. The target protein can comprise a protease. The payload protein can comprise a degron and a cut site the protease can be capable of cutting to expose the degron, and wherein the degron of the payload protein being exposed changes the payload protein to a payload protein destabilized state. The protease can comprise tobacco etch virus (TEV) protease, tobacco vein mottling virus (TVMV) protease, hepatitis C virus protease (HCVP), derivatives thereof, or any combination thereof. The payload protein can comprise a cage polypeptide. In some embodiments, the cage polypeptide comprises: (a) a helical bundle, comprising between 2 and 7 alpha-helices, wherein the helical bundle comprises: (i) a structural region; and (ii) a latch region, wherein the latch region comprises a degron located within the latch region, wherein the structural region interacts with the latch region to prevent activity of the degron; and (b) amino acid linkers connecting each alpha helix. The target protein can comprise a key polypeptide capable of binding to the cage polypeptide structural region, thereby displacing the latch region and activating the degron.

The payload protein and/or target protein can comprise a synthetic protein circuit component. In some embodiments, the payload comprises a bispecific T cell engager (BiTE). In some embodiments, the orthogonal signal triggers cellular differentiation. The payload protein can comprise fluorescence activity, polymerase activity, protease activity, phosphatase activity, kinase activity, SUMOylating activity, deSUMOylating activity, ribosylation activity, deribosylation activity, myristoylation activity demyristoylation activity, or any combination thereof. The payload protein can comprise nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, adenylation activity, deadenylation activity, or any combination thereof. The payload protein can comprise a CRE recombinase, GCaMP, a cell therapy component, a knock-down gene therapy component, a cell-surface exposed epitope, or any combination thereof. The payload protein can comprise a diagnostic agent (e.g., green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, mruby3, rsCherry, rsCherryRev, derivatives thereof, or any combination thereof).

In some embodiments, the target protein and/or payload protein can diminish immune cell function. The target protein and/or payload protein can be an activity regulator. The activity regulator can be capable of reducing T cell activity. The activity regulator can comprise a ubiquitin ligase involved in TCR/CAR signal transduction selected from the group comprising c-CBL, CBL-B, ITCH, R F125, R F128, WWP2, or any combination thereof. The activity regulator can comprise a negative regulatory enzyme selected from the group comprising SHP1, SHP2, SHTP1, SHTP2, CD45, CSK, CD148, PTPN22, DGKalpha, DGKzeta, DRAK2, HPK1, HPK1, STS1, STS2, SLAT, or any combination thereof. The activity regulator can be a negative regulatory scaffold/adapter protein selected from the group comprising PAG, LIME, NTAL, LAX31, SIT, GAB2, GRAP, ALX, SLAP, SLAP2, DOK1, DOK2, or any combination thereof. The activity regulator can be a dominant negative version of an activating TCR signaling component selected from the group comprising ZAP70, LCK, FYN, NCK, VAV1, SLP76, ITK, ADAP, GADS, PLCgammal, LAT, p85, SOS, GRB2, NFAT, p50, p65, API, RAP1, CRKII, C3G, WAVE2, ARP2/3, ABL, ADAP, RIAM, SKAP55, or any combination thereof. The activity regulator can comprise the cytoplasmic tail of a negative co-regulatory receptor selected from the group comprising CD5, PD1, CTLA4, BTLA, LAG3, B7-H1, B7-1, CD160, TFM3, 2B4, TIGIT, or any combination thereof. The activity regulator can be targeted to the plasma membrane with a targeting sequence derived from LAT, PAG, LCK, FYN, LAX, CD2, CD3, CD4, CD5, CD7, CD8a, PD1, SRC, LYN, or any combination thereof. In some embodiments, the activity regulator reduces or abrogates a pathway and/or a function selected from the group comprising Ras signaling, PKC signaling, calcium-dependent signaling, NF-kappaB signaling, NFAT signaling, cytokine secretion, T cell survival, T cell proliferation, CTL activity, degranulation, tumor cell killing, differentiation, or any combination thereof.

The payload protein and/or target protein can comprise a factor locally down-regulating the activity of endogenous immune cells. In some embodiments, the target protein and/or payload protein comprises a prodrug-converting enzyme (e.g., HSV thymidine kinase (TK), Cytosine Deaminase (CD), Purine nucleoside phosphorylase (PNP), Cytochrome p450 enzymes (CYP), Carboxypeptidases (CP), Caspase-9, Carboxylesterase (CE), Nitroreductase (NTR), Horse radish peroxidase (HRP), Guanine Ribosyltransferase (XGRTP), Glycosidase enzymes, Methionine-α,γ-lyase (MET), Thymidine phosphorylase (TP)).

In some embodiments, the payload gene encodes a payload RNA agent. A payload RNA agent can comprise one or more of dsRNA, siRNA, shRNA, pre-miRNA, pri-miRNA, miRNA, stRNA, lncRNA, piRNA, and snoRNA. In some embodiments, the payload gene encodes a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof.

The payload protein and/or target protein can comprise a cytokine. The cytokine can be selected from the group consisting of interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, granulocyte macrophage colony stimulating factor (GM-CSF), M-CSF, SCF, TSLP, oncostatin M, leukemia-inhibitory factor (LIF), CNTF, Cardiotropin-1, NNT-1/BSF-3, growth hormone, Prolactin, Erythropoietin, Thrombopoietin, Leptin, G-CSF, or receptor or ligand thereof.

The payload protein and/or target protein can comprise a member of the TGF-β/BMP family selected from the group consisting of TGF-β1, TGF-β2, TGF-β3, BMP-2, BMP-3a, BMP-3b, BMP-4, BMP-5, BMP-6, BMP-7, BMP-8a, BMP-8b, BMP-9, BMP-10, BMP-11, BMP-15, BMP-16, endometrial bleeding associated factor (EBAF), growth differentiation factor-1 (GDF-1), GDF-2, GDF-3, GDF-5, GDF-6, GDF-7, GDF-8, GDF-9, GDF-12, GDF-14, mullerian inhibiting substance (MIS), activin-1, activin-2, activin-3, activin-4, and activin-5. The payload protein and/or target protein can comprise a member of the TNF family of cytokines selected from the group consisting of TNF-alpha, TNF-beta, LT-beta, CD40 ligand, Fas ligand, CD 27 ligand, CD 30 ligand, and 4-1 BBL. The payload protein and/or target protein can comprise a member of the immunoglobulin superfamily of cytokines selected from the group consisting of B7.1 (CD80) and B7.2 (B70). The payload protein and/or target protein can comprise an interferon. The interferon can be selected from interferon alpha, interferon beta, or interferon gamma. The payload protein and/or target protein can comprise a chemokine. The chemokine can be selected from CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13, or CXCL15. The payload protein and/or target protein can comprise a interleukin. The interleukin can be selected from IL-10 IL-12, IL-1, IL-6, IL-7, IL-15, IL-2, IL-18 or IL-21. The payload protein and/or target protein can comprise a tumor necrosis factor (TNF). The TNF can be selected from TNF-alpha, TNF-beta, TNF-gamma, CD252, CD154, CD178, CD70, CD153, or 4-1BBL.

The payload protein and/or target protein can comprise a CRE recombinase, GCaMP, a cell therapy component, a knock-down gene therapy component, a cell-surface exposed epitope, or any combination thereof. The payload protein and/or target protein can comprise a chimeric antigen receptor.

The payload protein and/or target protein can comprise a programmable nuclease. In some embodiments, the programmable nuclease is selected from the group comprising: SpCas9 or a derivative thereof; VRER, VQR, EQR SpCas9; xCas9-3.7; eSpCas9; Cas9-HF1; HypaCas9; evoCas9; HiFi Cas9; ScCas9; StCas9; NmCas9; SaCas9; CjCas9; CasX; Cas9 H940A nickase; Cas12 and derivatives thereof; dcas9-APOBEC1 fusion, BE3, and dcas9-deaminase fusions; dcas9-Krab, dCas9-VP64, dCas9-Tet1, and dcas9-transcriptional regulator fusions; Dcas9-fluorescent protein fusions; Cas13-fluorescent protein fusions; RCas9-fluorescent protein fusions; Cas13-adenosine deaminase fusions. The programmable nuclease can comprise a zinc finger nuclease (ZFN) and/or transcription activator-like effector nuclease (TALEN). The programmable nuclease can comprise *Streptococcus pyogenes* Cas9 (SpCas9), *Staphylococcus aureus* Cas9 (SaCas9), a zinc finger nuclease, TAL effector nuclease, meganuclease, MegaTAL, Tev-m TALEN, MegaTev, homing endonuclease, Cas1, Cas1B, Cas2, Cas3, Cas4, Cas5, Cash, Cas7, Cas8, Cas9, Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb 1, Csb2, Csb3, Csx17, Csx14, Csx10, Csx16, CsaX, Csx3, Csx1, Csx15, Csf1, Csf2, Csf3, Csf4, Cpf1, C2c1, C2c3, Cas12a, Cas12b, Cas12c, Cas12d, Cas12e, Cas13a, Cas13b, Cas13c, derivatives thereof, or any combination thereof. The nucleic acid composition can comprise a polynucleotide encoding (i) a targeting molecule and/or (ii) a donor nucleic acid. The targeting molecule can be capable of associating with the programmable nuclease. The targeting molecule can comprise single strand DNA or single strand RNA. The targeting molecule can comprise a single guide RNA (sgRNA).

In some embodiments, the payload protein and/or target protein is a therapeutic protein or variant thereof. Non-limiting examples of therapeutic proteins include blood factors, such as β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-a), transforming growth factor beta (TGF-β), and the like; soluble receptors, such as soluble TNF-receptors, soluble VEGF receptors, soluble interleukin receptors (e.g., soluble IL-1 receptors and soluble type II IL-1 receptors), soluble γ/δ T cell receptors, ligand-binding fragments of a soluble receptor, and the like; enzymes, such as -glucosidase, imiglucarase, β-glucocerebrosidase, and alglucerase; enzyme activators, such as tissue plasminogen activator; chemokines, such as IP-10, monokine induced by interferon-gamma (Mig), Gro/IL-8, RANTES, MIP-1, MIP-I β, MCP-1, PF-4, and the like; angiogenic agents, such as vascular endothelial growth factors (VEGFs, e.g., VEGF121, VEGF165, VEGF-C, VEGF-2), transforming growth factor-beta, basic fibroblast growth factor, glioma-derived growth factor, angiogenin, angiogenin-2; and the like; anti-angiogenic agents, such as a soluble VEGF receptor; protein vaccine; neuroactive peptides, such as nerve growth factor (NGF), bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopressin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitrypsin; leukemia inhibitory factor (LIF); transforming growth factors (TGFs); tissue factors, luteinizing hormone; macrophage activating factors; tumor necrosis factor (TNF); neutrophil chemotactic factor (NCF); nerve growth factor; tissue inhibitors of metalloproteinases; vasoactive intestinal peptide; angiogenin; angiotropin; fibrin; hirudin; IL-1 receptor antagonists; and the like. Some other non-limiting examples of payload protein and/or target protein include ciliary neurotrophic factor (CNTF); brain-derived neurotrophic factor (BDNF); neurotrophins 3 and 4/5 (NT-3 and 4/5); glial cell derived neurotrophic factor (GDNF); aromatic amino acid decarboxylase (AADC); hemophilia related clotting proteins, such as Factor VIII, Factor IX, Factor X; dystrophin or mini-dystrophin; lysosomal acid lipase; phenylalanine hydroxylase (PAH); glycogen storage disease-related enzymes, such as glucose-6-phosphatase, acid maltase, glycogen debranching enzyme, muscle glycogen phosphorylase, liver glycogen phosphorylase, muscle phosphofructokinase, phosphorylase kinase (e.g., PHKA2), glucose transporter (e.g., GLUT2), aldolase A, β-enolase, and glycogen synthase; lysosomal enzymes (e.g., beta-N-acetylhexosaminidase A); and any variants thereof.

In some embodiments, the payload protein and/or target protein is an active fragment of a protein, such as any of the aforementioned proteins. In some embodiments, the payload protein and/or target protein is a fusion protein comprising some or all of two or more proteins. In some embodiments a fusion protein can comprise all or a portion of any of the aforementioned proteins.

In some embodiments, the payload protein and/or target protein is a multi-subunit protein. For examples, the payload protein and/or target protein can comprise two or more subunits, or two or more independent polypeptide chains. In some embodiments, the payload protein and/or target protein can be an antibody. Examples of antibodies include, but are not limited to, antibodies of various isotypes (for example, IgG1, IgG2, IgG3, IgG4, IgA, IgD, IgE, and IgM); monoclonal antibodies produced by any means known to those skilled in the art, including an antigen-binding fragment of a monoclonal antibody; humanized antibodies; chimeric antibodies; single-chain antibodies; antibody fragments such as Fv, F(ab')2, Fab', Fab, Facb, scFv and the like; provided that the antibody is capable of binding to antigen. In some embodiments, the antibody is a full-length antibody.

In some embodiments, the payload protein and/or target protein is a pro-survival protein (e.g., Bcl-2, Bcl-XL, Mcl-1 and A1). In some embodiments, the payload gene encodes a apoptotic factor or apoptosis-related protein such as, for example, AIF, Apaf (e.g., Apaf-1, Apaf-2, and Apaf-3), oder APO-2 (L), APO-3 (L), Apopain, Bad, Bak, Bax, Bcl-2, Bcl-$x_L$, Bcl-$x_S$, bik, CAD, Calpain, Caspase (e.g., Caspase-1, Caspase-2, Caspase-3, Caspase-4, Caspase-5, Caspase-6, Caspase-7, Caspase-8, Caspase-9, Caspase-10, and Caspase-11), ced-3, ced-9, c-Jun, c-Myc, crm A, cytochrom C, CdR1, DcR1, DD, DED, DISC, DNA-PKcs, DR3, DR4, DR5, FADD/MORT-1, FAK, Fas (Fas-ligand CD95/fas (receptor)), FLICE/MACH, FLIP, fodrin, fos, G-Actin, Gas-2, gelsolin, granzyme A/B, ICAD, ICE, JNK, Lamin A/B, MAP, MCL-1, Mdm-2, MEKK-1, MORT-1, NEDD, NF-$_{kappa}$B, NuMa, p53, PAK-2, PARP, perforin, PITSLRE, PKCdelta, pRb, presenilin, prICE, RAIDD, Ras, RIP, sphingomyelinase, thymidinkinase from herpes simplex, TRADD, TRAF2, TRAIL-R1, TRAIL-R2, TRAIL-R3, and/or transglutaminase.

In some embodiments, the payload protein and/or target protein is a cellular reprogramming factor capable of converting an at least partially differentiated cell to a less differentiated cell, such as, for example, Oct-3, Oct-4, Sox2, c-Myc, Klf4, Nanog, Lin28, ASCL1, MYT1 L, TBX3b, SV40 large T, hTERT, miR-291, miR-294, miR-295, or any combinations thereof. In some embodiments, the payload protein and/or target protein is a programming factor that is capable of differentiating a given cell into a desired differentiated state, such as, for example, nerve growth factor (NGF), fibroblast growth factor (FGF), interleukin-6 (IL-6), bone morphogenic protein (BMP), neurogenin3 (Ngn3), pancreatic and duodenal homeobox 1 (Pdx1), Mafa, or any combination thereof.

In some embodiments, the payload protein and/or target protein is a human adjuvant protein capable of eliciting an innate immune response, such as, for example, cytokines which induce or enhance an innate immune response, including IL-2, IL-12, IL-15, IL-18, IL-21CCL21, GM-CSF and TNF-alpha; cytokines which are released from macrophages, including IL-1, IL-6, IL-8, IL-12 and TNF-alpha; from components of the complement system including Clq, MBL, Clr, Cls, C2b, Bb, D, MASP-1, MASP-2, C4b, C3b, C5a, C3a, C4a, C5b, C6, C7, C8, C9, CR1, CR2, CR3, CR4, C1qR, C1INH, C4 bp, MCP, DAF, H, I, P and CD59; from proteins which are components of the signaling networks of the pattern recognition receptors including TLR and IL-1 R1, whereas the components are ligands of the pattern recognition receptors including IL-1 alpha, IL-1 beta, Beta-defensin, heat shock proteins, such as HSP10, HSP60, HSP65, HSP70, HSP75 and HSP90, gp96, Fibrinogen, Typ111 repeat extra domain A of fibronectin; the receptors, including IL-1 RI, TLR1, TLR2, TLR3, TLR4, TLR5, TLR6, TLR7, TLR8, TLR9, TLR10, TLR11; the signal transducers including components of the Small-GTPases signaling (RhoA, Ras, Racl, Cdc42 etc.), components of the PIP signaling (PI3K, Src-Kinases, etc.), components of the MyD88-dependent signaling (MyD88, IRAK1, IRAK2, etc.), components of the MyD88-independent signaling (TICAM1, TICAM2 etc.); activated transcription factors including e.g. NF-κB, c-Fos, c-Jun, c-Myc; and induced target genes including e.g. IL-1 alpha, IL-1 beta, Beta-Defensin, IL-6, IFN gamma, IFN alpha and IFN beta; from costimulatory molecules, including CD28 or CD40-ligand or PD1; protein domains, including LAMP; cell surface proteins; or human adjuvant proteins including CD80, CD81, CD86, trif, flt-3 ligand, thymopentin, Gp96 or fibronectin, etc., or any species homolog of any of the above human adjuvant proteins.

As described herein, the nucleotide sequence encoding the payload protein and/or target protein can be modified to improve expression efficiency of the protein. The methods that can be used to improve the transcription and/or translation of a gene herein are not particularly limited. For example, the nucleotide sequence can be modified to better reflect host codon usage to increase gene expression (e.g., protein production) in the host (e.g., a mammal).

The degree of payload protein and/or target protein expression in the cell can vary. The amount of the payload protein and/or target protein expressed in the subject (e.g., the serum of the subject) can vary. For example, in some embodiments the protein can be expressed in the serum of the subject in the amount of at least about 9 µg/ml, at least about 10 µg/ml, at least about 50 µg/ml, at least about 100 µg/ml, at least about 200 µg/ml, at least about 300 µg/ml, at least about 400 µg/ml, at least about 500 µg/ml, at least about 600 µg/ml, at least about 700 µg/ml, at least about 800 µg/ml, at least about 900 µg/ml, or at least about 1000 µg/ml. In some embodiments, the payload protein and/or target protein is expressed in the serum of the subject in the amount of about 9 µg/ml, about 10 µg/ml, about 50 µg/ml, about 100 µg/ml, about 200 µg/ml, about 300 µg/ml, about 400 µg/ml, about 500 µg/ml, about 600 µg/ml, about 700 µg/ml, about 800 µg/ml, about 900 µg/ml, about 1000 µg/ml, about 1500 µg/ml, about 2000 µg/ml, about 2500 µg/ml, or a range between any two of these values. A skilled artisan will understand that the expression level in which a payload protein and/or target protein is needed for the method to be effective can vary depending on non-limiting factors such as the particular payload protein and/or target protein and the subject receiving the treatment, and an effective amount of the protein can be readily determined by a skilled artisan using conventional methods known in the art without undue experimentation.

A payload protein and/or target protein encoded by a payload gene can be of various lengths. For example, the payload protein and/or target protein can be at least about 200 amino acids, at least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer in length. In some embodiments, the payload protein and/or target protein is at least about 480 amino acids in length. In some embodiments, the payload protein and/or target protein is at least about 500 amino acids in length. In some embodiments, the payload protein and/or target protein is about 750 amino acids in length.

The payload genes can have different lengths in different implementations. The number of payload genes can be different in different embodiments. In some embodiments, the number of payload genes in a nucleic acid composition can be, or can be about, 1, 2, 3, 4, 5, 6, 7, 8, 9, 10, 11, 12, 13, 14, 15, 16, 17, 18, 19, 20, 21, 22, 23, 24, 25, or a number or a range between any two of these values. In some embodiments, the number of payload genes in a nucleic acid composition can be at least, or can be at most, 1, 2, 3, 4, 5, 6, 7, 8, 9, 10, 11, 12, 13, 14, 15, 16, 17, 18, 19, 20, 21, 22, 23, 24, 25. In some embodiments, a payload genes is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3250, 3500, 3750, 4000, 4250, 4500, 4750, 5000, 5500, 6000, 6500, 7000, 7500, 8000, 8500, 9000, 9500, 10000, or a number or a range between any two of these values, nucleotides in length. In some embodiments, a payload gene is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3250, 3500, 3750, 4000, 4250, 4500, 4750, 5000, 5500, 6000, 6500, 7000, 7500, 8000, 8500, 9000, 9500, or 10000 nucleotides in length.

The payload can be an inducer of cell death. The payload can be induce cell death by a non-endogenous cell death pathway (e.g., a bacterial pore-forming toxin). In some embodiments, the payload can be a pro-survival protein. In some embodiments, the payload is a modulator of the immune system. The payload protein can comprise a CRE recombinase, GCaMP, a cell therapy component, a knock-down gene therapy component, a cell-surface exposed epitope, or any combination thereof.

Chimeric Antigen Receptors and Engineered T Cell Receptors

The payload protein(s) and/or target protein(s) can comprise a chimeric antigen receptor (CAR) or T-cell receptor (TCR). In some embodiments, the CAR comprises a T-cell receptor (TCR) antigen binding domain. The term "Chimeric Antigen Receptor" or alternatively a "CAR" refers to a set of polypeptides, typically two in the simplest embodiments, which when in an immune effector cell, provides the cell with specificity for a target cell, typically a cancer cell, and with intracellular signal generation. The terms "CAR" and "CAR molecule" are used interchangeably. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined below. In some embodiments, the set of polypeptides are in the same polypeptide chain (e.g., comprise a chimeric fusion protein). In some aspects, the set of polypeptides are contiguous with each other. In some embodiments, the set of polypeptides are not contiguous with each other, e.g., are in different polypeptide chains. In some embodiments, the set of polypeptides include a dimerization switch that, upon the presence of a dimerization molecule, can couple the polypeptides to one another, e.g., can couple an antigen binding domain to an intracellular signaling domain. In one aspect, the stimulatory molecule is the zeta chain associated with the T cell receptor complex. In one aspect, the cytoplasmic signaling domain further comprises one or more functional signaling domains derived from at least one costimulatory molecule as defined below. In some embodiments, the costimulatory molecule is chosen from the costimulatory molecules described herein, e.g., 4-1BB (i.e., CD137), CD27 and/or CD28. In some embodiments, the CAR comprises a chimeric fusion protein comprising an extracellular antigen binding domain, a transmembrane domain and an intracellular signaling domain comprising a functional signaling domain derived from a stimulatory molecule. In some embodiments, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule. In some embodiments, the CAR comprises a chimeric fusion protein comprising an extracellular antigen binding domain, a transmembrane domain and an intracellular signaling domain comprising two functional signaling domains derived from one or more costimulatory molecule(s) and a functional signaling domain derived from a stimulatory molecule. In some embodiments, the CAR comprises a chimeric fusion protein comprising an extracellular antigen binding domain, a transmembrane domain and an intracellular signaling domain comprising at least two functional signaling domains derived from one or more costimulatory molecule(s) and a functional signaling domain derived from a stimulatory molecule. In some embodiments the CAR comprises an optional leader sequence at the amino-terminus (N-ter) of the CAR fusion protein. In some embodiments, the CAR further comprises a leader sequence at the N-terminus of the extracellular antigen binding domain, wherein the leader sequence is optionally cleaved from the antigen binding domain (e.g., a scFv) during cellular processing and localization of the CAR to the cellular membrane.

The CAR and/or TCR can comprise one or more of an antigen binding domain, a transmembrane domain, and an intracellular signaling domain. The CAR or TCR further can comprise a leader peptide. The TCR further can comprise a constant region and/or CDR4. The term "signaling domain" refers to the functional portion of a protein which acts by transmitting information within the cell to regulate cellular activity via defined signaling pathways by generating second messengers or functioning as effectors by responding to such messengers. An "intracellular signaling domain," as the term is used herein, refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines. In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule. A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12.

The intracellular signaling domain can comprise a primary signaling domain, a costimulatory domain, or both of a primary signaling domain and a costimulatory domain.

The cytoplasmic domain or region of the CAR includes an intracellular signaling domain. An intracellular signaling domain is generally responsible for activation of at least one of the normal effector functions of the immune cell in which the CAR has been introduced. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

The term "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are contribute to an efficient immune response. Costimulatory molecules include, but are not limited to an MHC class I molecule, BTLA and a Toll ligand receptor, as well as OX40, CD27, CD28, CD5, ICAM-1, LFA-1 (CD11a/CD18), ICOS (CD278), and 4-1BB (CD137). Further examples of such costimulatory molecules include CD5, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. The intracellular signaling domain can comprise the entire intracellular portion, or the entire native intracellular signaling domain, of the molecule from which it is derived, or a functional fragment or derivative thereof.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability. It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain). A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs. The primary signaling domain can comprise a functional signaling domain of one or more proteins selected from the group consisting of CD3 zeta, CD3 gamma, CD3 delta, CD3 epsilon, common FcR gamma (FCER1G), FcR beta (Fc Epsilon Rib), CD79a, CD79b, Fcgamma RIIa, DAP10, and DAP12, or a functional variant thereof.

In some embodiments, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue. The costimulatory domain can comprise a functional domain of one or more proteins selected from the group consisting of CD27, CD28, 4-1BB (CD137), OX40, CD28-OX40, CD28-4-1BB, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB 1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D, or a functional variant thereof.

The portion of the CAR comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody, or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In some embodiments, the antigen binding domain of a CAR composition of the invention comprises an antibody fragment. In a further aspect, the CAR comprises an antibody fragment that comprises a scFv.

In some embodiments, the CAR of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen binding domain in a CAR of the invention include those associated with viral, bacterial and parasitic infections, autoimmune disease and cancer cells.

In some embodiments, the CAR-mediated T-cell response can be directed to an antigen of interest by way of engineering an antigen binding domain that specifically binds a desired antigen into the CAR. In some embodiments, the portion of the CAR comprising the antigen binding domain comprises an antigen binding domain that targets a tumor antigen, e.g., a tumor antigen described herein. The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, a T cell receptor (TCR), or a fragment there of, e.g., single chain TCR, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment. In some embodiments, the antigen binding domain comprises a humanized antibody or an antibody fragment. In some aspects, a non-human antibody is humanized, where specific sequences or regions of the antibody are modified to increase similarity to an antibody naturally produced in a human or fragment thereof. In some embodiments, the antigen binding domain is humanized.

The antigen binding domain can comprise an antibody, an antibody fragment, an scFv, a Fv, a Fab, a (Fab')2, a single domain antibody (SDAB), a VH or VL domain, a camelid VHH domain, a Fab, a Fab', a F(ab')2, a Fv, a scFv, a dsFv, a diabody, a triabody, a tetrabody, a multispecific antibody formed from antibody fragments, a single-domain antibody (sdAb), a single chain comprising cantiomplementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof.

In some embodiments, the antigen binding domain is a T cell receptor ("TCR"), or a fragment thereof, for example, a single chain TCR (scTCR). Methods to make such TCRs are known in the art. See, e.g., Willemsen R A et al, Gene Therapy 7: 1369-1377 (2000); Zhang T et al, Cancer Gene Ther 11: 487-496 (2004); Aggen et al, Gene Ther. 19(4): 365-74 (2012) (references are incorporated herein by its entirety). For example, scTCR can be engineered that contains the Vα and Vβ genes from a T cell clone linked by a linker (e.g., a flexible peptide). This approach is very useful to cancer associated target that itself is intracellar, however, a fragment of such antigen (peptide) is presented on the surface of the cancer cells by MHC.

In some embodiments, the antigen binding domain is a multispecific antibody molecule. In some embodiments, the multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

The antigen binding domain can be configured to bind to a tumor antigen. The terms "cancer associated antigen" or "tumor antigen" interchangeably refers to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, a tumor antigen is a marker expressed by both normal cells and cancer cells, e.g., a lineage marker, e.g., CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the CARs of the present invention includes CARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on CD8+T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Blood, 2011 117(16): 4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

The tumor antigen can be a solid tumor antigen. The tumor antigen can be selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8) aNeu5Ac(2-3)bDGalp(1-4)bDG1cp(1-1)Cer); TNF receptor family member B cell maturation (BCMA); Tn antigen ((Tn Ag) or (GalNAca-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Ab1) (bcr-ab1); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDG1cp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; survivin; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

The tumor antigen can be selected from the group comprising CD150, 5T4, ActRIIA, B7, BMCA, CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, GD2, GD3, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NY-ESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-1, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D1), ephrinB2, epithelial tumor antigen, estrogen receptor, fetal acethycholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, β2-Microglobulin, Fc Receptor-like 5 (FcRL5), or molecules expressed by HIV, HCV, HBV, or other pathogens.

The antigen binding domain can be connected to the transmembrane domain by a hinge region. In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge (e.g., an IgG4 hinge, an IgD hinge), a GS linker (e.g., a GS linker described herein), a KIR2DS2 hinge or a CD8a hinge.

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In some embodiments, the transmembrane domain is one that is associated with one of the other domains of the CAR e.g., in one embodiment, the transmembrane domain may be from the same protein that the signaling domain, costimulatory domain or the hinge domain is derived from. In some embodiments, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins, e.g., to minimize interactions with other members of the receptor complex. In some embodiments, the transmembrane domain is capable of homodimerization with another CAR on the cell surface of a CAR-expressing cell. In a different aspect, the amino acid sequence of the transmembrane domain may be modified or substituted so as to minimize interactions with the binding domains of the native binding partner present in the same CAR-expressing cell.

The transmembrane domain can comprise a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7Ra, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C, or a functional variant thereof. The transmembrane domain may be derived either from a natural or from a recombinant source. Where the source is natural, the domain may be derived from any membrane-bound or transmembrane protein. In some embodiments the transmembrane domain is capable of signaling to the intracellular domain(s) whenever the CAR has bound to a target.

Pro-Growth Proteins and Pro-Death Proteins

The pro-growth protein can be essential for survival and/or cell cycle progression (e.g., a cell-cycle regulator). The pro-growth protein can be essential for survival and/or cell cycle progression in the presence of an exogenous agent. The exogenous agent can be an antibiotic. In some embodiments, the pro-growth protein provides antibiotic resistance. The pro-growth protein can comprise a cyclin-dependent kinase (CDK), cyclin, an aurora kinase, a cell division cycle (CDC) protein, or any combination thereof. The pro-growth protein can comprise lamin B1, lamin B2, NUP153, GAS41, ARC21, cytoplasmic dynein, the protein kinase cdk1, β-actin, and γ-actin, Cdk1, Cdk2, Cdk3, Cdk4, Cdk6, Cyclin A, Cyclin D, Cyclin D, Cyclin E, Cyclin B, or any combination thereof. The pro-growth protein can comprise FoxO1, HDAC, DP-1, E2F, ABL, AMPK, BRK, BRSK I, BRSK2, BTK, CAMKK1, CAMKK alpha, CAMKK beta, Rb, Suv39HI, SCF, p19INK4D, GSK-3, pi 8 INK4, myc, cyclin E, CDK2, CDK9, CDG4/6, Cycline D, p16 INK4A, cdc25A, BMI1, SCF, Akt, CHK1/2, C 1 delta, CK1 gamma, C 2, CLK2, CSK, DDR2, DYRK1A/2/3, EF2K, EPH-A2/A4/B1/B2/B3/B4, EIF2A3, Smad2, Smad3, Smad4, Smad7, p53, p21 Cip1, PAX, Fyn, CAS, C3G, SOS, Tal, Raptor, RACK-1, CRK, Rap1, Rac, KRas, NRas, HRas, GRB2, FAK, PI3K, spred, Spry, mTOR, MPK, LKB1, PAK 1/2/4/5/6, PDGFRA, PYK2, Src, SRPK1, PLC, PKC, PKA, PKB alpha/beta, PKC alpha/gamma/zeta, PKD, PLK1, PRAK, PRK2, RIPK2, WAVE-2, TSC2, DAPK1, BAD, IMP, C-TAK1, TAK1, TAO1, TBK1, TESK1, TGFBR1, TIE2, TLK1, TrkA, TSSK1, TTBK1/2, TTK, Tp12/cotl, MEK1, MEK2, PLDL Erk1, Erk2, Erk5, Erk8, p9ORSK, PEA-15, SRF, p27 KIP1, TIF 1a, HMGN1, ER81, MKP-3, c-Fos, FGF-R1, GCK, GSK3 beta, HER4, HIPK1/2/3/, IGF-1R, cdc25, UBF, LAMTOR2, Stat1, StaO,CREB, JAK, Src, PTEN, NF-kappaB, HECTH9, Bax, HSP70, HSP90, Apaf-1, Cyto c, BCL-2, Bc1-xL, Smac, XIAP, Caspase-9, Caspase-3, Caspase-6, Caspase-7, CDC37, TAB, IKK, TRADD, TRAF2, R1P1, FLIP, TAK1, JNK1/2/3, Lck, A-Raf, B-Raf, C-Raf, MOS, MLK1/3, MN 1/2, MSK1, MST2/3/4, MPSK1, MEKK1, ME K4, MEL, ASK1, MINK1, MKK 1/2/3/4/6/7, NE 2a/6/7, NUAK1, OSR1, SAP, STK33, Syk, Lyn, PDK1, PHK, PIM 1/2/3, Ataxin-1, mTORC1, MDM2, p21 Waf1, Cyclin Dl, Lamin A, Tp12, Myc, catenin, Wnt, IKK-beta, IKK-gamma, IKK-alpha, IKK-epsilon, ELK, p65RelA, IRAKI, IRA 2, IRAK4, IRR, FADD, TRAF6, TRAF3, MKK3, MKK6, ROCK2, RSK1/2, SGK 1, SmMLCK, SIK2/3, ULK1/2, VEGFR1, WNK 1, YES1, ZAP70, MAP4K3, MAP4K5, MAPK1b, MAPKAP-K2 K3, p38 alpha/beta/delta/gamma MAPK, Aurora A, Aurora B, Aurora C, MCAK, Clip, MAPKAPK, FAK, MARK 1/2/3/4, Mud, SHC, CXCR4, Gap-1, Myc, beta-catenin/TCF, Cb1, BRM, Mcl1, BRD2, BRD3, BRD4, AR, RAS, ErbB3, EGFR, IRE1, HPK1, RIPK2, Era, or any combination thereof.

The pro-death protein can be capable of halting cell growth and/or inducing cell death. The pro-death protein can comprise cytosine deaminase, thymidine kinase, Bax, Bid, Bad, Bak, BCL2L11, p53, PUMA, Diablo/SMAC, S-TRAIL, Cas9, Cas9n, hSpCas9, hSpCas9n, HSVtk, cholera toxin, diphtheria toxin, alpha toxin, anthrax toxin, exotoxin, pertussis toxin, Shiga toxin, shiga-like toxin Fas, TNF, caspase 2, caspase 3, caspase 6, caspase 7, caspase 8, caspase 9, caspase 10, caspase 11, caspase 12, purine nucleoside phosphorylase, or any combination thereof. The pro-death protein can be capable of halting cell growth and/or inducing cell death in the presence of a pro-death agent.

Suicide Genes and Prodrugs

The exogenous agent and/or pro-death agent can be a prodrug. The target protein(s), payload protein(s), pro-growth protein, and/or pro-death protein can be the product of a suicide gene. Any suitable suicide gene and prodrug is contemplated this disclosure, such as, for example, the suicide gene/prodrug combinations depicted in Table 1.

TABLE 1

SUICIDE GENES AND PRODRUGS

| Suicide Gene | Prodrug(s) |
| --- | --- |
| HSV thymidine kinase (TK) | Ganciclovir (GCV); Ganciclovir elaidic acid ester; Penciclovir (PCV); Acyclovir (ACV); Valacyclovir (VCV); (E)-5-(2-bromovinyl)-2'-deoxyuridine (BVDU); Zidovuline (AZT); 2'-exo-methanocarbathymidine (MCT) |
| Cytosine Deaminase (CD) | 5-fluorocytosine (5-FC) |
| Purine nucleoside phosphorylase (PNP) | 6-methylpurine deoxyriboside (MEP); fludarabine (FAMP) |
| Cytochrome p450 enzymes (CYP) | Cyclophosphamide (CPA); Ifosfamide (IFO); 4-ipomeanol (4-IM) |
| Carboxypeptidases (CP) | 4-[(2-chloroethyl)(2-mesyloxyethyl)amino]benzoyl-L-glutamic acid (CMDA); Hydroxy-and amino-aniline mustards; Anthracycline glutamates; Methotrexate α-peptides (MTX-Phe) |
| Caspase-9 | AP1903 |
| Carboxylesterase (CE) | Irinotecan (IRT); Anthracycline acetals |
| Nitroreductase (NTR) | dinitroaziridinylbenzamide CB1954; dinitrobenzamide mustard SN23862; 4-Nitrobenzyl carbamates; Quinones |
| Horse radish peroxidase (HRP) | Indole-3-acetic acid (IAA); 5-Fluoroindole-3-acetic acid (FIAA) |
| Guanine Ribosyltransferase (XGRTP) | 6-Thioxanthine (6-TX) |
| Glycosidase enzymes | HM1826; Anthracycline acetals |
| Methionine-α,γ-lyase (MET) | Selenomethionine (SeMET) |
| Thymidine phosphorylase (TP) | 5'-Deoxy-5-fluorouridine (5'-DFU) |

Cell Populations

Disclosed herein include populations of cells. In some embodiments, the population of cells comprises: one or more sender cells comprising one or more of the nucleic acid compositions (e.g., circuits) provided herein; one or more receiver cells comprising one or more of the nucleic acid compositions (e.g., circuits) provided herein; and/or one or more sender-receiver cells comprising one or more of the nucleic acid compositions (e.g., circuits) provided herein.

Disclosed herein include populations of cells. In some embodiments, the population of cells comprises: a first cell type comprising one or more of the nucleic acid compositions (e.g., circuits) provided herein; and a second cell type comprising one or more of the nucleic acid compositions (e.g., circuits) provided herein, wherein the first cell type and second cell type are sender-receiver cells configured to grow in the presence of both cell types.

One or more cells of the population of cells can be capable of actively sensing, responding to, and/or controlling the cell population size and/or density. The sender cells and/or the sender-receiver cells can be configured to secrete the orthogonal signal at a constant rate. The sender cells and/or the sender-receiver cells can be configured to secrete the orthogonal signal in response to an intracellular state and/or extracellular environment. The orthogonal signal can be capable of stimulating and inhibiting net cell growth of the population of cells at different concentrations of the orthogonal signal. In some embodiments, sender-receiver cells can be capable of simultaneous production and perception of the orthogonal signal. The sender cells and/or the sender-receiver cells can be capable of secreting the orthogonal signal to generate a shared orthogonal signal pool. The shared orthogonal signal pool can be capable of being sensed by the receiver cells and/or the sender-receiver cells. Sender cells can be capable of secreting an orthogonal signal (e.g., auxin). Receiver cells can be capable of sensing the orthogonal signal. Sender-receiver cells can be capable of secreting an orthogonal signal as well as sensing the orthogonal signal. In some embodiments, sender cells and/or sender-receiver cells express a first synthase, a second synthase, and/or a transporter provided herein. In some embodiments, receiver cells and/or sender-receiver cells express a signal-binding protein, a first fusion protein, a second fusion protein, and/or third fusion protein provided herein.

In some embodiments, the orthogonal signal informs receiver cells about various types of 'information' concerning the senders (e.g., population size, location, cellular activity). The expression and/or activity of the first synthase, second synthase, and/or transporter can be configured to be responsive to changes in: cell localization; one or more signal transduction pathways regulating cell survival, cell growth, cell proliferation, cell adhesion, cell migration, cell metabolism, cell morphology, cell differentiation, apoptosis, or any combination thereof; and/or T cell activity (e.g., one or more of T cell simulation, T cell activation, cytokine secretion, T cell survival, T cell proliferation, CTL activity, T cell degranulation, and T cell differentiation). In some embodiments, a synthetic protein circuit component modulates the expression and/or activity of the first synthase, second synthase, and/or transporter. The expression and/or activity of the first synthase, second synthase, and/or transporter can be configured to be responsive to immune cell stimulation. Immune cell stimulation can comprise signal transduction induced by binding of a stimulatory molecule with its cognate ligand on the surface of an immune cell. The cognate ligand can be a CAR or a TCR. The first fusion protein, the second fusion protein, and/or the third fusion protein further can comprise a diagnostic agent (e.g., green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, mruby3, rsCherry, rsCherryRev, derivatives thereof, or any combination thereof).

In some embodiments, net growth of the population of cells occurs between a lower tuned orthogonal signal threshold and an upper tuned orthogonal signal threshold of a tuned orthogonal signal range. The lower tuned orthogonal signal threshold and/or the upper tuned orthogonal signal threshold of a tuned orthogonal signal range can be modulated by: adjusting the concentration of the first precursor molecule, the second precursor molecule, the exogenous agent, the pro-death agent, or any combination thereof; and/or adjusting the expression level of the signal-binding protein, the first fusion protein, the second fusion protein, the third fusion protein, the transporter, the first synthase, the second synthase, or any combination thereof. In some embodiments, the difference between the lower tuned orthogonal signal threshold and the upper tuned orthogonal signal threshold of the tuned orthogonal signal range is greater than about one order of magnitude. In some embodiments, the difference between the lower tuned orthogonal signal threshold and the upper tuned orthogonal signal threshold of the tuned orthogonal signal range is less than about one order of magnitude.

In some embodiments, one or more cells of the population of cells is configured to activate a therapeutic program in the presence of a critical orthogonal signal threshold (e.g., a local critical orthogonal signal threshold at a target site). The therapeutic program can comprise expression of one or more payloads (e.g., cytokines). For example, in some embodiments, (i) sender-receiver cells produce auxin constitutively and express an AID-tagged target protein that is capable of reducing the concentration, localization, stability, and/or activity of a cytokine payload, (ii) the shared pool of auxin that is collectively produced by the population of sender-receiver cells is sensed by each of the sender-receiver cells, (iii) at a critical orthogonal signal threshold, auxin concentrations are such that sufficient degradation of the target protein occurs and therapeutically effective levels of the cytokine payload are expressed.

One or more cells of the population of cells can be immune cells is configured to switch from an immune cell inactivated state to an immune cell activated state in the presence of a critical orthogonal signal threshold (e.g., a local critical orthogonal signal threshold at a target site). The sender cells and/or the sender-receiver cells can be detector cells capable of trafficking to a tumor site. The receiver cells and/or the sender-receiver cells can comprise a killer cell type.

One or more cells of the population of cells is configured to differentiate into one or more cell types in the presence of orthogonal signal threshold (e.g., a local critical orthogonal signal threshold at a target site).

One or more cells of the population of cells can be configured to differentiate into one or more cell types in the presence of a critical orthogonal signal threshold (e.g., a local critical orthogonal signal threshold at a target site).

In some embodiments, one or more cells of the population of cells is configured to switch cell states in the presence of orthogonal signal threshold (e.g., a local critical orthogonal signal threshold at a target site). For example, in some embodiments, (i) sender-receiver cells produce auxin constitutively and express an AID-tagged target protein that is capable of reducing the concentration, localization, stability, and/or activity of a cellular differentiation payload protein, (ii) the shared pool of auxin that is collectively produced by the population of sender-receiver cells is sensed by each of the sender-receiver cells, (iii) at a critical orthogonal signal threshold, auxin concentrations are such that sufficient degradation of the target protein occurs and the cellular differentiation payload protein can induce differentiation of the sender-receiver cells.

The population of cells can be configured such that steady state population size and/or density remains between a lower tuned threshold and an upper tuned threshold of a tuned cell population size and/or density range. In some embodiments, the population of cells remains within the tuned cell population size and/or density range for at least about 10 days, about 20 days, about 40 days, about 80 days, about 80 days, or about 100 days, of continuous culture and/or presence in a subject. In some embodiments, the population of cells oscillate between a lower tuned threshold and an upper tuned threshold of a tuned cell population size and/or density range. The lower tuned threshold and/or the upper tuned threshold of a tuned cell population size and/or density range can be modulated by: adjusting the concentration of the first precursor molecule, the second precursor molecule, the exogenous agent, the pro-death agent, or any combination thereof; and/or adjusting the expression level of the signal-binding protein, the first fusion protein, the second fusion protein, the third fusion protein, the transporter, the first synthase, the second synthase, or any combination thereof. The difference between the lower untuned threshold and the upper untuned threshold of the tuned cell population size and/or density range can be greater than about one order of magnitude. The difference between the lower tuned threshold and the upper tuned threshold of the tuned cell population size and/or density range can be less than about one order of magnitude.

One or more cells of the population of cells can be configured to activate a therapeutic program upon the cell population reaching a critical cell population size and/or density threshold. The therapeutic program can comprise expression of one or more payloads (e.g., cytokines). For example, in some embodiments, (i) sender-receiver cells produce auxin constitutively and express an AID-tagged target protein that is capable of reducing the concentration, localization, stability, and/or activity of a cytokine payload, (ii) the shared pool of auxin that is collectively produced by the population of sender-receiver cells is sensed by each of the sender-receiver cells, (iii) at a critical cell population size and/or density threshold, auxin concentrations are such that sufficient degradation of the target protein occurs and therapeutically effective levels of the cytokine payload are expressed.

One or more cells of the population of cells can be immune cells can be configured to switch from an immune cell inactivated state to an immune cell activated state upon the cell population reaching a critical cell population size and/or density threshold (e.g., a local critical cell population size and/or density threshold at a target site). The sender cells and/or the sender-receiver cells can be detector cells capable of trafficking to a tumor site. In some embodiments, receiver cells and/or the sender-receiver cells can comprise a killer cell type.

One or more cells of the population of cells can be configured to differentiate into one or more cell types upon the cell population reaching a critical cell population size and/or density threshold (e.g., a local critical cell population size and/or density threshold at a target site). One or more cells of the population of cells can be configured to differentiate into one or more cell types upon the cell population reaching a critical cell population size and/or density threshold (e.g., a local critical cell population size and/or density threshold at a target site). One or more cells of the population of cells can be configured to switch cell states upon the cell population reaching a critical cell population size and/or density threshold (e.g., a local critical cell population size and/or density threshold at a target site). For example, in some embodiments, (i) sender-receiver cells produce auxin constitutively and express an AID-tagged target protein that is capable of reducing the concentration, localization, stability, and/or activity of a cellular differentiation payload protein, (ii) the shared pool of auxin that is collectively produced by the population of sender-receiver cells is sensed by each of the sender-receiver cells, (iii) at a critical cell population size and/or density threshold, auxin concentrations are such that sufficient degradation of the target protein occurs and the cellular differentiation payload protein can induce differentiation of the sender-receiver cells.

The population of cells can be capable of being employed in synthetic organogenesis and/or tissue repair. The population of cells can be evolutionarily robust to mutations reducing or abrogating orthogonal signal-based control of population size and/or density. The population of cells can be robust to said mutations for at least about 10 days, about 20 days, about 40 days, about 80 days, about 80 days, or about 100 days, of continuous culture and/or presence in a subject.

The first cell type, second cell type, sender cell, receiver cell, and/or sender-receiver cell can comprise a eukaryotic cell. The eukaryotic cell can comprise an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, myoblast, myocyte, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, a zymogenic cell, or any combination thereof. The stem cell can comprise an embryonic stem cell, an induced pluripotent stem cell (iPSC), a hematopoietic stem/progenitor cell (HSPC), or any combination thereof.

Targeting

The first cell type, second cell type, sender cell, receiver cell, and/or sender-receiver cell further can comprise one or more targeting moieties configured to bind a component of a target site of a subject. The critical cell population size and/or density threshold can comprise a local critical cell population size and/or density threshold at a target site. The one or more targeting moieties can be selected from the group comprising mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, and an RGD peptide or RGD peptide mimetic. The one or more targeting moieties can comprise one or more of the following: an antibody or antigen-binding fragment thereof, a peptide, a polypeptide, an enzyme, a peptidomimetic, a glycoprotein, a lectin, a nucleic acid, a monosaccharide, a disaccharide, a trisaccharide, an oligosaccharide, a polysaccharide, a glycosaminoglycan, a lipopolysaccharide, a lipid, a vitamin, a steroid, a hormone, a cofactor, a receptor, a receptor ligand, and analogs and derivatives thereof.

The antibody or antigen-binding fragment thereof can comprise a Fab, a Fab', a F(ab')2, a Fv, a scFv, a dsFv, a diabody, a triabody, a tetrabody, a multispecific antibody formed from antibody fragments, a single-domain antibody (sdAb), a single chain comprising complementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof.

The one or more targeting moieties can be configured to bind one or more of the following: CD3, CD4, CD5, CD6, CD7, CD8, CD9, CD10, CD1 1a, CD1 1b, CD1 1c, CD12w, CD14, CD15, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49b, CD49c, CD51, CD52, CD53, CD54, CD55, CD56, CD58, CD59, CD61, CD62E, CD62L, CD62P, CD63, CD66, CD68, CD69, CD70, CD72, CD74, CD79, CD79a, CD79b, CD80, CD81, CD82, CD83, CD86, CD87, CD88, CD89, CD90, CD91, CD95, CD96, CD98, CD100, CD103, CD105, CD106, CD109, CD117, CD120, CD125, CD126, CD127, CD133, CD134, CD135, CD137, CD138, CD141, CD142, CD143, CD144, CD147, CD151, CD147, CD152, CD154, CD156, CD158, CD163, CD166, CD168, CD174, CD180, CD184, CDw186, CD194, CD195, CD200, CD200a, CD200b, CD209, CD221, CD227, CD235a, CD240, CD262, CD271, CD274, CD276 (B7-H3), CD303, CD304, CD309, CD326, 4-1BB, 5 AC, 5T4 (Trophoblast glycoprotein, TPBG, 5T4, Wnt-Activated Inhibitory Factor 1 or WAIF1), Adenocarcinoma antigen, AGS-5, AGS-22M6, Activin receptor like kinase 1, AFP, AKAP-4, ALK, Alpha integrin, Alpha v beta6, Amino-peptidase N, Amyloid beta, Androgen receptor, Angiopoietin 2, Angiopoietin 3, Annexin A1, Anthrax toxin protective antigen, Anti-transferrin receptor, AOC3 (VAP-1), B7-H3, *Bacillus anthracis* anthrax, BAFF (B-cell activating factor), B-lymphoma cell, bcr-abl, Bombesin, BORIS, C5, C242 antigen, CA125 (carbohydrate antigen 125, MUC16), CA-IX (CAIX, carbonic anhydrase 9), CALLA, CanAg, *Canis lupus familiaris* IL31, Carbonic anhydrase IX, Cardiac myosin, CCL11(C-C motif chemokine 11), CCR4 (C-C chemokine receptor type 4, CD194), CCR5, CD3E (epsilon), CEA (Carcinoembryonic antigen), CEACAM3, CEACAM5 (carcinoembryonic antigen), CFD (Factor D), Ch4D5, Cholecystokinin 2 (CCK2R), CLDN18 (Claudin-18), Clumping factor A, CRIPTO, FCSF1R (Colony stimulating factor 1 receptor, CD 115), CSF2 (colony stimulating factor 2, Granulocyte-macrophage colony-stimulating factor (GM-CSF)), CTLA4 (cytotoxic T-lymphocyte-associated protein 4), CTAA16.88 tumor antigen, CXCR4 (CD 184), C—X—C chemokine receptor type 4, cyclic ADP ribose hydrolase, Cyclin B 1, CYP1B 1, Cytomegalovirus, Cytomegalovirus glycoprotein B, Dabigatran, DLL4 (delta-like-ligand 4), DPP4 (Dipeptidyl-peptidase 4), DR5 (Death receptor 5), *E. coli* Shiga toxin type-1, *E. coli* Shiga toxin type-2, ED-B, EGFL7 (EGF-like domain-containing protein 7), EGFR, EGFRII, EGFRvIII, Endoglin (CD 105), Endothelin B receptor, Endotoxin, EpCAM (epithelial cell adhesion molecule), EphA2, Episialin, ERBB2 (Epidermal Growth Factor Receptor 2), ERBB3, ERG (TMPRSS2 ETS fusion gene), *Escherichia coli*, ETV6-AML, FAP (Fibroblast activation protein alpha), FCGR1, alpha-Fetoprotein, Fibrin II, beta chain, Fibronectin extra domain-B, FOLR (folate receptor), Folate receptor alpha, Folate hydrolase, Fos-related antigen 1.F protein of respiratory syncytial virus, Frizzled receptor, Fucosyl GM1, GD2 ganglioside, G-28 (a cell surface antigen glycolipid), GD3 idiotype, GloboH, Glypican 3, N-glycolylneuraminic acid, GM3, GMCSF receptor α-chain, Growth differentiation factor 8, GP100, GPNMB (Transmembrane glycoprotein NMB), GUCY2C (Guanylate cyclase 2C, guanylyl cyclase C(GC-C), intestinal Guanylate cyclase, Guanylate cyclase-C receptor, Heat-stable enterotoxin receptor (hSTAR)), Heat shock proteins, Hemagglutinin, Hepatitis B surface antigen, Hepatitis B virus, HER1 (human epidermal growth factor receptor 1), HER2, HER2/neu, HER3 (ERBB-3), IgG4, HGF/SF (Hepatocyte growth factor/scatter factor), HHGFR, HIV-1, Histone complex, HLA-DR (human leukocyte antigen), HLA-DR10, HLA-DRB, HMWMAA, Human chorionic gonadotropin, HNGF, Human scatter factor receptor kinase, HPV E6/E7, Hsp90, hTERT, ICAM-1 (Intercellular Adhesion Molecule 1), Idiotype, IGF1R (IGF-1, insulin-like growth factor 1 receptor), IGHE, IFN-γ, Influenza hemagglutinin, IgE, IgE Fc region, IGHE, IL-1, IL-2 receptor (interleukin 2 receptor), IL-4, IL-5, IL-6, IL-6R (interleukin 6 receptor), IL-9, IL-10, IL-12, IL-13, IL-17, IL-17A, IL-20, IL-22, IL-23, IL31RA, ILGF2 (Insulin-like growth factor 2), Integrins (α4, $α_\nu β3$, αvβ3, $α_4β_7$, α5β1, α6β4, α7β7, α11β3, α5β5, αvβ5), Interferon gamma-induced protein, ITGA2, ITGB2, KIR2D, LCK, Le, Legumain, Lewis-Y antigen, LFA-1(Lymphocyte function-associated antigen 1, CD1 1a), LHRH, LINGO-1, Lipoteichoic acid, LIV1A, LMP2, LTA, MAD-CT-1, MAD-CT-2, MAGE-1, MAGE-2, MAGE-3, MAGE A1, MAGE A3, MAGE 4, MARTI, MCP-1, MIF (Macrophage migration inhibitory factor, or glycosylation inhibiting factor (GIF)), MS4A1 (membrane-spanning 4-domains subfamily A member 1), MSLN (mesothelin), MUC1 (Mucin 1, cell surface associated (MUC1) or polymorphic epithelial mucin (PEM)), MUC1-KLH, MUC16 (CA125), MCP1 (monocyte chemotactic protein 1), MelanA/MART1, ML-IAP, MPG, MS4A1 (membrane-spanning 4-domains subfamily A), MYCN, Myelin-associated glycoprotein, Myostatin, NA17, NARP-1, NCA-90 (granulocyte antigen), Nectin-4 (ASG-22ME), NGF, Neural apoptosis-regulated proteinase 1, NOGO-A, Notch receptor, Nucleolin, Neu oncogene product, NY-BR-1, NY-ESO-1, OX-40, OxLDL (Oxidized low-density lipoprotein), OY-TES 1, P21, p53 nonmutant, P97, Page4, PAP, Paratope of anti-(N-glycolylneuraminic acid), PAX3, PAX5, PCSK9, PDCD1 (PD-1, Programmed cell death protein 1, CD279), PDGF-Ra (Alpha-type platelet-derived growth factor receptor), PDGFR-β, PDL-1, PLAC1, PLAP-like testicular alkaline phosphatase, Platelet-derived growth factor receptor beta, Phosphate-sodium co-transporter, PMEL 17, Polysialic acid, Proteinase3 (PR1), Prostatic carcinoma, PS (Phosphatidylserine), Prostatic carcinoma cells, *Pseudomonas aeruginosa*, PSMA, PSA, PSCA, Rabies virus glycoprotein, RHD (Rh polypeptide 1 (RhPI), CD240), Rhesus factor, RANKL, RhoC, Ras mutant, RGS5, ROBO4, Respiratory syncytial virus, RON, Sarcoma translocation breakpoints, SART3, Sclerostin, SLAMF7 (SLAM family member 7), Selectin P, SDC1 (Syndecan 1), sLe(a), Somatomedin C, SIP (Sphingosine-1-phosphate), Somatostatin, Sperm protein 17, SSX2, STEAP1 (six-transmembrane epithelial antigen of the prostate 1), STEAP2, STn, TAG-72 (tumor associated glycoprotein 72), Survivin, T-cell receptor, T cell transmembrane protein, TEM1 (Tumor endothelial marker 1), TENB2, Tenascin C (TN-C), TGF-a, TGF-β (Transforming growth factor beta), TGF-βI, TGF-β2 (Transforming growth factor-beta 2), Tie (CD202b), Tie2, TIM-1 (CDX-014), Tn, TNF, TNF-a, TNFRSF8, TNFRSF10B (tumor necrosis factor receptor superfamily member 10B), TNFRSF13B (tumor necrosis factor receptor superfamily member 13B), TPBG (trophoblast glycoprotein), TRAIL-R1 (Tumor necrosis apoptosis Inducing ligand Receptor 1), TRAILR2 (Death receptor 5 (DR5)), tumor-associated calcium signal transducer 2, tumor specific glycosylation of MUC1, TWEAK receptor, TYRP1 (glycoprotein 75), TRP-2, Tyrosinase, VCAM-1 (CD 106), VEGF, VEGF-A, VEGF-2 (CD309), VEGFR-1, VEGFR2, or vimentin, WT1, XAGE 1, or cells expressing any insulin growth factor receptors, or any epidermal growth factor receptors.

Methods of Treating a Disease or Disorder

Disclosed herein include methods for treating a disease or disorder in a subject. In some embodiments, the method comprises: introducing into two or more cells one or more of the nucleic acid compositions (e.g., circuits) provided herein or one or more of the compositions provided herein, thereby generating a population of cells; and administering to the subject an effective amount of the population of cells. The method can comprise: isolating the two or more cells from the subject prior to the introducing step. In some embodiments, the introducing step is performed in vivo, in vitro, and/or ex vivo. In some embodiments, the introducing step comprises calcium phosphate transfection, DEAE-dextran mediated transfection, cationic lipid-mediated transfection, electroporation, electrical nuclear transport, chemical transduction, electrotransduction, Lipofectamine-mediated transfection, Effectene-mediated transfection, lipid nanoparticle (LNP)-mediated transfection, or any combination thereof. Disclosed herein include methods for treating a disease or disorder in a subject. In some embodiments, the method comprises: administering to the subject an effective amount of a population of cells provided herein.

The subject can be a mammal. In some embodiments, the disease is associated with expression of a tumor antigen, wherein the disease associated with expression of a tumor antigen is selected from the group consisting of a proliferative disease, a precancerous condition, a cancer, and a non-cancer related indication associated with expression of the tumor antigen. The disease or disorder can be a cancer (e.g., a solid tumor). The cancer can be selected from the group consisting of colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers.

The cancer can be a hematologic cancer chosen from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or pre-leukemia.

The disease or disorder can be an autoimmune disorder. An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, antiphospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barre syndrome, Hashimoto's thyroiditis, and cardiomyopathy.

In some embodiments, the method comprises: administering to the subject an effective amount of the first precursor molecule, the second precursor molecule, the exogenous agent, the pro-death agent, or any combination thereof, to the subject prior to, during, and/or after administration of the disclosed engineered cells. The administration of said agents can modulate the population size/density and/or behavior of the engineered cells in the subject as described herein, and can be adjusted as needed throughout treatment. In some embodiments, the population of engineered cells does not exceed a desired population size and/or density in the subject. In some embodiments, the population of engineered cells activates a therapeutic program in the subject, such as, for example, killing of target cells at a target site (e.g., a target site-specific therapeutic program).

Administering can comprise aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, intradermal injection, or any combination thereof. The disclosed engineered cells can be administered at a therapeutically effective amount. For example, a therapeutically effective amount of the disclosed engineered cells can be at least about $10^2$ cells, at least about $10^3$ cells, at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the disclosed engineered cells is about $10^4$ cells, about $10^5$ cells, about $10^6$ cells, about $10^7$ cells, or about $10^8$ cells. In one particular embodiment, the therapeutically effective amount of the disclosed engineered cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

The disclosed engineered cells described herein may be included in a composition for therapy. In some embodiments, the composition comprises a population of disclosed engineered cells. The composition may include a pharmaceutical composition and further include a pharmaceutically acceptable carrier. A therapeutically effective amount of the pharmaceutical composition comprising the disclosed engineered cells may be administered. The cells provided herein may be administered either alone, or as a pharmaceutical composition in combination with diluents and/or with other components such as IL-2 or other cytokines or cell populations. Ex vivo procedures are well known in the art. Briefly, cells are isolated from a mammal (e.g., a human) and genetically modified (i.e., transduced or transfected in vitro) with a nucleic acid composition (e.g., a vector) disclosed herein or a composition disclosed herein, thereby generating an engineered population of cells. The disclosed engineered cells can be administered to a mammalian recipient to provide a therapeutic benefit. The mammalian recipient may be a human and the disclosed engineered cells can be autologous with respect to the recipient. Alternatively, the disclosed engineered cells can be allogeneic, syngeneic or xenogeneic with respect to the recipient.

Target Sites

In some embodiments, a target site of a subject comprises a site of disease or disorder or is proximate to a site of a disease or disorder. In some embodiments, the target site comprises a tissue. The target site can comprise a solid tumor. The target site can comprise a site of disease or disorder or can be proximate to a site of a disease or disorder. The location of the one or more sites of a disease or disorder can be predetermined, can be determined during the method, or both. The target site can be an immunosuppressive environment. The target site can comprise a tissue. The tissue can be inflamed tissue and/or infected tissue. The tissue can comprise adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue. The tissue can comprise: (i) grade I, grade II, grade III or grade IV cancerous tissue; (ii) metastatic cancerous tissue; (iii) mixed grade cancerous tissue; (iv) a sub-grade cancerous tissue; (v) healthy or normal tissue; and/or (vi) cancerous or abnormal tissue. In some embodiments, at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or a number or a range between any two of these values, of the disclosed engineered cells at the target site activate the target site-specific therapeutic program (e.g., CAR activation). In some embodiments, less than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or a number or a range between any two of these values, of the disclosed engineered cells at a site other than the target site activate the target site-specific therapeutic program (e.g., CAR activation).

The ratio of the concentration of payload protein at the subject's target site to the concentration of payload protein in subject's blood, serum, or plasma can be vary. In some embodiments, the ratio of the concentration of payload protein at the subject's target site to the concentration of payload protein in subject's blood, serum, or plasma can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio of the concentration of payload protein at the subject's target site to the concentration of payload protein in subject's blood, serum, or plasma can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1.

The target site can comprise target cells. The target cells can be tumor cells (e.g., solid tumor cells). In some embodiments, the administration of engineered cells provided herein results in the death of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or a number or a range between any two of these values, of the target cells. Non-target cells can comprise cells of the subject other than target cells. The ratio of target cell death to non-target cell death after administration of engineered cells provided herein can be at least about 2:1. In some embodiments, the ratio of target cell death to non-target cell death after administration of engineered cells provided herein can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio of target cell death to non-target cell death after administration of engineered cells provided herein can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1.

Additional Agents

In some embodiments, the method comprises administering one or more additional agents to the subject. In some embodiments, the one or more additional agents increases the efficacy of the population of cells. The one or more additional agents can comprise a protein phosphatase inhibitor, a kinase inhibitor, a cytokine, an inhibitor of an immune inhibitory molecule, and/or or an agent that decreases the level or activity of a TREG cell. The one or more additional agents can comprise an immune modulator, an anti-metastatic, a chemotherapeutic, a hormone or a growth factor antagonist, an alkylating agent, a TLR agonist, a cytokine antagonist, a cytokine antagonist, or any combination thereof. The one or more additional agents can comprise an agonistic or antagonistic antibody specific to a checkpoint inhibitor or checkpoint stimulator molecule such as PD1, PD-L1, PD-L2, CD27, CD28, CD40, CD137, OX40, GITR, ICOS, A2AR, B7-H3, B7-H4, BTLA, CTLA4, IDO, KIR, LAG3, PD-1, TIM-3.

The one or more additional agents can be selected from the group consisting of alkylating agents (nitrogen mustards, ethylenimine derivatives, alkyl sulfonates, nitrosoureas and triazenes); uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®); bendamustine (Treakisym®, Ribomustin®, Treanda®); chlormethine (Mustargen®); cyclophosphamide (Cytoxan®, Neosar®, Clafen®, Endoxan®, Procytox®, Revimmune™); ifosfamide (Mitoxana®); melphalan (Alkeran®); Chlorambucil (Leukeran®); pipobroman (Amedel®, Vercyte®); triethylenemelamine (Hemel®, Hexylen®, Hexastat®); triethylenethiophosphoramine; Temozolomide (Temodar®); thiotepa (Thioplex®); busulfan (Busilvex®, Myleran®); carmustine (BiCNU®); lomustine (CeeNU®); streptozocin (Zanosar®); estramustine (Emcyt®, Estracit®); fotemustine; irofulven; mannosulfan; mitobronitol; nimustine; procarbazine; ranimustine; semustine; triaziquone; treosulfan; and Dacarbazine (DTIC-Dome®); anti-EGFR antibodies (e.g., cetuximab (Erbitux®), panitumumab (Vectibix®), and gefitinib (Iressa®)); anti-Her-2 antibodies (e.g., trastuzumab (Herceptin®) and other antibodies from Genentech); antimetabolites (including, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), carmofur, cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®), decitabine (Dacogen®), enocitabine (Sunrabin®), sapacitabine, tegafur-uracil, tiazofurine, tioguanine, trofosfamide, and gemcitabine (Gemzar®); vinca alkaloids: vinblastine (Velban®, Velsar®), vincristine (Vincasar®, Oncovin®), vindesine (Eldisine®), vinorelbine (Navelbine®), vinflunine (Javlor®); platinum-based agents: carboplatin (Paraplat®, Paraplatin®), cisplatin (Platinol®), oxaliplatin (Eloxatin®), nedaplatin, satraplatin, and triplatin; anthracyclines: daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®), aclarubicin, amrubicin, liposomal doxorubicin, liposomal daunorubicin, pirarubicin, pixantrone, and zorubicin; topoisomerase inhibitors: topotecan (Hycamtin®), irinotecan (Camptosar®), etoposide (Toposar®, VePesid®), teniposide (Vumon®), lamellarin D, SN-38, camptothecin (e.g., IT-101), belotecan, and rubitecan; taxanes: paclitaxel (Taxol®), docetaxel (Taxotere®), larotaxel, cabazitaxel, ortataxel, and tesetaxel; antibiotics: actinomycin (Cosmegen®), bleomycin (Blenoxane®), hydroxyurea (Droxia®, Hydrea®), mitomycin (Mitozytrex®, Mutamycin®); immunomodulators: lenalidomide (Revlimid®), thalidomide (Thalomid®); immune cell antibodies: alemtuzamab (Campath®), gemtuzumab (Myelotarg®), rituximab (Rituxan®), tositumomab (Bexxar®); interferons (e.g., IFN-alpha (Alferon®, Roferon-A®, Intron®-A) or IFN-gamma (Actimmune®)); interleukins: IL-1, IL-2 (Proleukin®), IL-24, IL-6 (Sigosix®), IL-12; HSP90 inhibitors (e.g., geldanamycin or any of its derivatives). In certain embodiments, the HSP90 inhibitor is selected from geldanamycin, 17-alkylamino-17-desmethoxygeldanamycin ("17-AAG") or 17-(2-dimethylaminoethyl)amino-17-desmethoxygeldanamycin ("17-DMAG"); anti-androgens which include, without limitation nilutamide (Nilandron®) and bicalutamide (Caxodex®); antiestrogens which include, without limitation tamoxifen (Nolvadex®), toremifene (Fareston®), letrozole (Femara®), testolactone (Teslac®), anastrozole (Arimidex®), bicalutamide (Casodex®), exemestane (Aromasin®), flutamide (Eulexin®), fulvestrant (Faslodex®), raloxifene (Evista®, Keoxifene®) and raloxifene hydrochloride; anti-hypercalcaemia agents which include without limitation gallium (III) nitrate hydrate (Ganite®) and pamidronate disodium (Aredia®); apoptosis inducers which include without limitation ethanol, 2-[[3-(2,3-dichlorophenoxy)propyl]amino]-(9C1), gambogic acid, elesclomol, embelin and arsenic trioxide (Trisenox®); Aurora kinase inhibitors which include without limitation binucleine 2; Bruton's tyrosine kinase inhibitors which include without limitation terreic acid; calcineurin inhibitors which include without limitation cypermethrin, deltamethrin, fenvalerate and tyrphostin 8; CaM kinase II inhibitors which include without limitation 5-Isoquinolinesulfonic acid, 4-[{2S)-2-[(5-isoquinolinyl sulfonyl)methylamino]-3-oxo-3-{4-phenyl-1-piperazinyl) propyl]phenyl ester and benzenesulfonamide; CD45 tyrosine phosphatase inhibitors which include without limitation phosphonic acid; CDC25 phosphatase inhibitors which include without limitation 1,4-naphthalene dione, 2,3-bis [(2-hydroxyethyl)thio]-(9C1); CHK kinase inhibitors which include without limitation debromohymenialdisine; cyclooxygenase inhibitors which include without limitation 1H-indole-3-acetamide, 1-(4-chlorobenzoyl)-5-methoxy-2-methyl-N-(2-phenylethyl)-(9C1), 5-alkyl substituted 2-arylaminophenylacetic acid and its derivatives (e.g., celecoxib (Celebrex®), rofecoxib (Vioxx®), etoricoxib (Arcoxia®), lumiracoxib (Prexige®), valdecoxib (Bextra®) or 5-alkyl-2-arylaminophenylacetic acid); cRAF kinase inhibitors which include without limitation 3-(3,5-dibromo-4-hydroxybenzylidene)-5-iodo-1,3-dihydroindol-2-one and benzamide, 3-(dimethylamino)-N-[3-[(4-hydroxybenzoyl) amino]-4-methylphenyl]-(9C1); cyclin dependent kinase inhibitors which include without limitation olomoucine and its derivatives, purvalanol B, roascovitine (Seliciclib®), indirubin, kenpaullone, purvalanol A and indirubin-3'-monooxime; cysteine protease inhibitors which include without limitation 4-morpholinecarboxamide, N-[(1S)-3-fluoro-2-oxo-1-(2-phenylethyl)propyl]amino]-2-oxo-1-(phenylmethyl)ethyl]-(9C1); DNA intercalators which include without limitation plicamycin (Mithracin®) and daptomycin (Cubicin®); DNA strand breakers which include without limitation bleomycin (Blenoxane®); E3 ligase inhibitors which include without limitation N-((3,3,3-trifluoro-2-trifluoromethyl)propionyl)sulfanilamide; EGF Pathway Inhibitors which include, without limitation tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980; farnesyltransferase inhibitors which include without limitation a hydroxyfarnesylphosphonic acid, butanoic acid, 2-[(2 S)-2-[[(2 S,3 S)-2-[[(2R)-2-amino-3-mercaptopropyl] amino]-3-methylpent-yl]oxy]-1-oxo-3-phenylpropyl] amino]-4-(methylsulfonyl)-1-methylethylester (2S)-(9C1), tipifarnib (Zarnestra®), and manumycin A; Flk-1 kinase inhibitors which include without limitation 2-propenamide, 2-cyano-3-[4-hydroxy-3,5-bi s(1-methylethyl)phenyl]-N-(3-phenylpropyl)-(2E-)-(9C1); glycogen synthase kinase-3 (GSK3) inhibitors which include without limitation indirubin-3'-monooxime; histone deacetylase (HDAC) inhibitors which include without limitation suberoylanilide hydroxamic acid (SAHA), [4-(2-amino-phenylcarbamoyl)-benzyl]carbamic acid pyridine-3-ylmethylester and its derivatives, butyric acid, pyroxamide, trichostatin A, oxamflatin, apicidin, depsipeptide, depudecin, trapoxin, vorinostat (Zolinza®), and compounds disclosed in WO 02/22577; I-kappa B-alpha kinase inhibitors (IKK) which include without limitation 2-propenenitrile, 3-[(4-methylphenyl) sulfonyl]-(2E)-(9C1); imidazotetrazinones which include without limitation temozolomide (Methazolastone®, Temodar® and its derivatives (e.g., as disclosed generically and specifically in U.S. Pat. No. 5,260,291) and Mitozolomide; insulin tyrosine kinase inhibitors which include without limitation hydroxyl-2-naphthalenylmethylphosphonic acid; c-Jun-N-terminal kinase (JNK) inhibitors which include without limitation pyrazoleanthrone and epigallocatechin gallate; mitogen-activated protein kinase (MAP) inhibitors which include without limitation benzenesulfonamide, N-[2-[[[3-(4-chlorophenyl)-2-propenyl]methyl]amino] methyl]phenyl]-N-(2-hy-droxyethyl)-4-methoxy-(9C1); MDM2 inhibitors which include without limitation trans-4-iodo, 4'-boranyl-chalcone; MEK inhibitors which include without limitation butanedinitrile, bis[amino[2-aminophenyl)thio]methylene]-(9C1); MMP inhibitors which include without limitation Actinonin, epigallocatechin gallate, collagen peptidomimetic and non-peptidomimetic inhibitors, tetracycline derivatives marimastat (Marimastat®), prinomastat, incyclinide (Metastat®), shark cartilage extract AE-941 (Neovastat®), Tanomastat, TAA211, MMI270B or AAJ996; mTor inhibitors which include without limitation rapamycin (Rapamune®), and analogs and derivatives thereof, AP23573 (also known as ridaforolimus, deforolimus, or MK-8669), CCI-779 (also known as temsirolimus) (Torisel®) and SDZ-RAD; NGFR tyrosine kinase inhibitors which include without limitation tyrphostin AG 879; p38 MAP kinase inhibitors which include without limitation Phenol, 4-[4-(4-fluorophenyl)-5-(4-pyridinyl)-1H-imidazol-2-yl]-(9C1), and benzamide, 3-(dimethylamino)-N-[3-[(4-hydroxylbenzoyl)amino]-4-methylphenyl]-(9C1); p56 tyrosine kinase inhibitors which include without limitation damnacanthal and tyrphostin 46; PDGF pathway inhibitors which include without limitation tyrphostin AG 1296, tyrphostin 9, 1,3-butadiene-1,1,3-tricarbonitrile, 2-amino-4-(1H-indol-5-yl)-(9C1), imatinib (Gleevec®) and gefitinib (Iressa®) and those compounds generically and specifically disclosed in European Patent No.: 0 564 409 and PCT Publication No.: WO 99/03854; phosphatidylinositol 3-kinase inhibitors which include without limitation wortmannin, and quercetin dihydrate; phosphatase inhibitors which include without limitation cantharidic acid, cantharidin, and L-leucinamide; protein phosphatase inhibitors which include without limitation cantharidic acid, cantharidin, L-P-bromotetramisole oxalate, 2(5H)-furanone, 4-hydroxy-5-(hydroxymethyl)-3-(1-oxohexadecyl)-(5R)-(9C1) and benzylphosphonic acid; PKC inhibitors which include without limitation 1-H-pyrollo-2,5-dione, 3-[1-3-(dimethylamino)propyl]-1H-indol-3-yl]-4-(1H-indol-3-yl)-(9C1), Bisindolylmaleimide IX, Sphinogosine, staurosporine, and Hypericin; PKC delta kinase inhibitors which include without limitation rottlerin; polyamine synthesis inhibitors which include without limitation DMFO; PTP1B inhibitors which include without limitation L-leucinamide; protein tyrosine kinase inhibitors which include, without limitation tyrphostin Ag 216, tyrphostin Ag 1288, tyrphostin Ag 1295, geldanamycin, genistein and 7H-pyrrolo[2,3-d]pyrimidine derivatives as generically and specifically described in PCT Publication No.: WO 03/013541 and U.S. Publication No.: 2008/0139587; SRC family tyrosine kinase inhibitors which include without limitation PP1 and PP2; Syk tyrosine kinase inhibitors which include without limitation piceatannol; Janus (JAK-2 and/or JAK-3) tyrosine kinase inhibitors which include without limitation tyrphostin AG 490 and 2-naphthyl vinyl ketone; retinoids which include without limitation isotretinoin (Accutane®, Amnesteem®, Cistane®, Claravis®, Sotret®) and tretinoin (Aberel®, Aknoten®, Avita®, Renova®, Retin-A®, Retin-A MICRO®, Vesanoid®); RNA polymerase H elongation inhibitors which include without limitation 5, 6-dichloro-1-beta-D-ribofuranosylbenzimidazole; serine/Threonine kinase inhibitors which include without limitation 2-aminopurine; sterol biosynthesis inhibitors which include without limitation squalene epoxidase and CYP2D6; VEGF pathway inhibitors, which include without limitation anti-VEGF antibodies, e.g., bevacizumab, and small molecules, e.g., sunitinib (Sutent®), sorafinib (Nexavar®), ZD6474 (also known as vandetanib) (Zactima™), SU6668, CP-547632 and AZD2171 (also known as cediranib) (Recentin™).

EXAMPLES

Some aspects of the embodiments discussed above are disclosed in further detail in the following examples, which are not in any way intended to limit the scope of the present disclosure.

Example 1

Synthetic Mammalian Signaling Circuits for Robust Cell Population Control

In multicellular organisms, cells actively sense and control their own population density. Synthetic mammalian quorum sensing circuits could provide insight into principles of population control and improve cell therapies. However, a key challenge is avoiding their inherent sensitivity to "cheater" mutations that evade control. Here, the plant hormone auxin was repurposed to enable orthogonal mammalian cell-cell communication and quorum sensing. A paradoxical population control circuit was designed, termed Paradaux, in which auxin stimulates and inhibits net cell growth at different concentrations. This circuit was robust to cheater mutations, controlling growth for at least 43 days of continuous culture. By contrast, when operating in a non-paradoxical regime, the same cells limited population growth but were susceptible to mutational escape. These results establish auxin as a versatile 'private' communication system, and demonstrate that paradoxical circuit architectures can provide robust population control.

INTRODUCTION

Cells use intercellular communication systems to sense and control their own cell population density. In microbial communities, cells secrete diffusive signals to coordinate cooperative behaviors through the process of quorum sensing. In multicellular organisms, intercellular communication is essential to enable precise developmental patterning, control immunological responses, and coordinate organism-level physiology. Synthetic intercellular communication systems could similarly allow engineering of inherently multicellular behaviors not possible with cell-autonomous circuits.

In mammalian cells, an orthogonal, or "private" communication channel that allows specific communication between cells could enable engineering of analogous circuits (FIG. 1A). Mammalian cells have been engineered to produce, sense, and process signals from natural ligands by rewiring signaling pathways such as Nodal-Lefty, Sonic Hedgehog, and Notch, and by repurposing the amino acid tryptophan as a signaling molecule. However, these approaches are not orthogonal to endogenous systems. On the other hand, synthetic synNotch receptors allow multiple orthogonal communication channels, but depend on cell contact interactions to mediate diffusible signaling.

The ideal private communication system for mammalian population control would use a diffusible signal, avoid undesired interactions with non-engineered cells, permit external control over the strength of signaling, and operate in a broad variety of cell types. It should also allow direct, and rapid, control of diverse target protein activities to allow flexible interfacing within cells, and exhibit minimal immunogenicity to facilitate potential biomedical applications. Auxins, a class of plant-specific hormones that coordinate growth and behavior, including root initiation, embryogenesis, and tropism, represent an excellent candidate for this role. Molecularly, auxin induces protein-protein interactions between the F-box transport inhibitor response 1 (TIR1) protein and its target proteins. This leads to the assembly of a Skp, Cullin, F-box containing (SCF) complex, which in turn recruits E2 ubiquitin ligases that target specific proteins for degradation. Because TIR1 and its targets are absent in mammals, auxin does not regulate endogenous mammalian proteins. However, ectopic expression of TIR1 from rice (osTIR1) is sufficient to confer auxin-dependent degradation of proteins engineered to contain a minimal auxin inducible degron (mAID, or AID for simplicity in this paper). Thus, auxin is orthogonal to endogenous mammalian pathways but can enable direct control of key cellular activities through engineered protein targets. Additionally, in yeast, ectopic expression of bacterial indole-3-acetic acid hydrolase was shown to catalyze auxin production from an inactive precursor indole-3-acetamide (IAM), allowing controlled production of auxin. Nevertheless, a full auxin sending and receiving signaling system, which is necessary for population control, has not been established in mammalian cells.

A critical challenge for any population control circuit is evolutionary robustness. By limiting growth, a population control circuit inherently selects for 'cheater' mutations that escape regulation. In bacteria, toxin-antitoxin systems and periodic strain replacement can prevent cheater escape. However, these systems use components that do not function in mammalian cells or are not cell autonomous. In the mammalian context, a paradoxical architecture, in which a single signal stimulates both proliferation and death of the same target cell population, can actively select against cheaters. In this paradoxical design, mutations that diminish signal sensing lead to cell death and are eliminated. Despite its power and elegance, the paradoxical architecture has not, to our knowledge, been demonstrated synthetically in living cells.

The auxin pathway was engineered to act as a private mammalian communication channel, and it was used to construct and analyze synthetic population control circuits with different architectures. Combining auxin-synthesizing enzymes and auxin transporters, and employing alternative auxin precursors, it was shown that the auxin pathway can be used for synthetic quorum sensing in mammalian cells. Using this pathway, negative feedback and paradoxical control systems that regulate their own population size through auxin quorum sensing were constructed and compared. While both circuits limit population size, the paradoxical system enhances evolutionary stability, as predicted theoretically. Together, these results provide a versatile, diffusible synthetic signaling module for private-channel communication and demonstrate how paradoxical control schemes can enhance the evolutionary stability of population control systems.

Results

Engineered Mammalian Cell Lines Sense, Respond to, and Produce Auxin

Figure 1B:
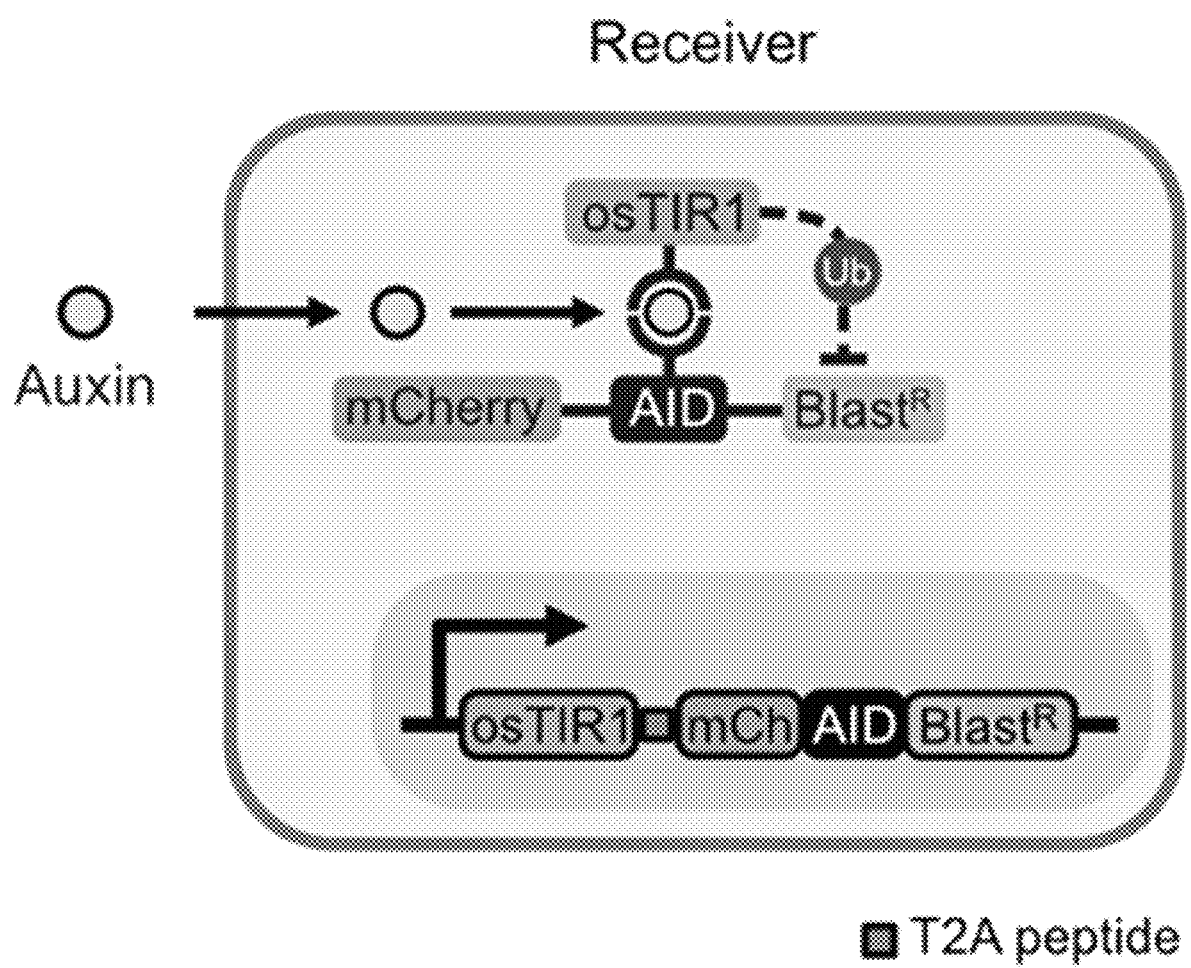

To establish and characterize auxin regulation of mammalian cell growth, auxin sensing was coupled to drug resistance and fluorescence. Specifically, blasticidin S deaminase (Blast R), whose protein product is necessary for survival in the presence of blasticidin, was fused to AID and mCherry domains, allowing auxin-dependent degradation and fluorescent readout of protein concentration, respectively. This chimeric gene was then stably integrated, along with a constitutively co-expressed osTIR1, in CHO-K1 cells to create an auxin-sensitive "Receiver" cell line (FIG. 1B).

Figure 1C:
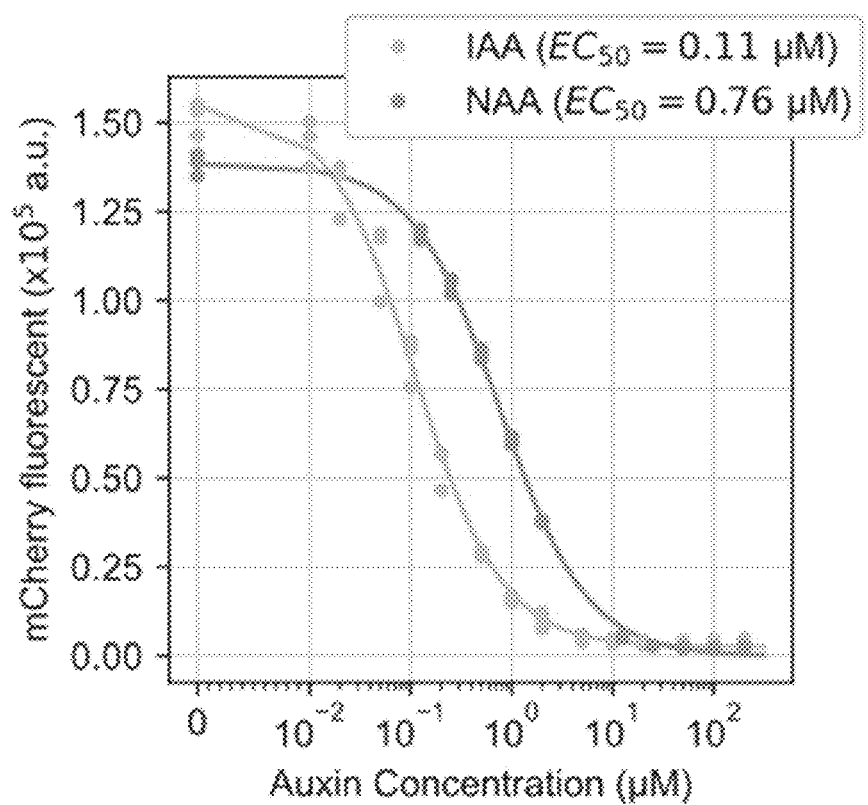
Figure 1D:
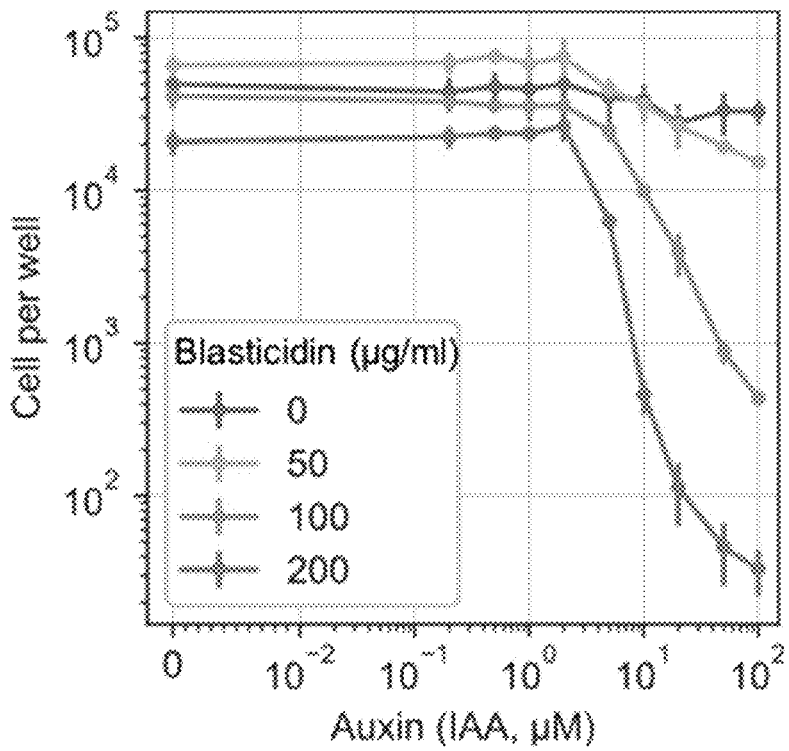

To validate auxin regulation of mCherry-AID-Blast R, Receivers were cultured in media containing varying concentrations of two auxin variants: either the major natural auxin, indole-3-acetic acid (IAA), or a synthetic auxin analog, 1-napthalenatic acid (NAA) (FIG. 1C). Both auxins reduced mCherry fluorescence in a dose-dependent manner, with EC50 values of 0.11 µM and 0.7604, respectively. Addition of IAA to media containing blasticidin was sufficient to degrade $Blast^R$ and inhibit cell survival (FIG. 1D). This effect was dose-dependent with both blasticidin and IAA. Comparing fluorescence of mCherry-AID-Blast$^R$ in FIG. 1C with cell survival in FIG. 1D shows that a small amount of mCherry-AID-Blast$^R$ is sufficient to enable survival in blasticidin. These results confirmed that the AID domain and osTIR1 together are sufficient to enable net growth regulation by auxin in mammalian cells.

Figure 2A:
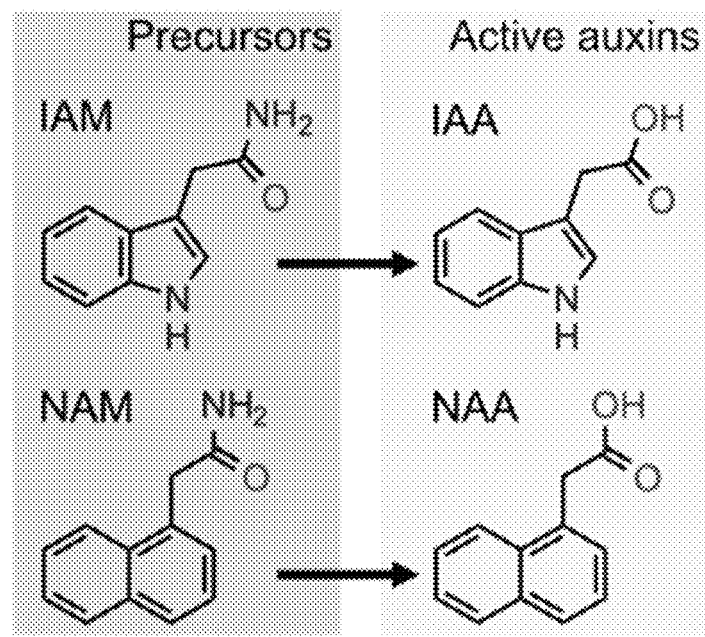
FIGS. 2A-2E depict non-limiting exemplary embodiments and data showing Sender-Receiver cells produce and respond to auxin.

In addition to sensing, a population control system can require that cells produce auxin at levels sufficient to trigger responses in receiving cells. Auxin can be synthesized in two enzymatic steps: (1) oxidation of L-tryptophan to indole-3-acetamide (IAM) and (2) hydrolysis of IAM to IAA (FIG. 6B). By itself, the second enzymatic step can produce either IAA or NAA from precursors IAM or 1-naphthaleneacetamide (NAM), respectively, enabling direct control of auxin production (FIG. 2A). To identify enzymes that efficiently catalyze this reaction, thirteen indole-3-acetamide hydrolases from bacteria and plants (FIG. 6A, left) were compared by transiently expressing them individually in Receivers and measuring their ability to downregulate AID-tagged mCherry fluorescence by flow cytometry.

Figure 2B:
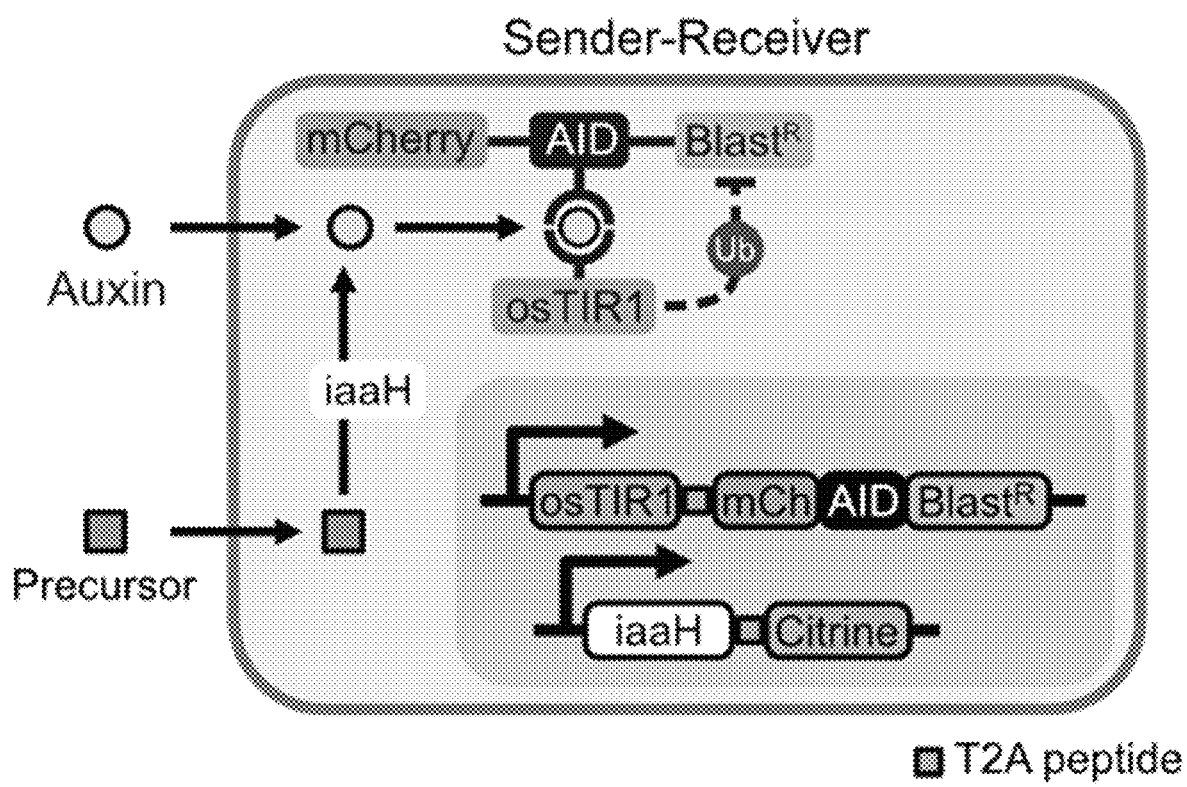
Figure 2C:
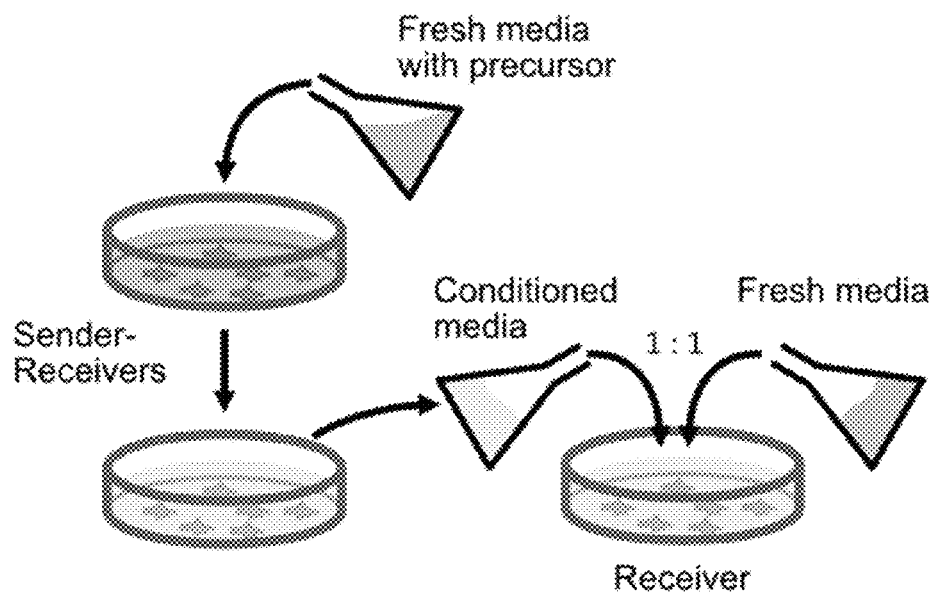
Figure 2D:
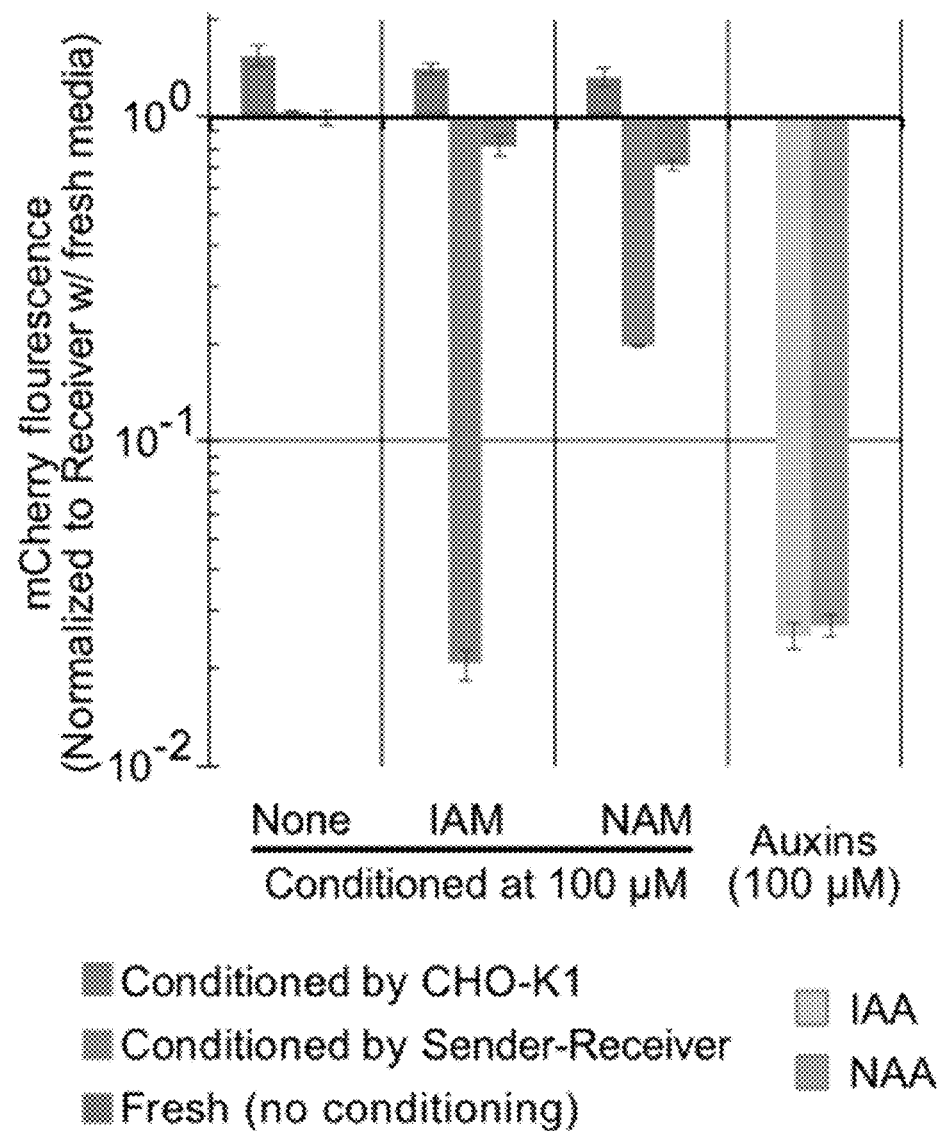
Figure 6A:
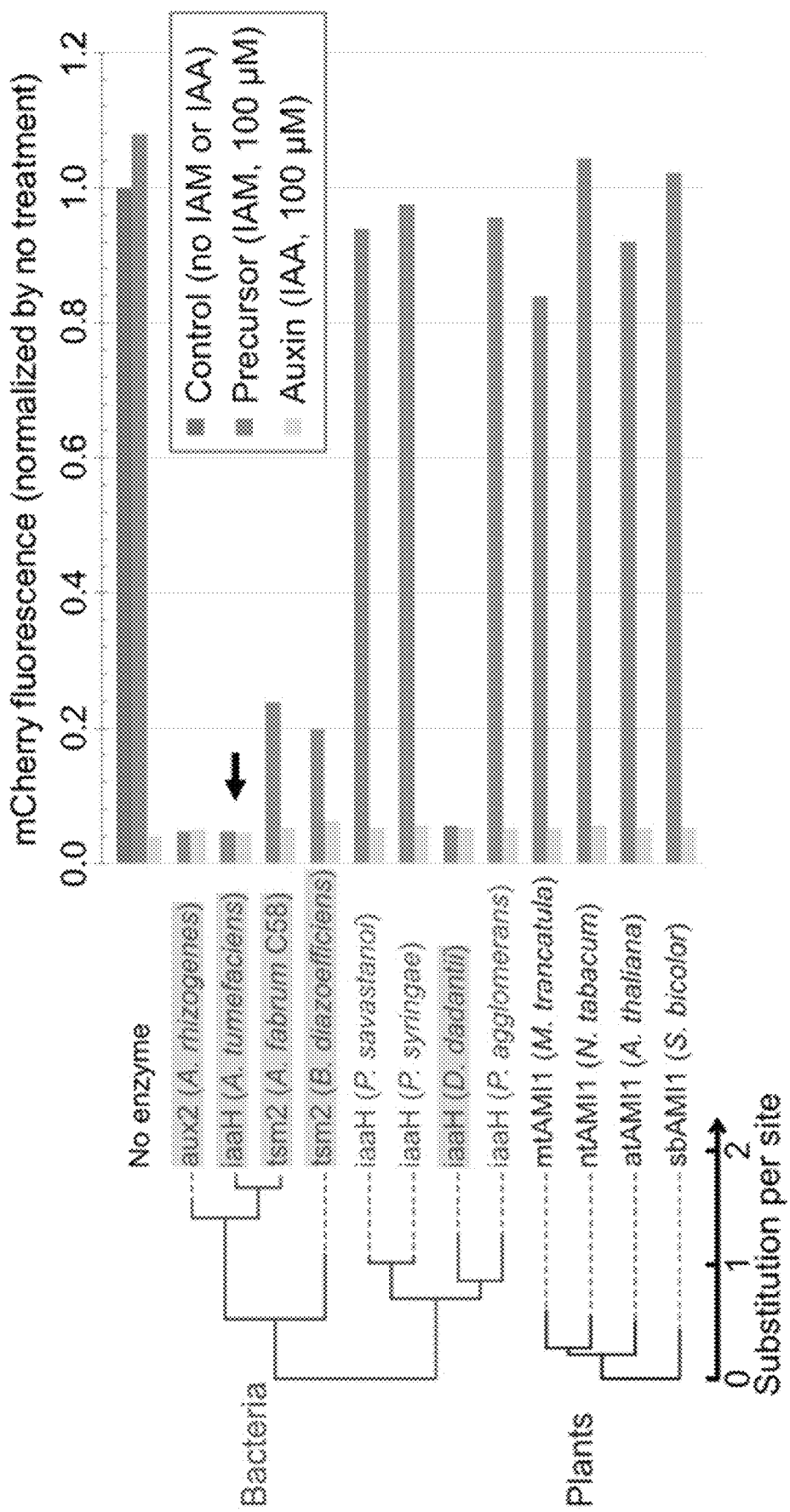
FIGS. 6A-6D depict non-limiting exemplary embodiments and data showing expression of auxin-synthesizing enzymes enables cells to produce auxin.

Three enzymes reduced mCherry to levels comparable to that produced by addition of IAA itself (FIG. 6A). Among these, A. tumefaciens iaaH was selected for further use. This was stably integrated in Receivers to create a Sender-Receiver cell line (FIG. 2B). After 2 days of culturing Sender-Receivers in media containing the IAM precursor, the resulting conditioned media, diluted into an equal volume of fresh media for optimum cell growth, reduced mCherry-AID-Blast$^R$ to levels comparable to those generated by saturating concentrations of IAA (FIGS. 2C and 2D). The Sender-Receiver line was also able to produce the auxin NAA (which, as shown below, has some advantages compared to IAA) from its corresponding precursor NAM (FIG. 2D), albeit with a diminished response compared to NAA, consistent with the higher $EC_{50}$ of NAA compared to IAA. These results show that iaaH expression in mammalian cells can efficiently produce both auxins from corresponding precursors.

Figure 6C:
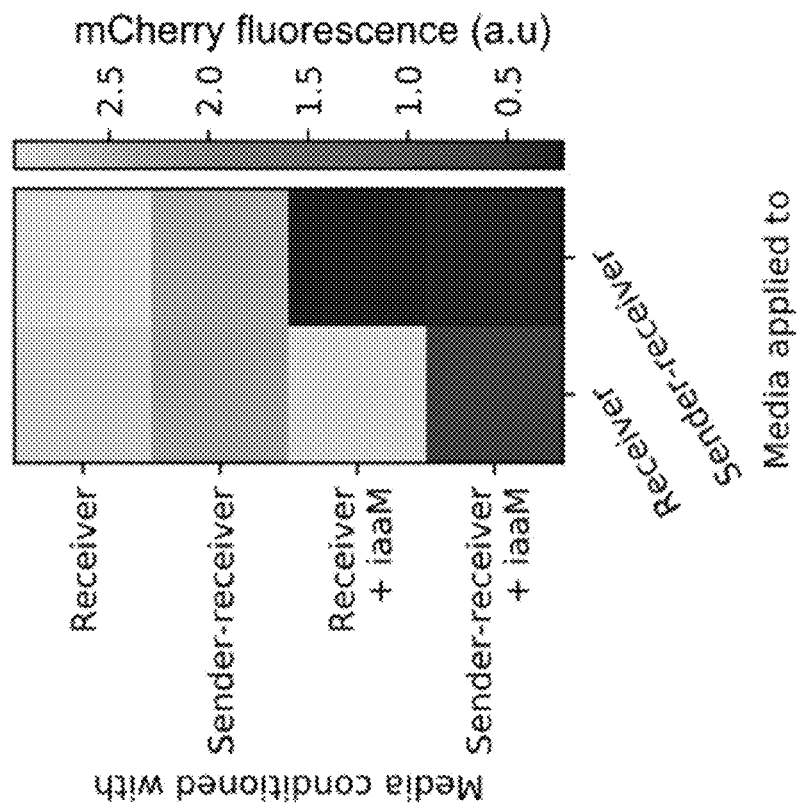
Figure 6B:
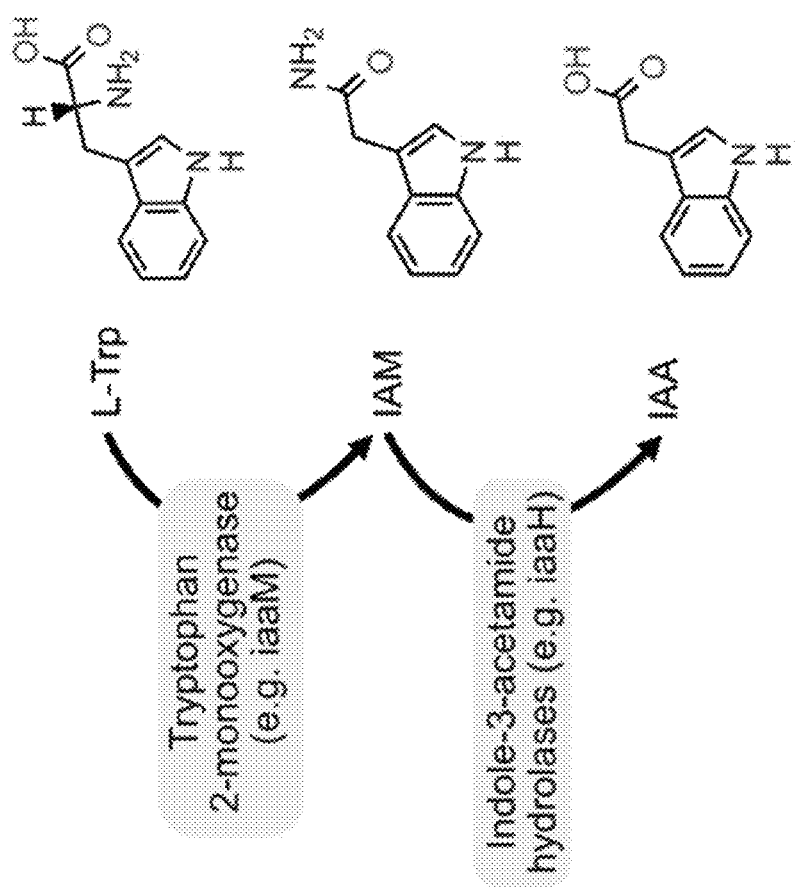

The ability to synthesize auxin in mammalian cells without exogenous precursors could facilitate in vivo applications of population control circuits. Bacterial auxin synthesis pathways use a tryptophan 2-monooxygenase, iaaM (also known as aux1 or TMO) to synthesize IAM from L-tryptophan (FIG. 6B). Sender-Receivers expressing iaaM, cultured in media without precursors, produced auxin concentrations in conditioned media that were sufficient to degrade the auxin reporter in Receiver cells (FIG. 6C). Furthermore, iaaM-expressing Receivers produced precursor in conditioned media, allowing auxin production by Sender-Receivers (FIG. 6C). These results demonstrate the two step iaaM-iaaH auxin synthesis pathway can operate in mammalian cells without exogenous precursors. However, in the following experiments, iaaH was used with added precursors to allow external control of auxin synthesis.

Figure 2E:
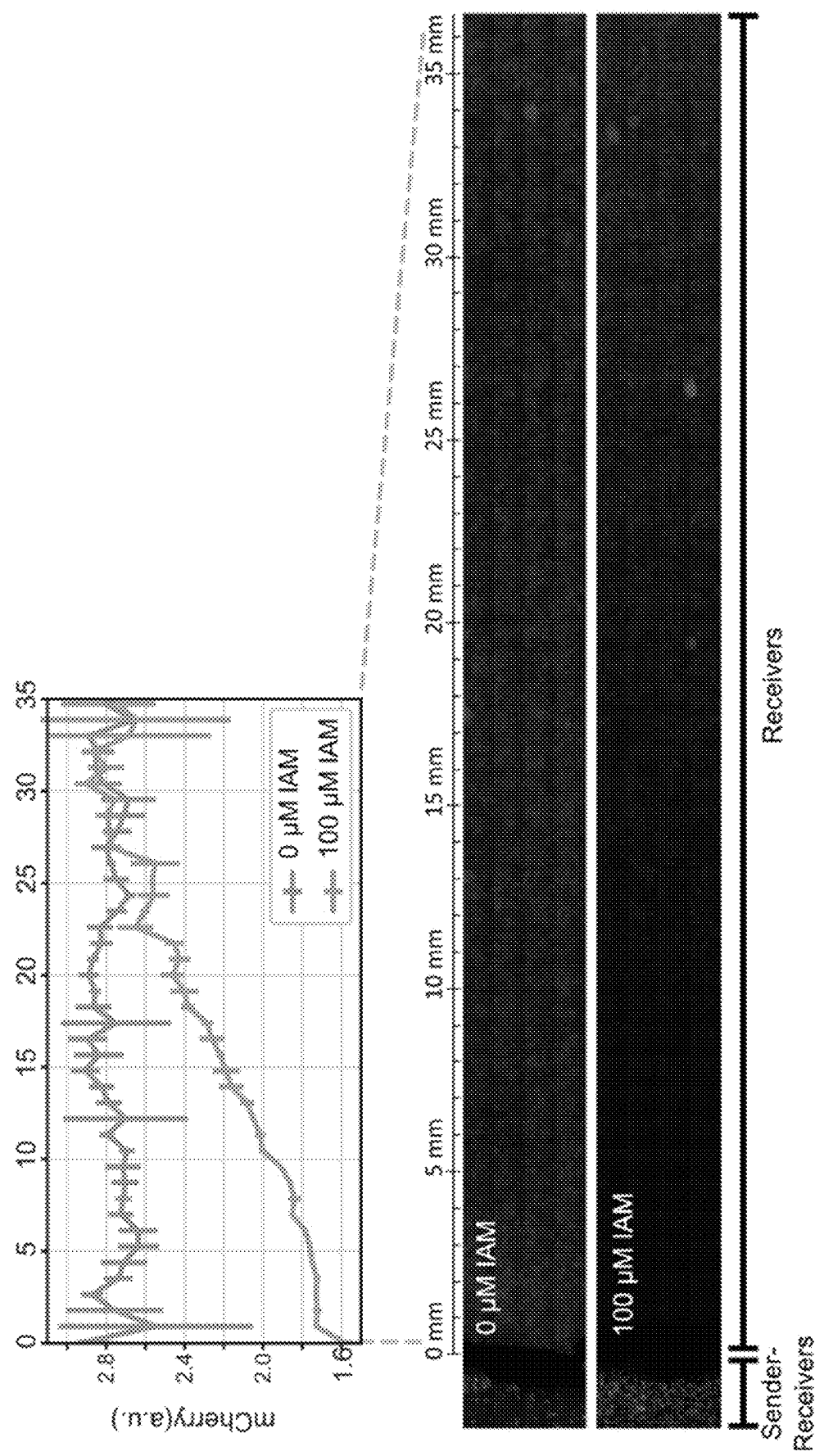
Figure 6D:
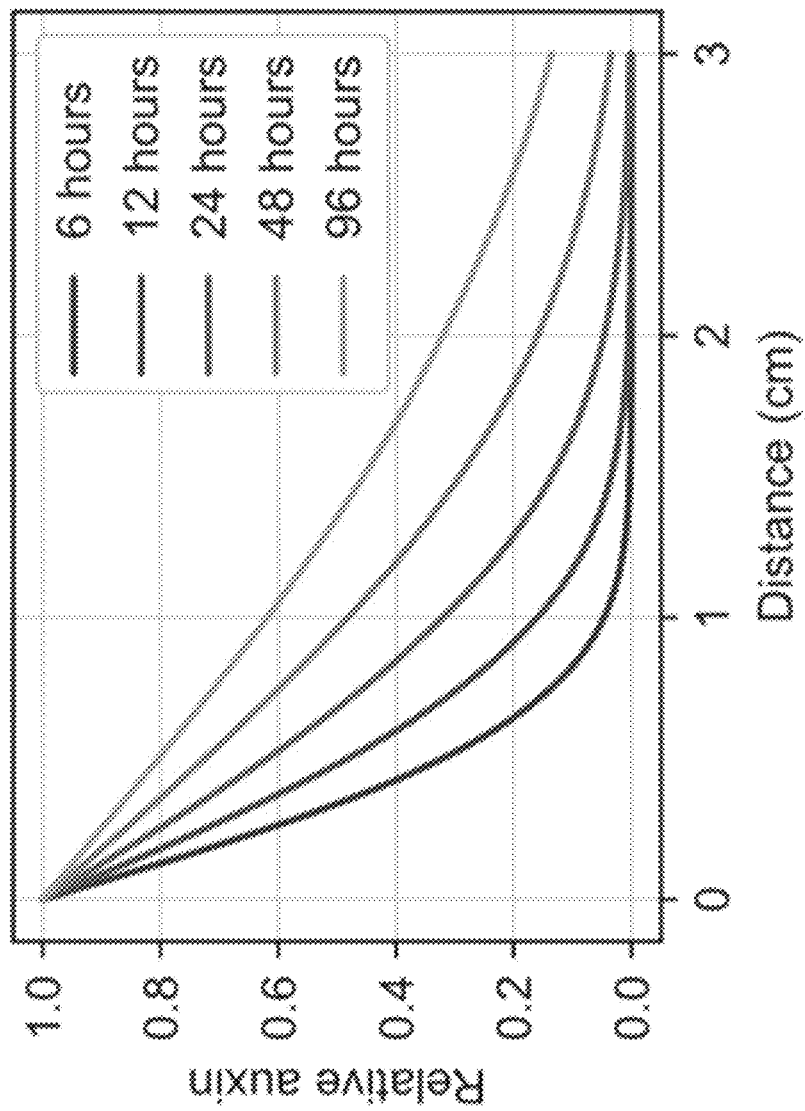

Population control can require integrating cell density over an extended spatial scale. To estimate the spatial range of auxin signaling, a field of Sender-Receivers was seeded adjacent to a larger region of Receivers, applying media in a 1.5% agarose gel to prevent non-diffusive transport (Methods). After 48 hours, mCherry fluorescence was reduced in Receivers proximal to the Sender-Receiver region, forming a long-range gradient. This effect occurred in the presence, but not the absence, of the IAM precursor, consistent with a dependence on IAA production (FIG. 2E, bottom). Image analysis revealed auxin response in Receivers declining to half its maximum value at a length scale of 15.6±0.85 millimeters (Methods), or approximately 750 cell diameters, from the source region, within 48 hours (FIG. 2E, top), consistent with expectations for a small molecule the size of auxin diffusing in buffered solutions (FIG. 6D and supplementary text). These results show that auxin can provide information about global cell density over an extended region, and further demonstrate the possibility of using auxin as a synthetic gradient-forming morphogen for applications in synthetic developmental biology.

Engineered Cell Lines Sense Population Density

Figure 3A:
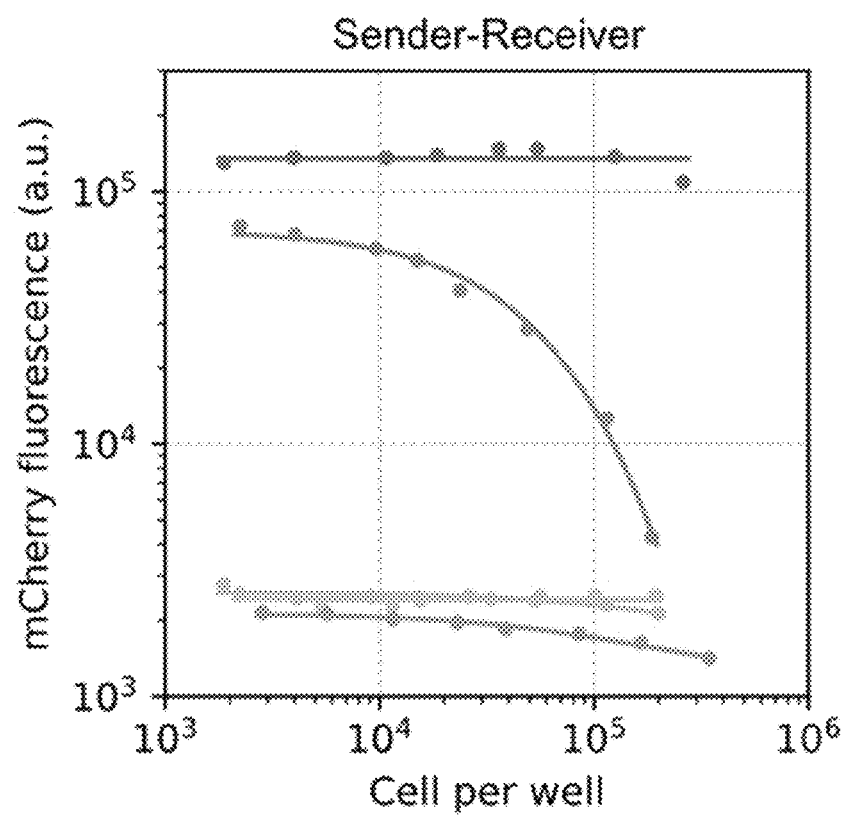
FIGS. 3A-3D depict non-limiting exemplary embodiments and data showing Sender-Receiver cells sense their population density and regulate survival accordingly.
Figure 3B:
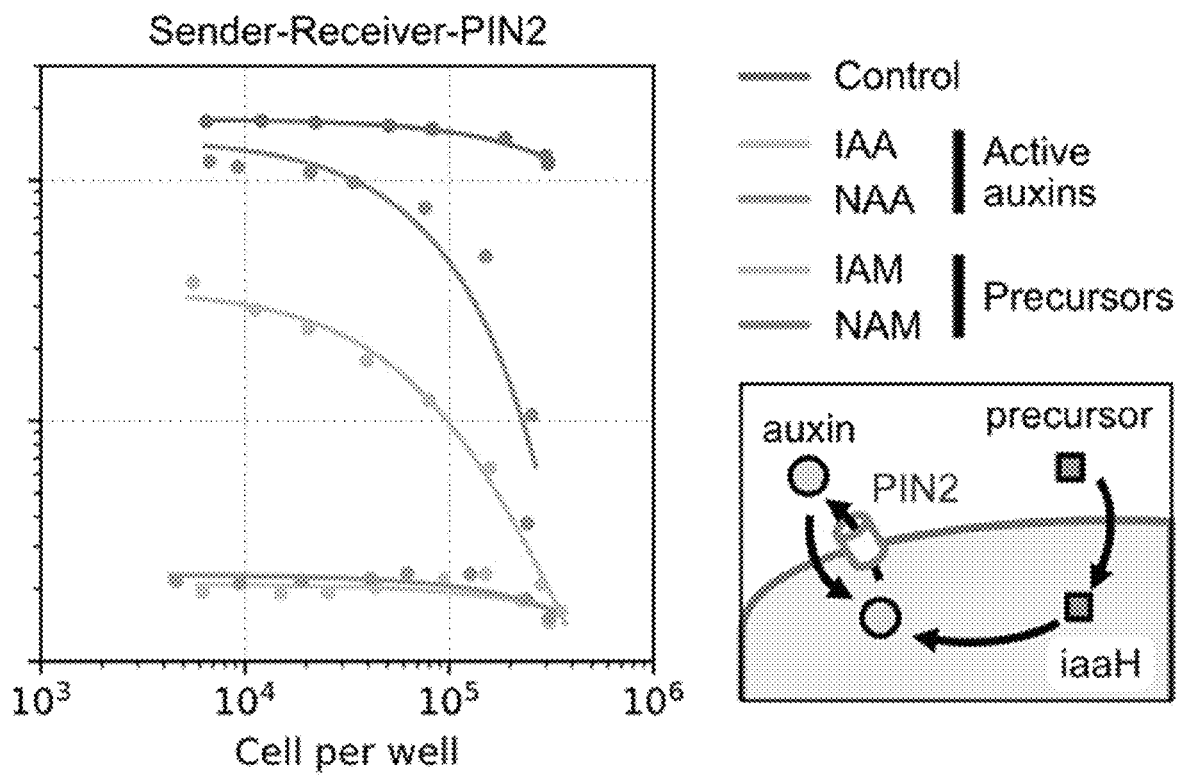
Figure 3C:
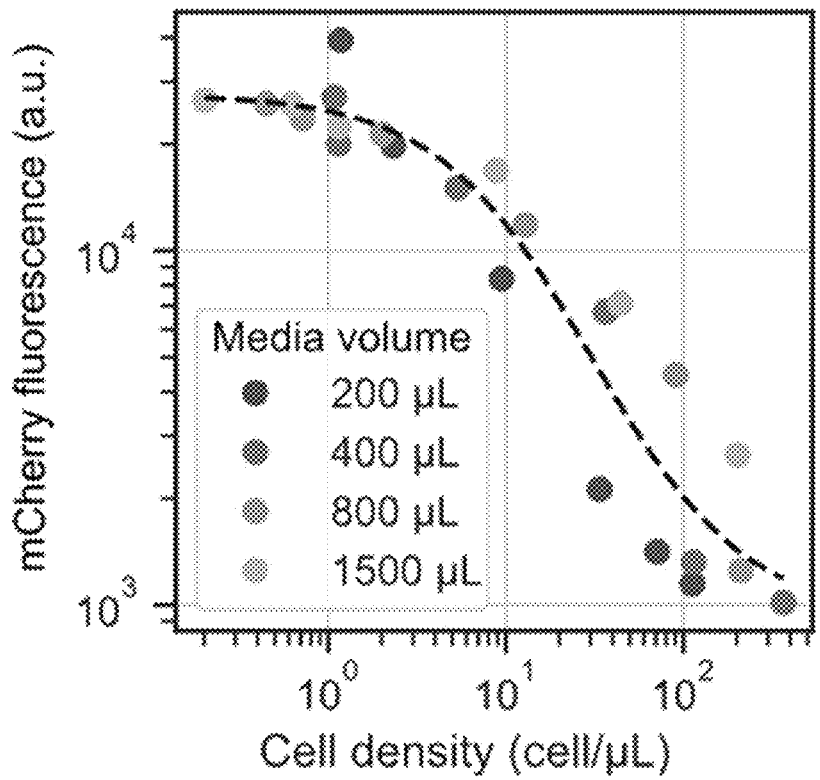
Figure 7A:
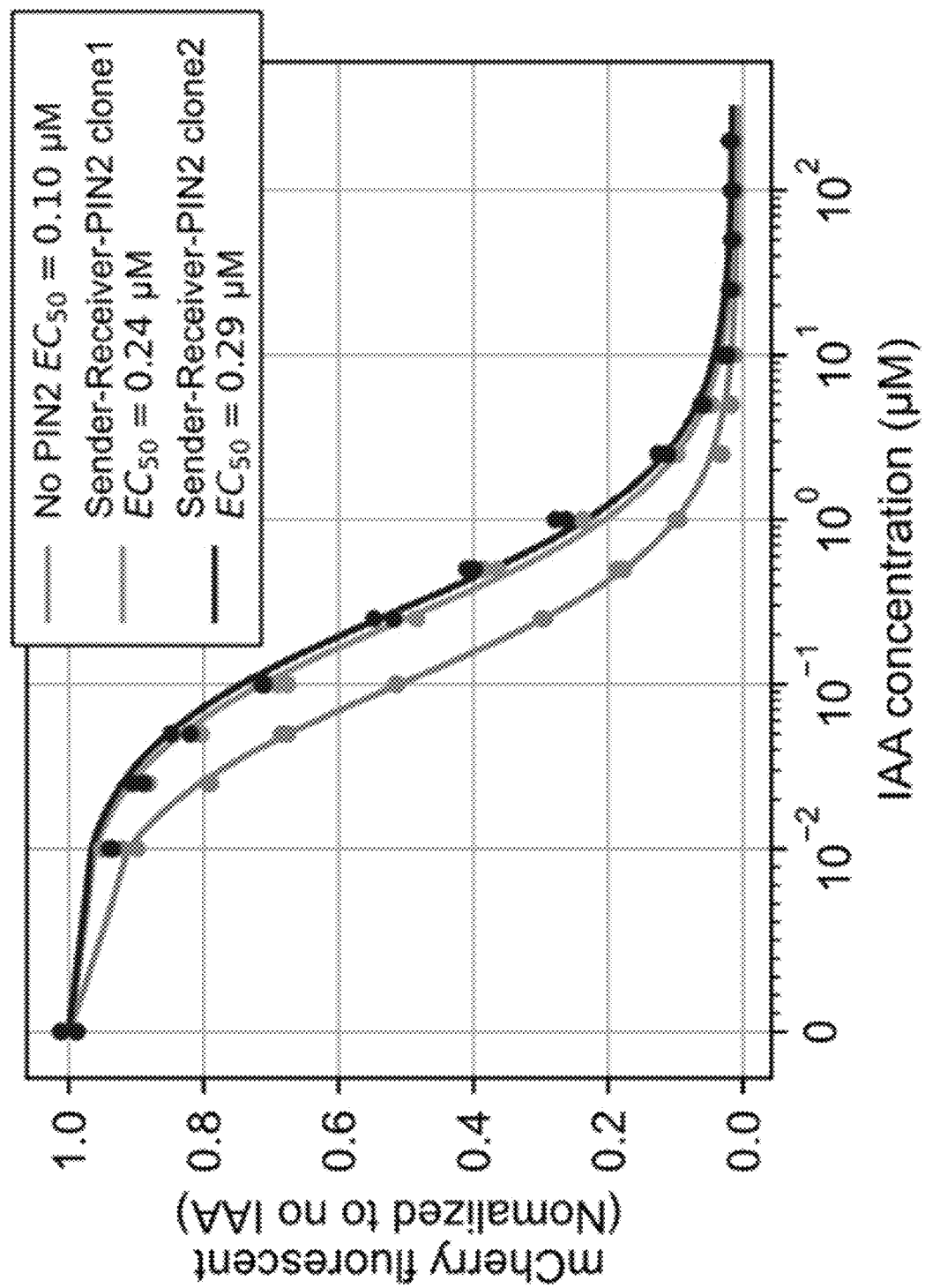
FIGS. 7A-7D depict non-limiting exemplary data showing Sender-Receiver cells sense their population density and regulate survival accordingly.
Figure 7B:
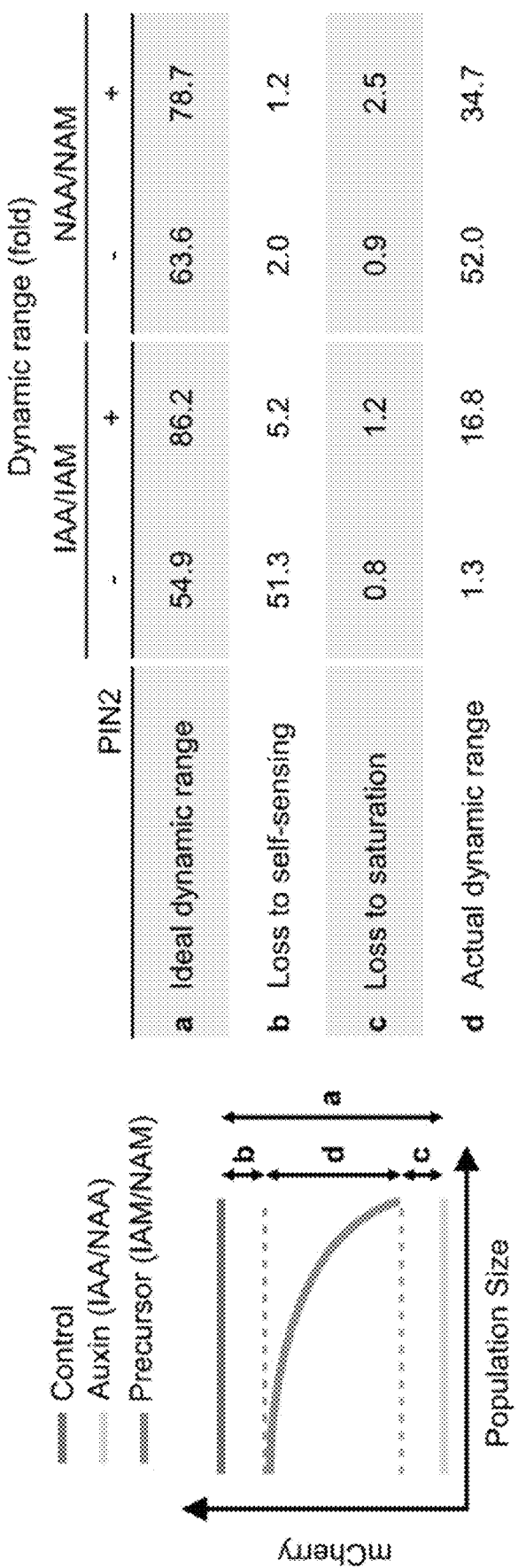

It was next asked whether Sender-Receiver cells could sense their own population density by producing auxin at a rate proportional to population size and sensing auxin concentration in the local environment (quorum sensing, FIG. 1A, middle panel). The dependence of reporter expression on cell population density in the presence of concentrations of each precursor sufficient to generate saturating levels of auxin was analyzed. With the NAM precursor, reporter fluorescence decreased in response to increasing population density (FIG. 3A, darker blue line). By contrast, addition of IAM generated a strong, but density-independent, decrease in fluorescence (FIG. 3A, light blue line). It was reasoned that this density-independence could result from IAA's limited membrane permeability at neutral pH, potentially causing newly synthesized IAA to accumulate intracellularly. Though the rate of exchange is sufficient to fully induce receiver cells (on the timescale of days, FIGS. 2D and 2E), it could be insufficient to prevent intracellular accumulation of auxin due to the faster rate of auxin production by iaaH (typically several 11M per minute) in the same cell. To overcome this issue, the auxin exporter PIN2 from *Arabidopsis thaliana* was stably expressed in Sender-Receiver cells (Sender-Receiver-PIN2 cells) (FIG. 3B, right). PIN2 expression produced a modest decrease in auxin sensing, suggesting the transporter was functional (FIG. 7A), but allowed quorum sensing across most of the full dynamic range of auxin concentration sensing (FIG. 3B; FIG. 7B). Cells responded similarly to cell density across different culture media volumes, indicating quorum sensing responded to cell density rather than absolute cell number (FIG. 3C). Together, these results establish that Sender-Receiver cells can sense their own population density in two ways: using NAM without PIN or using either precursor with PIN2.

The Paradaux Cell Line Implements Paradoxical Population Control

Figure 3D:
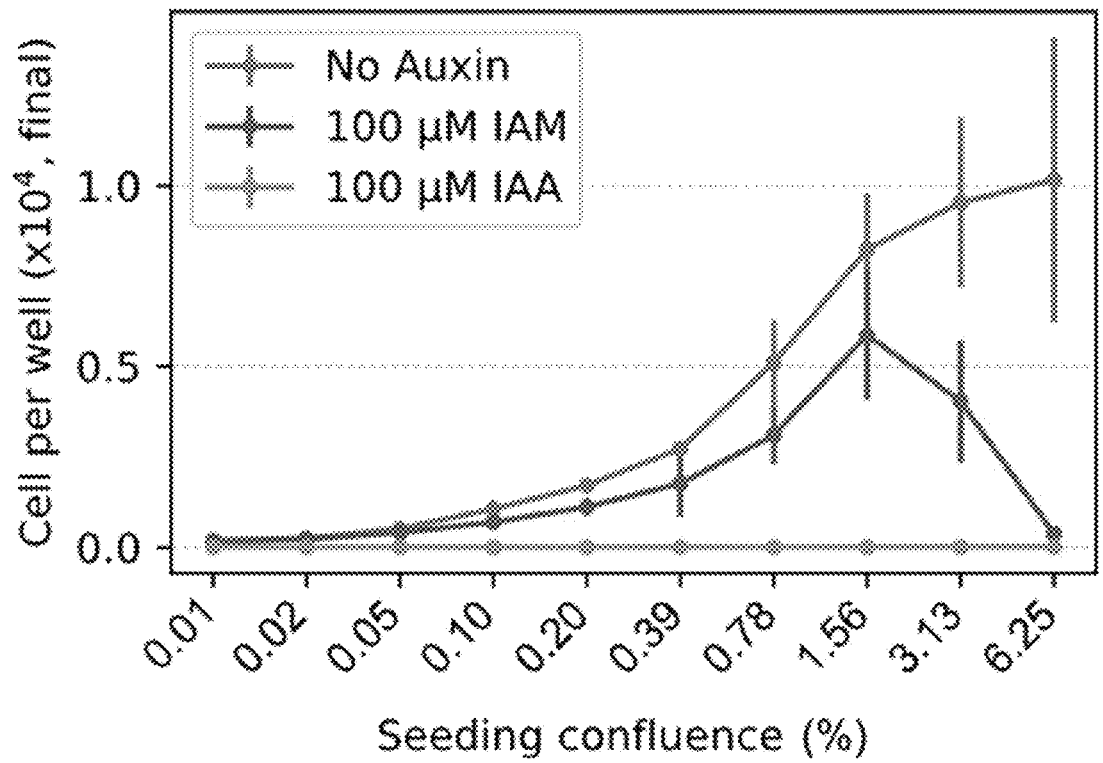

Linking quorum sensing to cell survival could enable cell population control (FIG. 1A, right). To test this possibility, cells were seeded at different densities in media containing blasticidin, to make cell growth dependent on BlastR levels, as well as the precursor IAM. After 4 days, cells seeded at high, but not low, densities exhibited reduced cell numbers compared to cells plated at the same density without IAM or IAA (FIG. 3D). These results demonstrate density-dependent control of cell survival.

Figure 7C:
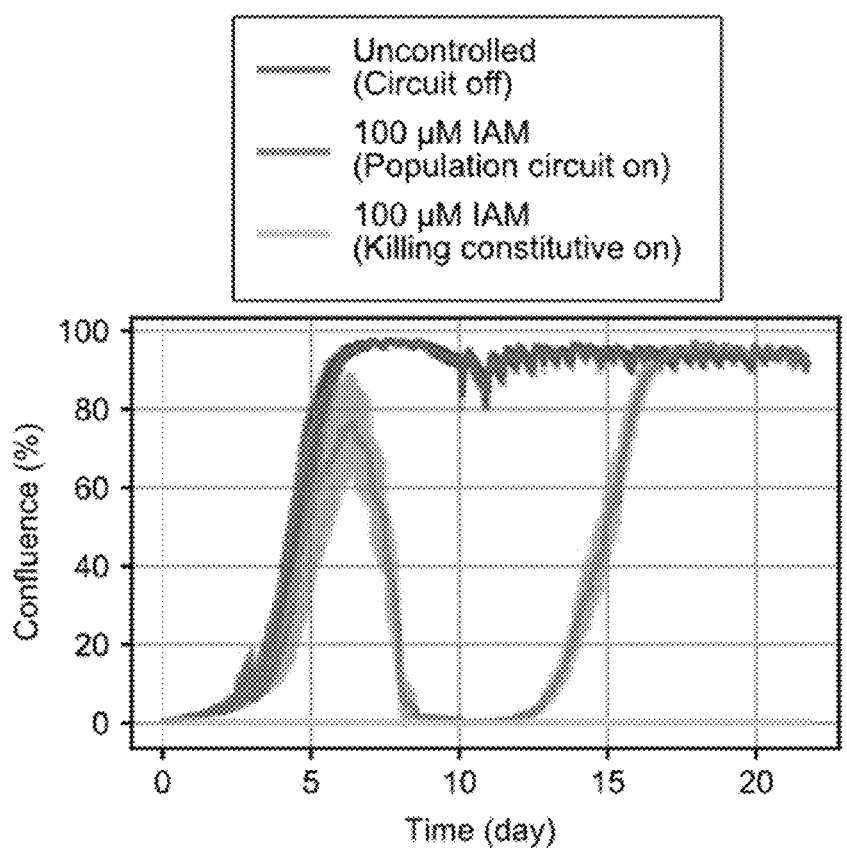
Figure 7D:
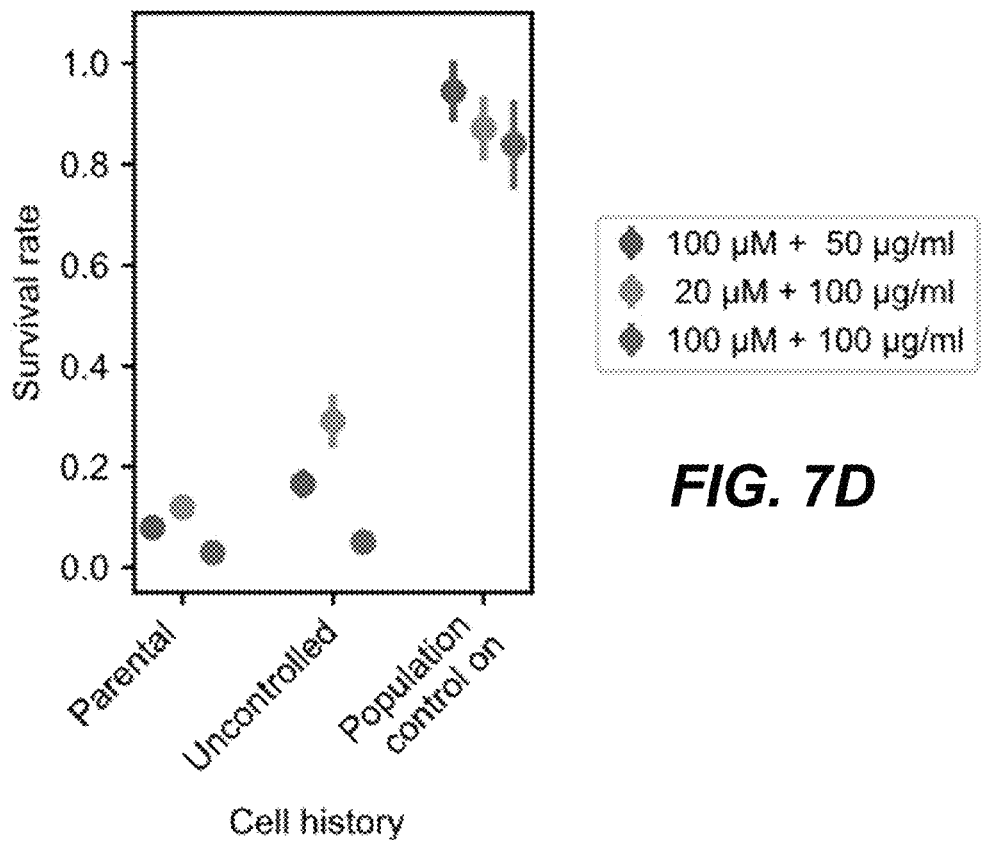

This negative autoregulatory feedback loop resembles a similar design in bacterial systems, where a quorum sensing signal induces cell killing. As with the bacterial circuit, this negative feedback circuit is inherently susceptible to 'cheater' mutations that allow cells to escape control. In fact, when the Sender-Receiver-PIN2 cell line was cultured in media containing blasticidin and IAM to activate the circuit, escape from population control was observed within 16 days (FIG. 7C) due to "cheater" cells that acquired the ability to proliferate in high auxin and blasticidin (FIG. 7D).

Figure 4A:
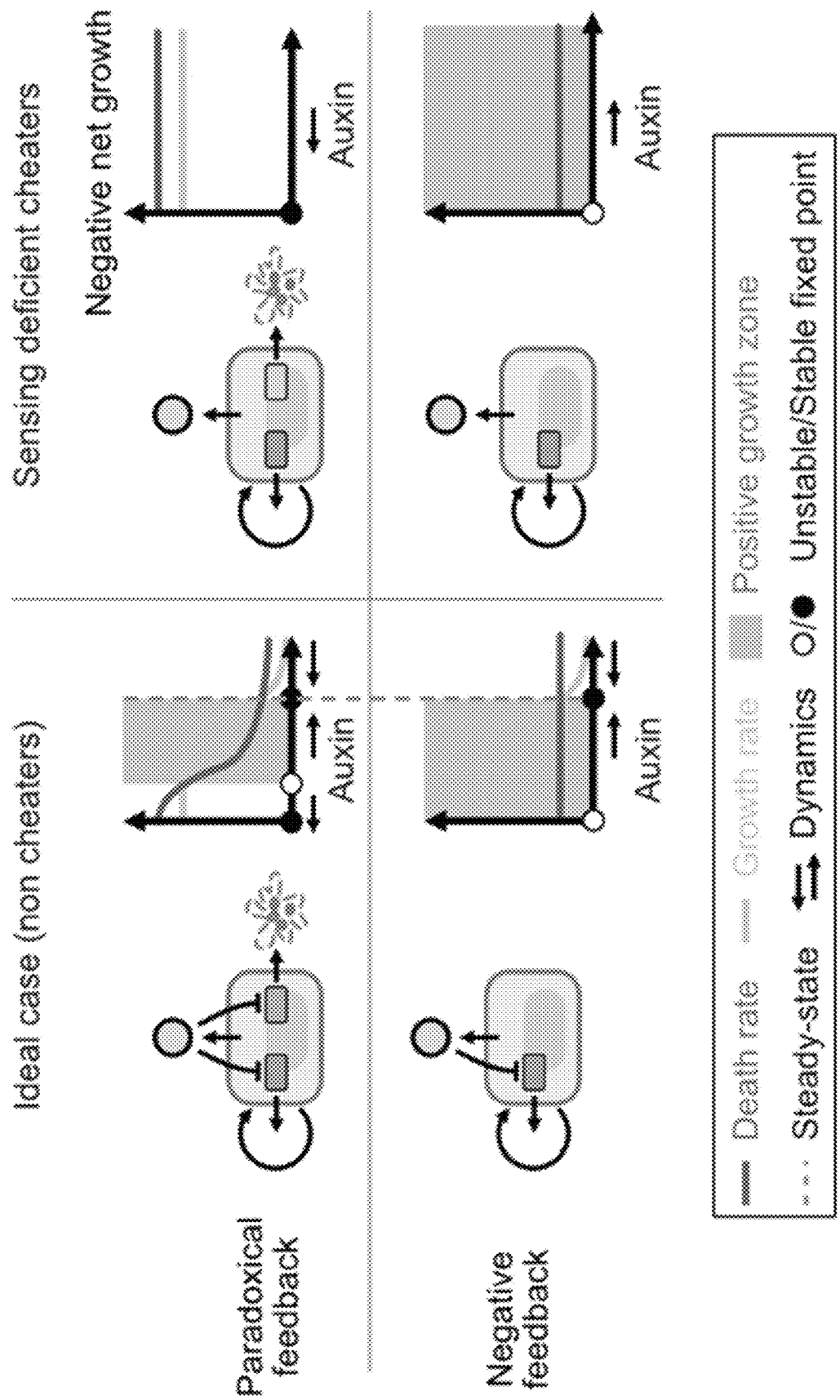

A 'paradoxical' circuit architecture, in which a quorum sensing signal either stimulates or inhibits both cell proliferation and cell death, can make population control more mutationally robust, by counter selecting against cheaters that lose signal sensing. In the paradoxical circuits, positive net growth can occur only at signal concentrations lying between two non-zero bounds, similar to the Allee effect in ecology (FIG. 4A, blue regions). By comparison, the simpler, non-paradoxical negative feedback architecture, in which signals only down-regulate growth, exhibits positive net growth at all signal concentrations below a single upper bound (FIG. 4A, lower left). While both circuits exhibit stable fixed points at the maximum of their positive growth zones, they respond differently to cheater mutations that reduce auxin sensitivity (the predominant cheater phenotype observed in FIGS. 7B and 7C). Specifically, with negative feedback alone, such cheater mutations extend the regime of positive net growth to higher signal concentrations and cell densities, providing a growth advantage over non-mutant cells (FIG. 4A, lower right). By contrast, in the paradoxical circuit, the same mutation would cause signal sensing to drop below the lower bound, activating the cell death arm of the circuit (FIG. 4A upper right). In this way, the paradoxical circuit design should suppress escape by cheater mutations that reduce or eliminate signal sensing.

A paradoxical circuit was designed in which auxin represses both proliferation and death, a configuration that is well-suited to the inhibitory nature of auxin-dependent protein degradation (FIG. 4A, upper left). In addition to auxin regulation of Blast R a parallel regulatory pathway was added, in which auxin negatively regulates cell death by inducing degradation of iCasp9, an ectopically expressed master regulator of apoptosis (caspase 9) activated by the small molecular dimerizer AP1903 (FIG. 4B). An AID domain in iCasp9 was added to provide auxin regulation, and fused it to the monomeric GFP variant mGFPmut3, to allow direct readout of its concentration (FIG. 4B). This design allows one to operate the same cell line in three regimes, depending on what combinations of blasticidin and AP1903 are added to the medium. With only blasticidin, the circuit operates in the pure negative feedback regime; with blasticidin and AP1903 it operates in the paradoxical regime; and with neither inducer it has unregulated growth. Because it implements paradoxical regulation through auxin, and this circuit was termed 'Paradaux.'

Figure 4D:
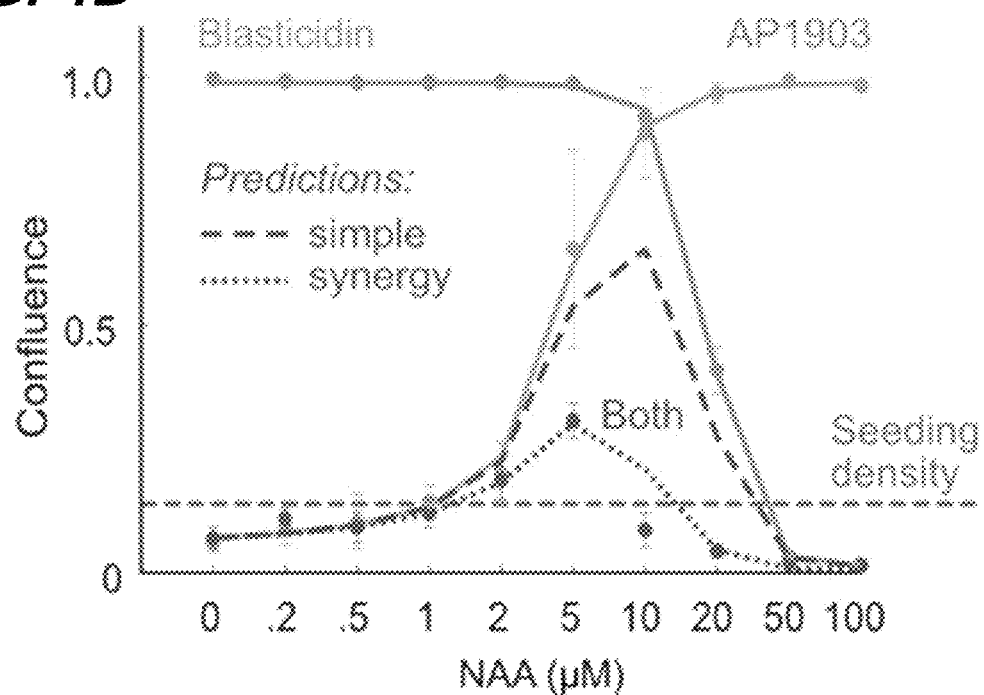

To encode the Paradaux circuit, a single multi-protein construct expressing osTIR1, the auxin-regulated iCasp9 system, and the auxin-regulated Blast R construct described above was designed (FIG. 4C). To eliminate one potential mechanism for evolutionary escape, Blast$^R$ was positioned at the C-terminal end of the construct, so that premature stop codon mutations would deactivate Blast®, decreasing survival. The construct was integrated to create stable monoclonal CHO-K1 cell lines for further analysis. Survival of these cells increased monotonically with auxin in the presence of AP1903 and decreased with auxin in the presence of blasticidin, demonstrating that both branches of the Paradaux circuit were individually functional (FIG. 4D, red and green lines). (An additional monoclonal line with an independent integration of the same circuit is shown in FIG. 8A). Further, including both blasticidin and AP1903 produced a biphasic survival curve (FIG. 4D, blue), which can, in some embodiments, be the key requirement for paradoxical population control.

Mathematical Modeling Identifies Parameter Regimes Required for Paradoxical Control To identify parameter regimes, including concentrations of blasticidin and AP1903, that optimize its population control capabilities, a mathematical model of the Paradaux circuit was developed and analyzed. Assuming rapid intracellular-extracellular auxin equilibration, as observed for NAA (FIG. 3A), and timescale separation between fast intracellular dynamics and the slower cell population dynamics (FIG. 8B, Supplementary Text), an approximate model based on two differential equations was derived. The first represents the extracellular auxin concentration shared by all cells, denoted A. The second describes the cell population size, denoted N, ranging from 0 to the environmental carrying capacity, normalized as 1 (Supplementary Text).

It was assumed auxin is produced at a constant rate per cell, $\lambda_A$, and diluted by periodic media changes, approximated as a continuous process with rate constant $\delta_A$:

$$\frac{dA}{dt} = \lambda_A \cdot N - \delta_A \cdot A \qquad \text{(Equation 1)}$$

It was also assumed cell growth can be described by a generalized logistic function (FIG. 8C, Supplementary Text), modified to incorporate the effects of blasticidin, B, and iCasp9, I, on growth:

$$\frac{dN}{dt} = R_g(B, I, A) \cdot N \cdot (1 - N^v) \quad \text{(Equation 2)}$$

Here, the exponent v is the non-linear correction parameter in the generalized logistic growth function. $R_g$ denotes the cellular growth rate, and can be written as a sum of two Hill-like terms representing the combined auxin dependent effects of blasticidin and iCasp9 on cell survival (See Equations S13, S14, and S15 for the exact form).

Figure 8D:
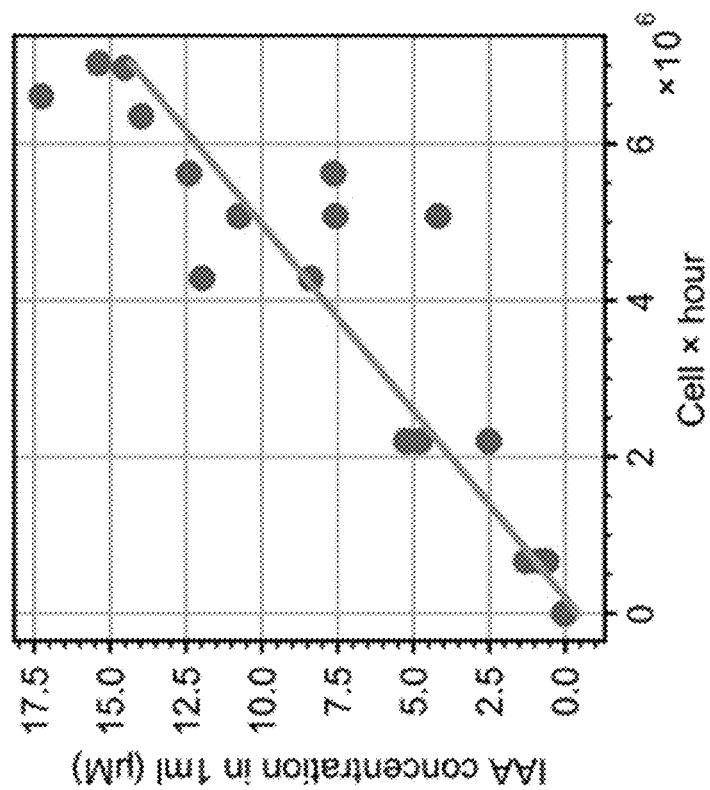
Figure 8C:
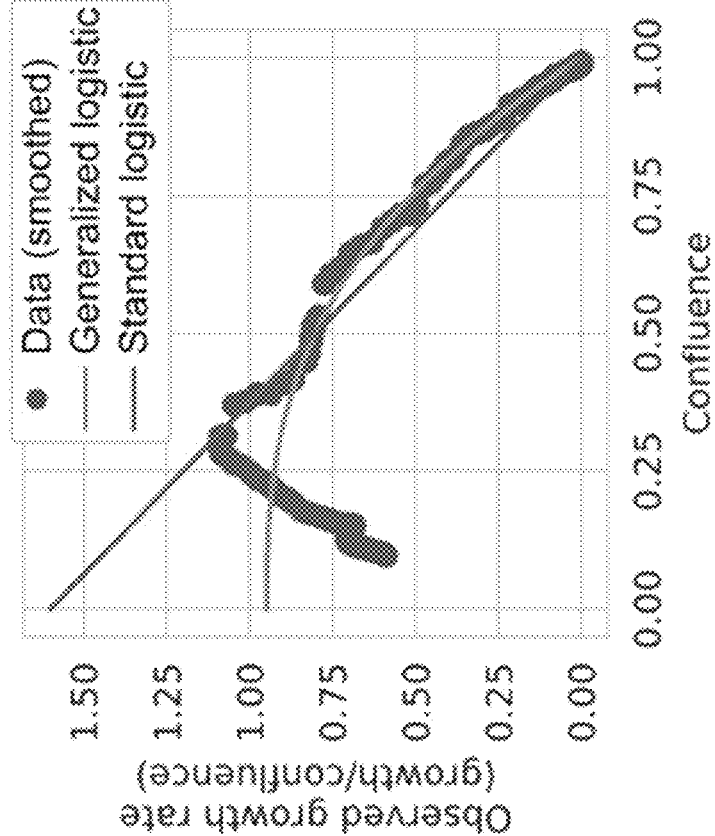

To constrain the effective biochemical parameter values in the model, experimentally measured values of the sensitivity of AID-tagged proteins to auxin, the unperturbed cell growth rate, the auxin secretion rate, and the non-linear growth correction parameter were incorporated (FIG. 1C; FIGS. 8C and 8D). Remaining parameters were fit using the auxin-dependent survival rates measured with either AP1903 or blasticidin (FIG. 4D, red and green line). The model initially overestimated actual growth rates when both arms of the circuit were simultaneously active (FIG. 4D, dashed blue lines), possibly due to previously reported synergy between apoptosis and blasticidin-dependent translational inhibition. A phenomenological synergistic interaction term was therefore added to the growth rate expression (Equation S17 and Supplementary text; Table 2, parameter set 1; FIG. 4D, dotted line). Finally, it was checked that experimental parameter values expected to be independent of integration site, such as maximum cell death and growth rates, as well as synergy and Hill coefficients, agreed, within ~2-fold, with those measured for a second Paradaux monoclonal cell line with an independent integration of the circuit construct (FIG. 8A; Table 2, parameter set 2).

Figure 4E:
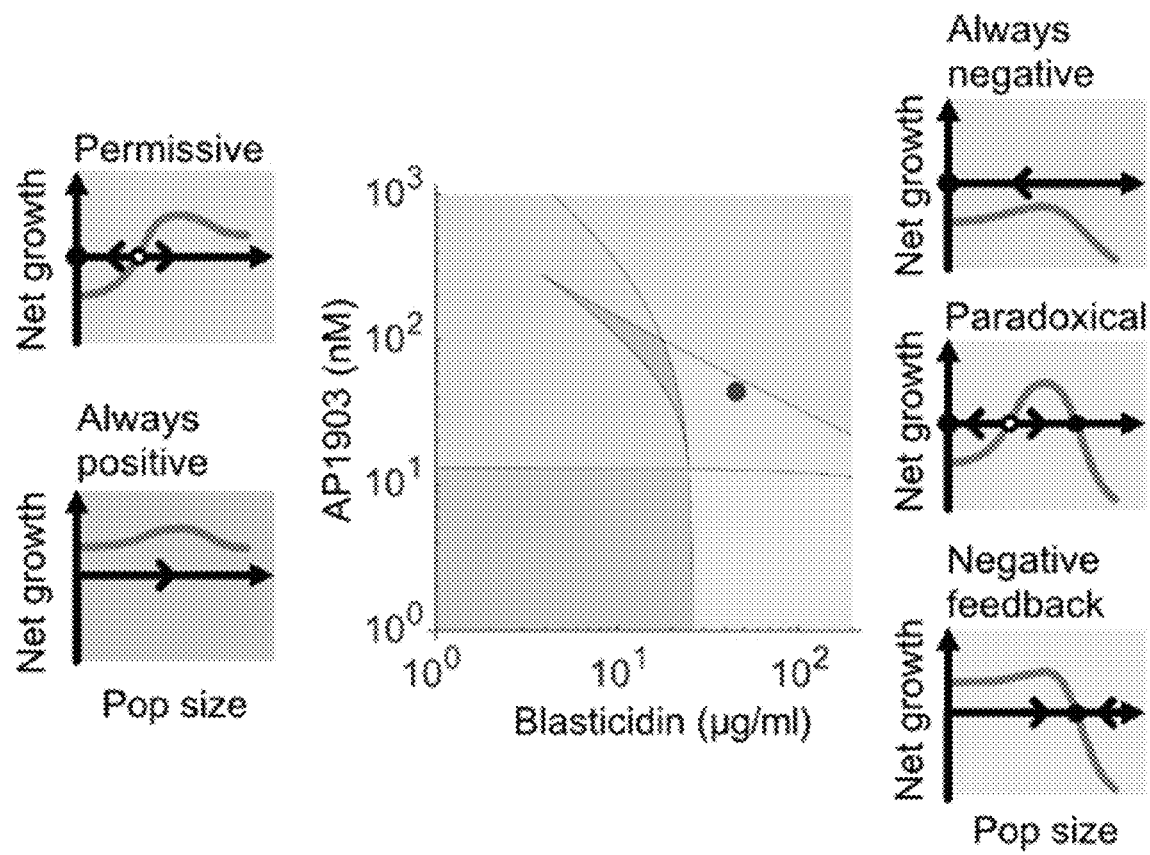
Figure 4F:
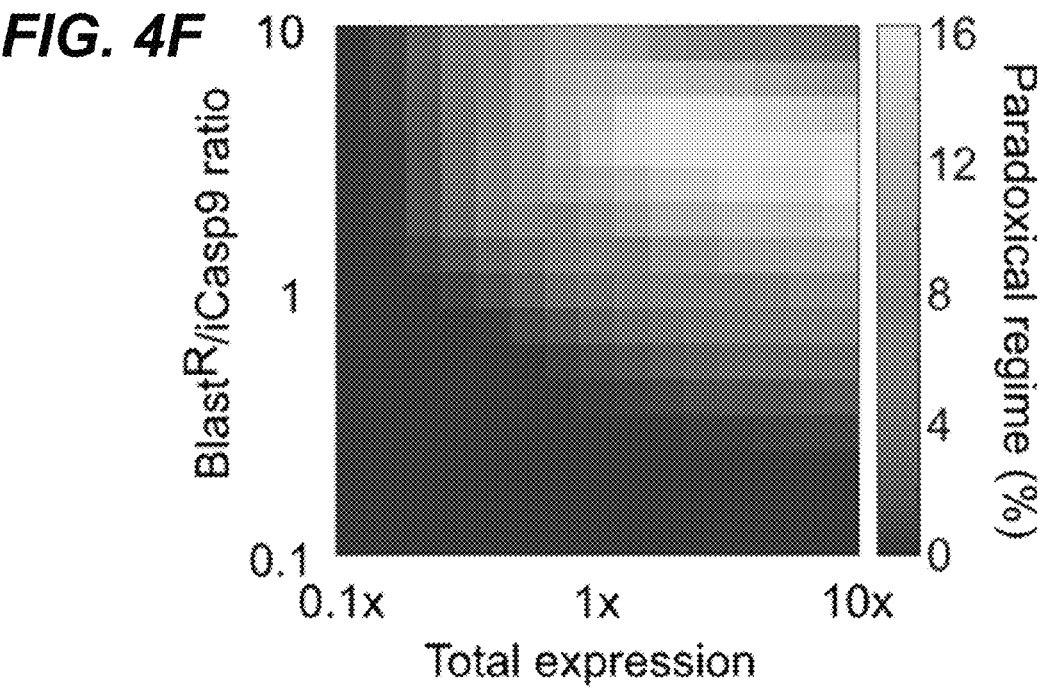
Figure 4G:
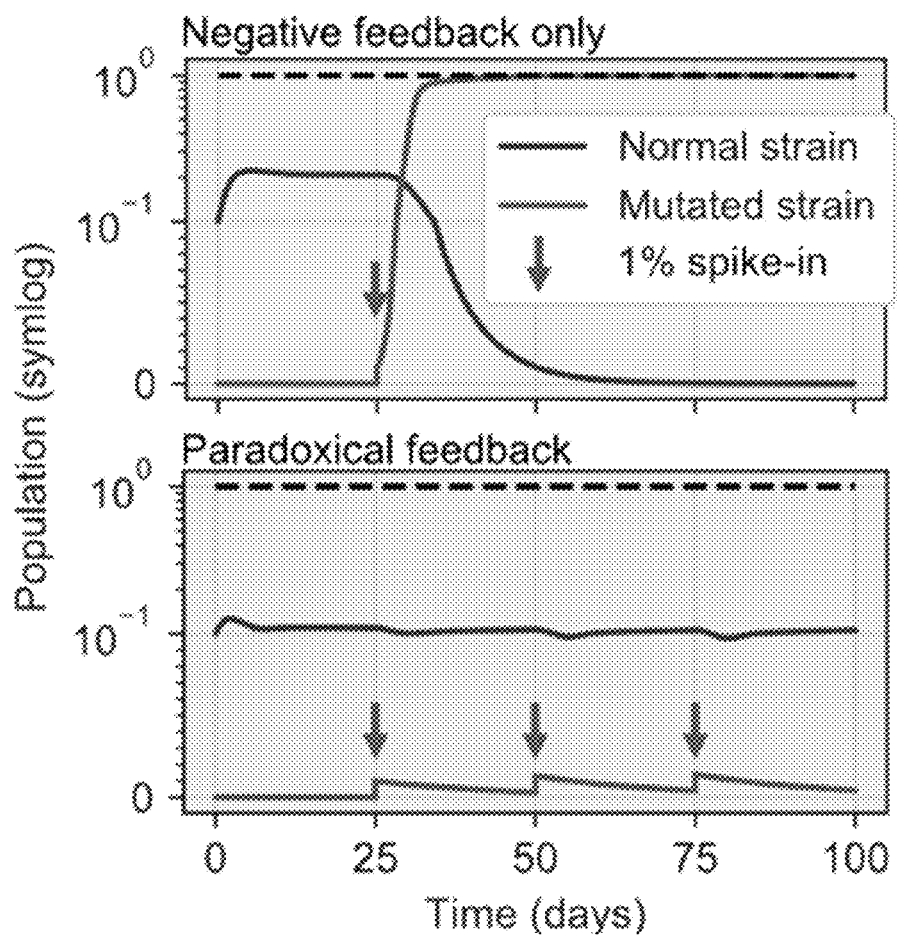
Figure 8E:
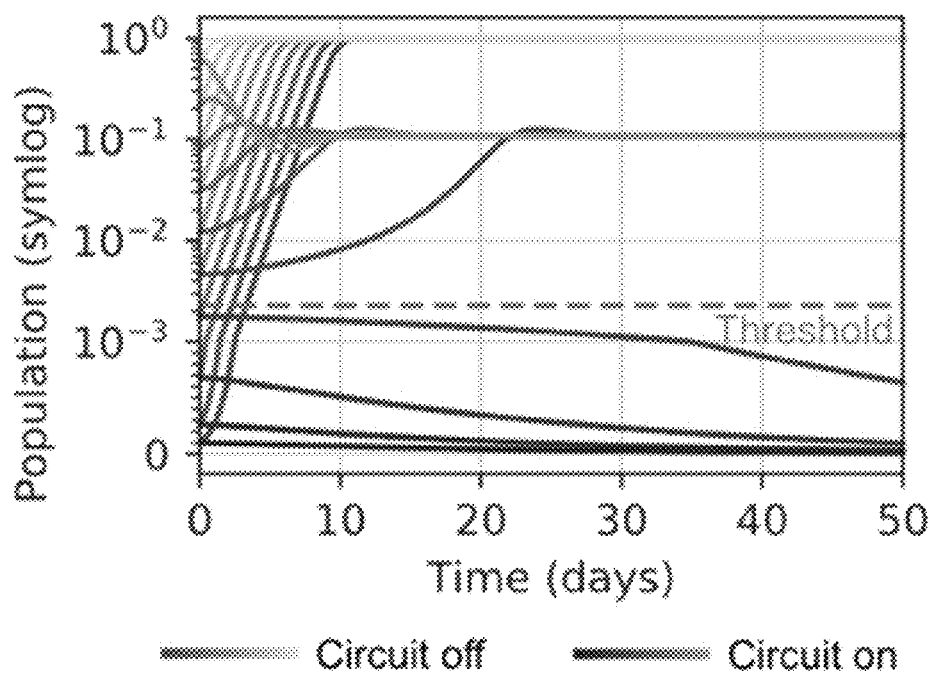

Before initiating challenging long-term analysis of population control, the model was used to systematically scan for AP1903 and blasticidin concentrations likely to favor paradoxical population control. For each pair of AP1903 and blasticidin concentrations, the dependence of cell survival on auxin was classified into one of five qualitatively distinct behaviors: (1) positive net cell growth across all auxin concentrations (FIG. 4E, purple background); (2) negative net cell growth across all auxin concentrations (FIG. 4E, green background); (3) permissive growth, in which cells proliferate only beyond a minimum auxin concentration (FIG. 4E, pink background); (4) simple negative feedback control, analogous to the Sender-Receiver behavior (FIG. 4E, yellow background); and (5) paradoxical control (FIG. 4E, blue background). Only the negative and paradoxical feedback regimes produce a non-zero, stable fixed point, allowing population control. The desired paradoxical regime occurred in a window of blasticidin and AP1903 concentrations centered around 50 µg/ml and 50 nM, respectively (FIG. 4E). Further, this paradoxical window could be enlarged by optimizing the expression levels of iCasp9 and $Blast^R$ (FIG. 4F). Within the paradoxical regime, the circuit produced the expected bistability of population size (FIG. 8E) and robustness to mutations that eliminate auxin sensing, which were implemented by setting sensed auxin to 0 (FIG. 4G).

Additionally, the effect of the 2-3 day time delay required for blasticidin to kill sensitive cells was explored. Time delays in negative feedback loops are known to produce oscillations under some conditions. In simulations of the paradoxical circuit, inclusion of a time delay led to oscillations of population density with periods of 2 weeks or more, depending on the value of the delay parameter, τ. A bifurcation between damped and sustained oscillations occurred at approximately τ=48 hrs. Taken together, these results provided insight into parameter dependence and expected dynamics of the circuit, and identified specific AP1903 and blasticidin concentrations for long timescale analysis of the experimental circuit.

Paradoxical Circuits Extend the Duration of Population Control

Figure 5A:
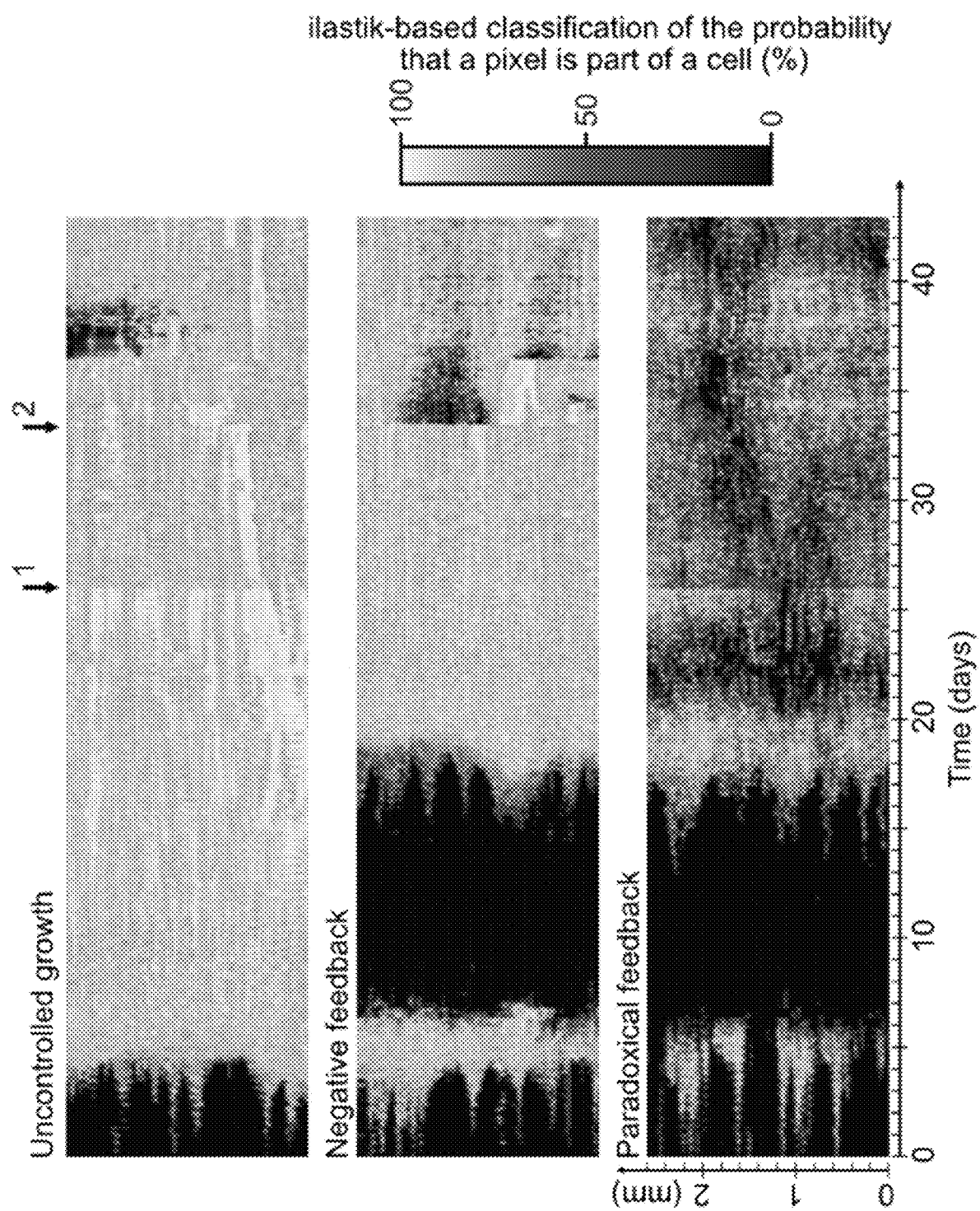
Figure 5B:
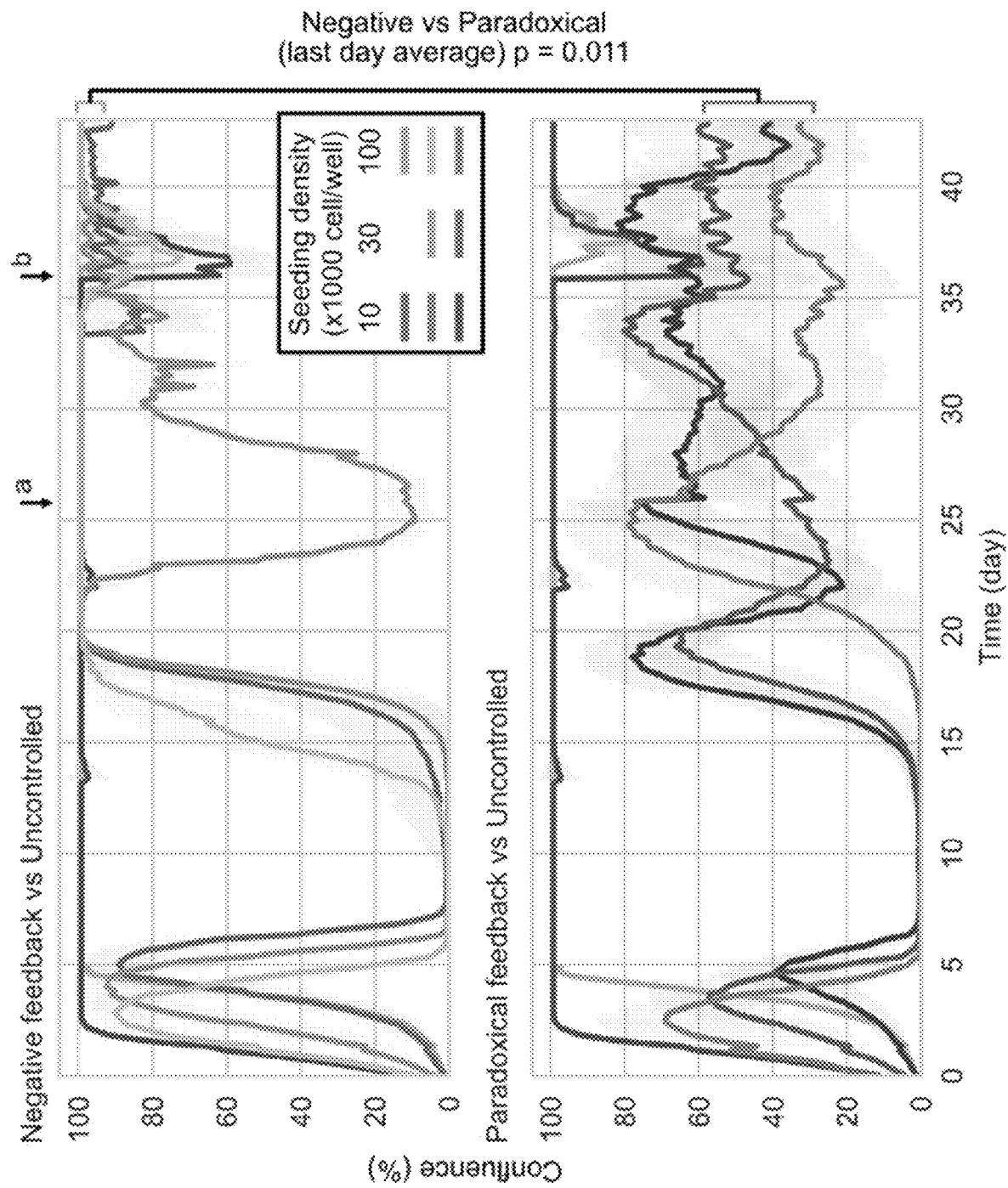
Figure 8F:
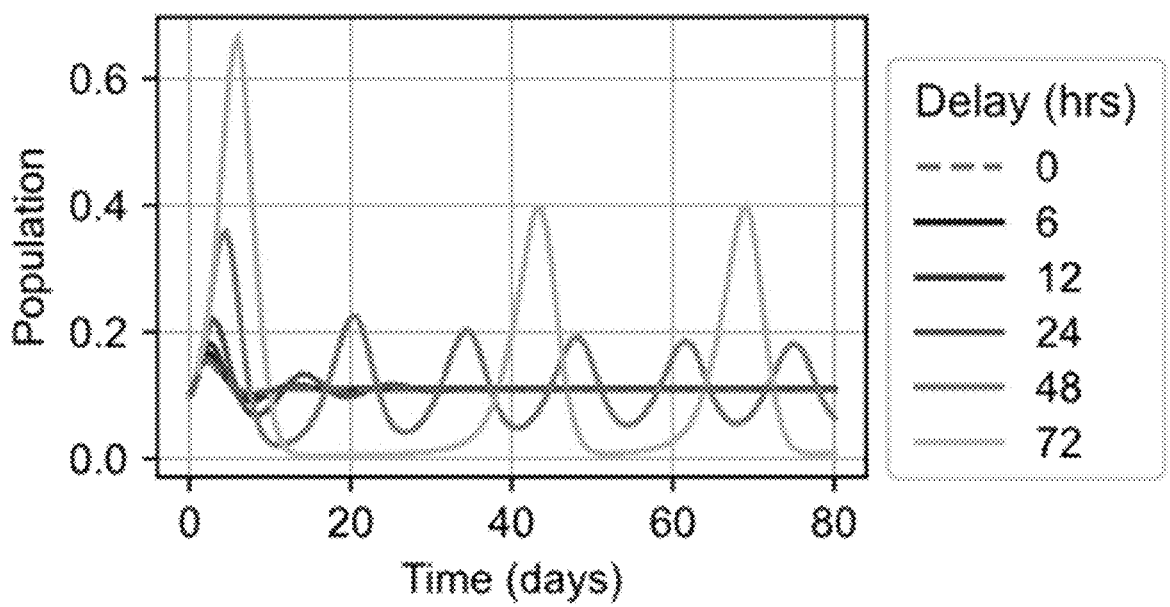

To experimentally analyze population control, cultures of the Paradaux cell line were continuously monitored for 43 days (an arbitrary time scale constrained by technical limitations). Cells were cultured in regimes of uncontrolled growth (no blasticin or AP1903), negative feedback (blasticidin added), or paradoxical feedback (both blasticidin and AP1903). In the uncontrolled regime, cells grew to, and remained at, full confluence for the duration of the movie (FIGS. 5A and 5B). In the latter two regimes, population dynamics exhibited oscillations, consistent with models incorporating time delays for blasticidin-dependent cell killing (FIG. 8F). Time-lapse imaging from FIG. 5A revealed robustness of the paradoxical population control architecture. In a time-course movie experiment, 10,000 cells were seeded per well into a 24-well imaging plate (FIG. 5A), with no control (100 µM NAM; left), negative feedback (100 µM NAM and 50 µg/ml blasticidin; middle), or paradoxical feedback (100 µM NAM, 50 µg/ml blasticidin, and 50 nM AP1903; right). Images of constitutively expressed mTagBFP2 were taken with a 20× inverted microscope every 4 hours, in a 5×5 grid, and stitched together (Methods). Robustness of the paradoxical population control architecture was observed.

Figures 9A, 9B:
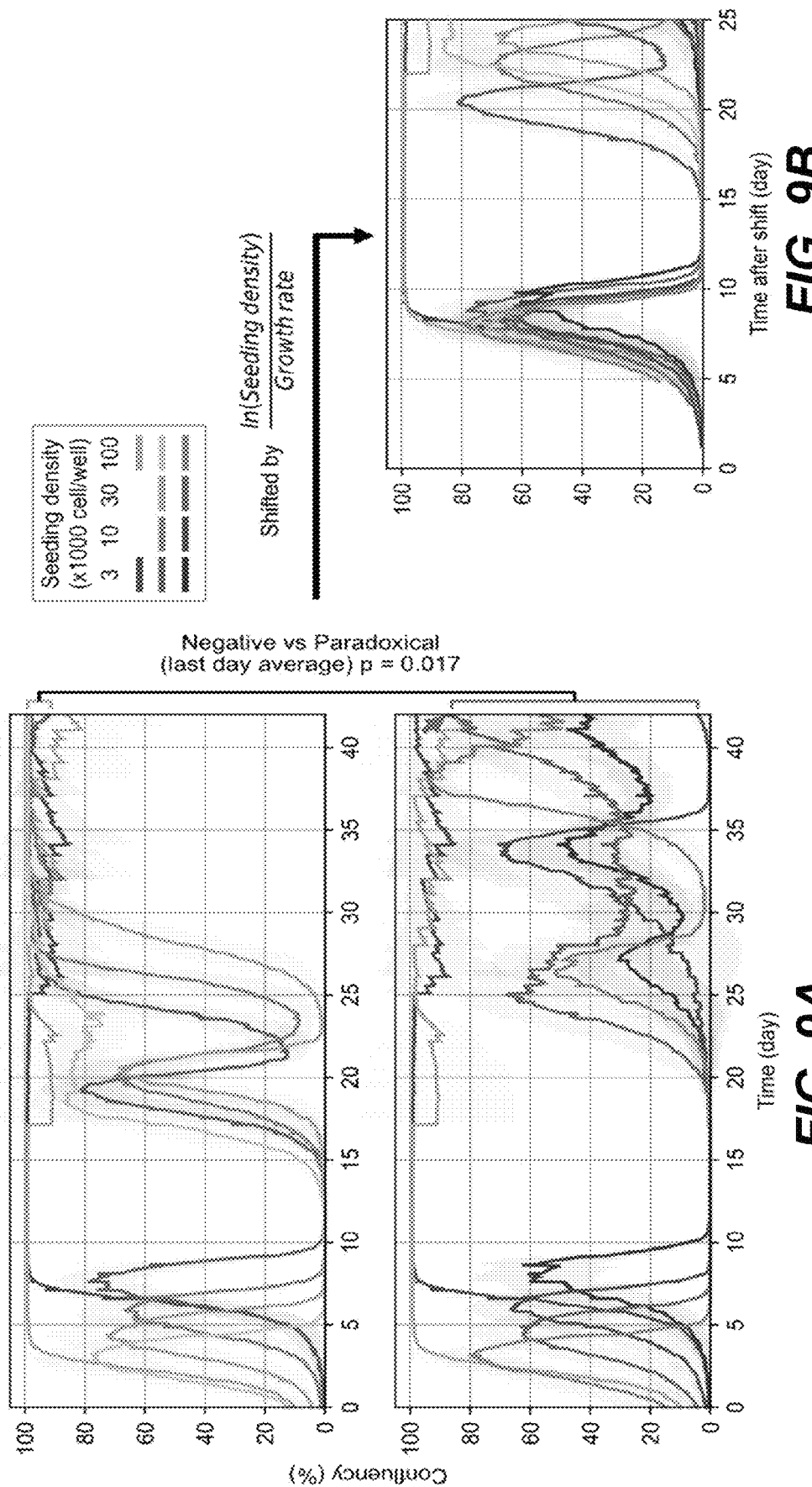
FIGS. 9A-9B depict non-limiting exemplary data showing the paradoxical circuit allows evolutionarily robust population control in a replicate time-lapse experiment.

The negative feedback regime limited population size for 1 or 2 oscillatory periods (~15-20 days), after which cells appeared to escape control, remaining confluent for the remainder of the movie (at least 10 subsequent days, FIG. 5B). This behavior is consistent with the experimentally observed susceptibility of simple negative feedback control to escape mutants (FIGS. 7C and 7D), and simulated responses to introduction of sensing mutants (FIG. 4G). By contrast, in the paradoxical regime, cultures exhibited oscillations in population density, but remained at sub-saturating densities for the full 43-day experiment (FIG. 5B, bottom). Similar results were observed in an independent experiment that used different starting population densities and a slightly different cell maintenance protocol (FIG. 10; Methods). In this case as well, the negative feedback conditions led to escape, while the paradoxical conditions did not (FIG. 9A). Independent cultures showed identical dynamics for their first ~10 days when shifted in time in time to compensate for their different initial seeding densities (FIG. 9B), suggesting that the circuit behaves consistently between cultures before acquiring random mutations. Across all experiments, only paradoxical feedback isolates successfully controlled population size for the full duration of the time-lapse movies (FIG. 5B and FIG. 9A), and only one of the paradoxical isolates approached confluence at the movie end-point of 43 days (FIG. 9A, turquoise arrow). Together, these results demonstrate that the paradoxical control circuit reproducibly extends the duration of population control.

Time-lapse imaging from FIG. 9A revealed robustness of the paradoxical population control architecture. In a time-course movie experiment, cells were seeded at 3000 cell per well into a 24-well imaging plate (FIG. 9A), with no control (100 µM NAM; left), negative feedback (100 µM NAM and 50 µg/ml blasticidin; middle), or paradoxical feedback (100 µM NAM, 50 µg/ml blasticidin, and 50 nM AP1903; right). Images were taken with a 20× inverted microscope with 1 hour interval (see Method), and the constitutively expressed mTagBFP2 channel was observed. The robustness of the paradoxical population control architecture was observed.

Figure 5C:
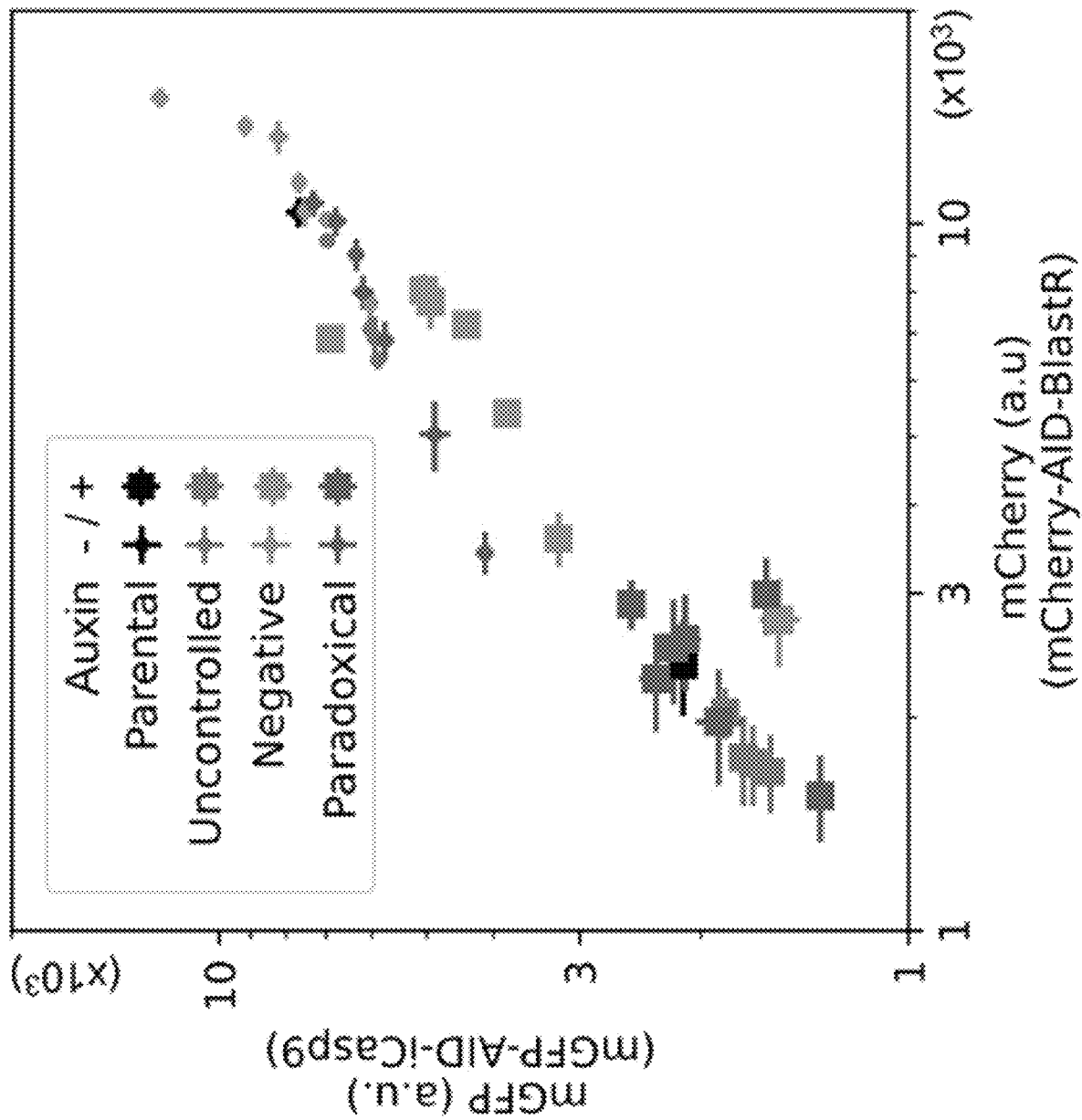

To gain insight into how cells evolved during long-term culture (FIG. 5B and FIG. 9A), cells isolated at the end of each of the 18 individual long-term cultures after passaging in standard media were analyzed. The fluorescence of mCherry and mGFP, which are co-expressed with the $Blast^R$ and iCasp9, respectively, varied substantially across all isolates, reflecting independently acquired changes in the expression of circuit components during long-term culture, rather than amplification of a common founder mutation already present in the parental cell line (FIG. 5C). The two fluorescent reporters expressed at a similar ratio in each isolate (FIG. 5C), suggesting that alterations occurred upstream of both circuit arms.

The two population control conditions produced different effects on circuit component expression and phenotypic behavior. In cells selected under negative feedback conditions, basal Blast R expression was upregulated by 57%, and showed 49% less responsiveness to auxin compared to the uncontrolled group (FIGS. 5D and 5E; p=0.014 and p<0.001, respectively). By contrast, isolates from the paradoxical feedback conditions showed significantly lower basal $Blast^R$ expression (p=0.012) and retained a larger dynamic range of $Blast^R$ regulation compared to negative feedback isolates (p=0.011). These differences in $Blast^R$ levels were also reflected in cell survival (FIGS. 5F and 5G). In a combination of blasticidin and auxin, mimicking high cell density, negative feedback isolates exhibited increased survival compared to the uncontrolled group (p=0.021) (FIG. 5F). By contrast, survival of paradoxical isolates was not significantly different on average from the uncontrolled growth isolates (p=0.17), although one individual isolate may have acquired the ability to escape in these conditions (FIG. 9A and FIG. 5F, turquoise arrows). Together, these results suggest that paradoxical conditions preserved more of the original $Blast^R$ regulation and function compared to negative feedback conditions.

The paradoxical architecture is designed to suppress sensing deficient mutations that reduce the responsiveness of both arms of the circuit to auxin. More specifically, cells that lose auxin sensing should no longer degrade $Blast^R$ (FIG. 5H, lower right), even in the presence of auxin, giving those cells a growth advantage. By contrast, in the paradoxical circuit, such sensing deficient cells would also be unable to degrade iCasp9, leading to their elimination (FIG. 5H, upper right). Thus, sensing deficient isolates from the negative feedback condition should become susceptible to killing through the iCasp9 arm, even in the presence of auxin. In fact, isolates from negative feedback conditions were sensitive to the combination of AP1903 and auxin, indicating that they had acquired the potential to be counter-selected under paradoxical conditions (FIG. 5G, p=0.021). Together, these results suggest that cells with reduced sensing gain a growth advantage in negative feedback conditions but are counter-selected under paradoxical conditions, consistent with the principle of paradoxical control.

Figure 10A:
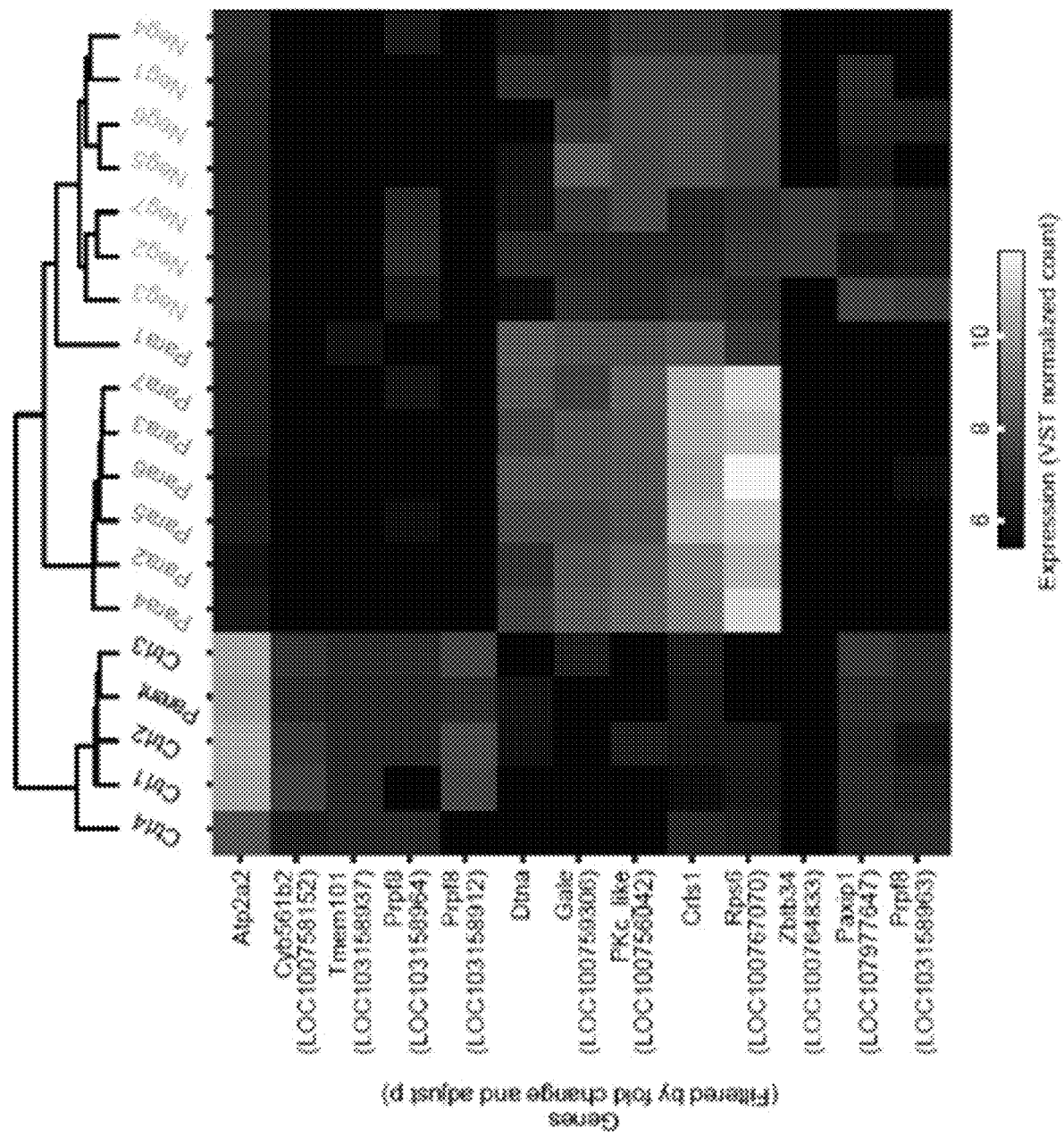
FIGS. 10A-10C depict non-limiting exemplary data showing whole genome expression profiling reveals effects of long term culture on gene expression.
Figure 10B:
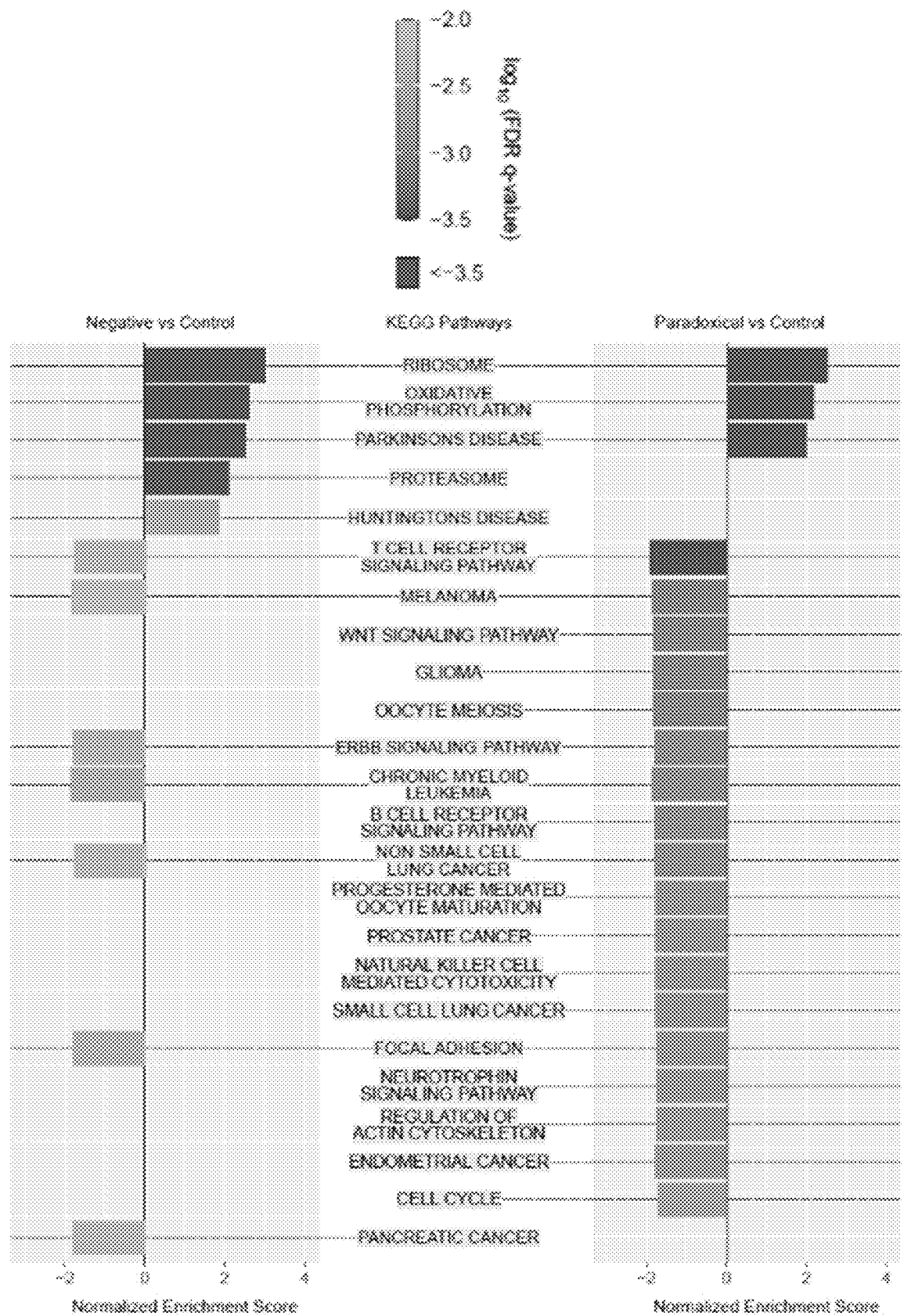
Figure 10C:
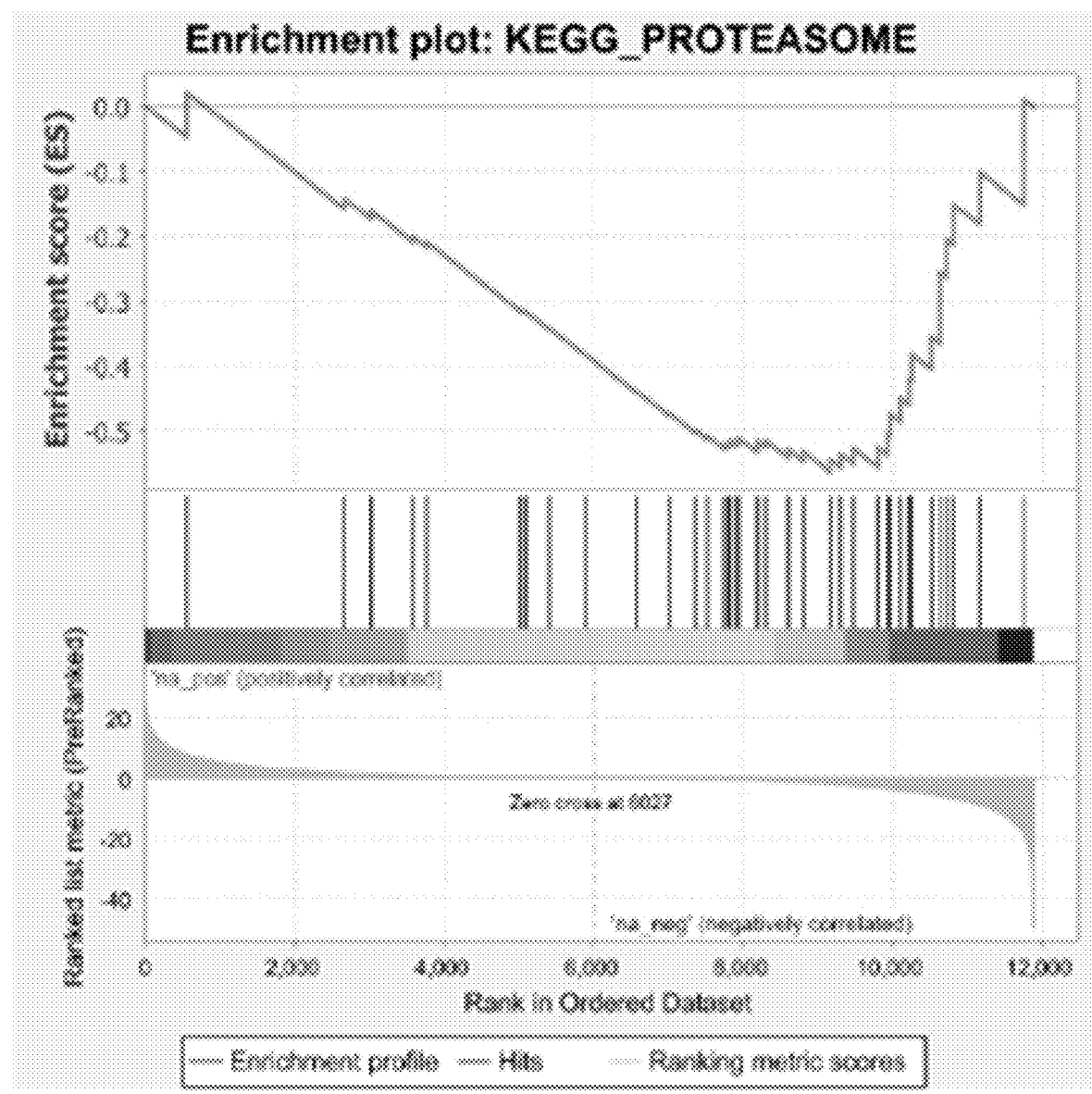

Finally, to characterize gene expression changes outside of the circuit during long-term culture, RNA sequencing analysis of the isolates was performed. RNA profiles generally clustered by circuit operating mode (uncontrolled, negative, or paradoxical feedback), although one paradoxical isolate exhibited an intermediate expression phenotype suggesting that the operating mode of the circuit largely drives gene expression changes (FIG. 10A). Isolates from the uncontrolled growth groups clustered with parental cells, suggesting that the uncontrolled conditions did not drive similar adaptations in gene expression. Pathway enrichment analysis revealed that ribosome components, the primary targets of blasticidin, were significantly upregulated in both negative feedback and paradoxical conditions (FIG. 10B). Differentially expressed proteasome components, on the other hand, were enriched in the negative feedback, but not in the paradoxical condition, and were expressed at lower levels in paradoxical compared to negative feedback conditions (FIG. 10C, nominal p=0.042, FDR q=0.085 and normalized enrichment score=−1.42), consistent with the opposite selection pressures on proteasome activity generated by auxin regulation of BlastR and iCasp9 in the paradoxical condition.

Together, these results suggest that diminished sensitivity to auxin provides a growth advantage in the negative feedback condition by upregulating and reducing the auxin-responsiveness of $Blast^R$, but are counter-selected in the paradoxical condition, in which they would trigger activation of iCasp9. While this analysis cannot rule out the possibility that other adaptations could eventually lead to escape in paradoxical conditions, it suggests that the paradoxical design can extend the duration of population control by suppressing the growth advantage of sensing deficient mutants.

In a time-course movie experiment, cells were seeded into a 24-well imaging plate with 50 µg/ml of blasticidin solely ("Uncontrolled") or with 100 µM IAM ("Population circuit on") or IAA ("Killing constitutive on"). Images of constitutively expressed NLS-citrine were taken with a 20× inverted microscope once per hour. Sender-Receiver-PIN2 cells were found escape after 15 days of continuous culture.

Numerical simulation revealed delay bifurcation between damped and limit cycle oscillations. This time course showed simulated dynamics of the paradoxical feedback model for different values of the delay parameter, τ. For each value of τ, the simulation showed two trajectories starting from different initial conditions. Note the transition from damped to limit cycle oscillations between 42 and 54 hours. Initial conditions were held fixed at a cell seeding density of 0.1 and auxin concentration of 40 µM and 16 µM for trajectory 1 and trajectory 2, respectively.

Additional Data

The Negative Feedback Population Control Circuit is Susceptible to Cheater Mutations at Long Timescales.

Figure 11A:
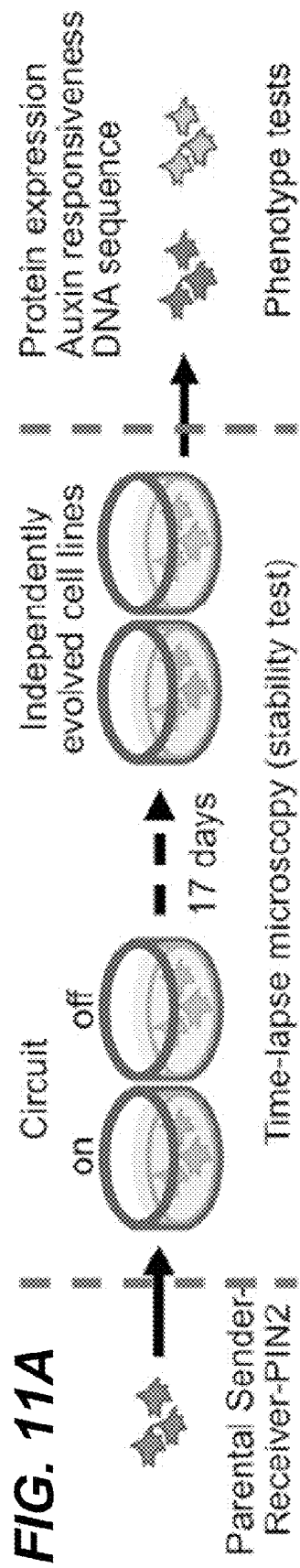
FIGS. 11A-11E depict non-limiting exemplary embodiments and data showing quorum sensing regulation of cell survival transiently limits population size.
Figure 11B:
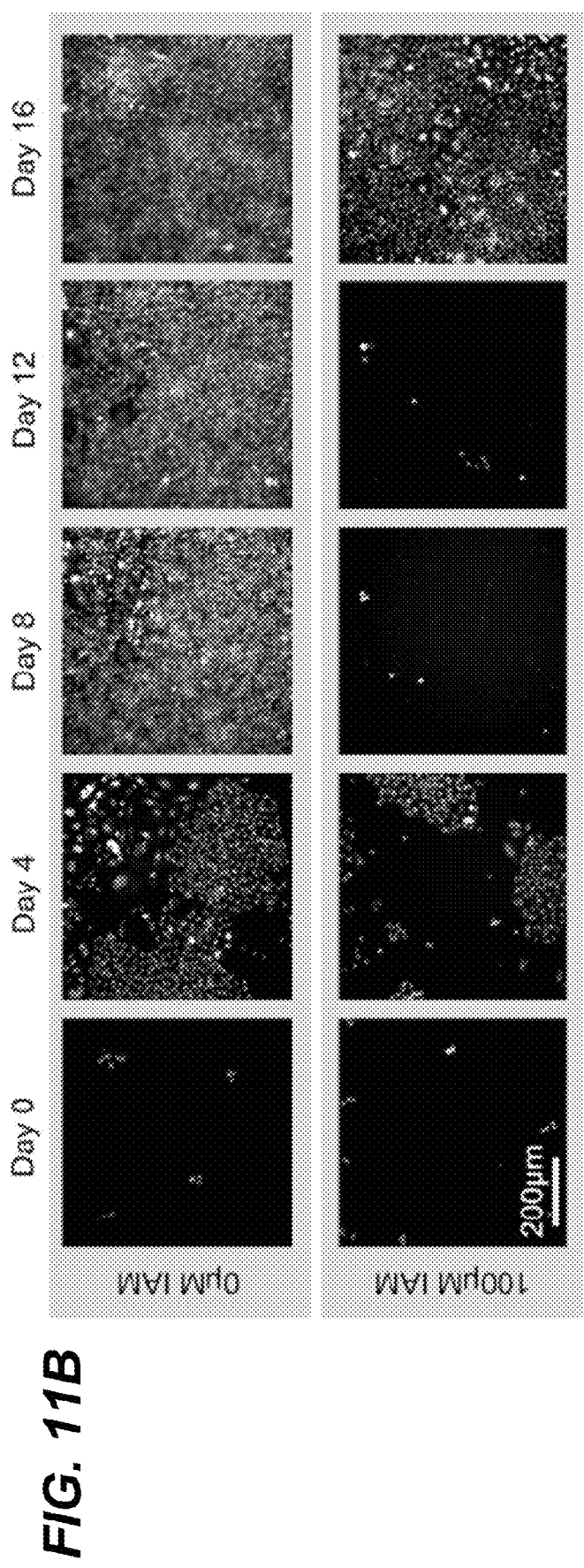
Figure 14A:
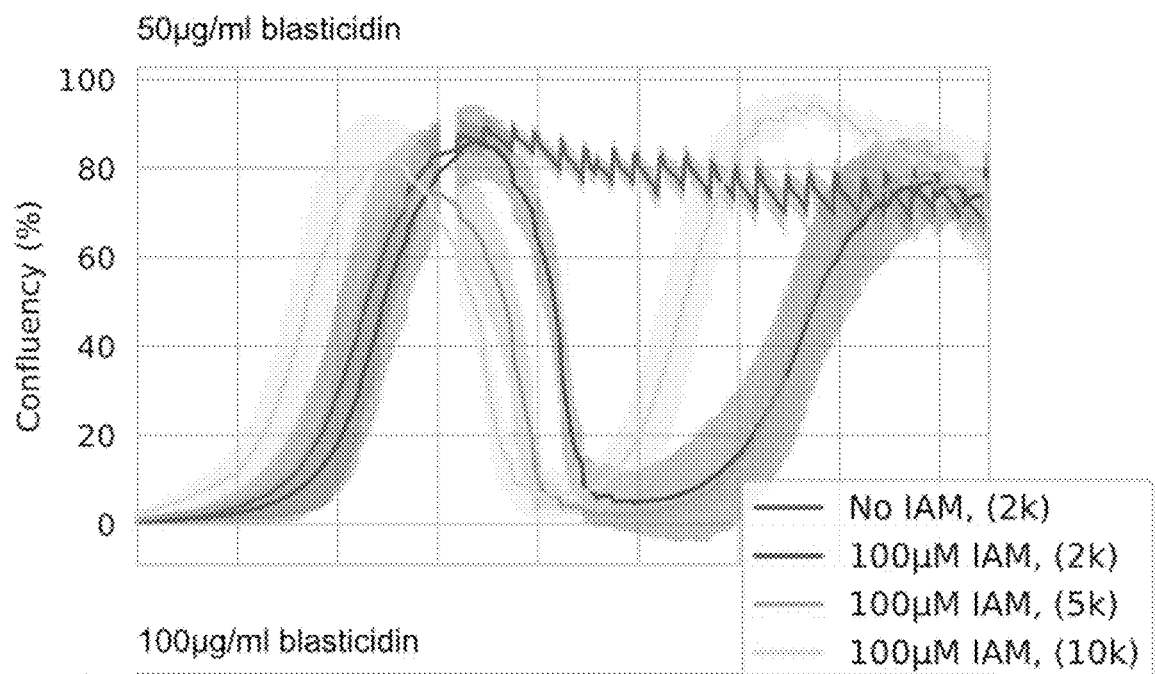
FIGS. 14A-14D depict non-limiting exemplary data showing simple negative feedback enables cell density-dependent killing.
Figure 14B:
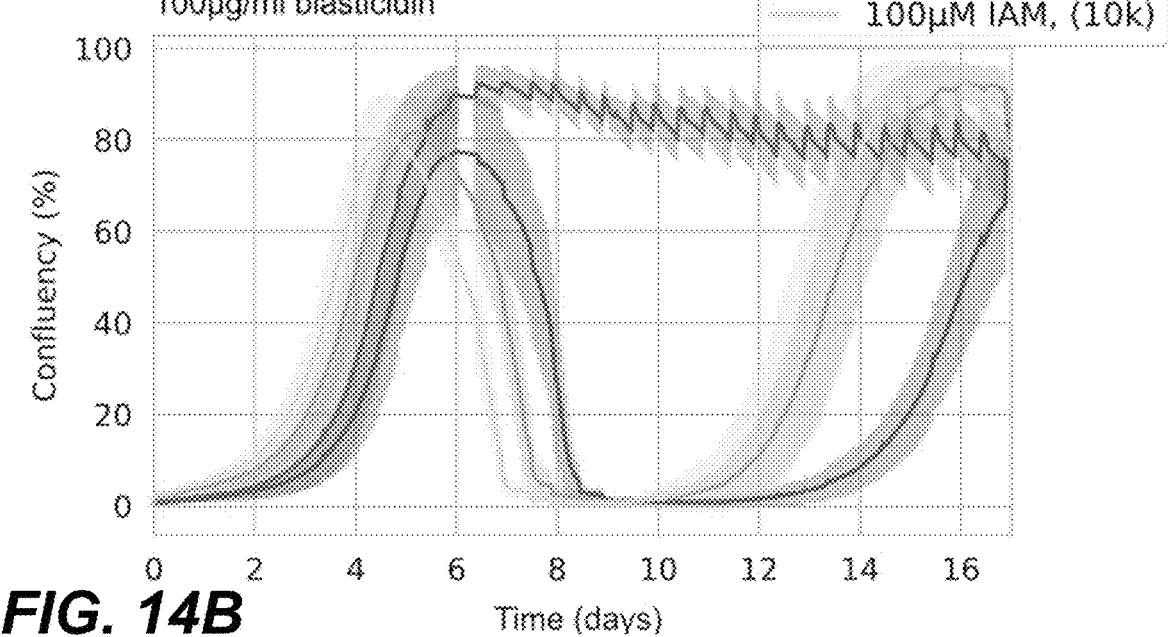

To better understand circuit dynamics and stability over longer timescales, time-lapse imaging of a continuous culture of Sender-Receiver-PIN2 cells was set up (FIG. 11A). Media was partially replaced twice daily to achieve a dilution rate of 50% per 24 hours, and acquired images of cells once per hour for 17 days (408 hours) (FIG. 11B). In the presence of precursor (IAM), cells grew to threshold (peak) densities, diminished due to cell death, and subsequently grew back. Further, the threshold densities that triggered cell death depended on blasticidin concentration but were independent of initial seeding density, consistent with quorum sensing (FIGS. 11C-11D; FIGS. 14A-14B). By contrast, in the absence of precursor, cells grew to and remained at a higher cell density. These results are broadly consistent with the pulsatile 'overshoot' dynamics expected from time-delayed negative feedback.

Figure 11C:
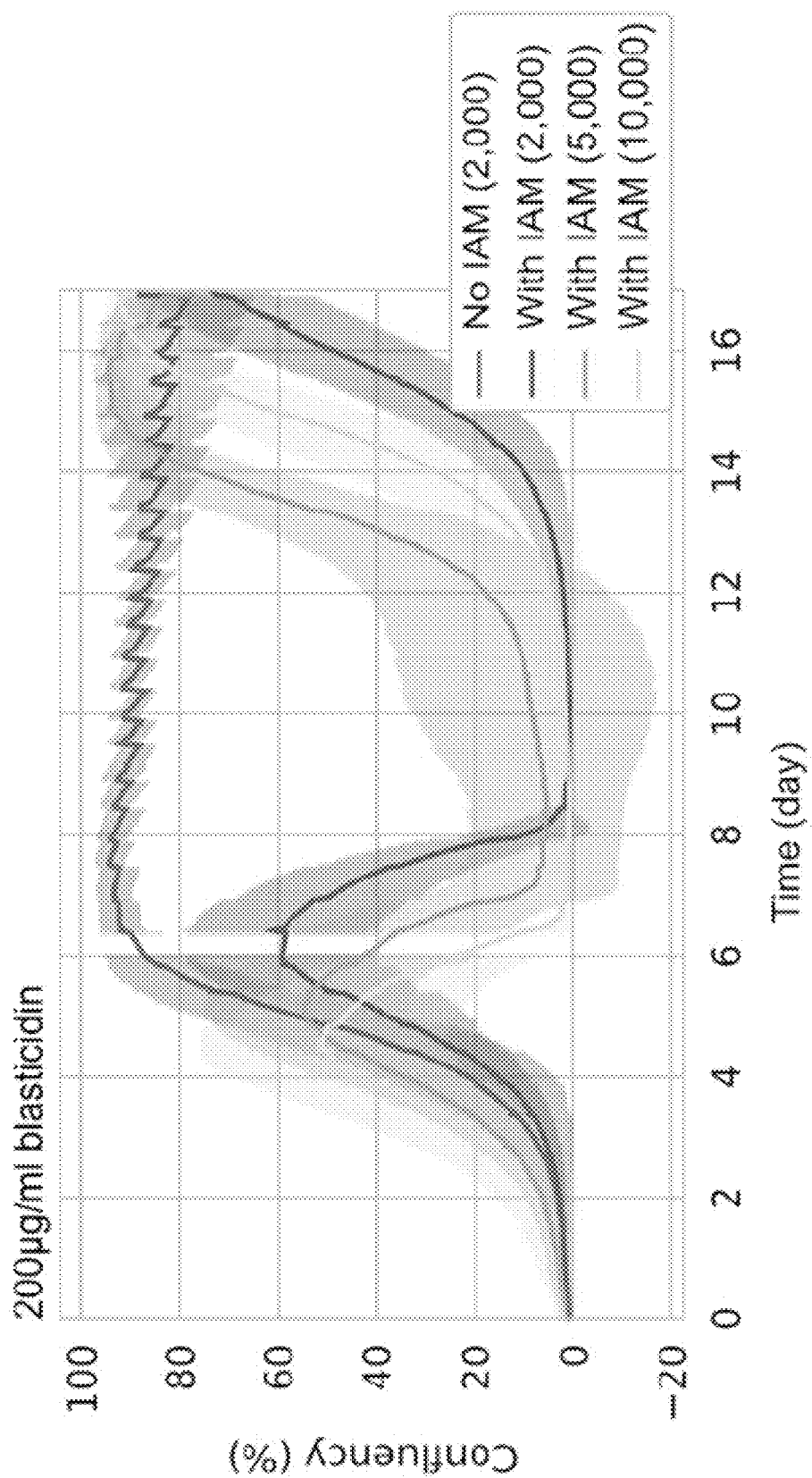
Figure 11D:
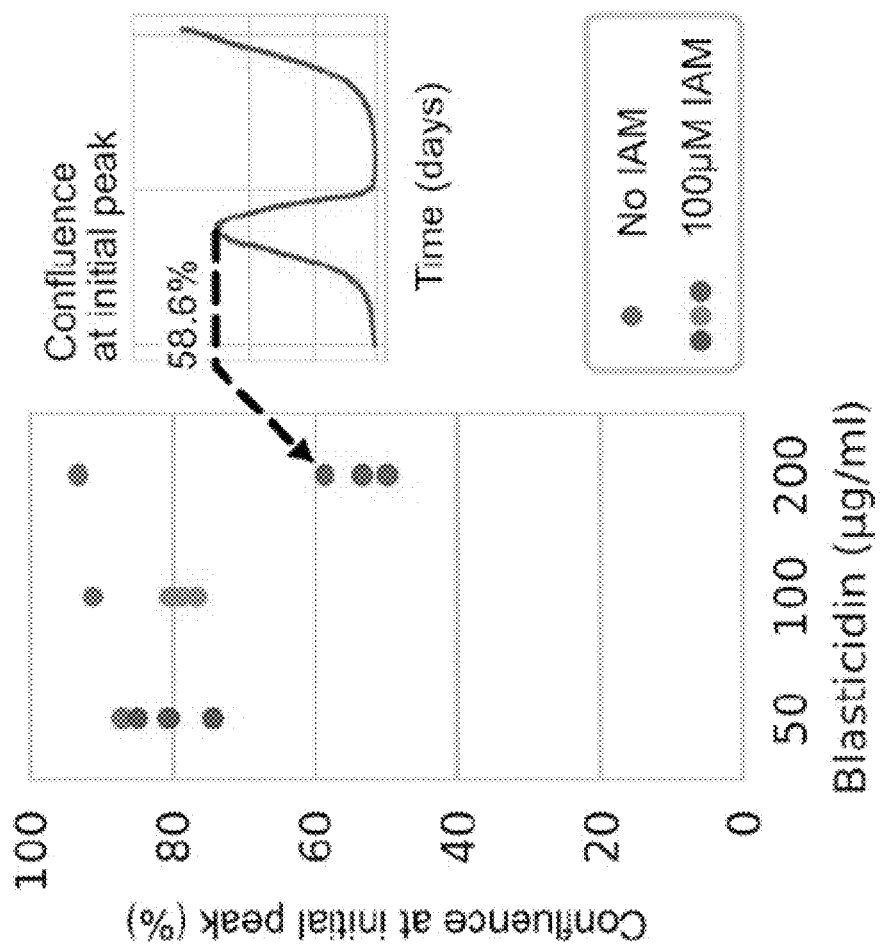
Figure 11E:
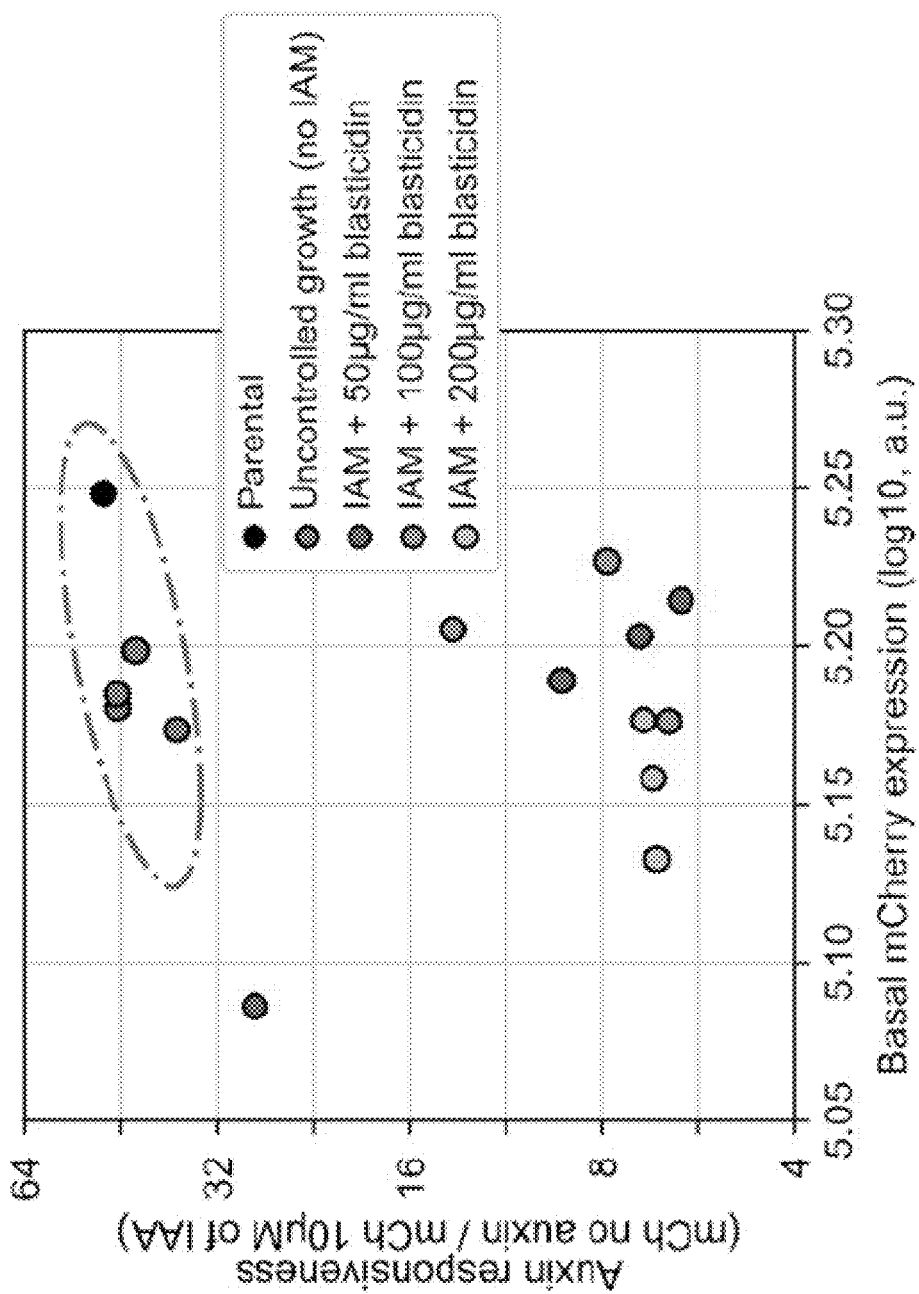
Figure 14C:
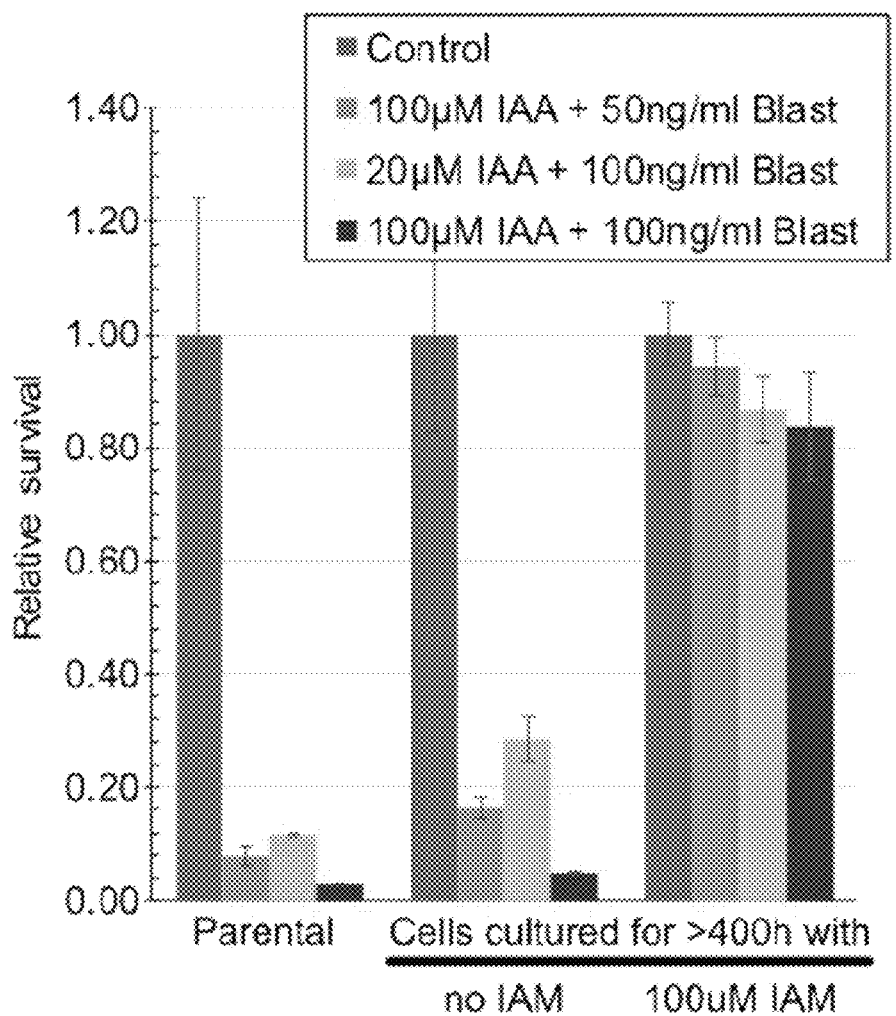

Although the circuit initially limited growth, at longer times, population sizes invariably reached those of cultures lacking blasticidin (FIG. 11C; FIGS. 14A-14B). This behavior could reflect not only pulses in population density but also the appearance and expansion of 'cheater' mutations that effectively disable population control over longer timescales. In fact, cells extracted at the endpoints of movies conducted with blasticidin were significantly less responsive to auxin compared parental or unregulated group (p<0.01 for each culture), and therefore more resistant to blasticidin than cells cultured in the absence of IAM, i.e. without activation of the circuit (FIG. 11E; FIG. 14C). These results suggest that cells acquired mutations (or other heritable changes) that effectively reduced auxin sensing.

Figure 14D:
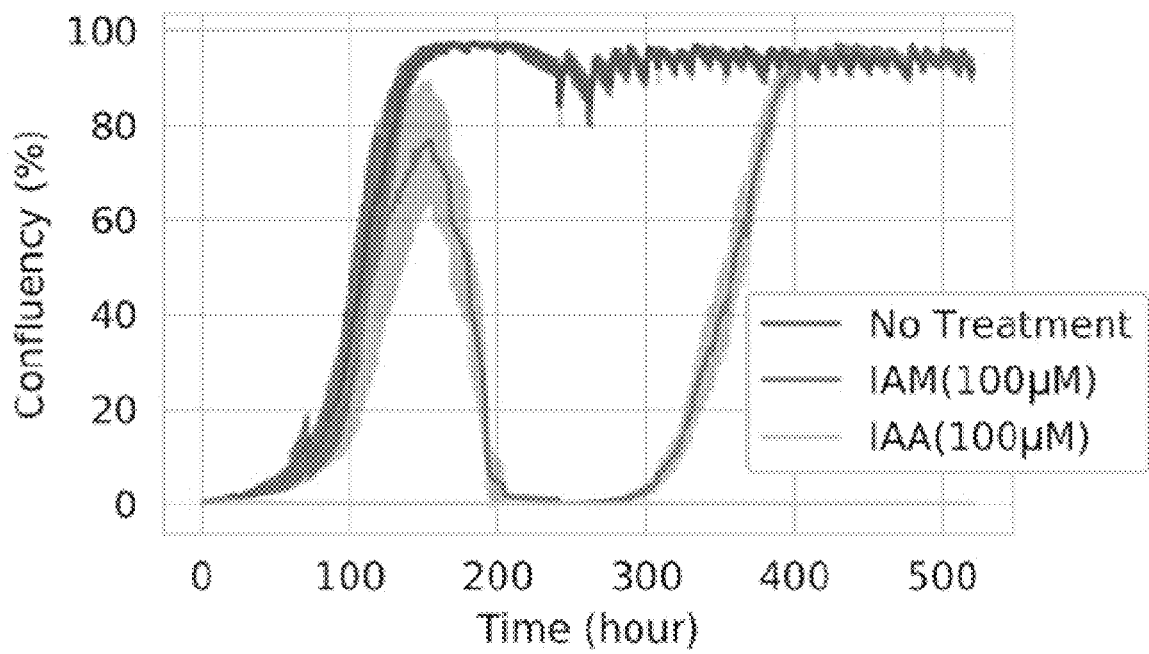

Several observations suggest that these effects originated from spontaneous, independent mutations. First, resistance mutations occurred in separately maintained, long-term cultures, and therefore could not spread from one culture to another. Second, parental cells cultured in the presence of IAA and blasticidin died within 3 days, with no cells observed to escape selection for at least 20 days of further observation (FIG. 14D), indicating that adaptive mutants were not present in the parental population. Finally, sequencing of the integrated osTIR1/$Blast^R$-AID-mCherry plasmid in ten escape mutant lines revealed three distinct, non-synonymous mutations within the AID sequence, consistent with a loss of auxin sensing. While sensing mutations are likely responsible at least in part for the mutant growth advantage, their specific effects in a parental background was not characterized. Together, these results suggest that the negative feedback population control circuit can be circumvented by de novo mutations or other heritable changes in the circuit. However, as described herein, a paradoxical circuit designs provide robust population control.

Figure 12A:
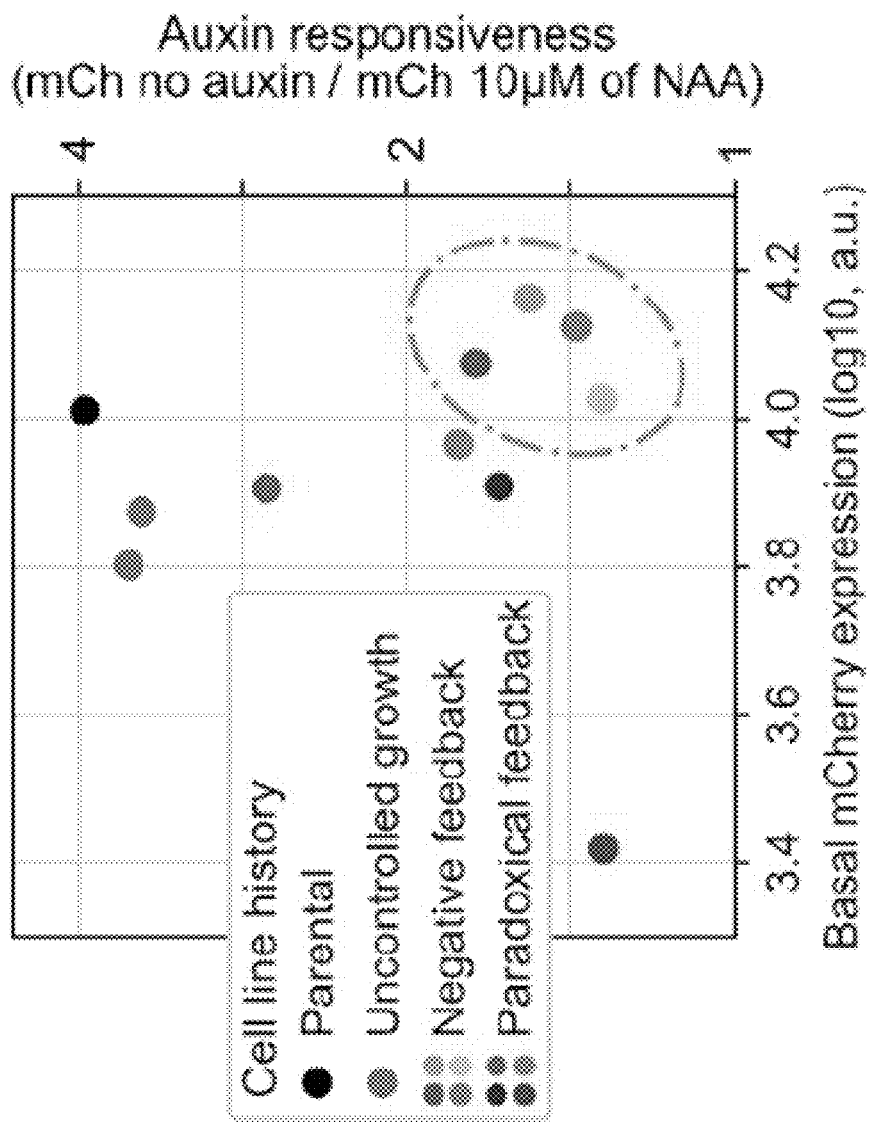
FIGS. 12A-12C depict non-limiting exemplary data showing the paradoxical circuit allows mutationally robust population control.
Figure 12C:
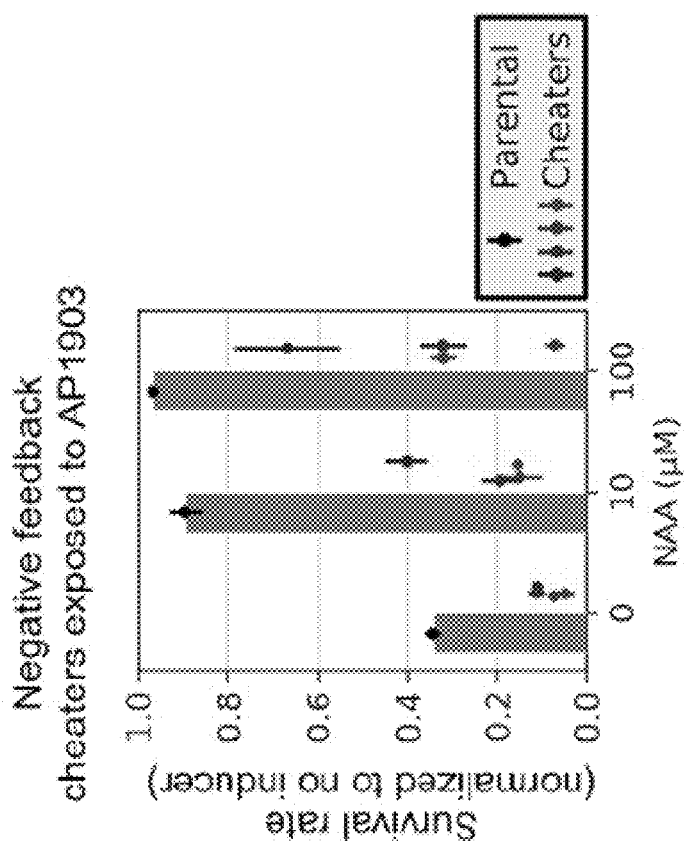
Figure 12B:
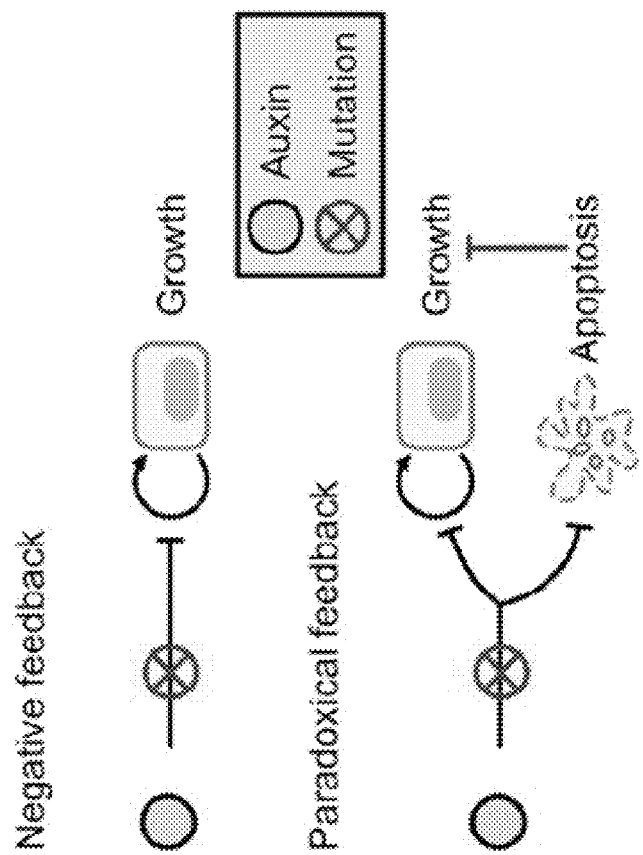
Figure 13:
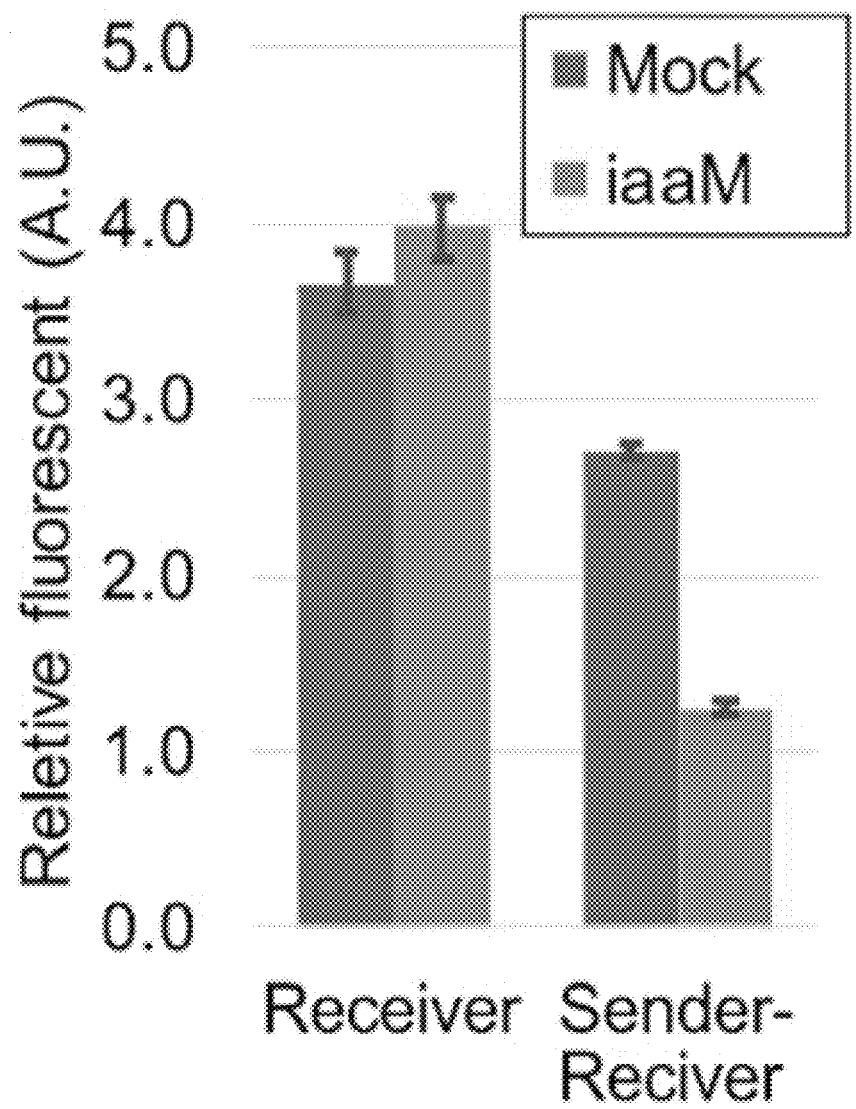
FIG. 13 depicts non-limiting exemplary data showing expression of auxin-synthesizing enzymes enables cells to produce auxin. iaaM expression enables auxin production in Sender-Receivers in the absence of precursor. Receiver or Sender-Receiver cells were transfected and fluorescence was assayed by flow cytometry 48 hours later.

Finally, it was asked whether the paradoxical architecture could suppress cheater mutants for the reasons predicted by the model. Loss of auxin sensing is the predominant cheating mode under negative feedback conditions. This was observed above with Sender-Receiver-PIN2 cells (FIG. 11E), and again, independently, with Paradoxical Control cells cultured under negative feedback conditions (without AP1903) (FIG. 12A). In the paradoxical circuit design, the expression of BlastR and iCasp9 are both up-regulated by loss of auxin perception. Consequently, most adaptive mutations that up-regulate BlastR should also increase iCasp9 expression, and thereby become susceptible to AP1903-dependent killing (FIG. 12C). For this reason, paradoxical conditions should select against loss of signal sensing. In fact, cells evolved under paradoxical conditions did exhibit significantly different basal expression and auxin-responsiveness than cheaters evolved under negative feedback alone (FIG. 12A, blue/green dots, all p<0.01). These results show that the paradoxical architecture achieved greater evolutionary robustness by successfully blocking the predominant mutational escape path to cheating.

DISCUSSION

Natural cytokine-based control circuits allow cells to regulate their own population dynamics, as well as those of other cell types. Synthetic circuits could provide analogous capabilities. To this end, simultaneous production and sensing of the plant hormone auxin was engineered in mammalian cells, and it was coupled to genes controlling cell proliferation and death. The enzymes iaaH and iaaM, together with PIN2, allow cells to produce and export auxin. osTIR1 together with AID domains provide a simple, direct means of sensing auxin and coupling it to arbitrary protein targets (FIGS. 1-2). These components thus provide a long-range private communication channel, and enable the foundational property of quorum sensing (FIG. 3). Coupling quorum sensing to cell survival opens up the possibility of creating population control circuits, provoking the question of what circuit architectures can provide robust, long-term control. Consistent with previous work, mathematical modeling showed that a paradoxical architecture, in which auxin inhibits survival mediated by $Blast^R$ and killing by iCasp9, can generate a range of qualitatively different behaviors and, in some regimes, can suppress cheaters (FIGS. 4E and 4G). To experimentally realize this capability, the "Paradaux" circuit was constructed, and was compared its operation in three distinct regimes—uncontrolled growth, negative feedback, and paradoxical—by using media with different combinations of blasticidin and AP1903 (FIG. 4B). Long-term culturing for up to 43 days revealed that while both negative and paradoxical feedback architectures can limit cell population size for weeks, the former is more susceptible to escape by sensing-deficient cheaters (FIG. 5, FIG. 7B, and FIG. 9). By contrast, the paradoxical design suppressed these cheaters, as predicted theoretically (FIGS. 4 and 5), and provided more robust population control for the conditions and timescales explored here.

In some embodiments of the circuits provided herein, the Paradaux cell line can comprise addition of the auxin precursors IAM or NAM for auxin synthesis. Though this provides a good external control method for our experimental setup, it might be suboptimal in some embodiments. In some embodiments, complete biosynthesis of IAA can be achieved by expressing tryptophan 2-monooxygenase (iaaM), in conjunction with iaaH (FIGS. 6B and 6C). In some embodiments of the circuits provided herein, blasticidin and its auxin-regulated resistance gene for growth control is replaced with corresponding growth control proteins and agents provided herein. For example, in some embodiments, enzyme-prodrug systems provide an alternative approach with fewer non-specific effects on host cells. Alternatively, a more generalizable, cell-autonomous system could be achieved by coupling auxin to a cell-cycle regulator, such as Cdk1, 2 or 3, or other genes essential for survival and/or cell cycle progression. In some embodiments of the circuits provided herein, due to the inherent time delays within the feedback loop, the Paradaux circuit exhibits oscillatory behaviors (FIG. 8F), similar to earlier synthetic population control circuits in bacteria. Provided herein are methods and compositions for reducing feedback delays and/or implementing more sophisticated control systems that can facilitate non-oscillatory homeostatic dynamics. Finally, although the paradoxical control system successfully extended the duration of population control, cells nevertheless accumulated changes (FIG. 5 and FIG. 9). In some embodiments of the circuits provided herein, the paradoxical design can extend the duration of control in the presence of strong selection pressure to subvert it for even longer timescales.

In addition to quorum sensing and population control, the auxin cell-cell communication system provided herein enables the engineering more complex multi-cell type communication and control systems disclosed herein. For example, to track the relative distance between two groups of cells, there are provided circuits to engineer receivers that permanently activate in response to auxin secreted by a second cell type. Alternatively, circuits provided herein, in some embodiments, take advantage of the two-step nature of auxin biosynthesis (FIGS. 6B and 6D) by separating the steps into distinct cells, thereby enabling a proximity-dependent AND gate. More complex cytokine-like, multi-channel circuits can be achieved by the circuits provided herein by combining the auxin with additional diffusible, orthogonal signals. This approach enables synthetic bidirectional signaling or even Turing-like spatial pattern formation in some embodiments. In some embodiments, molecules for additional channels include the plant hormones abscisic acid and gibberellin, both of which have partially mapped biosynthetic pathways and were previously engineered to induce protein-protein interactions, enabling them to regulate transcription or protein localization in mammalian cells. The plant IP-CRE1, which has been successfully ported to yeast, uses an ATP related metabolite specific to plants as diffusible signal to induce phosphorylation and further transcriptional activation, providing an additional signaling system employed in the methods and compositions disclosed herein. Bacterial autoinducers and synthetic proteins are also additional orthogonal signaling channels employed in the methods and compositions that are provided herein.

With these developments, the private communication channels, population sensing, and population control methods and compositions provided herein could improve engineered cell therapies by allowing cells to coordinate their responses and localize activities at target sites. In some embodiments of the private auxin-based communication channels disclosed herein allow engineered cells to not only specifically sense and limit their own local population size but also to enable conditional activation only beyond a minimum density. Accordingly, the incorporation of synthetic population control systems provided herein in future generations of engineered cell therapies is anticipated.

Materials, Methods, and Supplementary Text

TABLE 2

List of parameters and fitted values

| Parameter | Description | Fitted value | Unit |
|---|---|---|---|
| A | Production rate of auxin at 100% confluence | 4.18 | µM/hr |
| $\delta_A$ | Dilution rate of auxin | 0.0289 | $hr^{-1}$ |
| v | Generalized logistic growth coefficient | 2.69 | DL |
| α | Maximum natural cell proliferation rate | 0.0395(1); 0.0327(2) | $hr^{-1}$ |
| $\beta_B$ | Maximum net growth reduction by blasticidin | 0.0874(1); 0.147(2) | $hr^{-1}$ |
| $\beta_C$ | Maximum death rate induced by iCasp9 | 0.0451(1); 0.0375(2) | $hr^{-1}$ |
| $\beta_{syn}$ | The synergetic coefficient | 1.12(1); 1.70(2) | $hr^{-1}$ |
| $\kappa_A$ | Effective strength of auxin | 1.316 | $µM^{-1}$ |
| $\kappa_B$ | Effective strength of blasticidin | 0.045(1); 0.069(2) | $(µg/ml)^{-1}$ |
| $P_R$ | Effective expression rate of BlastR | 1.77(1); 0.716(2) | DL |
| $\kappa_1^{-n2} \cdot P_C$ | Effective expression rate of iCasp9 | 8.54e–4(1); 1.23(2) | DL |
| $n_1$ | Cooperativity of the blasticidin regulation | 2.26(1); 2.28(2) | DL |
| $n_2$ | Cooperativity of the iCasp9 regulation | 1.41(1); 1.67(2) | DL |

Fitted values are labeled as (1) or (2), in cases where the major Paradaux line (labeled as 1), and the one used from confirming the model (labeled as 2) were fit with different values. Dimensionless values are labeled as "DL" in the "Unit" column.

Estimation of Auxin Diffusion Coefficient

To estimate the auxin diffusion coefficient, the system was modeled as a fixed concentration source, with the standard result for one-dimensional diffusion:

$$n(x, t) = n_0 \cdot \text{erfc}\left(\frac{x}{2\sqrt{Dt}}\right) \quad \text{(Equation S1)}$$

In which, n is the concentration as a function of time(t) and space(x), $n_0$ is the fixed concentration source, erfc the complementary error function and D is the diffusion coefficient. The diffusion coefficient of auxin has been previously measured to be 5.58×10[31][6] $cm^2/s$. Therefore after 48 hours, the diffusion will expand to approximately 3 to 4 centimeters (FIG. 6D). Compared to this ideal fixed concentration source model, the in vitro experimental gradient (FIG. 2E) is expected to exhibit delays in both auxin production and auxin sensing. Nevertheless, the experimentally observed gradient length scale was similar to the theoretical model prediction (tens of millimeters).

Fitting for the Auxin and Population Responsive Curves

To fit the mCherry's response curve to auxin and population (FIG. 1C, FIGS. 3A and 3B; FIGS. 7A and 7B), it was assumed the log of fluorescence (F) follows an inverted Michaelis-Menten's equation as follow:

$$\log(F) = F_{max} - Amp \cdot \frac{X}{EC_{50} + x} \quad \text{(Equation S2)}$$

In which, $F_{max}$ represents the basal level of fluorescence in log; Amp represents the max amplitude the population or auxin (represented by a) could reduce the fluorescent; and $EC_{50}$ represents the concentration, or population number when the reduction is half of the Amp.

In FIG. 7B, to avoid the problem that the above function (Equation S2) does not extrapolate well when fitted with flat lines (controls and samples treated with auxin), $x=10^3$ and $x=3 \cdot 10^5$ was used for the extreme values. More specifically, the "ideal dynamic range" is defined as $$\frac{F_{control}(x = 10^3)}{F_{auxin}(x = 10^3)},$$

the "loss to self-sensing" is defined as $$\frac{F_{control}(x = 10^3)}{F_{precursor}(x = 10^3)},$$

the "loss to saturation" is defined as $$\frac{F_{precursor}(x = 3 \cdot 10^5)}{F_{auxin}(x = 3 \cdot 10^5)},$$

and the "actual dynamic range" is defined as $$\frac{F_{precursor}(x = 10^3)}{F_{precursor}(x = 3 \cdot 10^5)}.$$

Model of the Paradoxical Population Control Circuit

Herein is described a dynamical model of the paradoxical population control circuit. The model is based on the following biochemical reactions, interactions, and assumptions:

Auxin, denoted A, is synthesized from its precursor through an iaaH-catalyzed hydrolysis reaction at a constant synthesis rate per cell $\lambda_A$, eliminated at a rate $\delta_A$, which is dominated by dilution due to media changes. Auxin diffuses rapidly in and out of the cell, and its concentration is therefore assumed to be at quasi-steady state (Equation 1).

iCasp9, denoted C, and Blast$^R$, denoted R, are produced at rates $\lambda_C$ and $\lambda_R$, respectively.

Auxin binds reversibly to osTIR1 to form an auxin-osT1R1 complex, which ubiquitylates and degrades iCasp9 and Blast R via their attached AID domains. These reactions are described using classical enzyme kinetics with the auxin-osTIR1 complex as the activating enzyme, described as a constant rate $v_{ub}$, In addition to auxin-induced active degradation, iCasp9 and Blast$^R$ are also eliminated at rate $\delta$ due to dilution (Equations S3 and S4).

The concentrations of iaaH and osTIR1 are assumed to be constant. Auxin precursor is assumed to remain at excess, saturating concentration.

osT1R1 is assumed to be present at excess concentration compared to the iCasp9-auxin-osTIR1 and Blast$^R$-auxin-osTIR1 complexes, and therefore potential competition between iCasp9 and BlastR for osTIR1 can be neglected.

With these assumptions, the dynamics of iCasp9 and Blast R can be described with the following differential equations:

$$\frac{dR}{dt} = \lambda_R - v_{ub} \cdot R \cdot A - \delta \cdot R \quad \text{(Equation S3)}$$

$$\frac{dC}{dt} = \lambda_C - v_{ub} \cdot C \cdot A - \delta \cdot C \quad \text{(Equation S4)}$$

The model represents blasticidin and AP1903 interactions as follows:

Extracellular Blasticidin, denoted B, diffuses into the cell, where it is denoted $B_{int}$, and undergoes subsequent enzymatic inactivation by Blast$^R$, with a threshold concentration of $K_B$, and a Hill coefficient $n_1$:

$$B_{int} = B \cdot \frac{(K_B)^{n_1}}{(K_B)^{n_1} + R^{n_1}} \quad \text{(Equation S5)}$$

AP1903 forms an active caspase complex, $[I:C_{n_2}]$ with iCasp9, with a threshold concentration of $K_d^C$ and a Hill coefficient $n_2$:

$$[I:C_{n_2}] = \frac{1}{(K_d^C)^{n_2}} \cdot I \cdot C^{n_2} \quad \text{(Equation S6)}$$

In these two cases, the more general Hill kinetics was allowed to account for potential intermediate reaction mechanisms that could influence the effective cooperativity in the final expressions. Additionally, it was assumed that both inactivation of Blasticidin and iCasp9 binding to AP1903 are rapid and have reached steady state.

As described above, the overall population dynamics can be described using a generalized logistic function, with the growth rate represented as a linear combination of blasticidin-dependent and iCasp9-dependent terms (Equation 2). The Blasticidin-dependent growth rate, $F_G$, is a sum of two terms. The first describes attenuation of the maximum natural cell proliferation rate, $\alpha$, with increasing blasticidin, while the second represents an increase in the cell death rate, $\beta$, with increased blasticidin. These terms are associated with half-maximal blasticidin concentrations of $K_g$ and $K_d$, respectively:

$$F_G = \alpha \frac{K_g}{K_g + B_{int}} - \beta \frac{B_{int}}{K_d + B_{int}} \quad \text{(Equation S7)}$$

For simplicity, it is assumed $K_g = K_d = K$. Thus, Equation S7 can be reduced to the following form:

$$F_G = (\alpha + \beta) \frac{K}{K + B_{int}} - \beta \quad \text{(Equation S8)}$$

Herein is similarly described the iCasp9-dependent cell death rate, $F_D$, with a Hill function dependence on the concentration of the AP1903-iCasp9 (I) complex:

$$F_D = \beta_C \frac{[I:C_{n_2}]}{[I:C_{n_2}] + \kappa_{[I:C]}} \quad \text{(Equation S9)}$$

Adding Equations S8 and S9 together and substituting the corresponding terms from Equations S5 and S6, generates the complete form of the growth rate function R(B, I, A) in Equation 2:

$$R_g(B, I, A) = (\alpha + \beta) \frac{\kappa[(K_B)^{n_1} + R^{n_1}]}{\kappa[(K_B)^{n_1} + R^{n_1}] + B(K_B)^{n_1}} - \\ \beta - \beta_C \frac{\frac{1}{(K_d^C)^{n_2}} \cdot I \cdot C^{n_2}}{\frac{1}{(K_d^C)^{n_2}} \cdot I \cdot C^{n_2} + \kappa_{[I:C]}} \quad \text{(Equation S10)}$$

To simplify this description, it was assumed a time-scale separation between the faster auxin-population dynamics and the slower intracellular reactions involving R and C. Using singular perturbation theory, the system can then be approximated by a simpler system that retains only the slower dynamics (Equation 1 and 2), while the faster dynamics (Equation S3 and S4) are considered to be at equilibrium:

$$\frac{dR}{dt} = \frac{dC}{dt} \approx 0.$$

With this approximation, one can write R and C in terms of the auxin concentration, A.

$$R = \frac{\lambda_R}{\delta + v_{ub} A} \quad \text{(Equation S11)}$$

$$C = \frac{\lambda_C}{\delta + v_{ub} A} \quad \text{(Equation S12)}$$

The following additional parameter combinations were also defined for simplicity (see Table 2):

$$\kappa_A = \frac{v_{ub}}{\delta}; \kappa_B = \frac{1}{\kappa}; P_R = \frac{\lambda_R}{K_B}; P_C = \frac{\lambda_C}{K_d^C}; \kappa_1 = \frac{1}{\kappa_{[I:C]}} \quad \text{(Equation S13)}$$

One can then substitute R and C in Equation S10 to obtain the following:

$$R_g(B,I,A) = (\alpha+\beta) \cdot G(B,A) - \beta - \beta_C \cdot D(I,A) \quad \text{(Equation S14)}$$

in which:

$$G(B,A) = \frac{(\kappa_A A + 1)^{n_1} + \left(\frac{P_R}{\delta}\right)^{n_1}}{(\kappa_A A + 1)^{n_1}(\kappa_B B + 1) + \left(\frac{P_R}{\delta}\right)^{n_1}} \quad \text{(Equation S15)}$$

$$D(I,A) = \frac{\kappa_I I \cdot \left(\frac{P_C}{\delta}\right)^{n_2}}{\kappa_I I \cdot \left(\frac{P_C}{\delta}\right)^{n_2} + (\kappa_A A + 1)^{n_2}} \quad \text{(Equation S16)}$$

To verify the validity of the approximation, the full model (Equations 1, 2, S3, and S4) was compared to the approximate model, where Equations S3 and S4 are set to 0. Both models were simulated using the parameter values in Table 2 (the Paradaux set). The two sets of traces closely followed each other (FIG. 8B), indicating that the approximate system accurately reproduced the dynamics of the full model.

(1) Representing Synergy Between iCasp9 and Blasticidin Control of Cell Survival As discussed above, the model above overestimated actual survival rates when both arms of the circuit were simultaneously active (FIG. 4D; FIG. 8A, dashed blue lines), likely due to synergy between apoptosis and blasticidin-dependent translational inhibition. Therefore a phenomenological synergistic interaction term was added: $-\beta_{syn} \cdot [1-G(B,A)] \cdot D(I,A)$ to the growth rate expression ($R_g$ in Equation S10):

$$R_g(B,I,A) = (\alpha+\beta_B) \cdot G(B,A) - \beta - \beta_C \cdot D(I,A) - \beta_{syn} \cdot [1-G(B,A)] \cdot D(I,A) \quad \text{(Equation S17)}$$

Equation S17 gives the final form of the paradoxical growth curve with the synergistic correction, and is used to improve data fitting (FIG. 4D; FIG. 8A, dotted blue lines). Together with the fitted parameters, the reduced system (Equations 1 and 2, with $R_g$ defined as Equation S17) was used to run parameter screens and dynamic simulations (FIGS. 5E-5G, FIGS. 8E-8F).

(2) Parameter Screening and Stability Analysis

For numerical parameter screening and stability analysis, some terms were computed analytically to make the process faster and more efficient. The Jacobian of the reduced dynamical system (Equations 1 and 2) can be expressed as follows:

$$J = \begin{pmatrix} -\delta_A & \lambda_A \\ R'(A) \cdot L(N) & R(A) \cdot L'(N) \end{pmatrix} \quad \text{(Equation S18)}$$

Here, L(N)=N(1−N"). Note that in the operating range 0<N<1, L(N)>0 and L'(N)>0. Thus R(A)=0 is required to achieve dN/dt=0 (the equilibrium point condition). With this assumption, the eigenvalues of the Jacobian at equilibrium are the roots of the following quadratic characteristic equation:

$$\lambda \cdot (\delta_A + \lambda) - \lambda_A \cdot R' \cdot L' = 0 \quad \text{(Equation S19)}$$

Thus the sign of eigenvalues (root of $\lambda$) of the matrix (Equation S18) can be solely determined by the sign of R'(A). If it is greater than zero, at least one of the eigenvalues has a real part greater than zero, making the associated equilibrium point unstable. If R'(A) is less than zero, it's straightforward to deduce that the real parts of all eigenvalues are less than zero, making the equilibrium point stable. Based on this analysis, the equilibrium points of the system and the corresponding sign of R'(A) was screened to determine the stability and type of each condition (FIG. 4E).

Figure 8G:
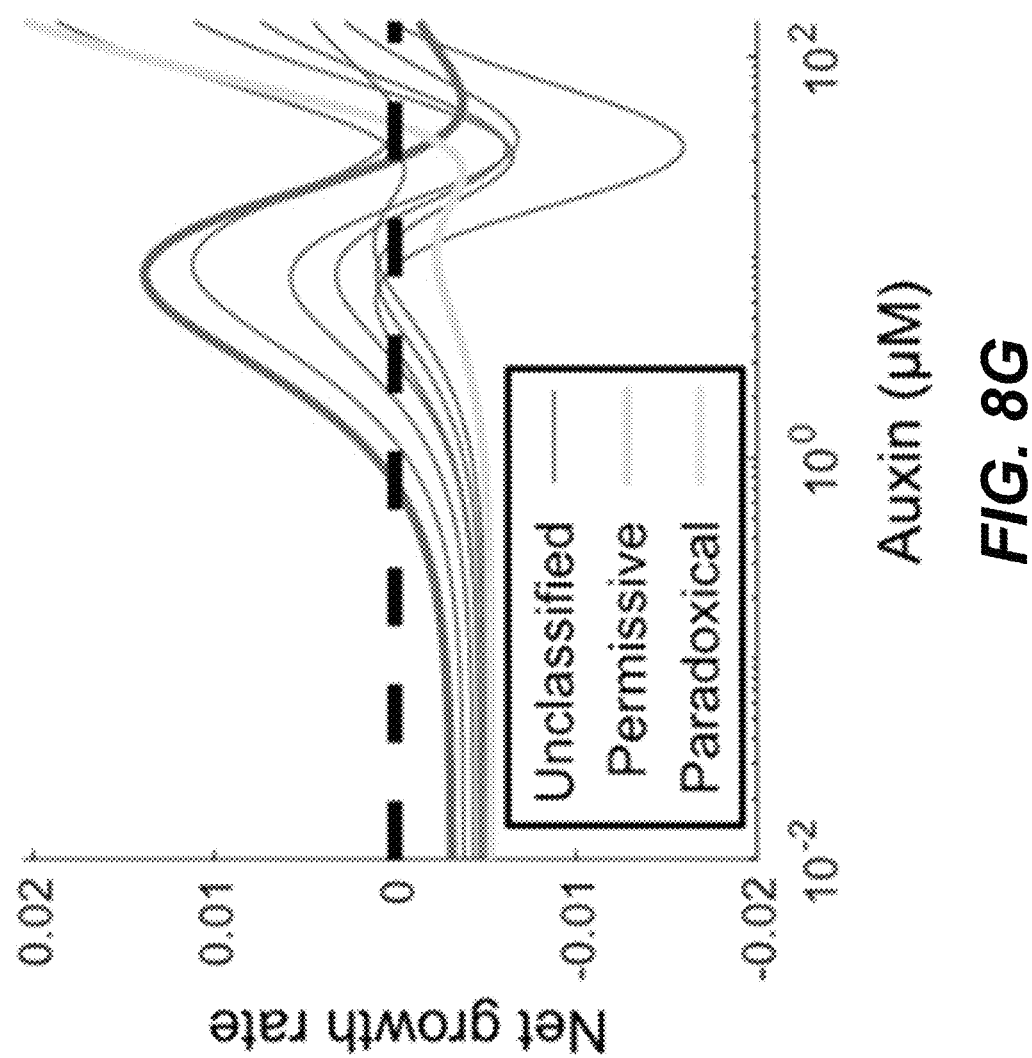

Besides the five major behavior categories described above (FIG. 4E, surrounding plots), a small but significant portion (0.68% of total) of conditions appearing at the border between "permissive" and "paradoxical" types, could not be classified into any of the five types. To further investigate these cases the space was down-sampled from 201×201 to 21×21 conditions and plotted all the six (0.62% or total) unclassified curves, as well the permissive and paradoxical types next to this region (FIG. 8G; grey, pink, and light blue respectively). Inspection of these curves revealed a transitional type between permissive and paradoxical, with the unusual equilibrium points caused by the nonlinearity of the introduced synergetic term. Note that the range of net growth rate of the system is around 0.09-0.04 defined by $\alpha$, $\alpha-\beta_B$ and $\alpha-\beta_C$. The net growth rates of these curves around the unusual equilibrium points is significantly lower (−0.01~0.02), indicating those points are unstable. Therefore, those curves' dynamics, although not mathematically classified, will behave similarly to either permissive or paradoxical types.

Resources

TABLE 3

Resources

| REAGENT OR RESOURCE | SOURCE | IDENTIFIER |
|---|---|---|
| Chemicals, peptides, and recombinant proteins | | |
| Indole-3-acetic acid | Sigma Aldrich | I2886; CAS#87-51-4 |
| Indole-3-actetamide | Sigma Aldrich | 286281; CAS#879-37-8 |
| 1-Naphthylacetic acid | Sigma Aldrich | N0640; CAS#86-87-3 |
| 1-Naphylacetamide | Sigma Aldrich | 36732; CAS#86-86-2 |
| AP1903 (Rimiducid) | MedChemExpress | HY-16046; CAS#195514-63-7 |
| Blasticidin S HCl | Gibco | R21001; CAS#3513-03-9 |

TABLE 3-continued

Resources

| REAGENT OR RESOURCE | SOURCE | IDENTIFIER |
|---|---|---|
| *Deposited data* | | |
| The plasmid GenBank files, raw data, and processing/plotting scripts for generating the figures | This application | http://dx.doi.org/10.22002/D1.1613 |
| *Experimental models: cell lines* | | |
| CHO-K1 (ATCC ® CCL-61 ™ | ATCC | Lot# CCL-61 |
| *Recombinant DNA* | | |
| vYM073_PB-pEF-osTIR1-T2A-mCherry-AID-Flag-BlastR | This application | Addgene #160042 |
| vYM082_PB-pEF1s(min)-3xNLS-Citrine-T2A-iaaH (Hygro) | This application | Addgene #160044 |
| vYM140_PB-pEFa1-iaaM(P.s)-Hygro | This application | Addgene #160043 |
| vYM140_PB-pEF1a-optiPIN2-HA(Hygro) | This application | Addgene #160045 |
| vYM133_PB-pEF-osTIR1-T2A-iaaH-T2A-mGFPmut3-mAID-iCasp9-T2A-mCh-AID-BlastR | This application | Addgene #160046 |
| *Software and algorithms* | | |
| Easyflow | Y. Antebi | https://github.com/AntebiLab/easyflow |
| Fiji | (Schindelin et at. 2012) | https://inagej.net/Fiji |
| Ilastik | (Berg et al. 2019) | https://www.ilastik.org/ |
| Kallisto | (Bray et el. 2016) | https://pachterlab.github.io/kallisto/ |
| DEseq2 | (Love, Huber, and Anders 2014) | https://bioconductor.org/packages/release/bioc/html/DESeq2.htm |
| GSEA | (Subramanian et at. 2005) | https://www.gsea-msigdb.org/gsea/index.jsp |
| *Other* | | |
| The python library used for processing the images and the movies | This application | https://github.com/labowitz/MovieTools |
| The code for the mathematical modeling section (FIG. 4 and FIG. 8) | This application | https://github.com/labowitz/auxin_paradox_matlab_code |

Experimental Model and Details

Tissue Culture and Cell Lines

CHO-K1 (Hamster cells, RRID:CVCL_0214, ATCC Catalog No. CCL-61) cells and their derivatives were grown on tissue culture grade plastic plates (Thermo Scientific) in Alpha MEM Earle's Salts (Irvine Scientifics), supplemented with 10% Tet System Approved FBS (ClonTech, or VWR), 100 U/ml penicillin, 100 µg/ml streptomycin, 0.292 mg/ml L-glutamine (GIBCO) or 1× GlutaMax (GIBCO). The complete media is filtered with 0.22 micron filters (Falcon).

For long-term culturing demonstrated in FIG. 5 and FIG. 9, cells were seeded in 24-well TC-treated plates (total media 500 µL per well) with imaging-grade plastic bottoms (ibidi inc. #82406), and media was changed every 12 hours with one of the following methods: 1) adding and mixing 200 µL fresh media into the well, taking out the media, and putting back 500 µL, or 2) taking out the media, adding back 350 µL and adding 150 µL of fresh media. Both methods simulate a media refreshing rate of 0.693/day (equivalent to media half-life=1 day). For results in FIG. 5, an additional centrifuge at around 2000 xg is applied for the old media to remove floating cells. This likely dampened the oscillation in FIG. 5 compared to FIG. 9, as iaaH proteins have been shown to work in cell lysate (data not shown).

Method Details

Gene Constructs

All constructs created in this work were assembled using standard restriction enzyme-based cloning and/or Gibson cloning. mAID and osTIR1 coding sequences were amplified from addgene #72827 and #72834. iCasp9 coding sequence was amplified from addgene #15567. PIN2, mGFP, and iaaM coding sequences (CDS) were codon optimized for expressing in mice and synthesized as dsDNA at Integrated DNA Technology together with all oligos for cloning. Coding sequences for screening indole-3-hydrolases were synthesized as cloning plasmid at Twist Bioscience. All constructs were cloned into the piggyBac plasmids (System Biosciences Inc.) driven by a synthetic version of human EF1A promoter.

Cell Line Engineering

All cell lines used in this paper contained stable integrations of transgenes, and were typically clonal populations. To create each stable cell line, the following steps were followed: 1) Cells were first transfected with 800-1000 ng of plasmid DNA using Lipofectamine 2000 or Lipofectamine LTX according manufacturer's instruction. 2) 24-48 hours later, cells were transferred to selection media containing 10~50 ug/ml Blasticidin as appropriate for 1-2 weeks. 3) Single clones were isolated through the technique of limiting dilution. For piggyBac constructs, the initial transfection consisted of the target plasmid along with the construct expressing the piggyBac transposase in a 1:4 mass ratio.

Flow Cytometry

Flow cytometry by trypsinizing 0.25% trypsin-EDTA (GIBCO) for 1 min at room temperature. The mixture was then neutralized by culture media and cells were resuspended in Hank's Balanced Salt Solution (GIBCO) with 2.5 mg/ml Bovine Serum Albumin (BSA). Cells were then filtered through a 40 µm cell strainer and analyzed by flow cytometry (MACSQuant VYB, Miltenyi or CytoFLEX, Beckman Coulter). EasyFlow, a Matlab-based software package developed by Yaron Antebi (https://github.com/AntebiLab/easyflow), was used to process flow cytometry data. All fluorescence data were acquired as the median value of the gated population. For counting cells, 1000 CountBright beads (Life Technologies) were spiked into the sample before filtering, gated out by their fluorescence in analysis and used to estimate cell number in each sample.

Conditioned Media

The process is described in FIG. 2C. Cells were first seeded at about 20% confluence with fresh media for conditioning, and cultured for 2 days. The supernatant was collected as "conditioned media", and further filtered with 0.22 micron filter or centrifuged at 300 g for 3 minutes to remove any remaining cells. The conditioned media was then combined with fresh culture media at 1:1 ratio, and applied to receiving cells.

Cell Imaging

For imaging experiments, cells were seeded at 24 or 96-well TC-treated plates with imaging grade plastic bottoms (ibidi inc.), as described above.

Snapshots were acquired on the EVOS imaging system (ThermoFisher) with the EVOS AMG 4× objective (0.13 NA), or a 10× olympus objective (0.30 NA), with the system's default auto-scanning function.

Time-lapse images were acquired on an inverted Olympus IX81 fluorescence microscope with Zero Drift Control (ZDC), an ASI 2000XY automated stage, iKon-M CCD camera (Andor, Belfast, NIR), and a 20× olympus objective (0.70 NA). Fluorophores were excited with an X-Cite XLED1 light source (Lumen Dynamics). Cells were kept in a custom-made environmental chamber enclosing the microscope, with humidified 5% $CO_2$ flow at 37° C. Microscope and image acquisition were controlled by Metamorph software (Molecular Devices). For results in FIG. 5, in each well, 25 positions (about 665 um×665 um each) was imaged in a 5×5 grid with 600 um intervals, every 4 hours. The images were stitched using Fiji's stitching plugin. For results in FIG. 9, 12 individual positions were imaged per well every hour.

Images were background-subtracted and masked by the constitutive mTagBFP2 fluorescent in blue channel (not shown) and quantified by summing up intensities of pixels that passed the mask. Error bars are standard deviations of four images at the same distance.

Long-Range Gradient Setup

Silicone-based inserts (ibidi inc. #80269) were first attached to the bottom of TC-treated 6 cm dishes (Thermo Scientific). Sender-receiver cells were seeded inside the inserts and allowed to settle down for 2 hours. The inserts are removed and the whole dish is washed with PBS twice to remove non-attached Sender-Receiver cells. Receiver cells were then seeded in the dish at approximately 20% confluence, and allowed to settle down for another 6 hours. To prepare agarose infused media, 2% low melting point agarose (EMD) was melted in alpha-MEM at 95° C. for 10 minutes, and temperature was cooled to 42° C., before IAM and other ingredients of complete media (described above) were mixed in. Agarose infused media was applied to dishes with original media removed and allowed to solidify at room temperature for 20 minutes, before moved into the incubator.

Bulk RNA Sequencing of Isolates

Cells were cultured for 2 days at under 80% confluence before harvested for bulk RNA extrusion (Qiagen #74104). The library preparation and sequencing was performed at Millard and Muriel Jacobs Genetics and Genomics Laboratory at Caltech as service. Specifically, RNA integrity was assessed using Bioanalyzer (Agilent Technologies #5067-1513) and mRNA was isolated using NEBNext Poly(A) mRNA Magnetic Isolation Module (NEB #E7490). RNA-seq libraries were constructed using NEBNext Ultra II RNA Library Prep Kit for Illumina (NEB #E7770) following manufacturer's instructions. Libraries were quantified with Qubit dsDNA HS Kit (ThermoFisher Scientific #Q32854) and the size distribution was confirmed with Bioanalyzer (Agilent Technologies #5067-4626). Libraries were sequenced on Illumina HiSeq2500 in single read mode with the read length of 50 nt to the depth of 15 million reads per sample following manufacturer's instructions. Base calls were performed with RTA 1.13.48.0 followed by conversion to FASTQ with bcl2fastq 1.8.4.

Quantification and Statistical Analysis

Confluence Estimation

Images, regardless of acquisition conditions, were converted to grey-scale for analysis in cases where pseudo-color was applied by the software automatically (a 2×2 binning is applied if acquired using the EVOS system). For each experiment, around 5 images were used in Ilastik pixel classification mode to train a classifier (decision tree-based), that classifies each pixel as cell or not cell (the trained models are available with the full data set). The classifier was then applied to the entire set of images, and output as probability masks. The masks were then analyzed to determine the fractions of "cell" pixels in the image. This value was then used to estimate confluence.

RNA-Sequencing Analysis

The reads were first trimmed and filtered by Trim Galore! (Babraham Institute) and then counted with kallisto with the CHO transcriptome (RefSeq GCF_000223135.1) as a reference. Genes that are differentially expressed were determined with DESeq2 and exported as ranked lists, with sign(log2FoldChange)·−log(padj) as weights. The top 30 genes in each of the three comparisons (negative vs control, paradoxical vs control and paradoxical vs negative), if not annotated with a symbol in the RefSeq file, are manually annotated by looking up their gene products in RSCB PDB (RSCB.org). The ranked gene list is then input into the GSEA to perform pathway enrichment analysis, against the curated KEGG pathway annotation (MSigDB: c2.cp.kegg.v7.4.symbols), with mapping from mouse gene symbol to human orthologs.

Bootstrapping and Significant Tests

Figure 5E:
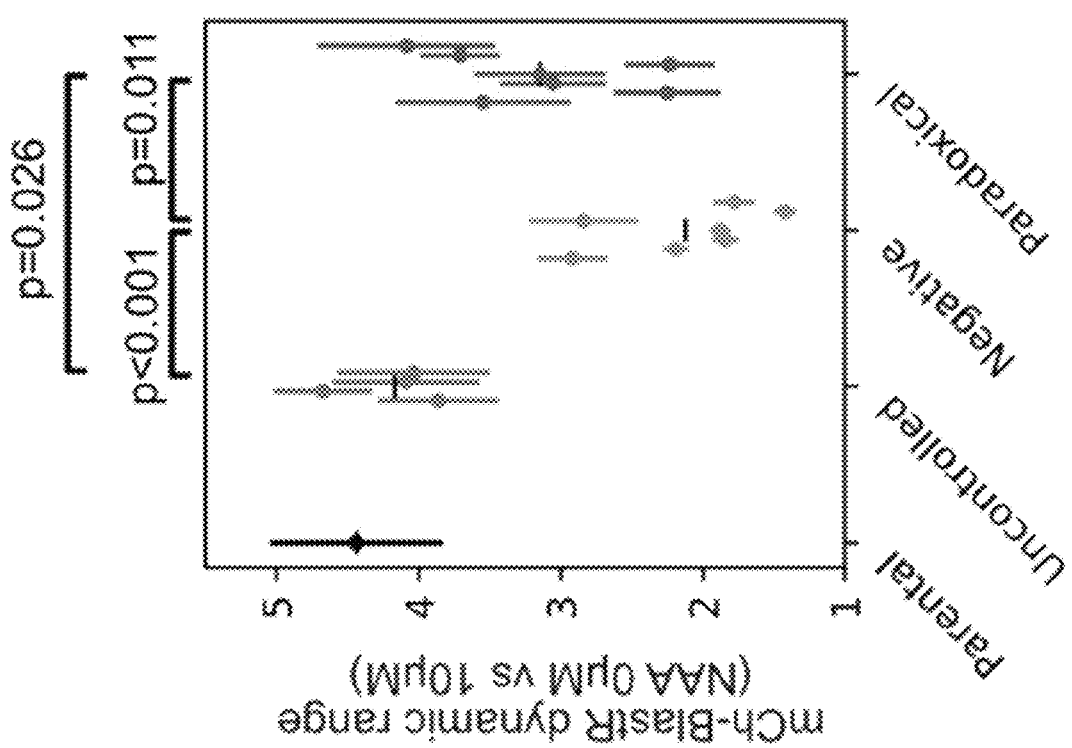
Figure 5D:
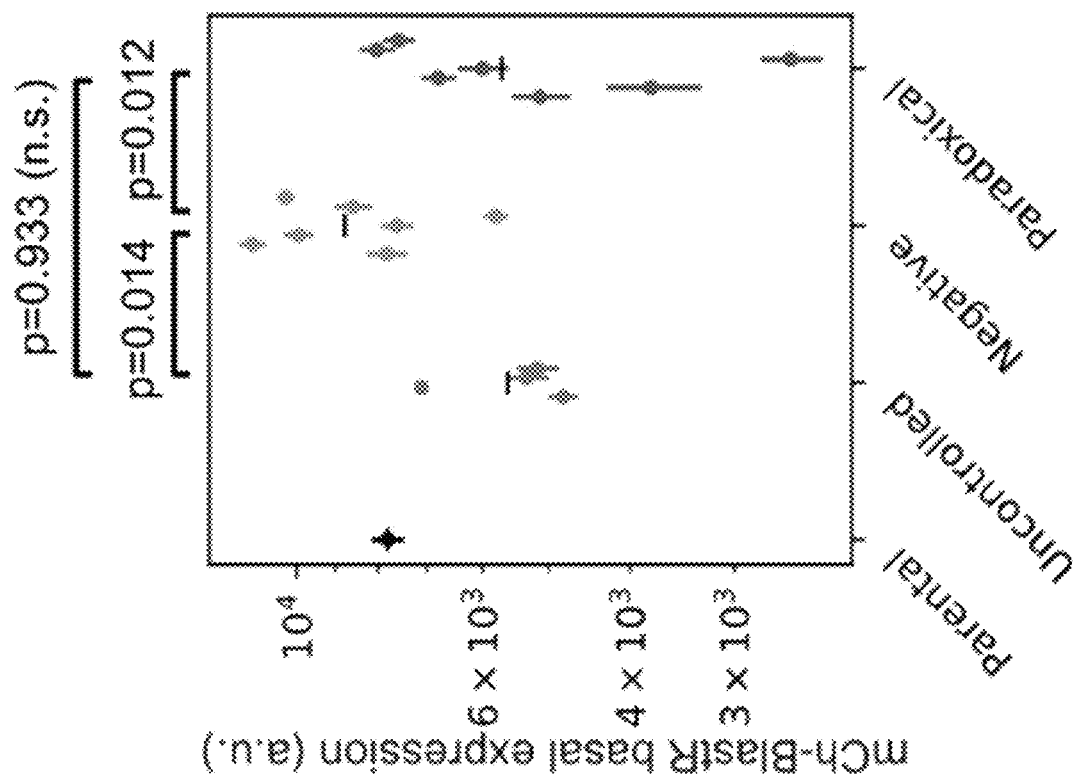
Figure 5G:
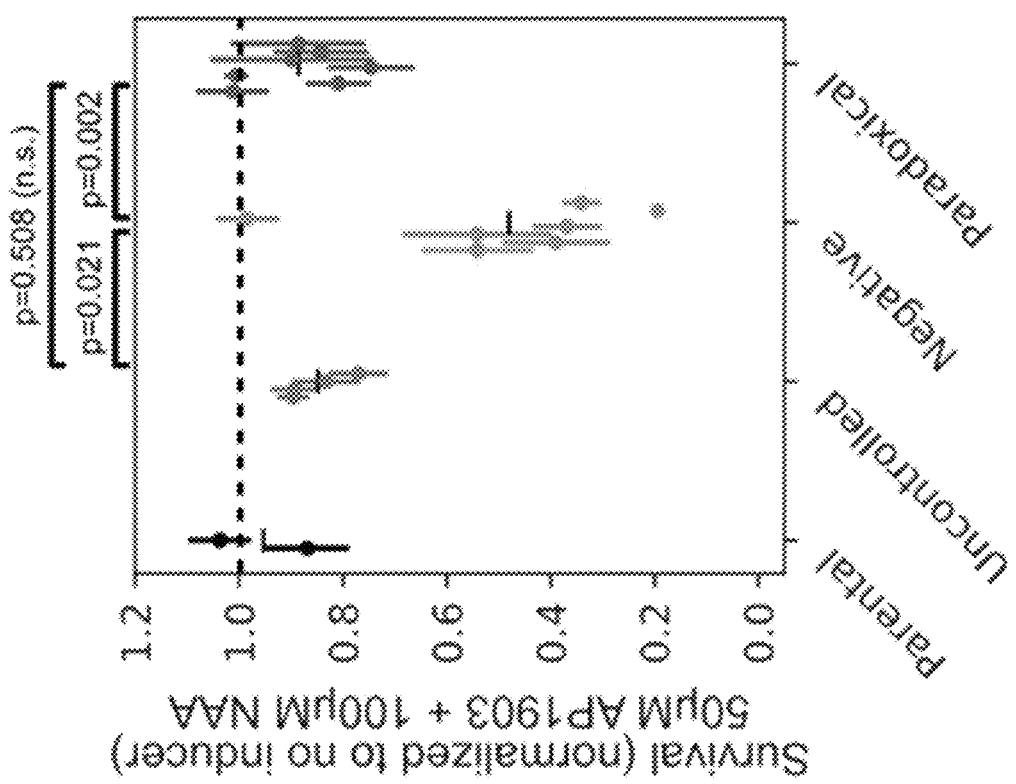
Figure 5F:
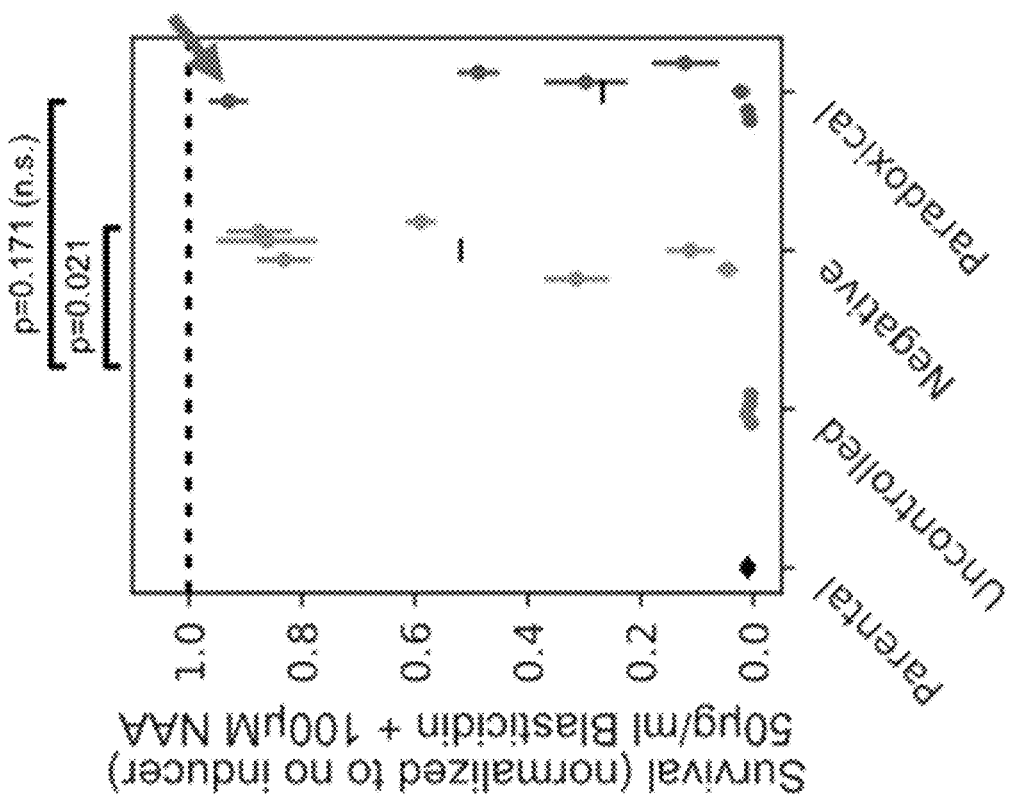
Figure 5H:
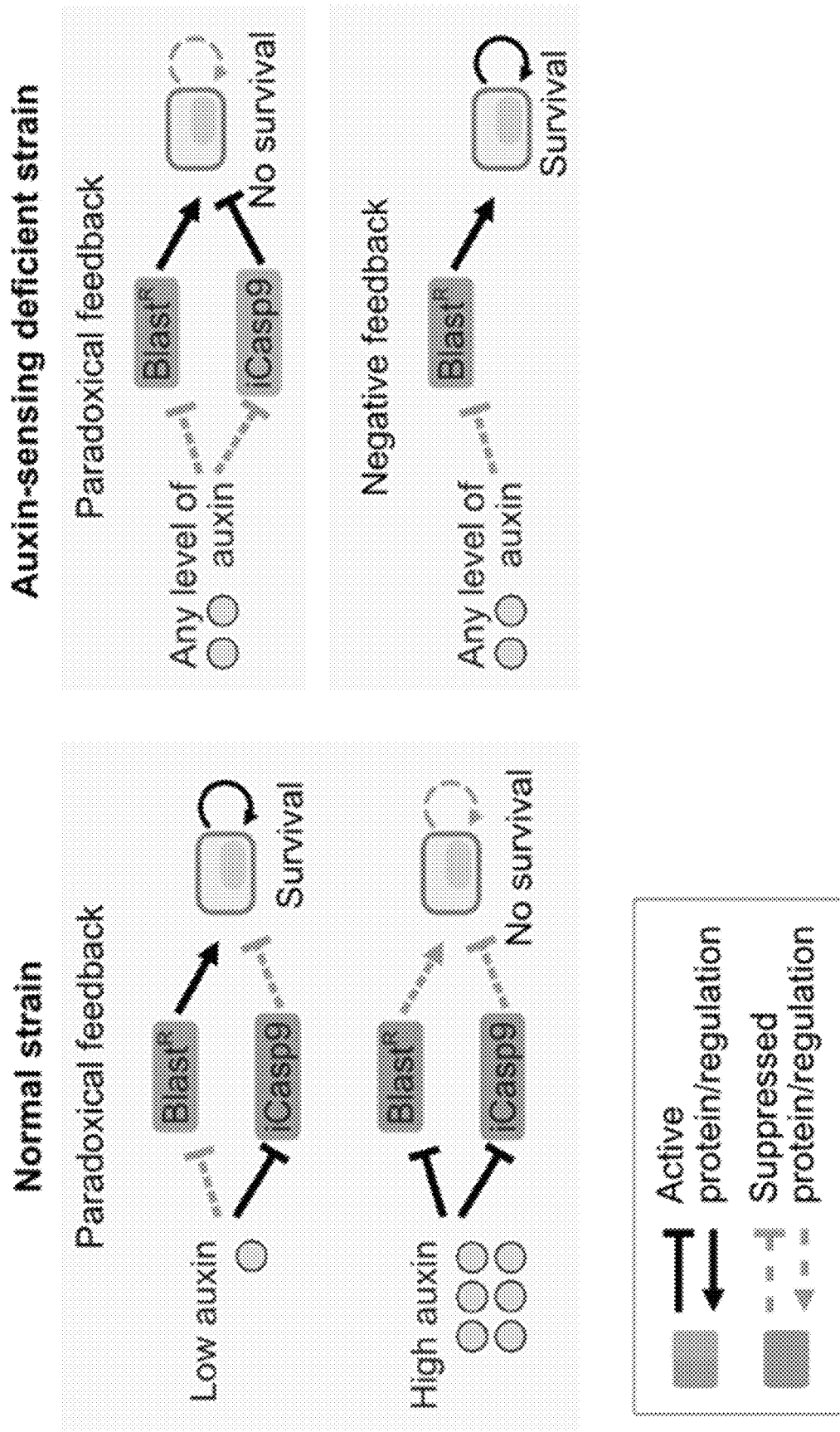

Bootstrapping is used in FIGS. 5E-5G, where the experimental group is normalized to a normalizer. For M experiment replicates and N normalizer replicates, all possible combinations of normalizing (M×N values) is calculated and the mean and standard deviation is reported as a data point with bar in the figures.

Significance tests in FIGS. 5D-5G are from double-ended Student's T test, with a null hypothesis that assumes the mean values of the means from each individual isolate are not different. The tests in FIG. 5B and FIG. 9A are Student's T tests with null hypothesis assuming the mean values of each group, averaged for the last day, are not different.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A nucleic acid composition, comprising:
   a first polynucleotide encoding a first synthase, wherein the first synthase comprises an indole-3 acetic acid hydrolase capable of catalyzing the synthesis of an orthogonal signal from a first precursor molecule;
   a second polynucleotide encoding a second synthase, wherein the second synthase is capable of catalyzing the synthesis of the first precursor molecule from a second precursor molecule; and
   a third polynucleotide encoding a transporter capable of transporting the orthogonal signal across a cell membrane;
   wherein the first polynucleotide, the second polynucleotide, and the third polynucleotide are operably linked to a ubiquitous mammalian promoter.

2. The nucleic acid composition of claim 1, comprising: a fourth polynucleotide encoding a signal-binding protein comprising the F-box transport inhibitor response 1 (TIR1) wherein the TIR1 protein is capable of binding the orthogonal signal; a fifth polynucleotide encoding a first fusion protein comprising a signal-responsive domain and a pro-growth protein; and optionally a sixth polynucleotide encoding a second fusion protein comprising a signal-responsive domain and a pro-death protein, wherein the signal-responsive domain comprises an auxin inducible degron (AID); and wherein the signal-binding protein bound to the orthogonal signal is capable of reducing the stability of the first and/or second fusion protein comprising a signal-responsive domain; wherein the fourth polynucleotide, the fifth polynucleotide, and the sixth polynucleotide are operably linked to a ubiquitous mammalian promoter.

3. The nucleic acid composition of claim 2, wherein the auxin inducible degron (AID) comprises a minimal auxin inducible degron (mAID).

4. The nucleic acid composition of claim 2, wherein the pro-growth protein is essential for survival and/or cell cycle progression, optionally a cell-cycle regulator, and/or wherein the pro-growth protein is essential for survival and/or cell cycle progression in the presence of an exogenous agent, optionally the exogenous agent is an antibiotic, further optionally the pro-growth protein provides antibiotic resistance.

5. The nucleic acid composition of claim 2, wherein the pro-death protein is capable of halting cell growth and/or inducing cell death, and/or wherein the pro-death protein is capable of halting cell growth and/or inducing cell death in the presence of a pro-death agent.

6. The nucleic acid composition of claim 2, wherein the signal-binding protein bound to the orthogonal signal is capable of triggering the ubiquitylation and proteasomal degradation of the protein comprising a signal-responsive domain.

7. The nucleic acid composition of claim 1, wherein the indole-3 acetic acid hydrolase comprises iaaH, aux2 and/or AMI1.

8. The nucleic acid composition of claim 1, wherein the transporter is auxin exporter PIN2, optionally *Arabidopsis thaliana* PIN2.

9. The nucleic acid composition of claim 1, wherein the second precursor molecule is an endogenous molecule of a cell, optionally L-tryptophan.

10. The nucleic acid composition of claim 1, wherein the orthogonal signal is an auxin.

11. The nucleic acid composition of claim 1, wherein the nucleic acid composition is comprised within one or more vectors; optionally at least one of the one or more vectors is a viral vector, a plasmid, a naked DNA vector, a lipid nanoparticle, or any combination thereof; and further optionally the viral vector is an AAV vector, a lentivirus vector, a retrovirus vector, an integration-deficient lentivirus (IDLV) vector.

\* \* \* \* \*